US012758494B2

(12) United States Patent
Shenoy et al.

(10) Patent No.: US 12,758,494 B2
(45) Date of Patent: *Oct. 13, 2026

(54) ORAL POLYPEPTIDE FORMULATIONS

(71) Applicant: Bhami's Research Laboratory, Pvt. Ltd., Mangalore (IN)

(72) Inventors: Bhami Shenoy, Mangalore (IN); Suryakanth Motilal Pai, Mangalore (IN)

(73) Assignee: Bhami's Research Laboratory, Pvt. Ltd., Mangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/339,808

(22) Filed: Jun. 22, 2023

(65) Prior Publication Data

US 2024/0122847 A1 Apr. 18, 2024

(30) Foreign Application Priority Data

Oct. 14, 2022 (IN) ............................. 202241058760
Mar. 27, 2023 (IN) ............................. 202341022048

(51) Int. Cl.
*A61K 9/00* (2006.01)
*A61K 38/12* (2006.01)
(Continued)

(52) U.S. Cl.
CPC ............ *A61K 9/0056* (2013.01); *A61K 38/12* (2013.01); *A61K 38/26* (2013.01); *A61K 38/27* (2013.01);
(Continued)

(58) Field of Classification Search
CPC ...... A61K 9/0056; A61K 38/12; A61K 38/26; A61K 38/27; A61K 38/28; A61K 38/29;
(Continued)

(56) References Cited

U.S. PATENT DOCUMENTS 10,646,569 B2 5/2020 Shenoy
2006/0178296 A1* 8/2006 Goldberg ............... A61K 38/28
514/5.9

(Continued)

FOREIGN PATENT DOCUMENTS

RU 2 117 488 C1 8/1998
WO WO-1987/005505 A1 * 9/1987 ............... A61K 9/64

(Continued)

OTHER PUBLICATIONS

Puhl, Sebastian et al. "Recent advances in crystalline and amorphous particulate protein formulations for controlled delivery". Asian Journal of Pharmaceutical Sciences, vol. 11, No. 4, Elsevier BV, Aug. 2016, pp. 469-477. https://doi.org/10.1016/j.ajps.2016.06.003. (Year: 2016).*

(Continued)

*Primary Examiner* — Sahana S Kaup
*Assistant Examiner* — Lucy M Tien
(74) *Attorney, Agent, or Firm* — Choate, Hall & Stewart LLP; Brenda Herschbach Jarrell; Beejan Asady

(57) ABSTRACT

The present disclosure provides, among other things, methods and compositions for the oral administration of polypeptides. Many polypeptides are typically administered in liquid solutions by intravenous or subcutaneous injection. The present disclosure provides methods and compositions that include a polypeptide formulation, e.g., truffle, tablet, globule, or candy formulation suitable for buccal/sublingual administration, where the formulation includes an amorphous polypeptide composition or a crystallized polypeptide composition and a pharmaceutically acceptable carrier.

18 Claims, 71 Drawing Sheets

Hollow Sugar Truffles

(51) Int. Cl.

| | |
|---|---|
| ***A61K 38/26*** | (2006.01) |
| ***A61K 38/27*** | (2006.01) |
| ***A61K 38/28*** | (2006.01) |
| ***A61K 38/29*** | (2006.01) |
| ***A61K 39/395*** | (2006.01) |
| ***A61K 47/26*** | (2006.01) |

(52) U.S. Cl.
CPC .............. *A61K 38/28* (2013.01); *A61K 38/29* (2013.01); *A61K 39/39558* (2013.01); *A61K 47/26* (2013.01)

(58) Field of Classification Search
CPC .............. A61K 39/39558; A61K 47/26; A61K 2039/54; A61K 38/08; A61K 39/39591; A61K 47/02; A61K 47/10; A61K 9/1682; A61K 9/1688; C07K 2317/24; C07K 14/62; C07K 14/635; C07K 14/61; C07K 16/32
See application file for complete search history.

(56) References Cited

U.S. PATENT DOCUMENTS

| | | | | |
|---|---|---|---|---|
| 2006/0204626 | A1* | 9/2006 | Talbot | A23G 1/507 426/383 |
| 2010/0166914 | A1* | 7/2010 | Herron | A23G 1/48 426/103 |
| 2014/0135263 | A1* | 5/2014 | Pohl | A61K 9/0056 514/5.9 |
| 2014/0162965 | A1 | 6/2014 | Maggio | |
| 2016/0263047 | A1* | 9/2016 | Kaufman | A61K 31/198 |
| 2020/0254094 | A1 | 8/2020 | Shenoy | |
| 2022/0211070 | A1* | 7/2022 | Liang | A23G 1/46 |
| 2022/0339114 | A1 | 10/2022 | Pai et al. | |

FOREIGN PATENT DOCUMENTS

| | | | |
|---|---|---|---|
| WO | WO-2007/143367 | A1 | 12/2007 |
| WO | WO-2018/211517 | A1 | 11/2018 |
| WO | WO-2022/219646 | A1 | 10/2022 |
| WO | WO-2024/079738 | A1 | 4/2024 |

OTHER PUBLICATIONS

U.S. Appl. No. 18/339,706, filed Jun. 22, 2023, Shenoy et al.

Renukuntla, J. et al., Approaches for Enhancing Oral Bioavailability of Peptides and Proteins, Int. J. Pharm., 447:75-93 (2013).

International Search Report for PCT/IN2023/050599, 4 pages (mailed Oct. 2, 2023).

Mallik, J. et al., Hard Gelatin Capsules (Two Piece)—A Unique Pharmaceutical Dosage Form—An Exhaustive Review, Asian Jrnl. Pharm. Res. Dev., 1(4):1-9 (2013).

Written Opinion for PCT/IN2023050599, 7 pages (mailed Oct. 2, 2023).

* cited by examiner

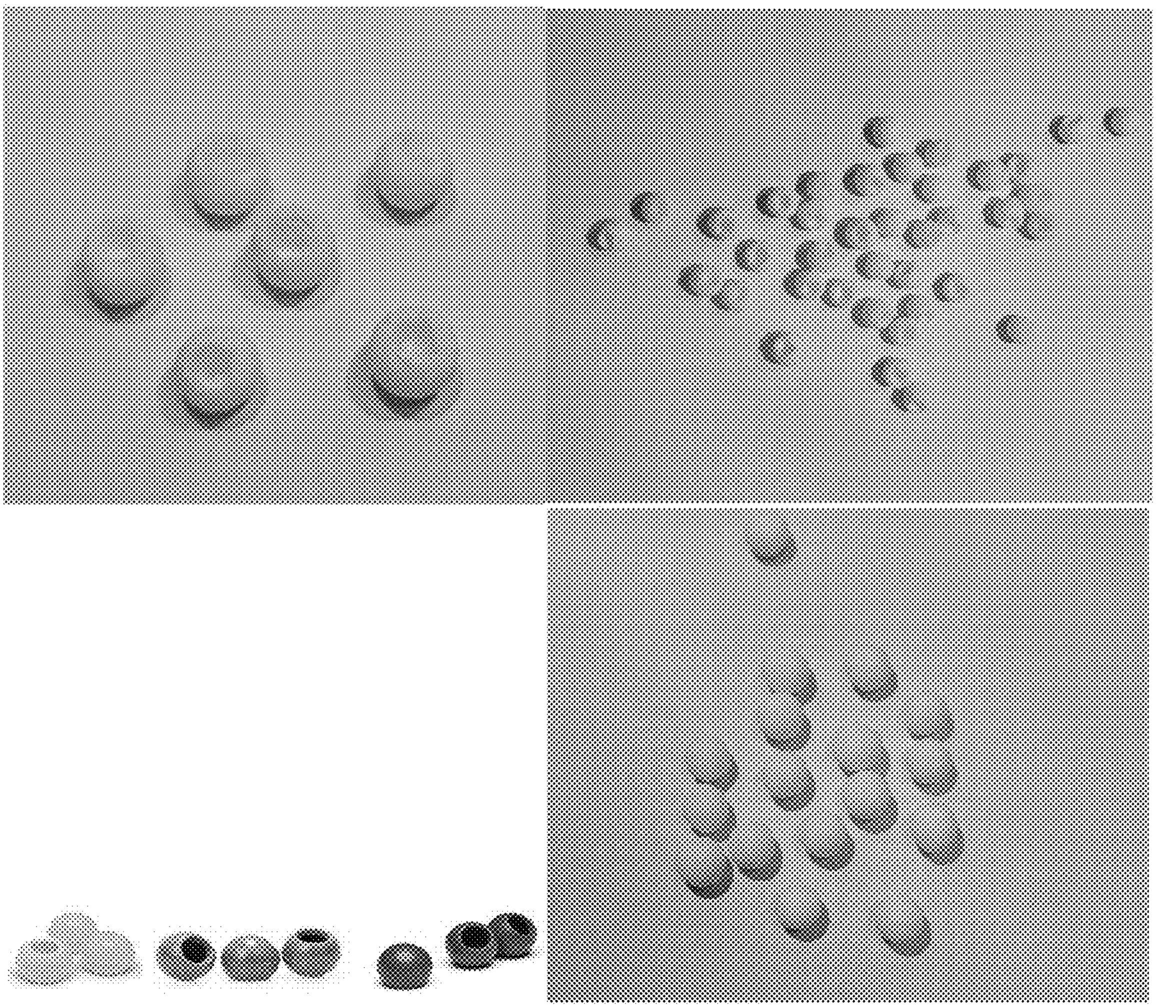
FIG. 1 Hollow Sugar Truffles

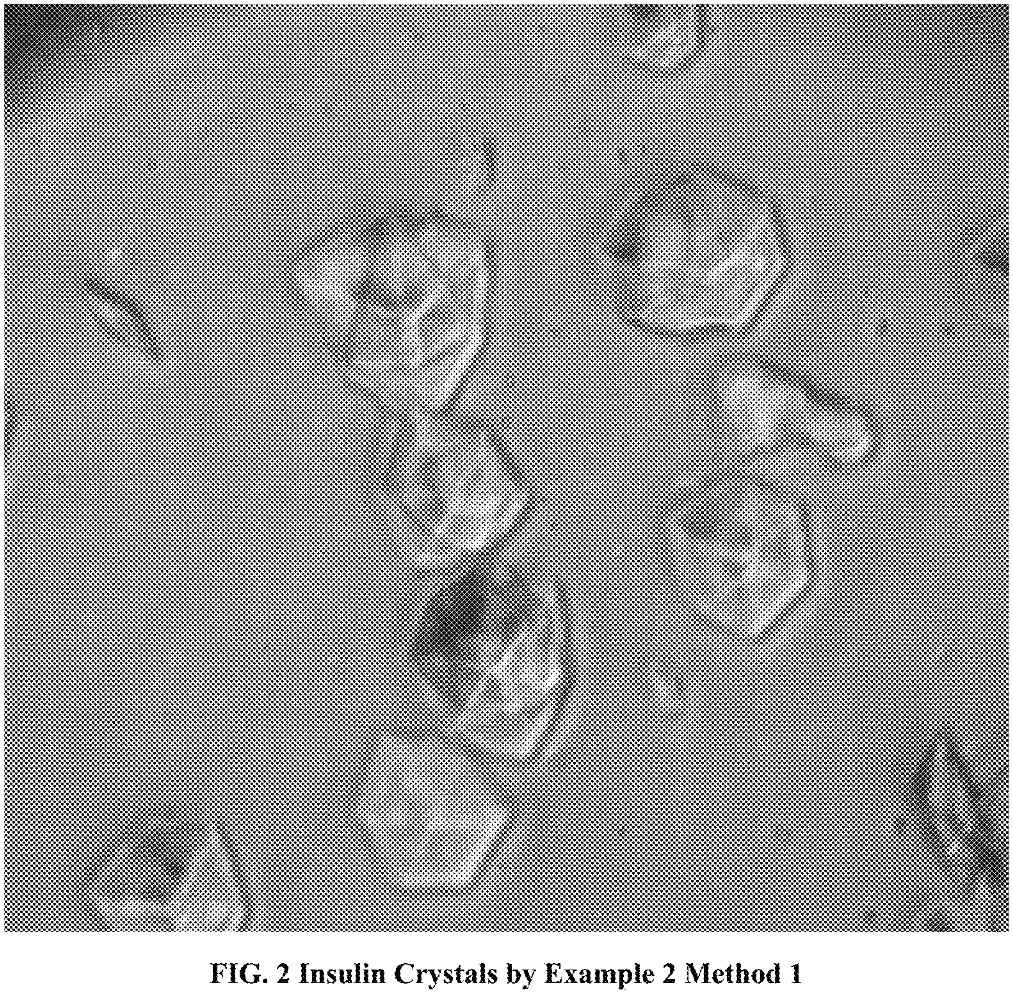
FIG. 2 Insulin Crystals by Example 2 Method 1

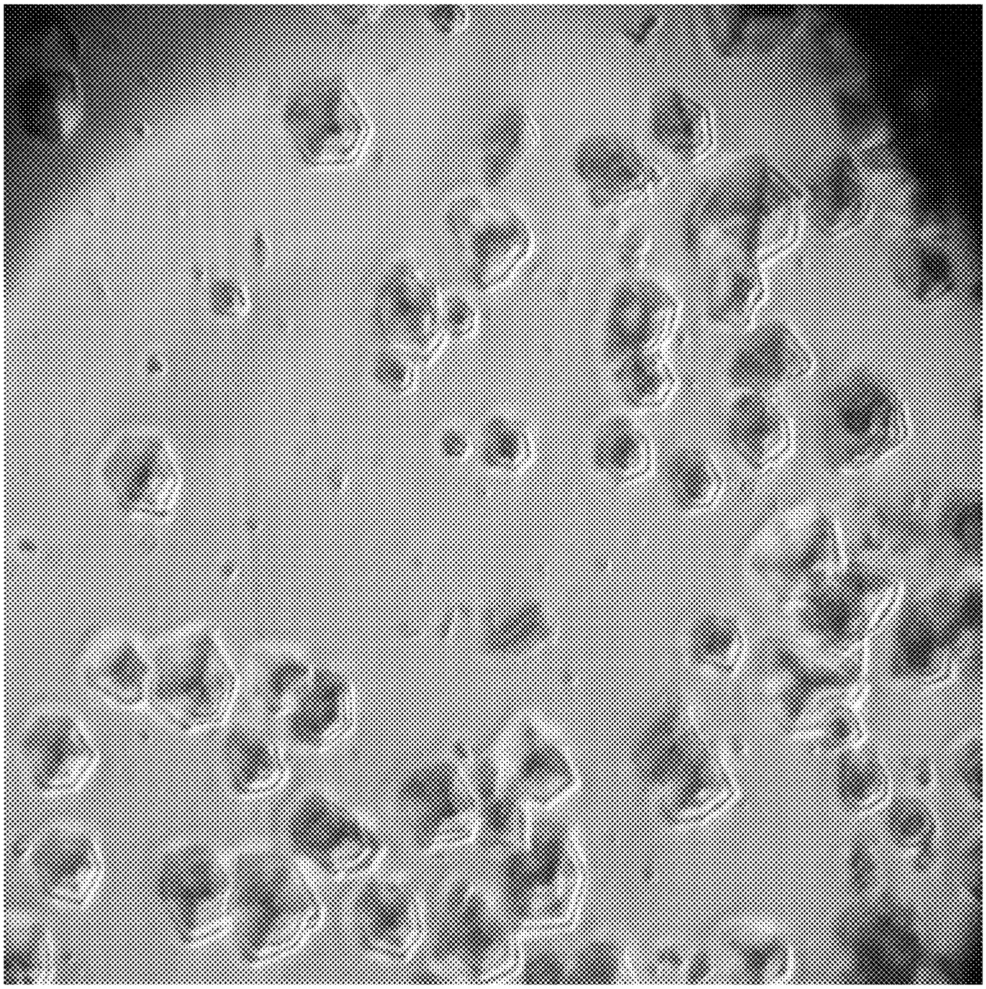
FIG. 3 Insulin Crystals by Example 2 Method 2

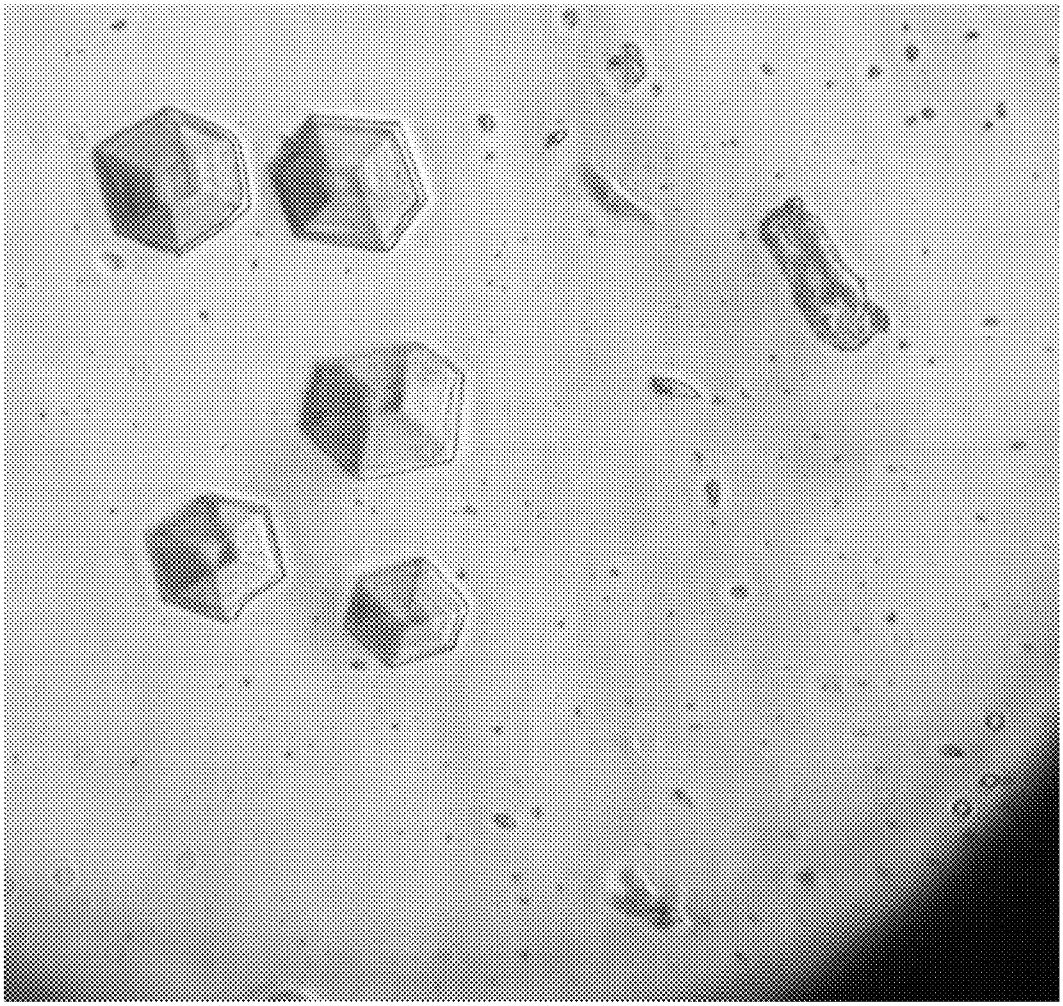
FIG. 4 Insulin Crystals by Example 2 Method 3

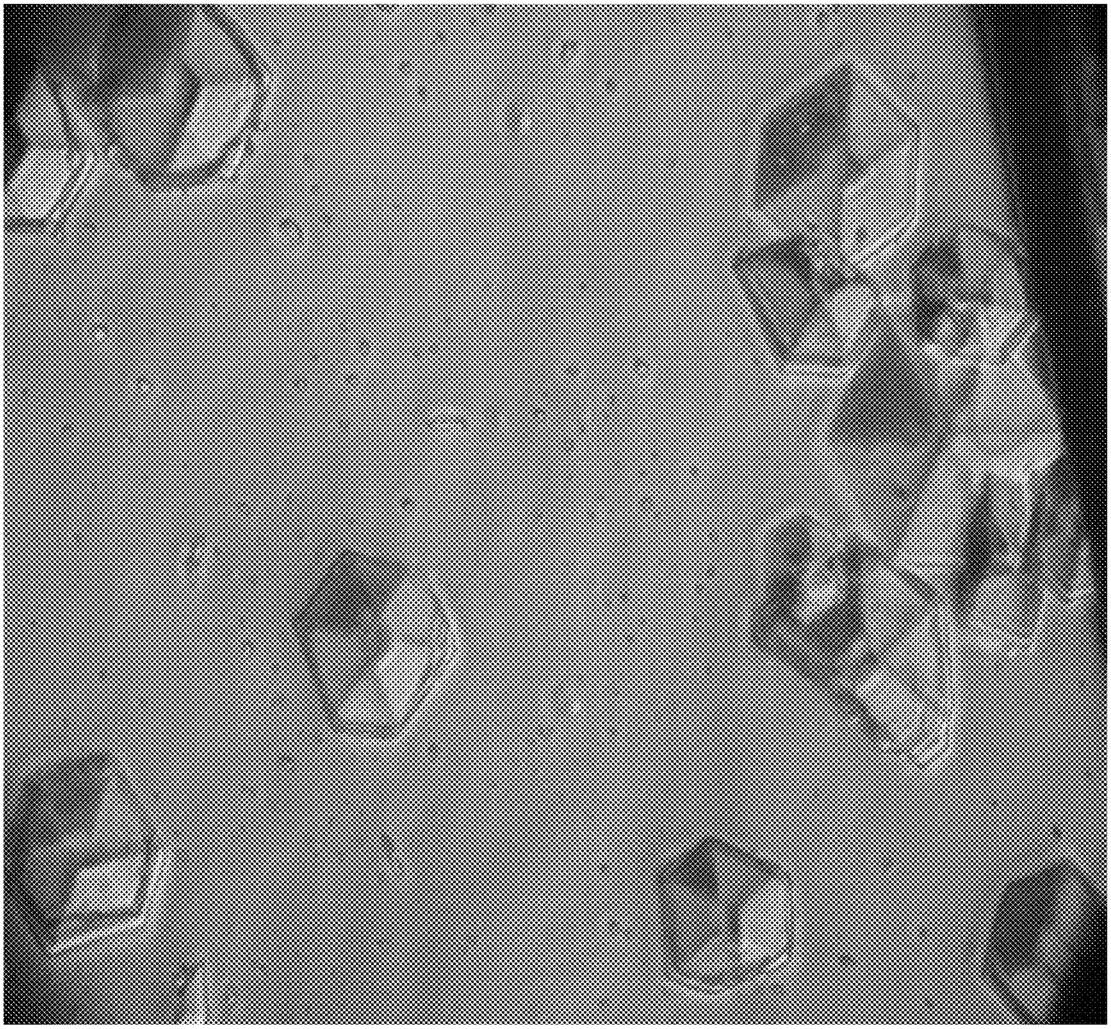
FIG. 5 Insulin Crystals by Example 2 Method 4

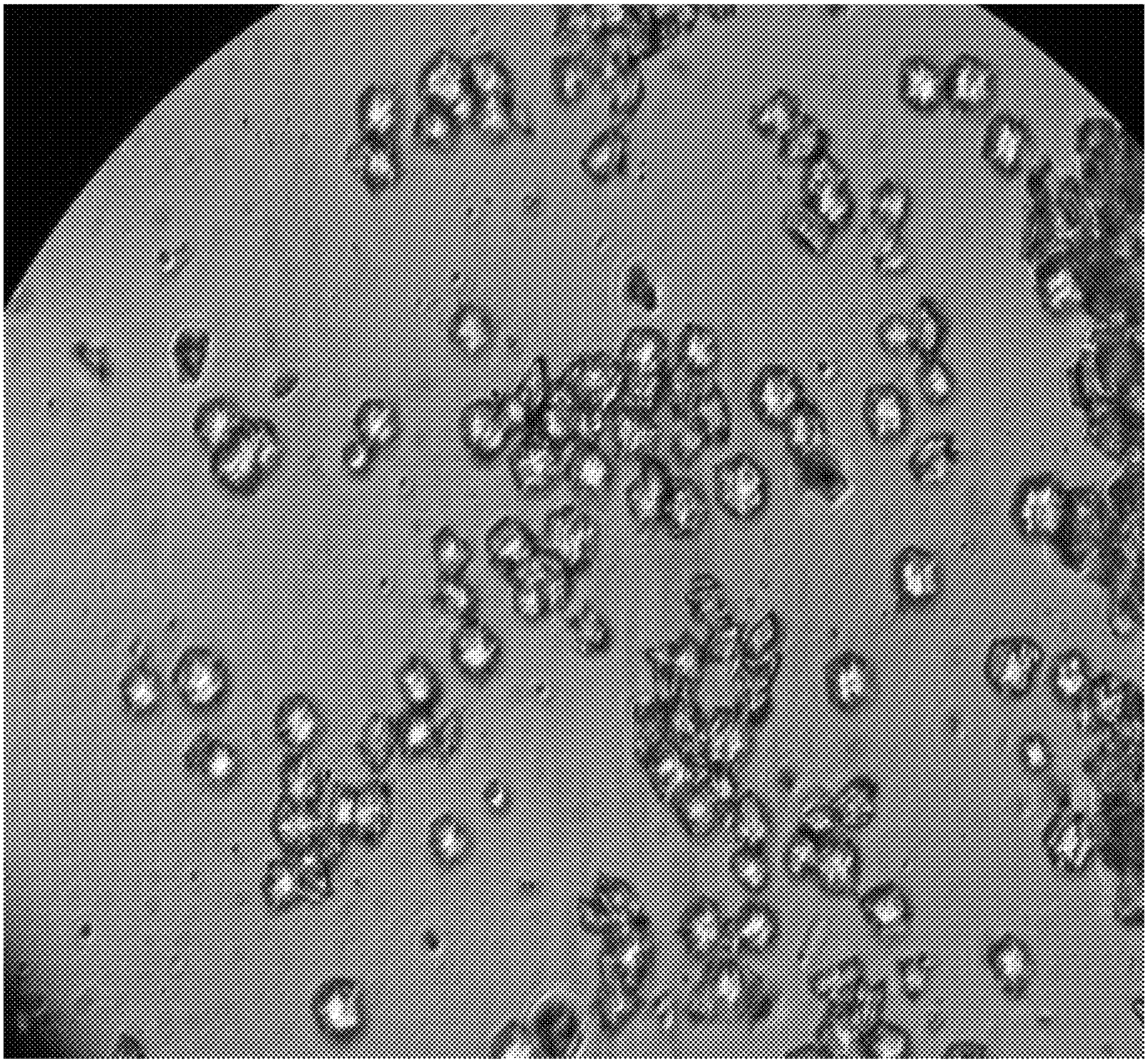
FIG. 6 Insulin Crystals by Example 2 Method 5

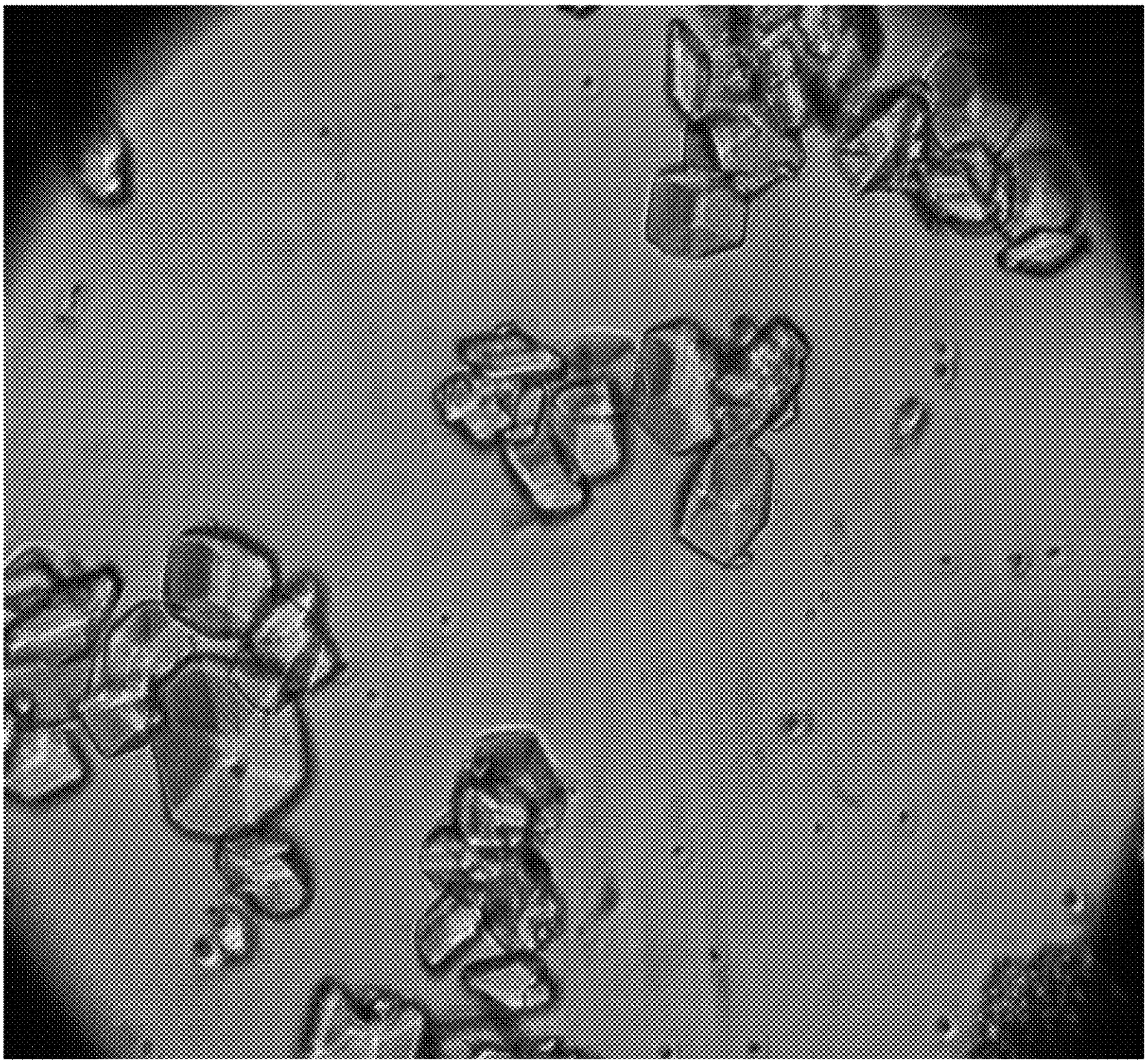
FIG. 7 Insulin Crystals by Example 2 Method 6

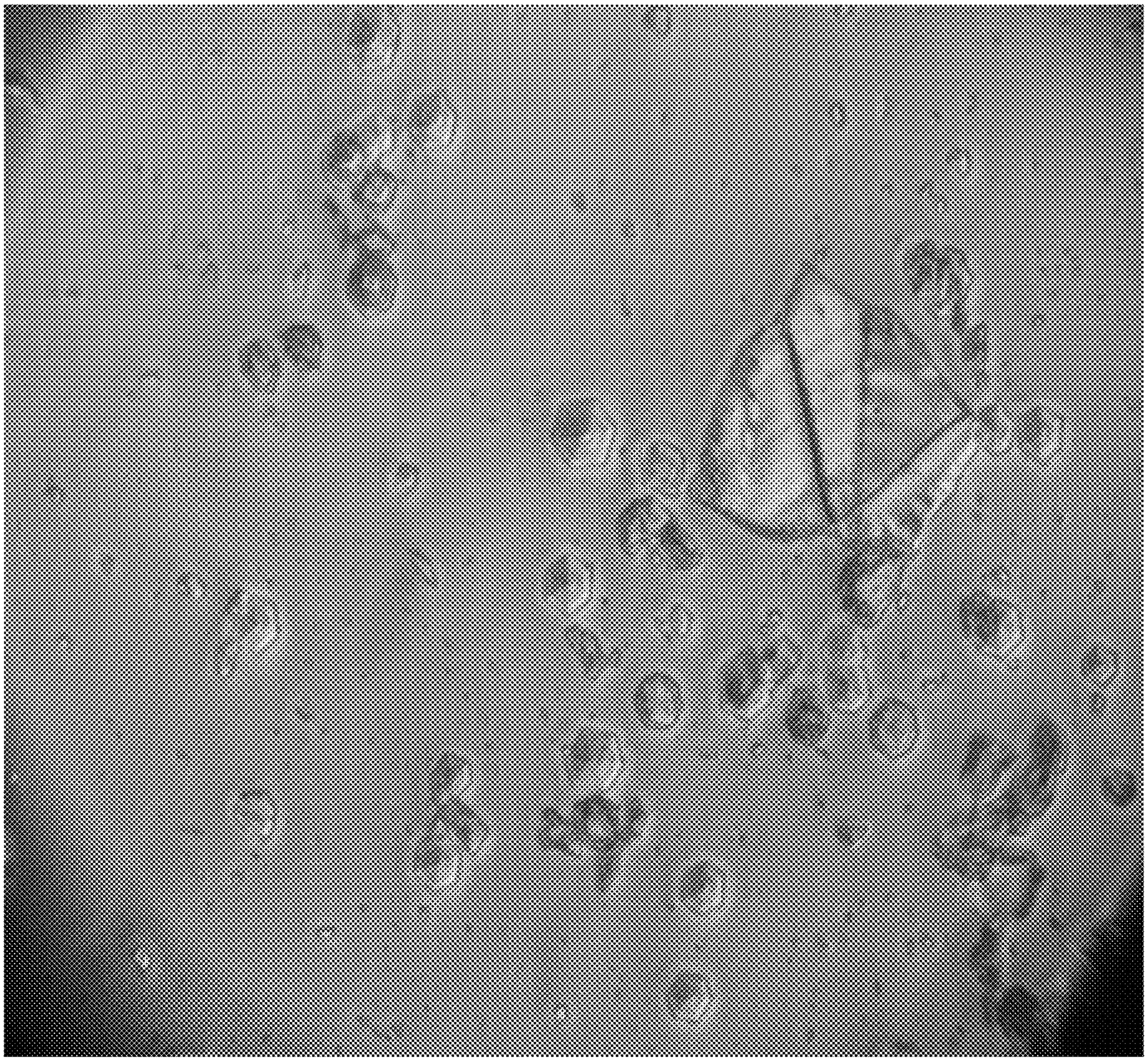
FIG. 8 Insulin Crystals by Example 2 Method 7

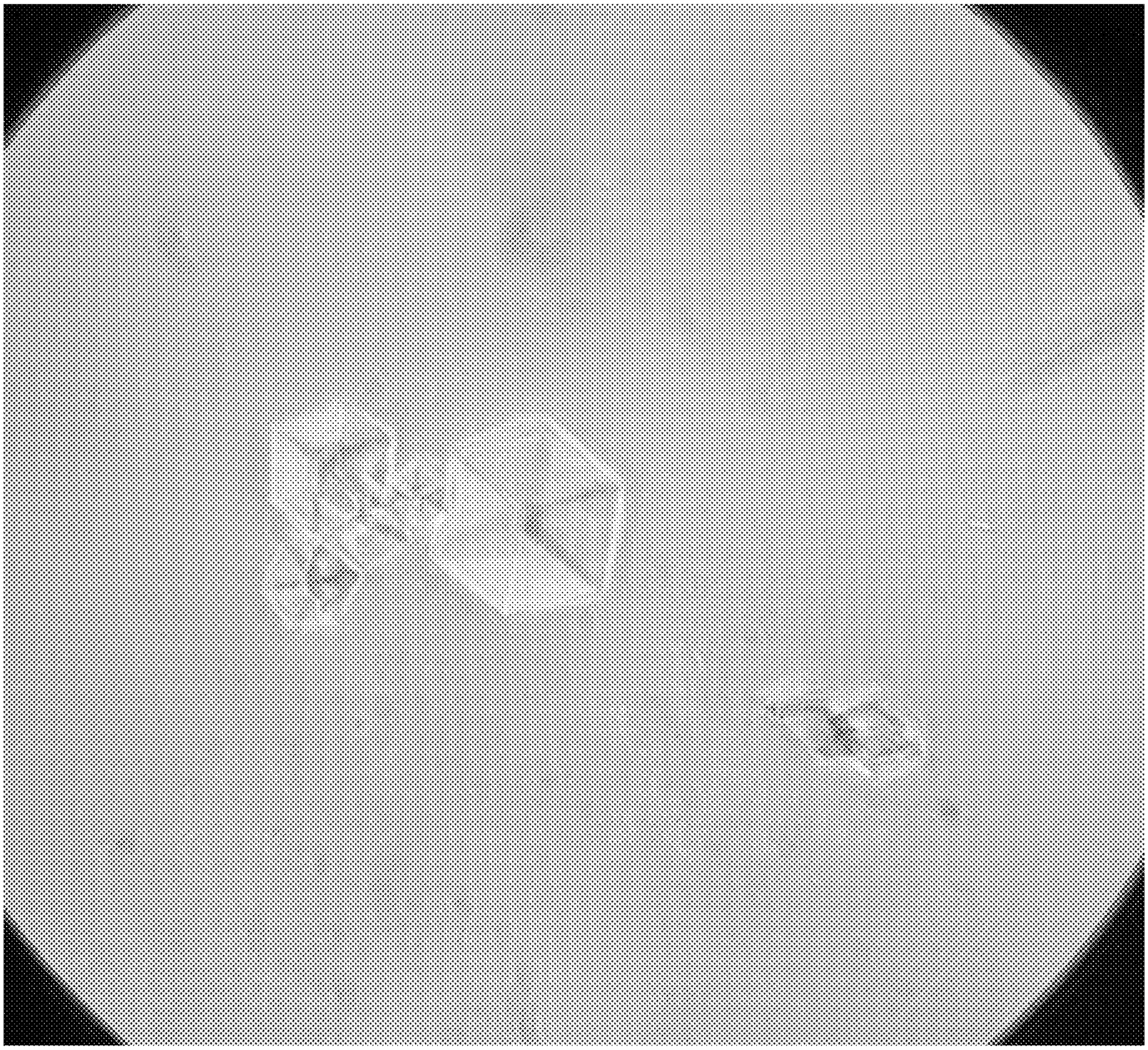
FIG. 9 Insulin Crystals by Example 2 Method 8

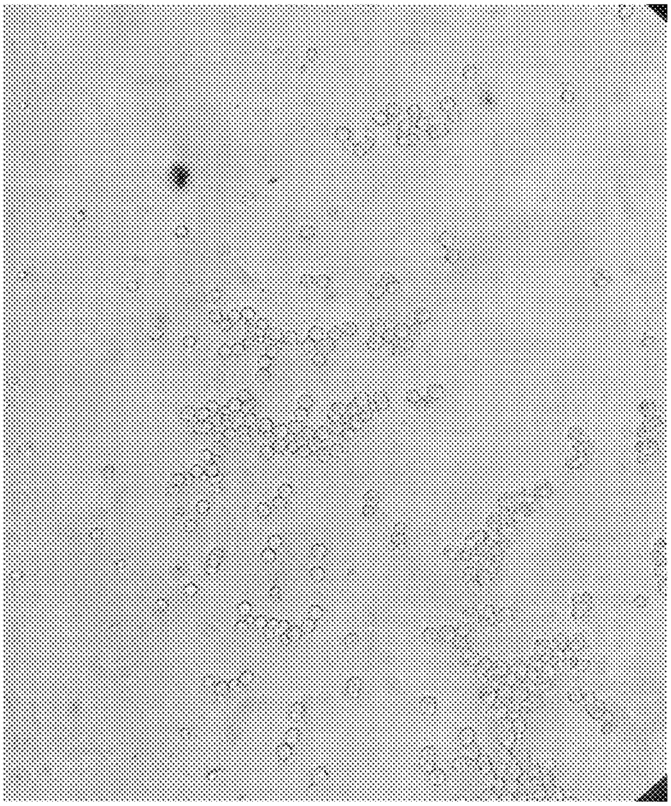
FIG. 10A Lantus/Insulin Glargine Crystals
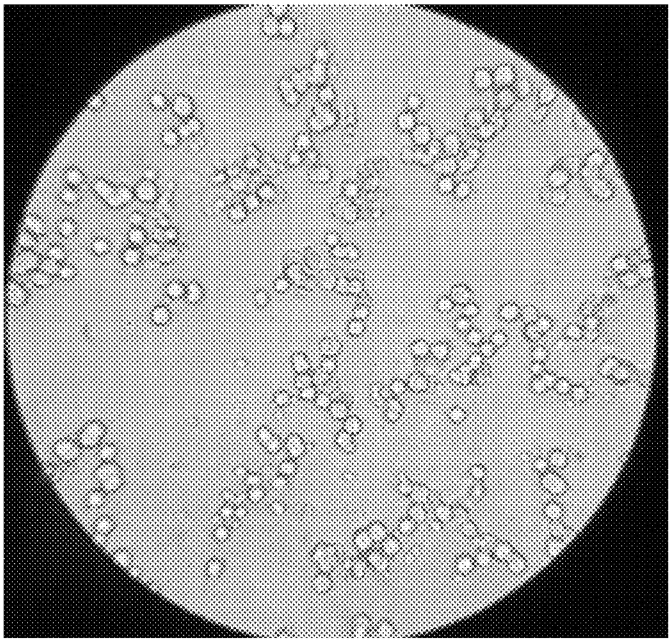
FIG. 10B Lantus/Insulin Glargine Crystals

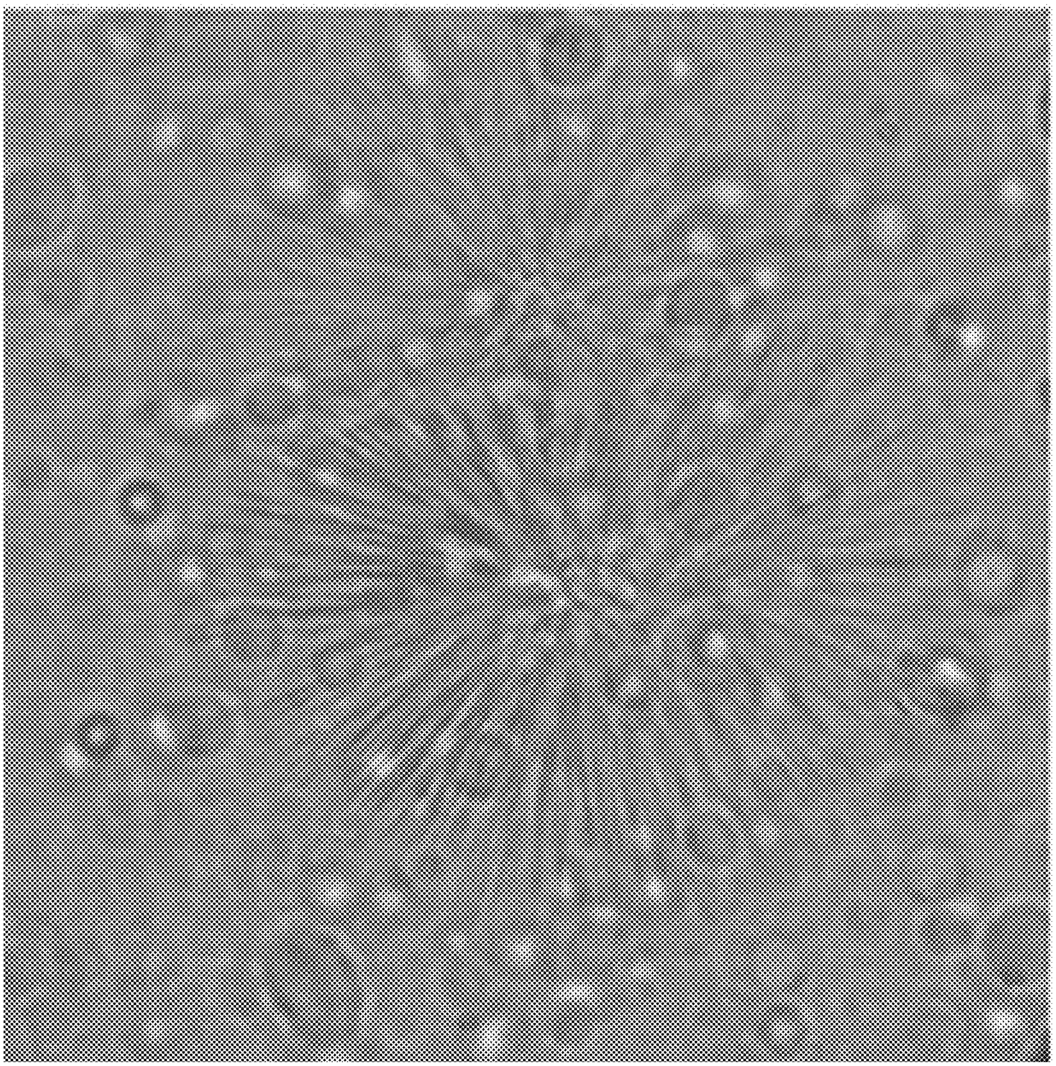
FIG. 11 PTH Crystals by Example 4 Method 1

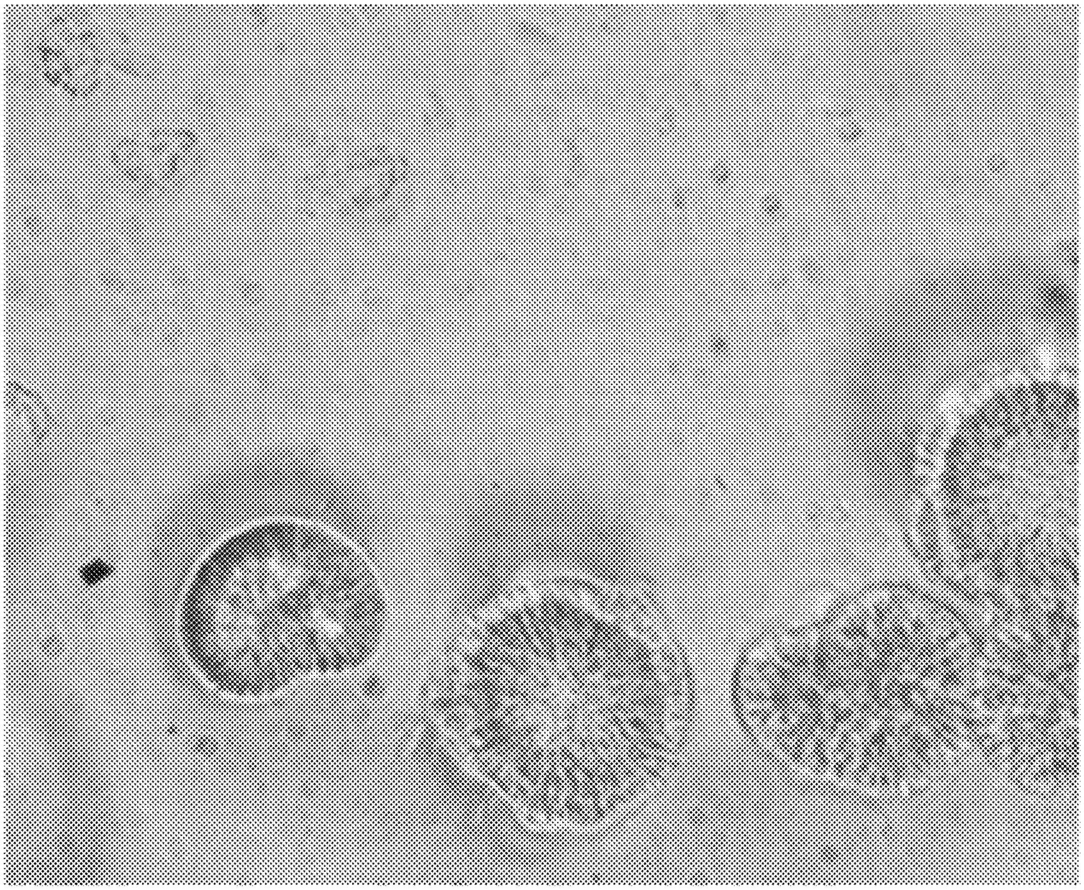
FIG. 12 PTH Crystals by Example 4 Method 2

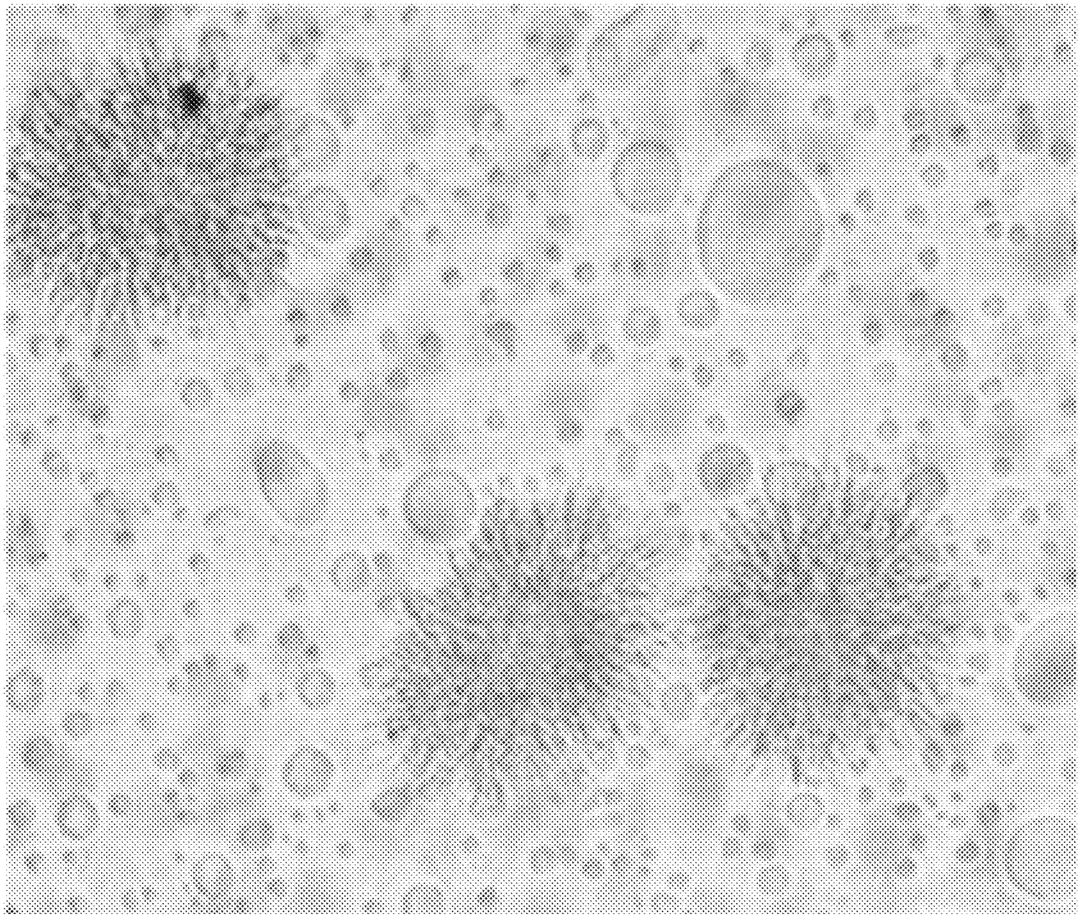
FIG. 13 PTH Crystals by Example 4 Method 3

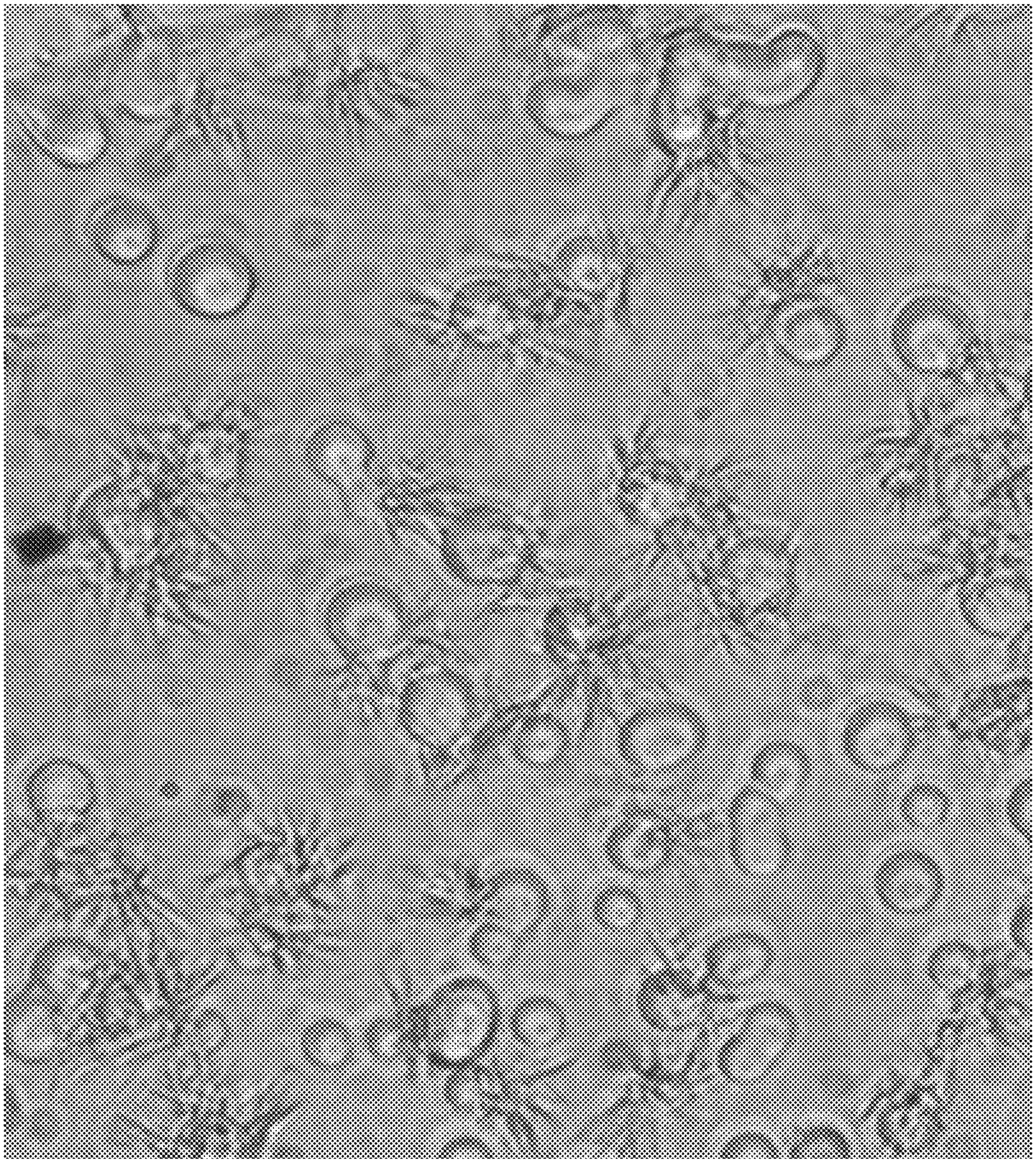
FIG. 14 PTH Crystals by Example 4 Method 4

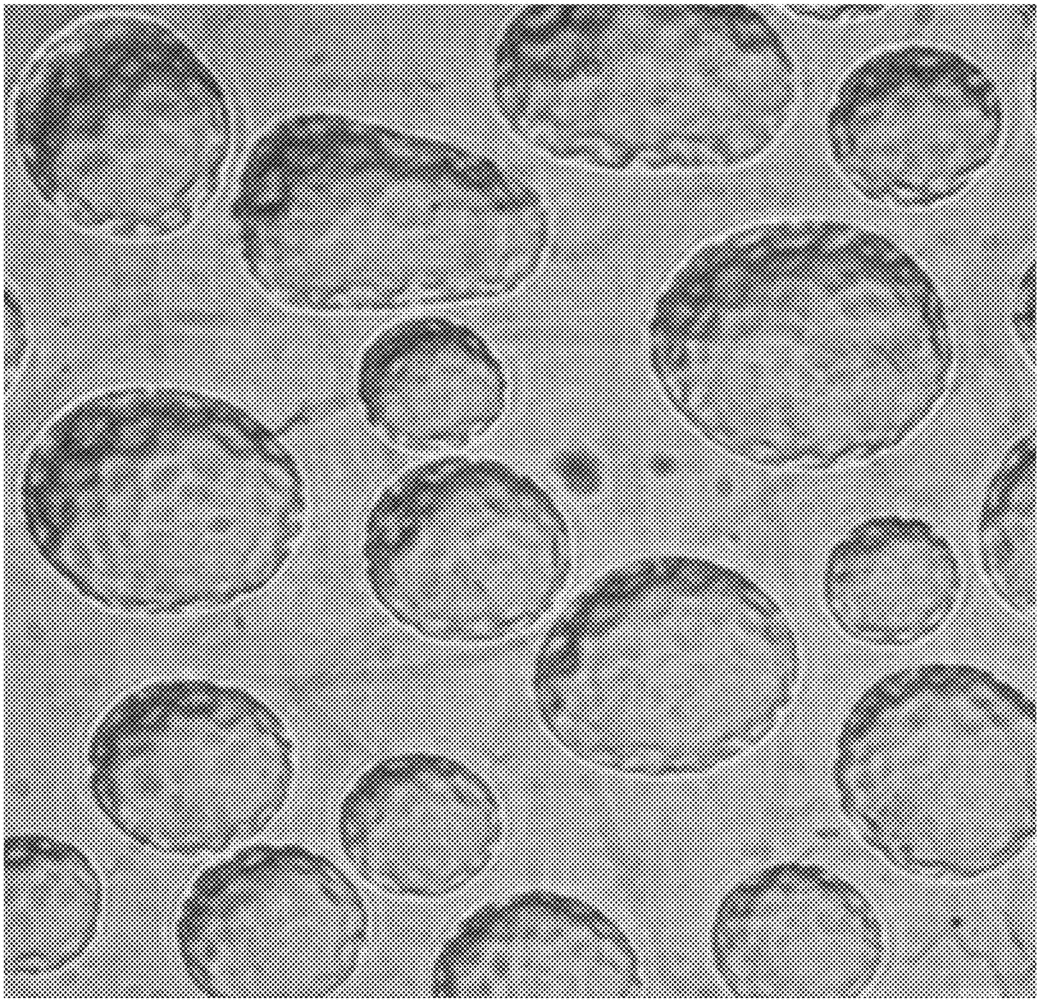
FIG. 15 PTH Crystals by Example 4 Method 5

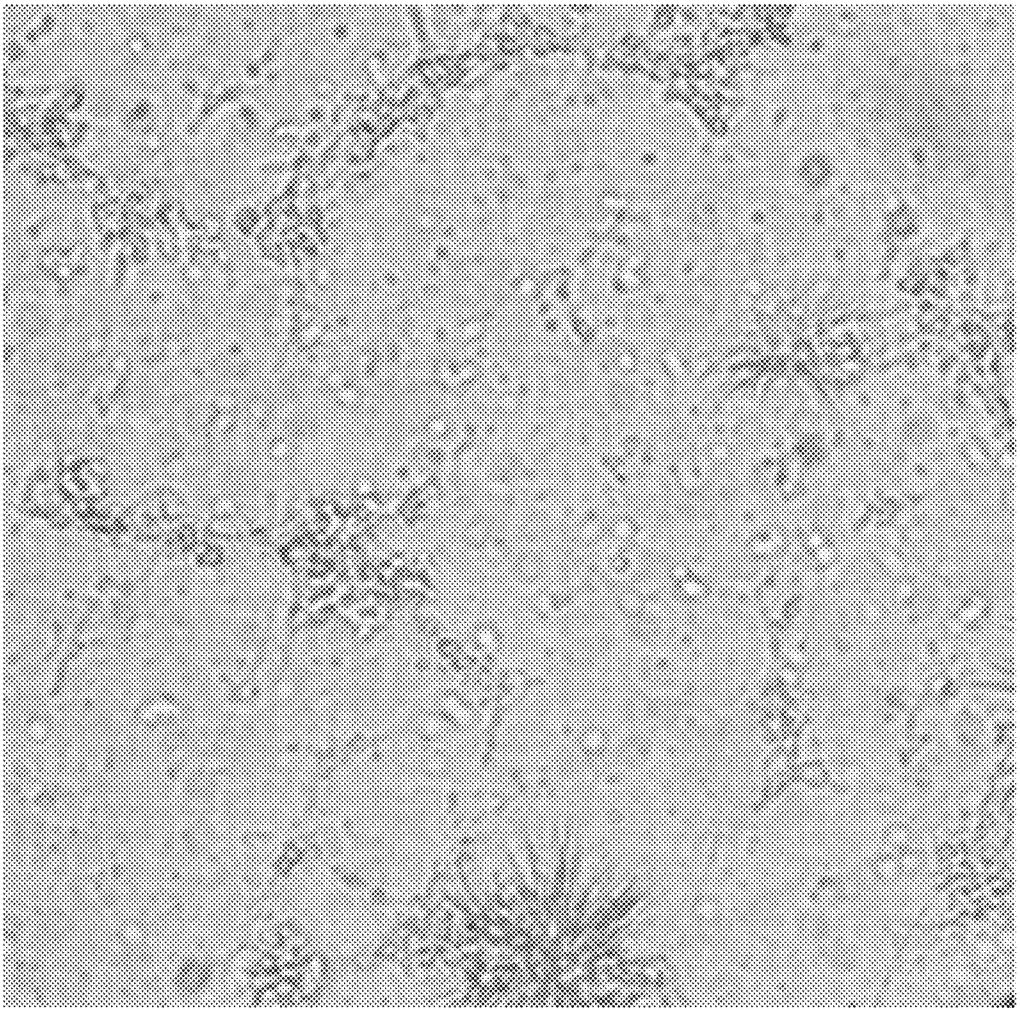
FIG. 16 PTH Crystals by Example 4 Method 6

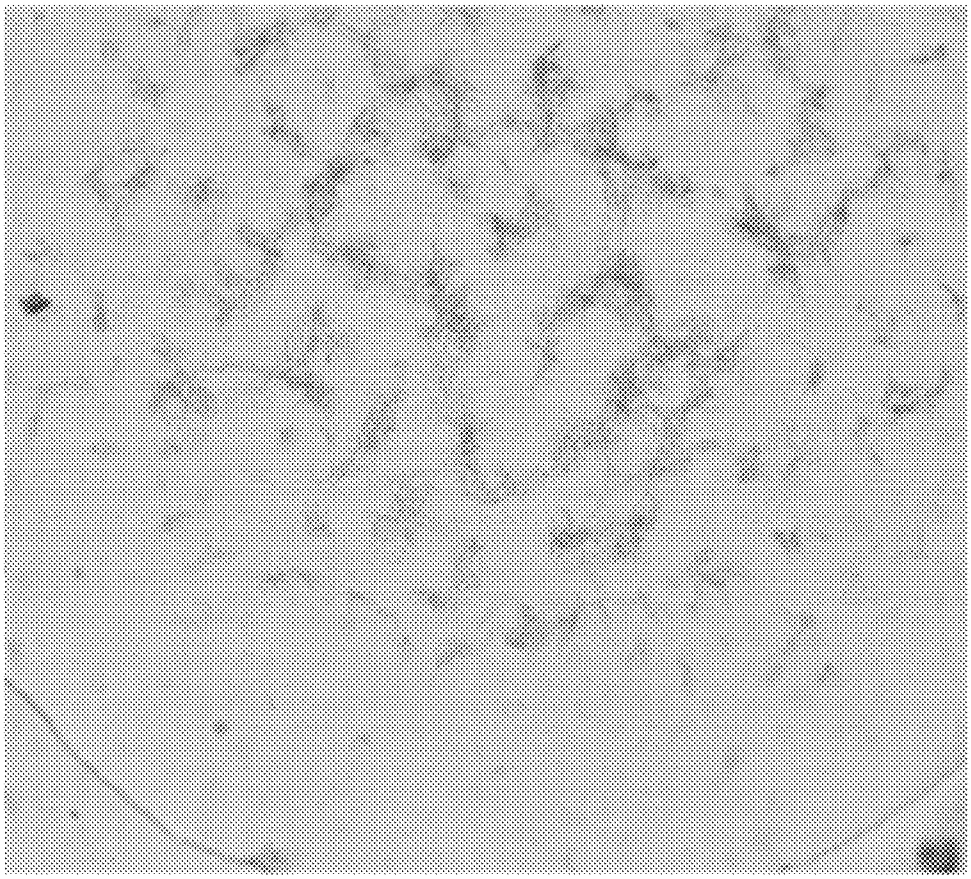
FIG. 17 PTH Crystals by Example 4 Method 7

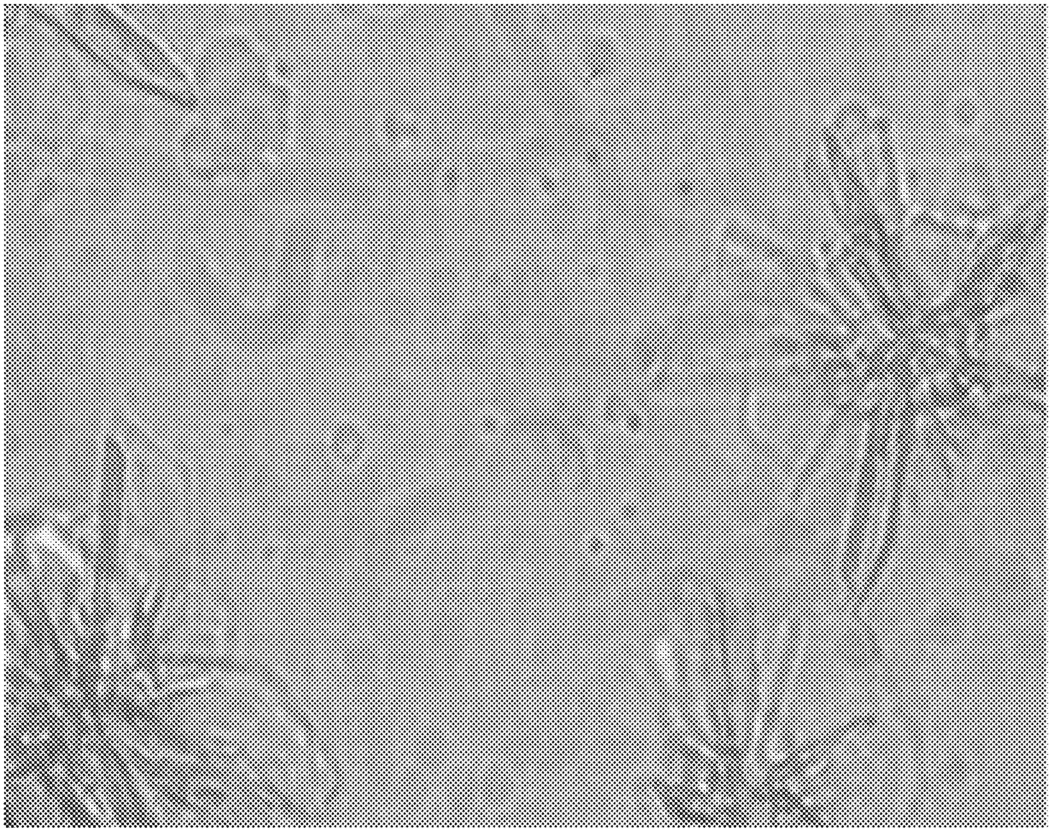
FIG. 18 PTH Crystals by Example 4 Method 8

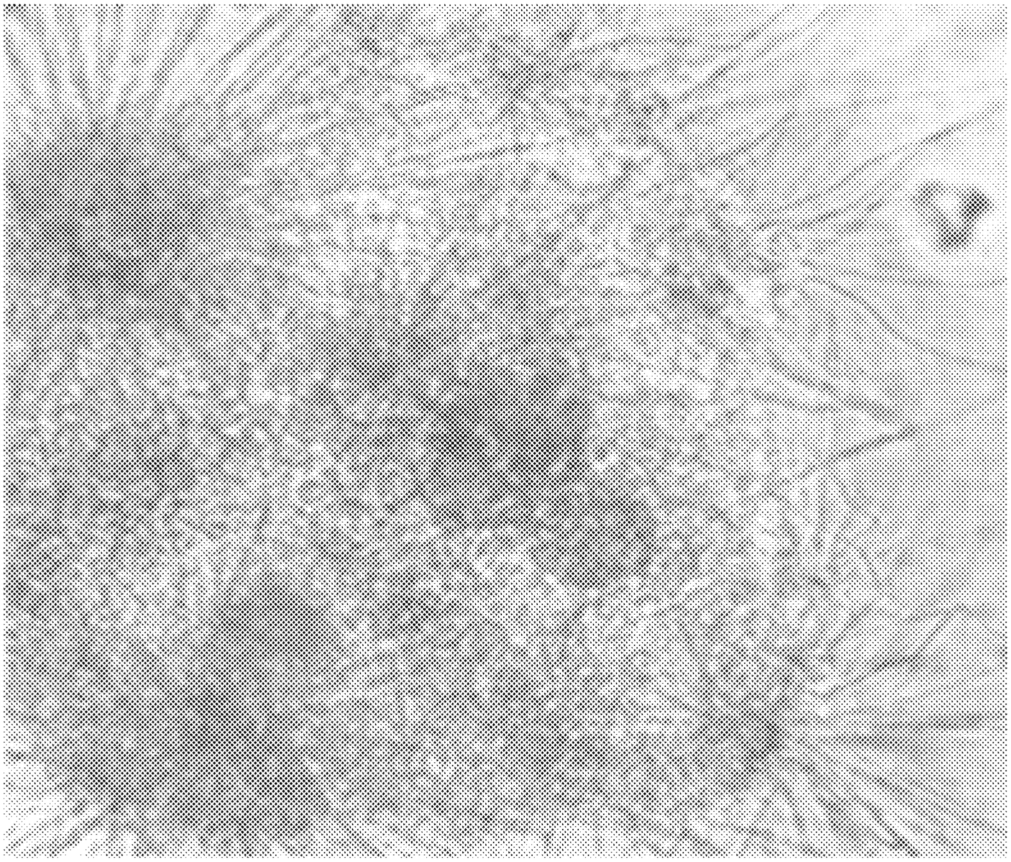
FIG. 19 PTH Crystals by Example 4 Method 9

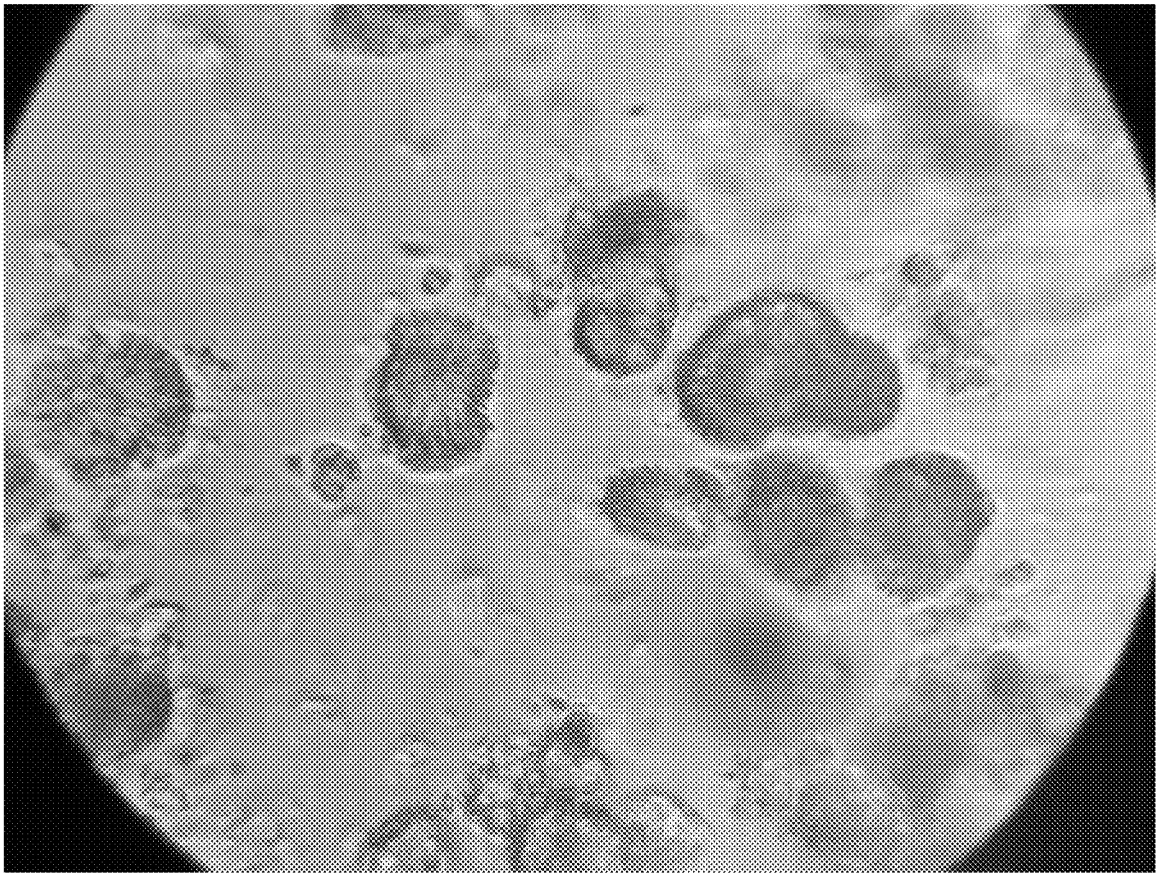
FIG. 20 PTH Crystals by Example 4 Method 20

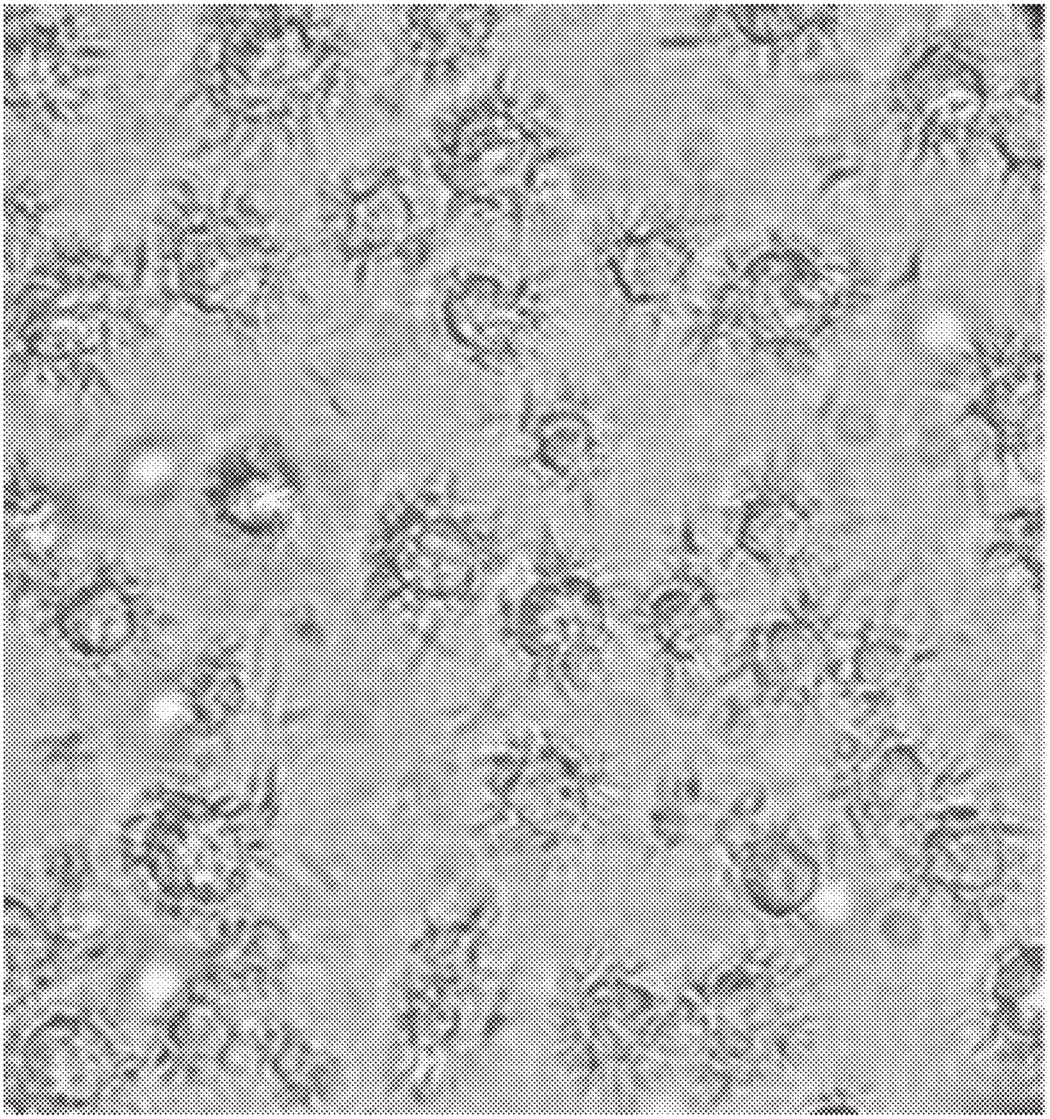
FIG. 21 Liraglutide Crystals by Example 5 Method 1

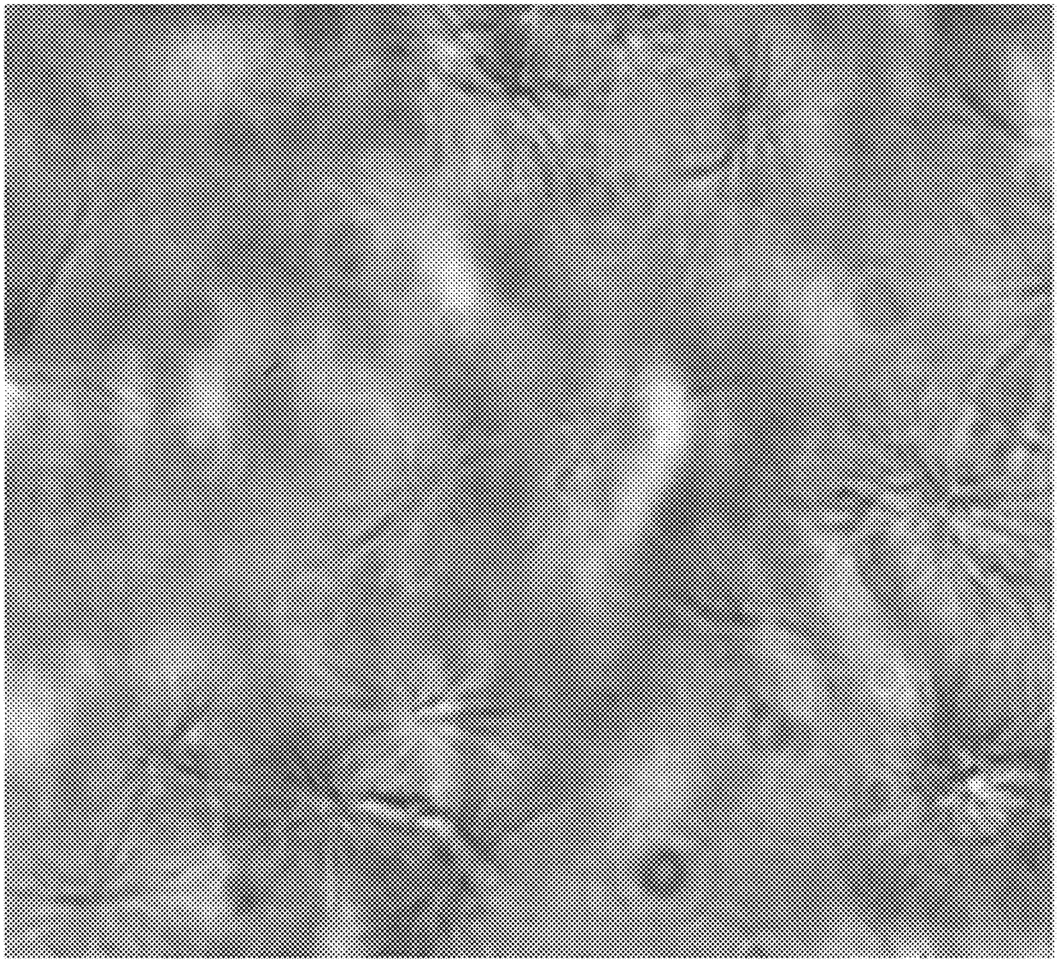
FIG. 22 Liraglutide Crystals by Example 5 Method 2

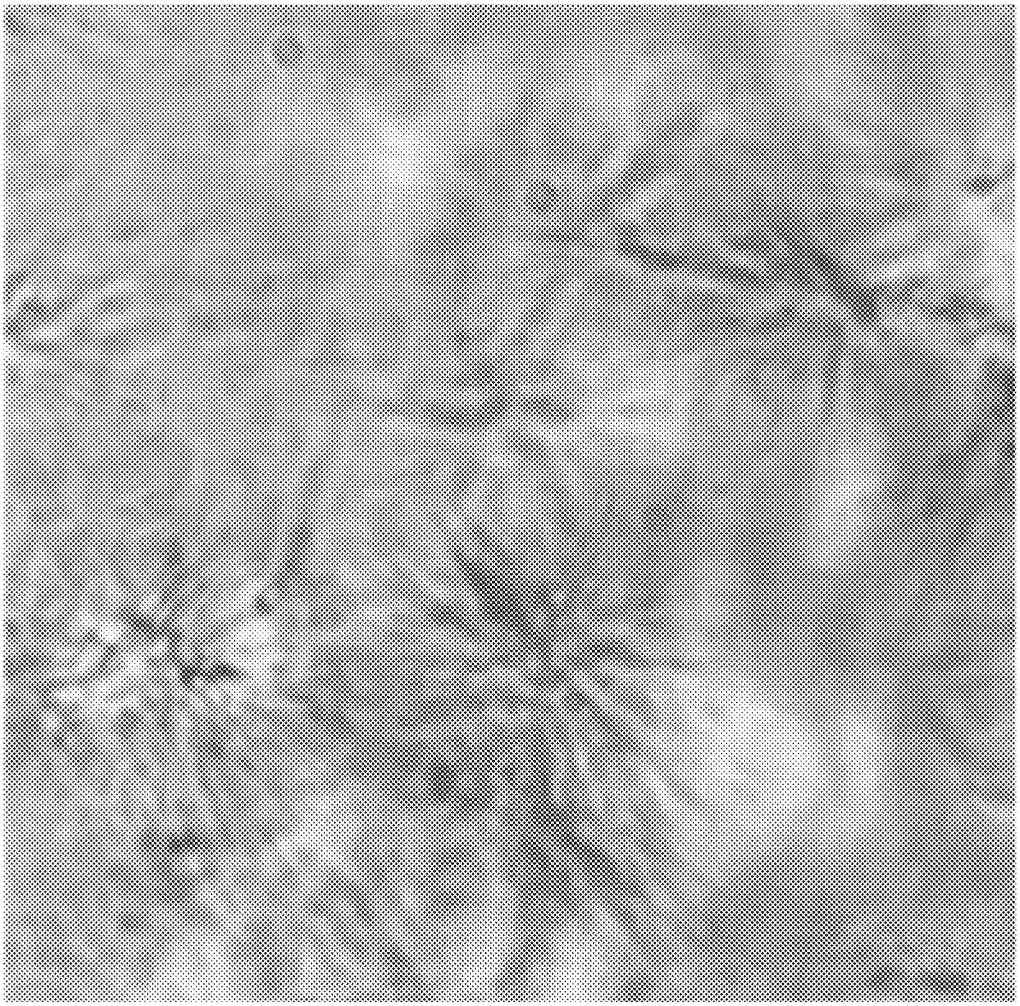
FIG. 23 Liraglutide Crystals by Example 5 Method 3

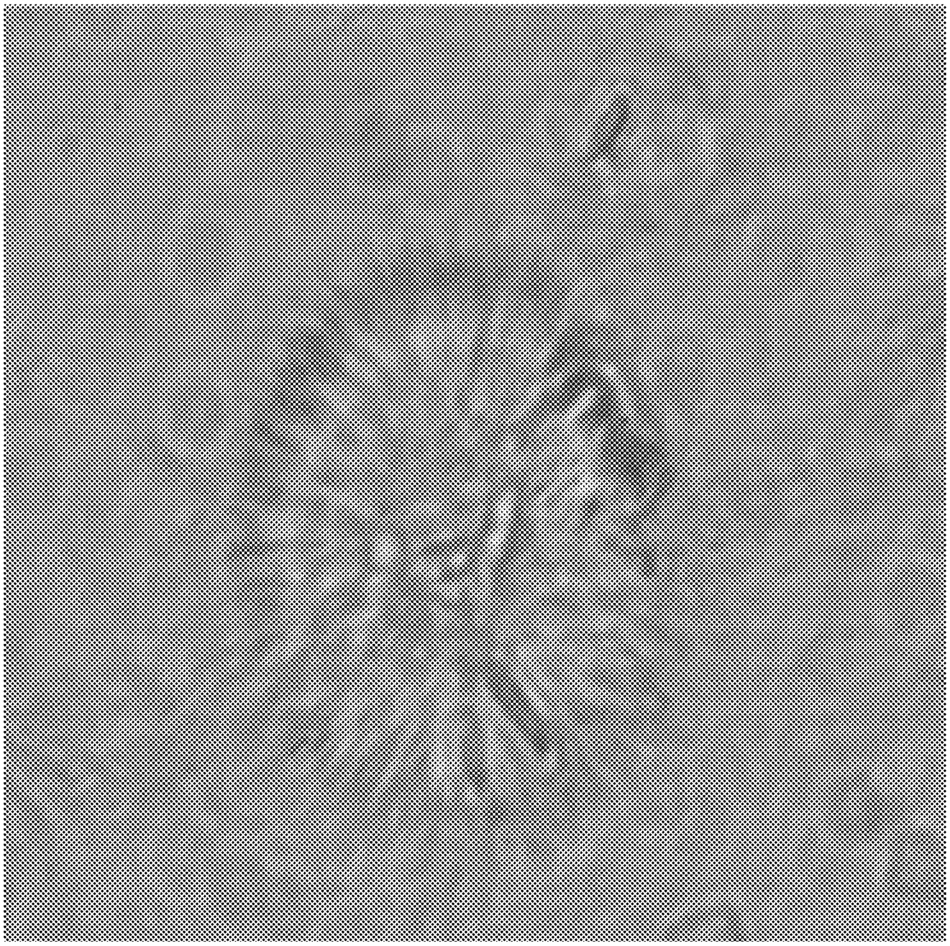
FIG. 24 Liraglutide Crystals by Example 5 Method 4

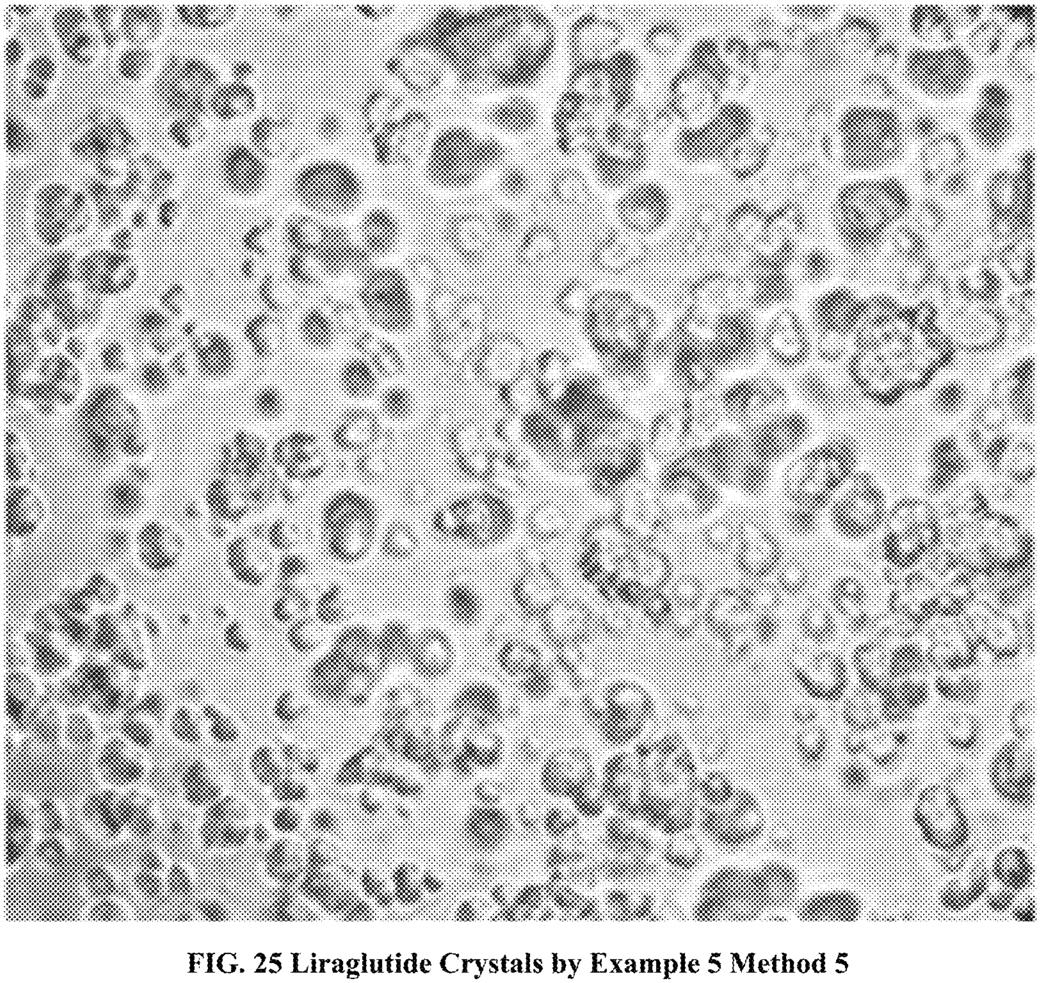
FIG. 25 Liraglutide Crystals by Example 5 Method 5

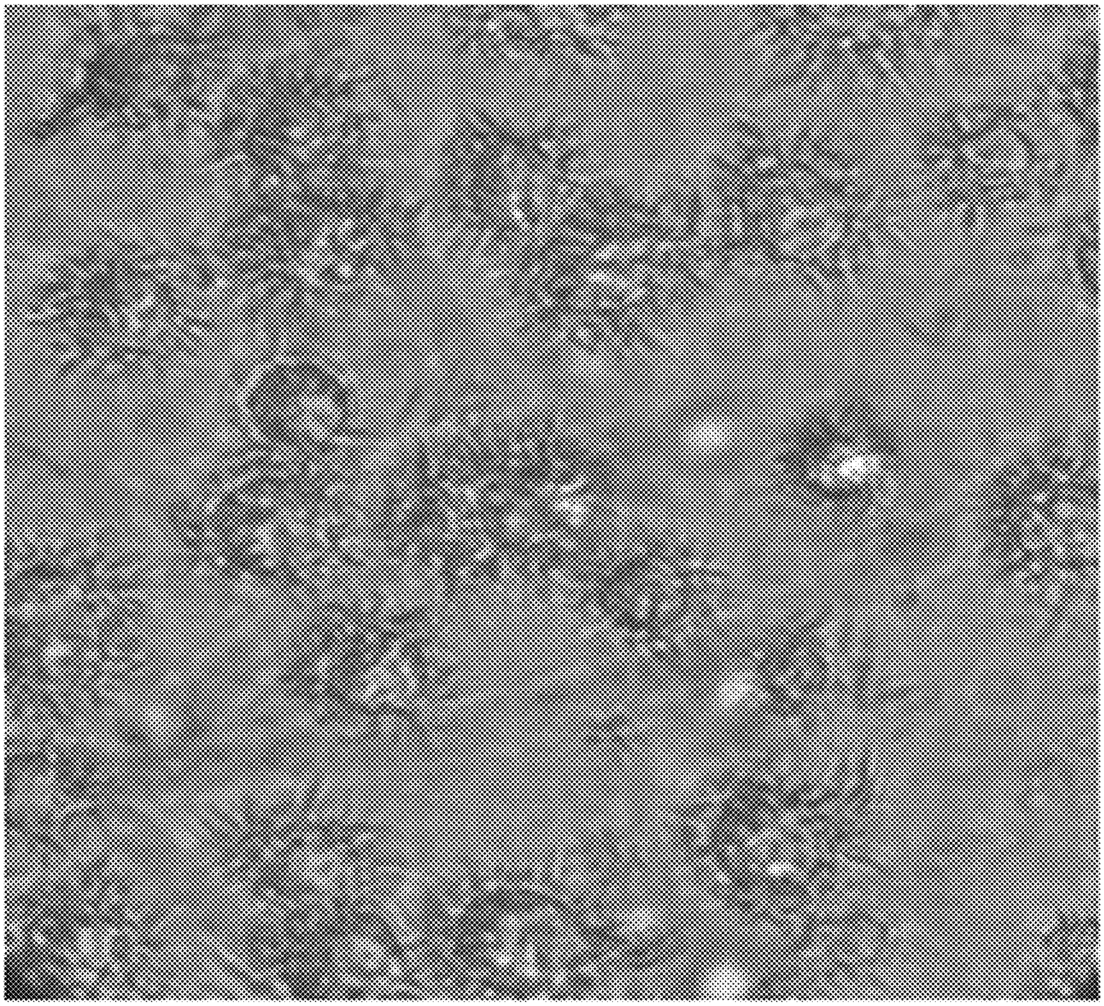
FIG. 26 Liraglutide Crystals by Example 5 Method 6

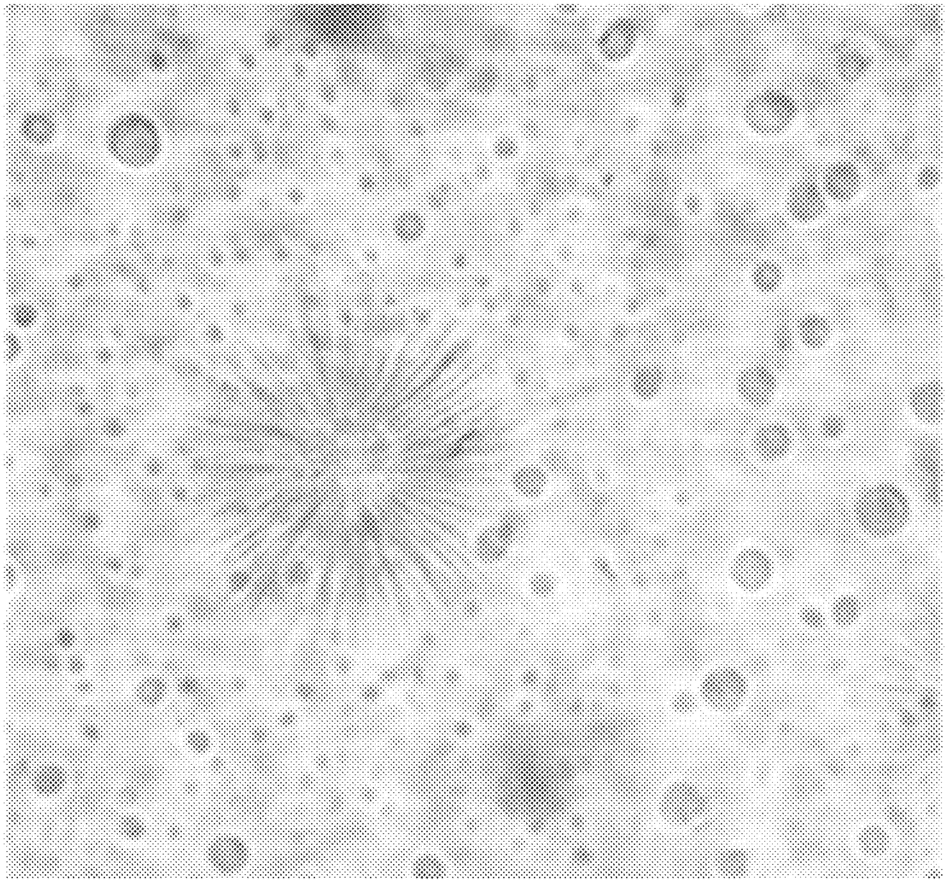
FIG. 27 Liraglutide Crystals by Example 5 Method 7

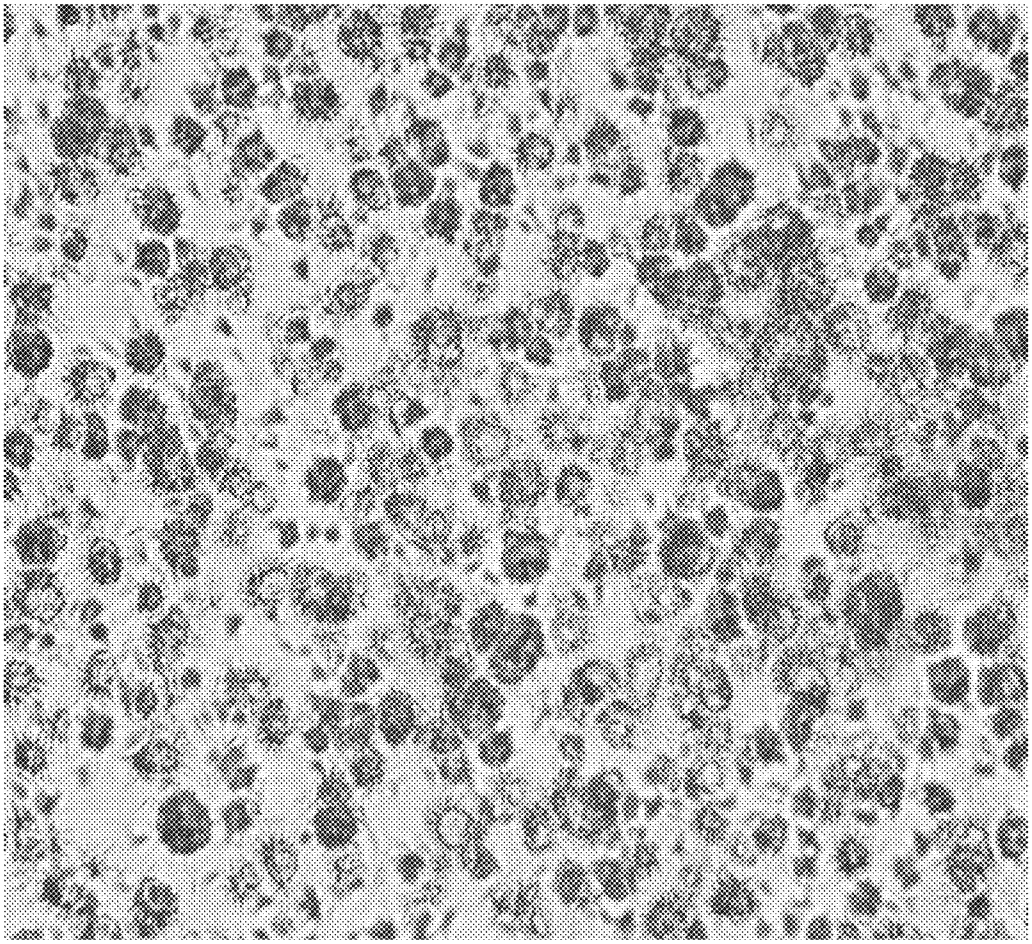
FIG. 28 Liraglutide Crystals by Example 5 Method 8

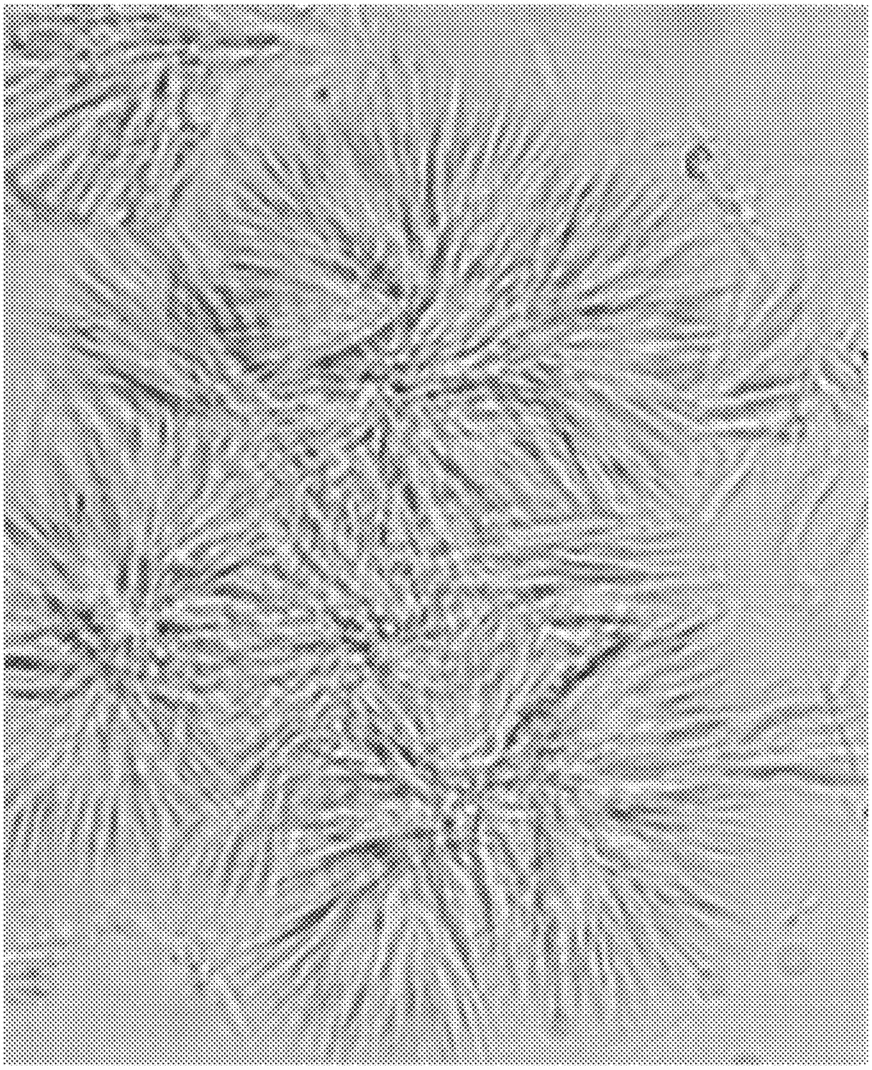
FIG. 29 Liraglutide Crystals by Example 5 Method 9

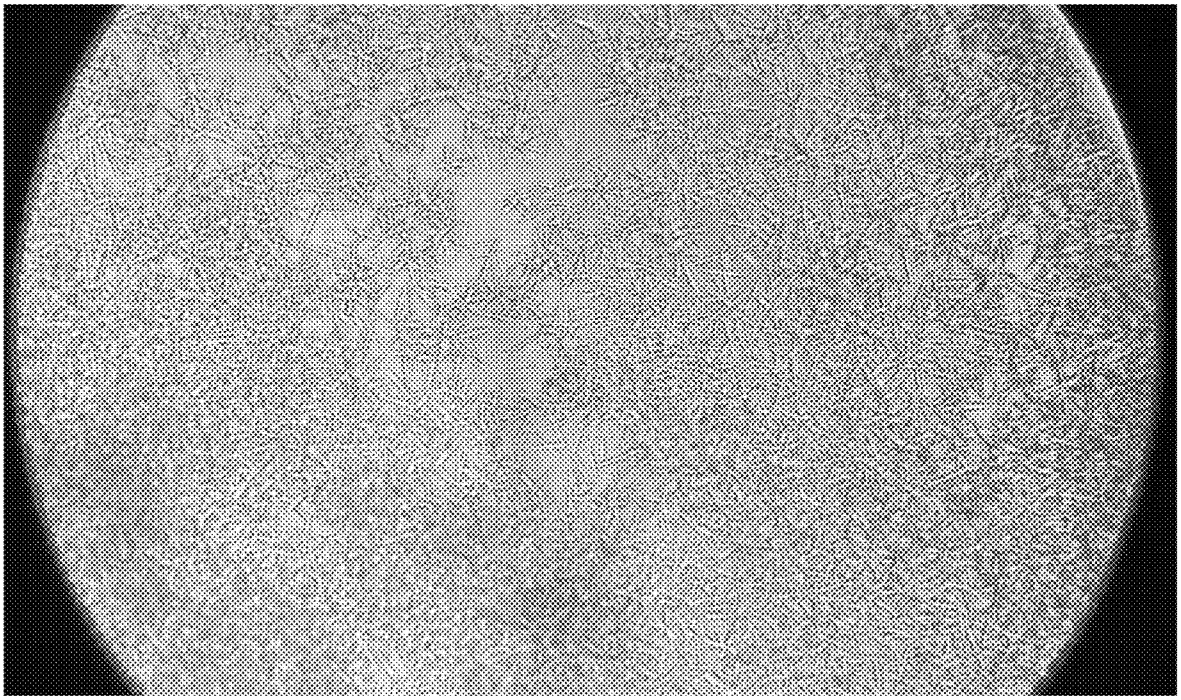
FIG. 30 Octreotide Crystals by Example 6 Method 1

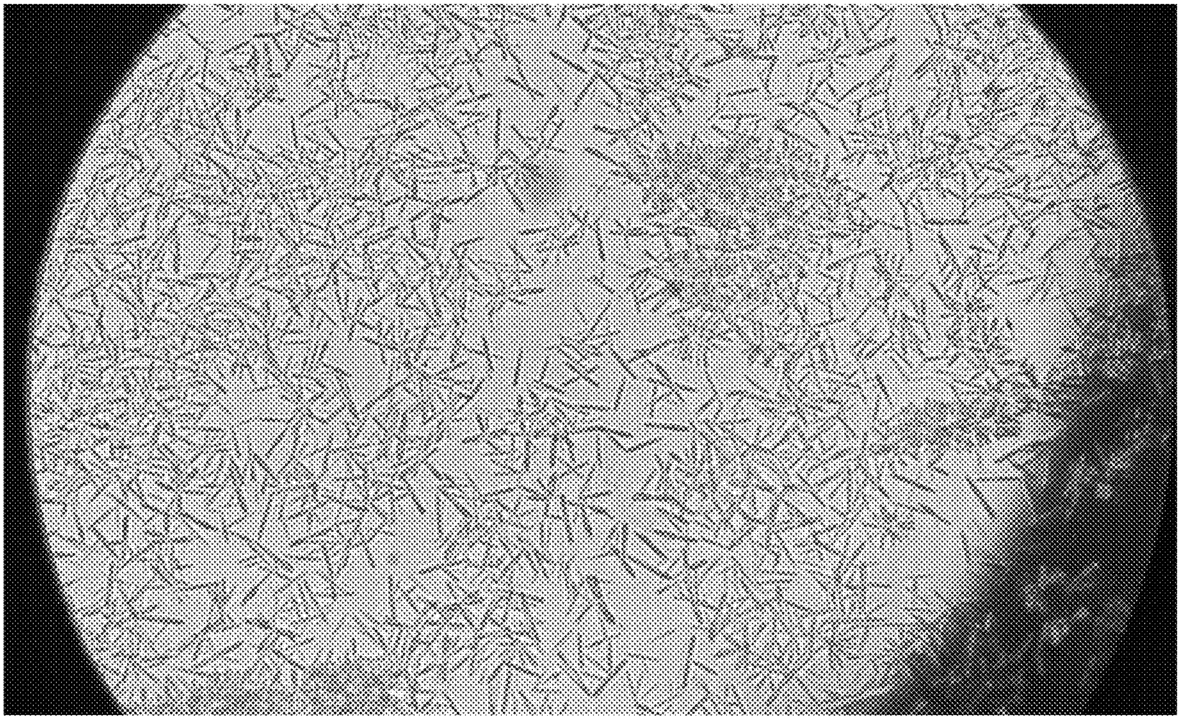
FIG. 31 Octreotide Crystals by Example 6 Method 2

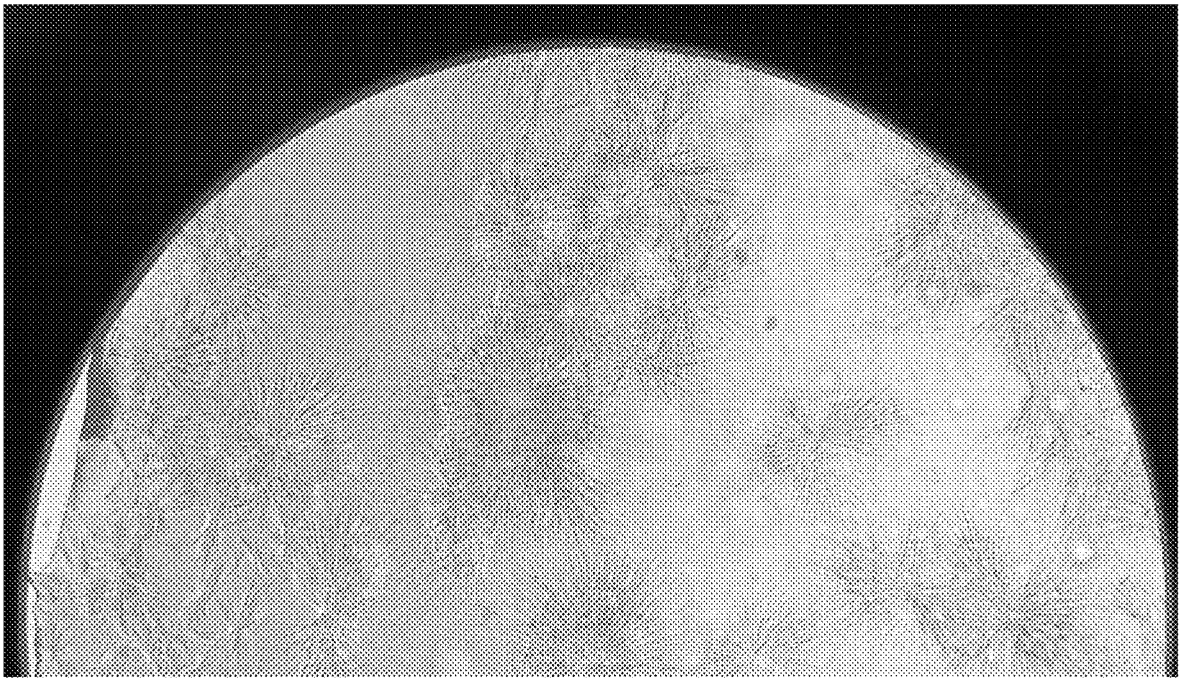
FIG. 32 Octreotide Crystals by Example 6 Method 3

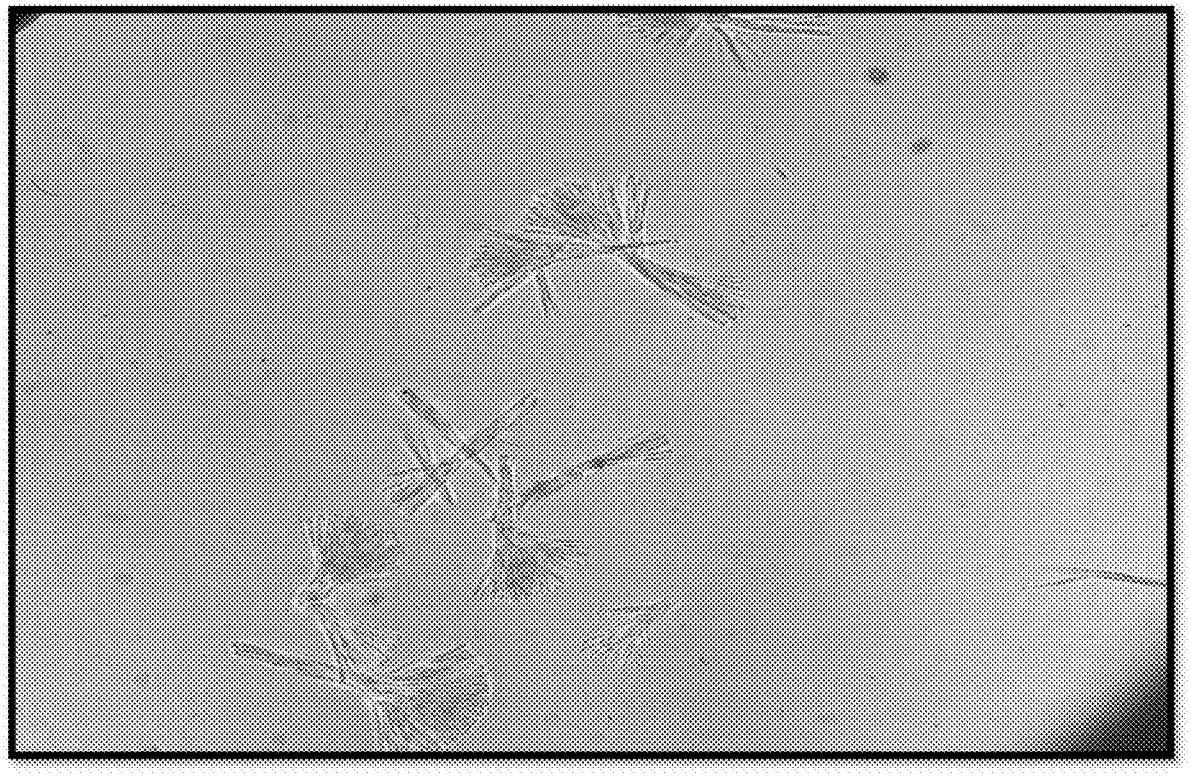
FIG. 33 Octreotide Crystals by Example 6 Method 4

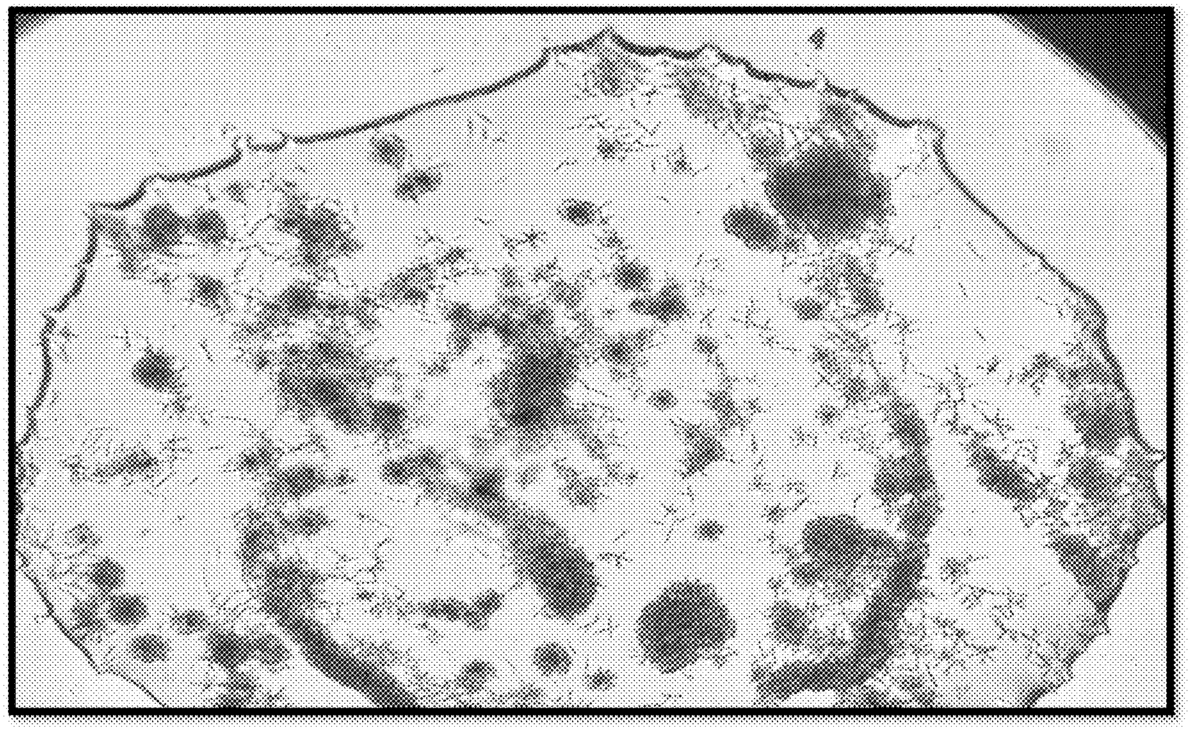
FIG. 34 Octreotide Crystals by Example 6 Method 5

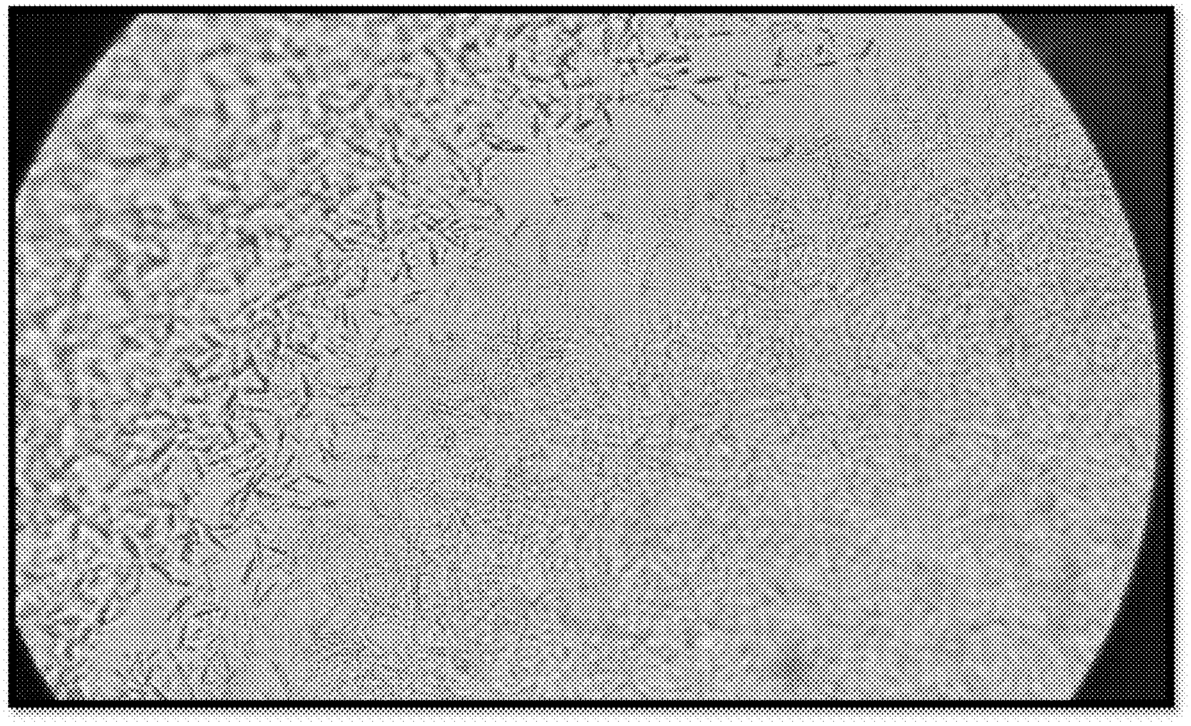
FIG. 35 Octreotide Crystals by Example 6 Method 6

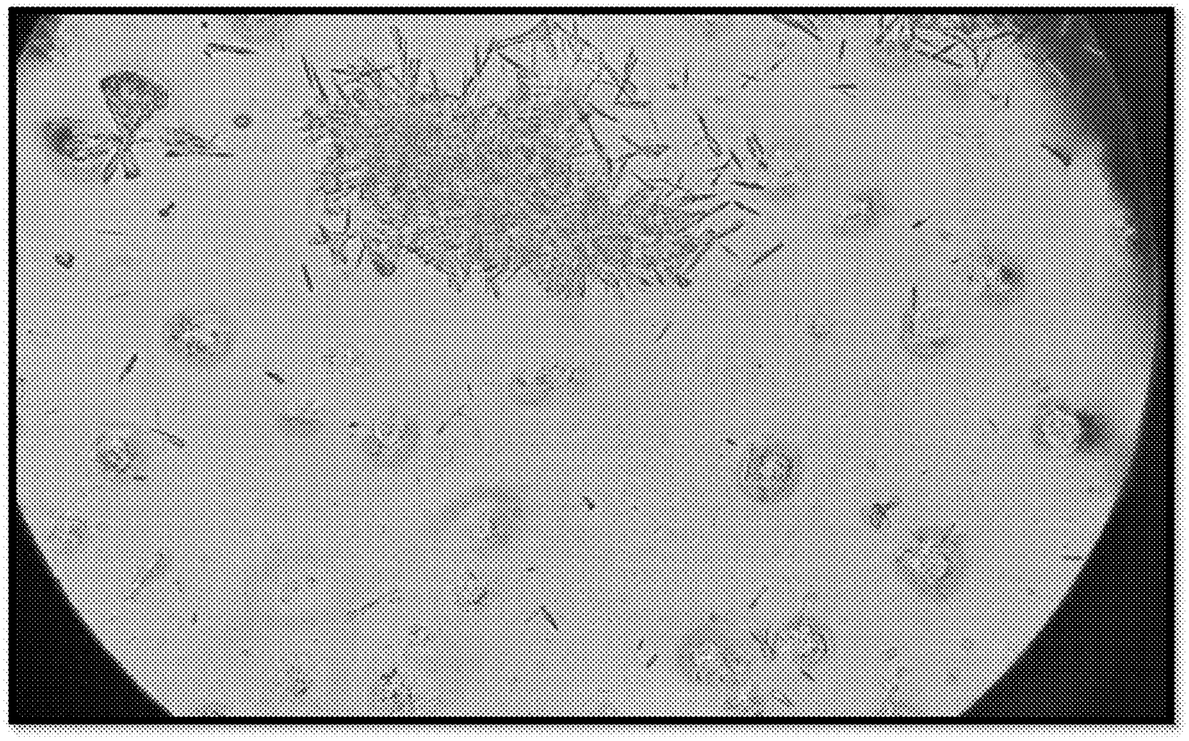
FIG. 36 Octreotide Crystals by Example 6 Method 7

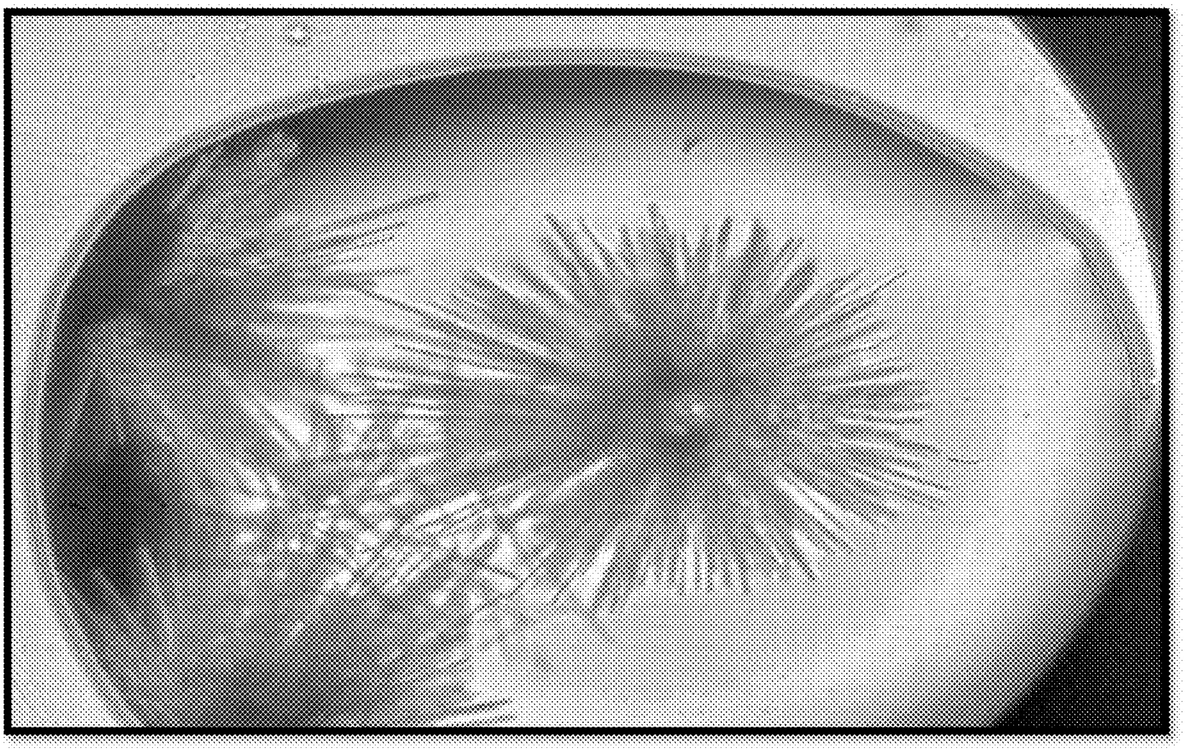
FIG. 37 Octreotide Crystals by Example 6 Method 8

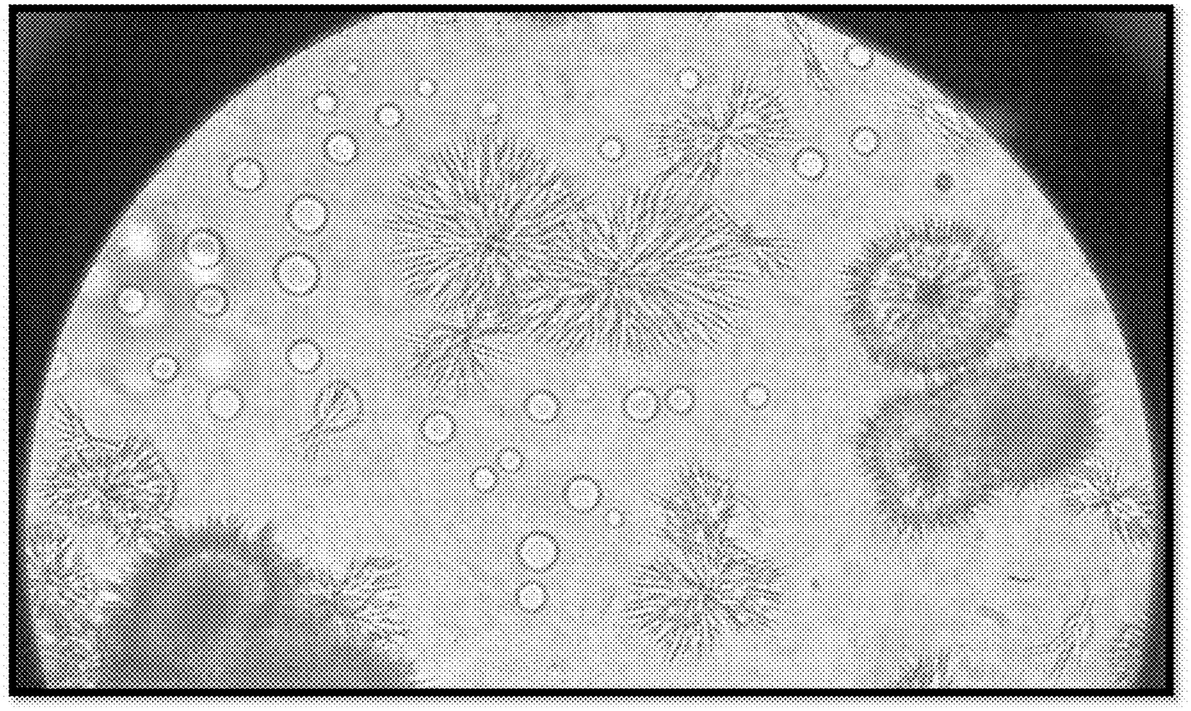
FIG. 38 Octreotide Crystals by Example 6 Method 9

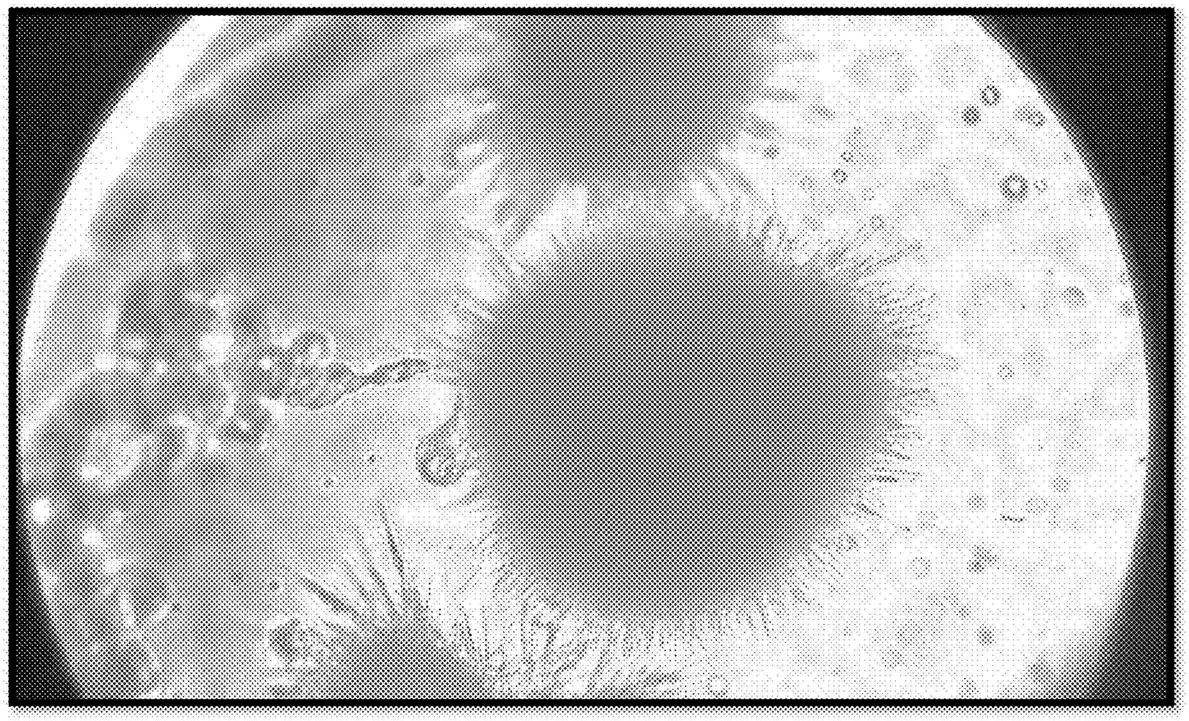
FIG. 39 Octreotide Crystals by Example 6 Method 10

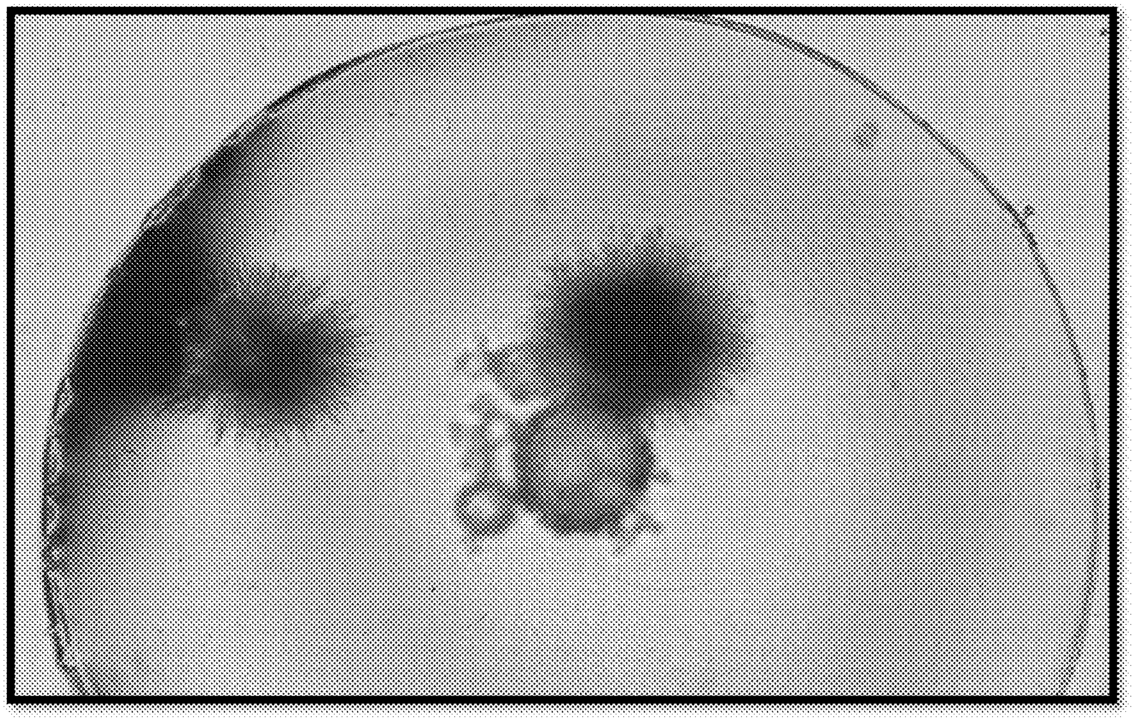
FIG. 40 Octreotide Crystals by Example 6 Method 11

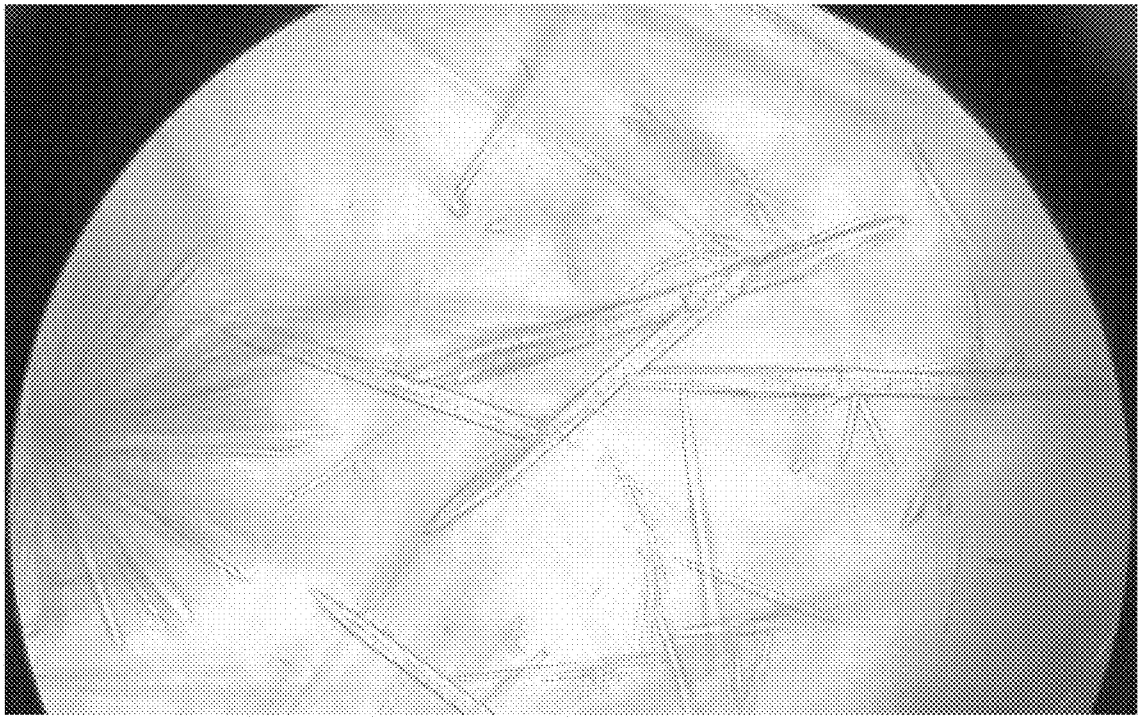
FIG. 41 Octreotide Crystals by Example 6 Method 12

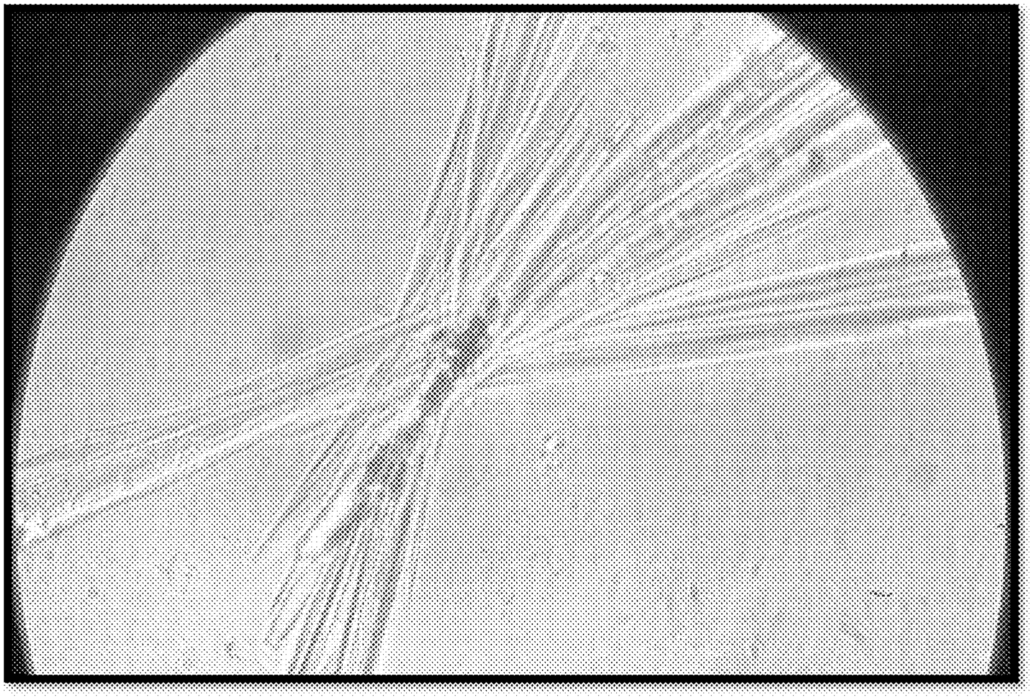
FIG. 42 Octreotide Crystals by Example 6 Method 13

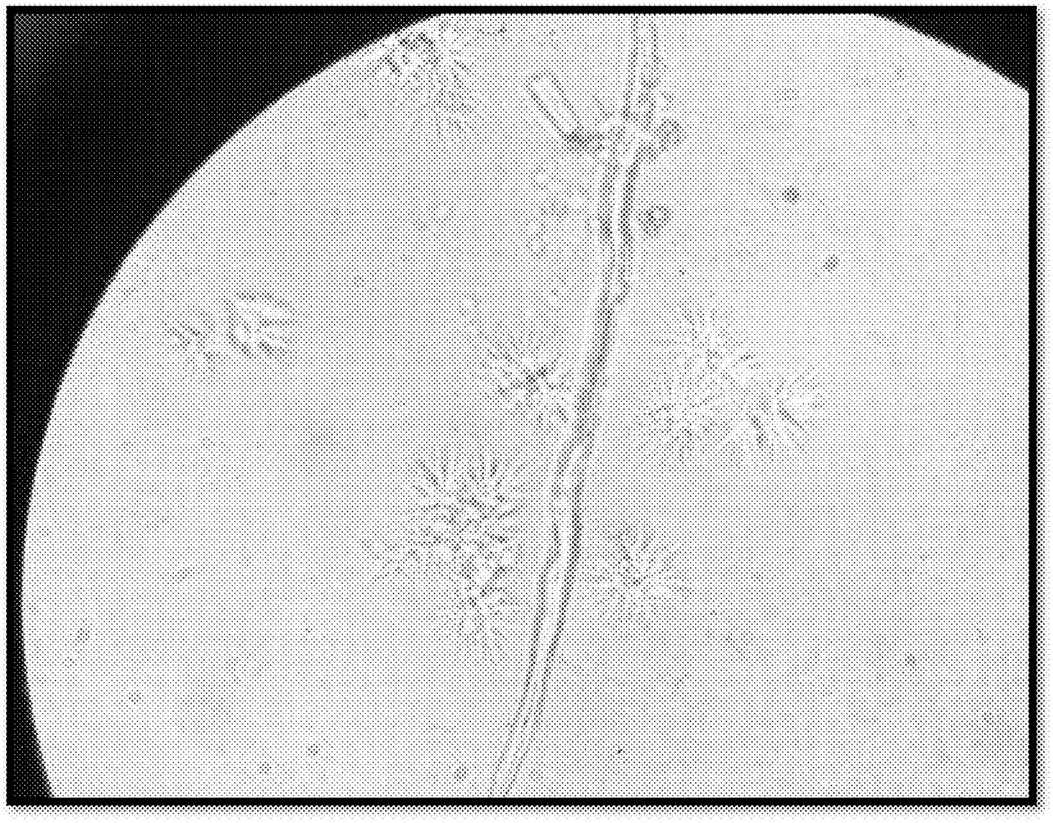
FIG. 43 Octreotide Crystals by Example 6 Method 14

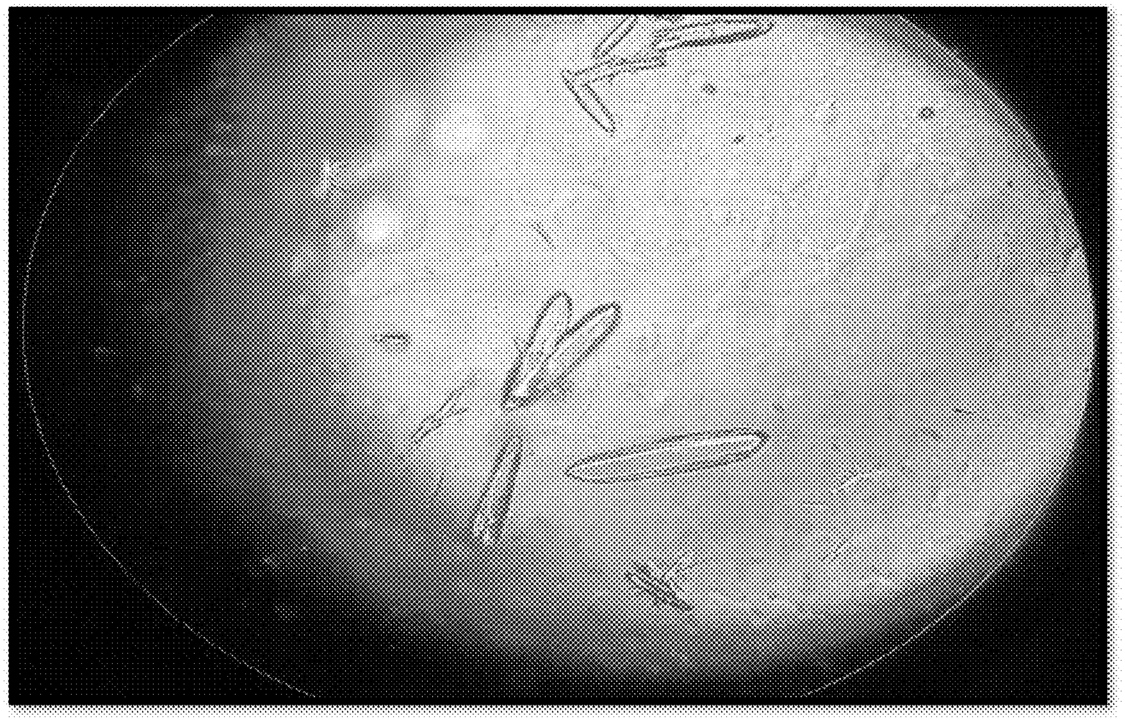
FIG. 44 Octreotide Crystals by Example 6 Method 15

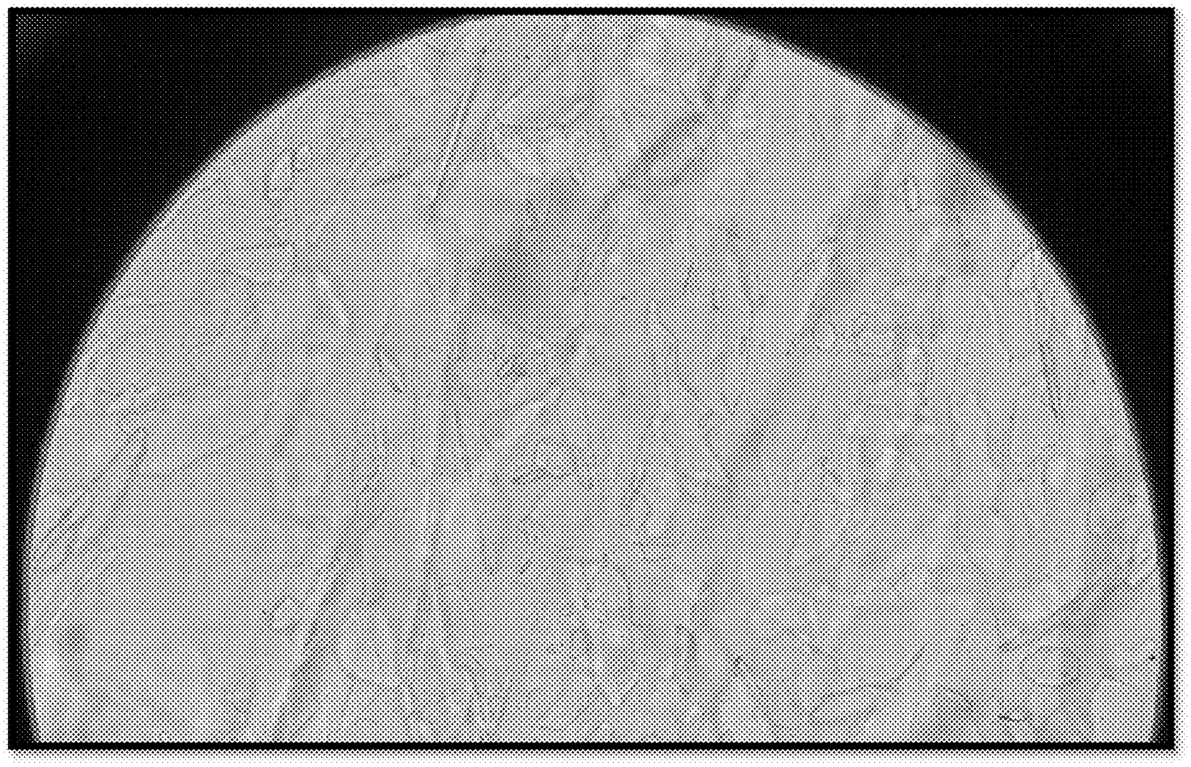
FIG. 45 Octreotide Crystals by Example 6 Method 16

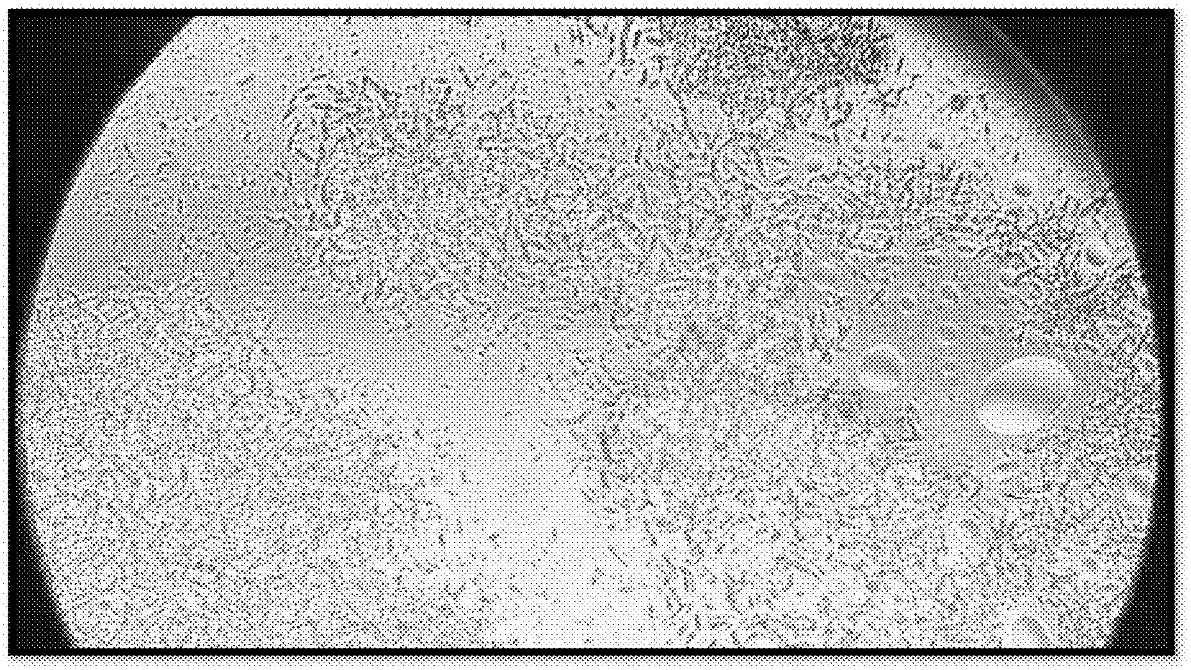
FIG. 46 Octreotide Crystals by Example 6 Method 17

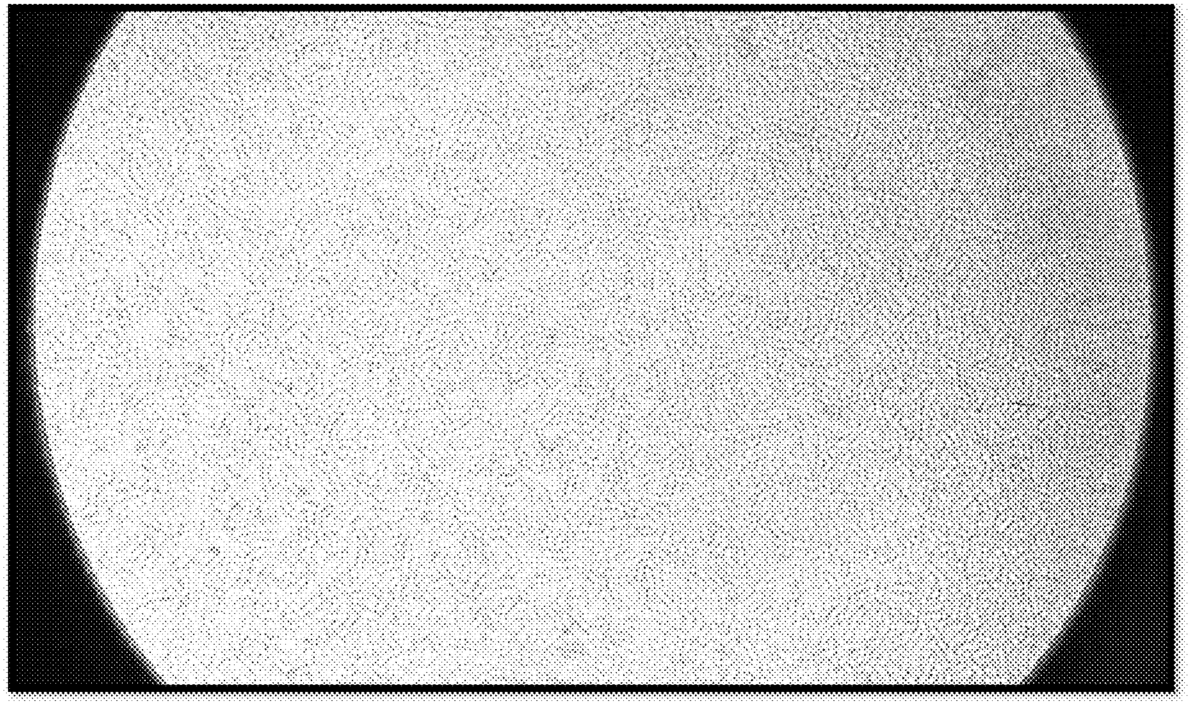
FIG. 47 Octreotide Crystals by Example 6 Method 18

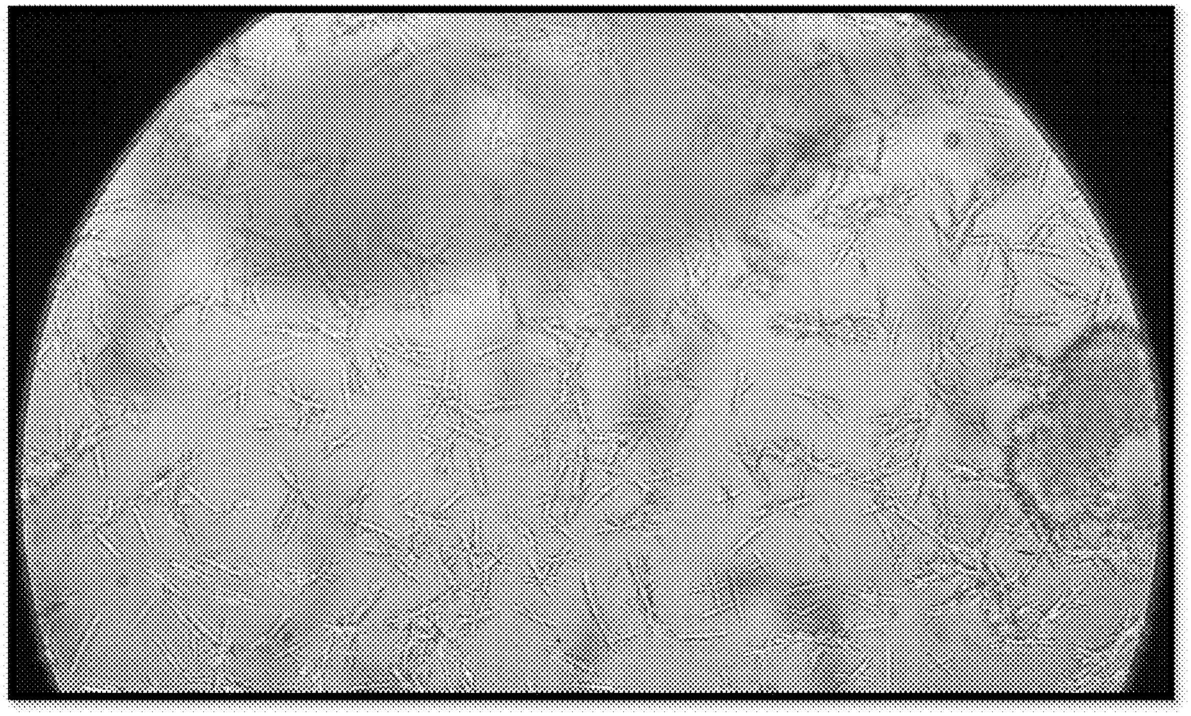
FIG. 48 Octreotide Crystals by Example 6 Method 19

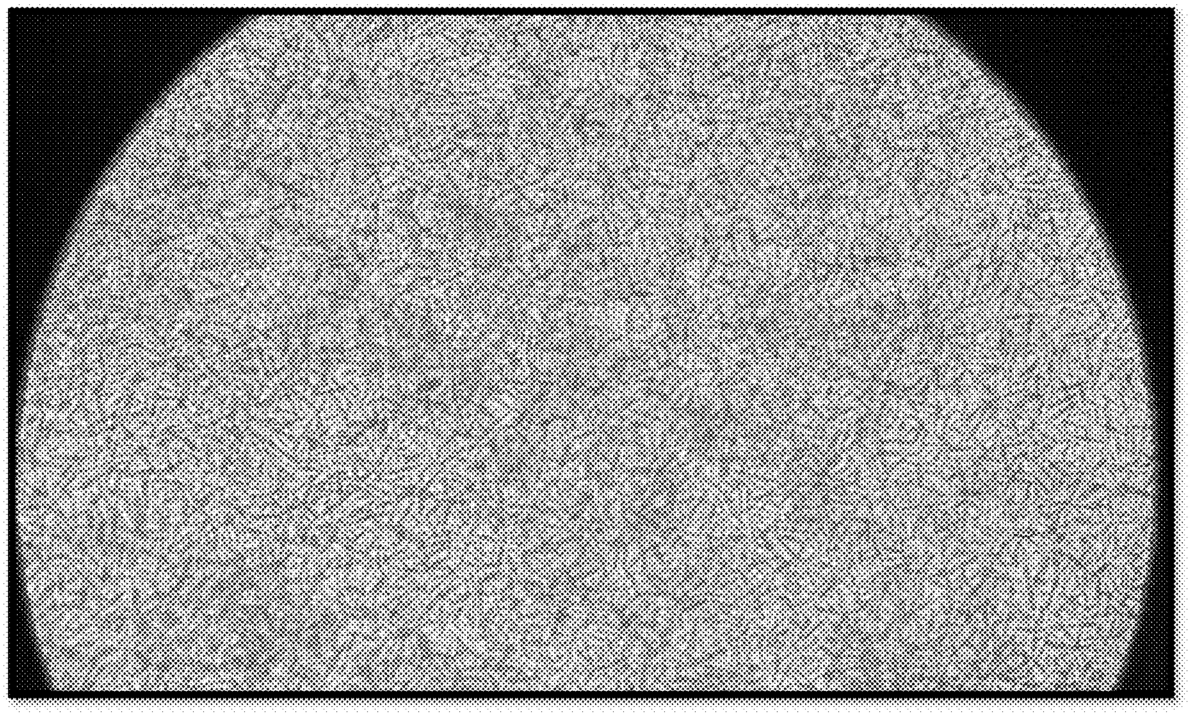
FIG. 49 Octreotide Crystals by Example 6 Method 20

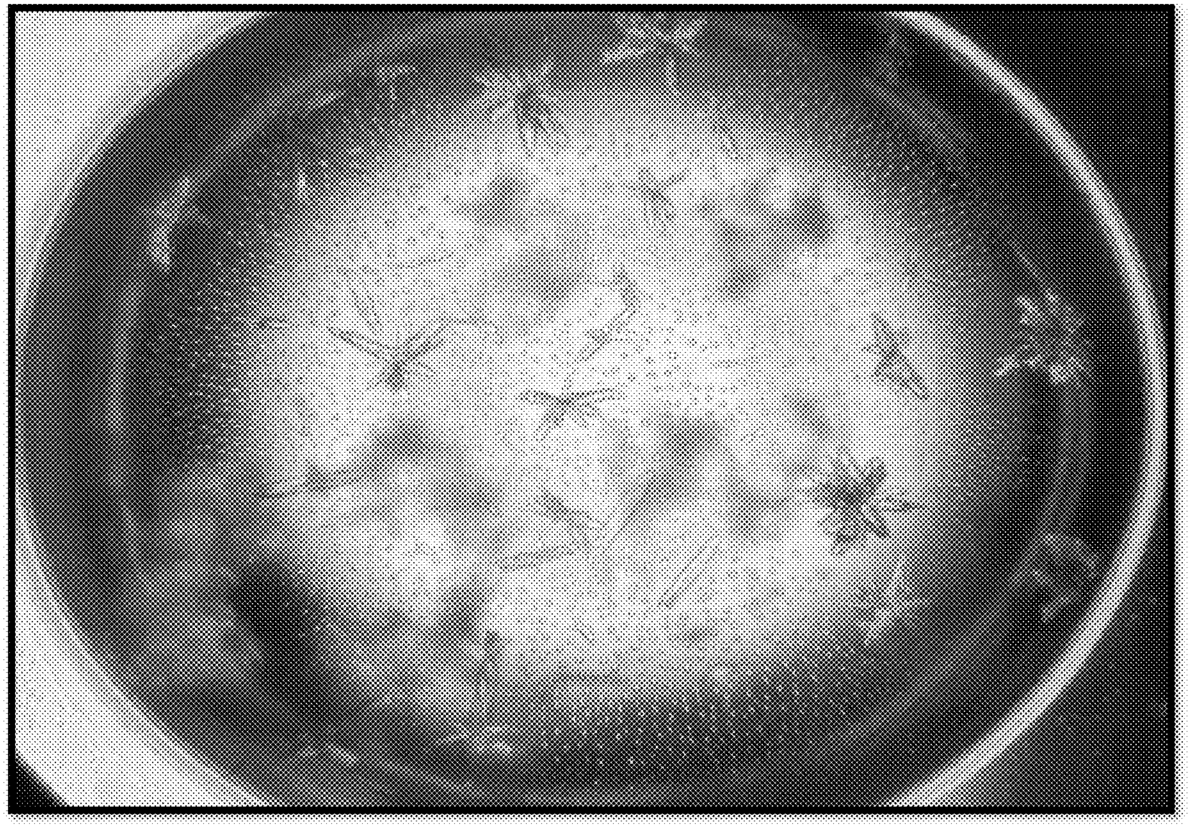
FIG. 50 Octreotide Crystals by Example 6 Method 21

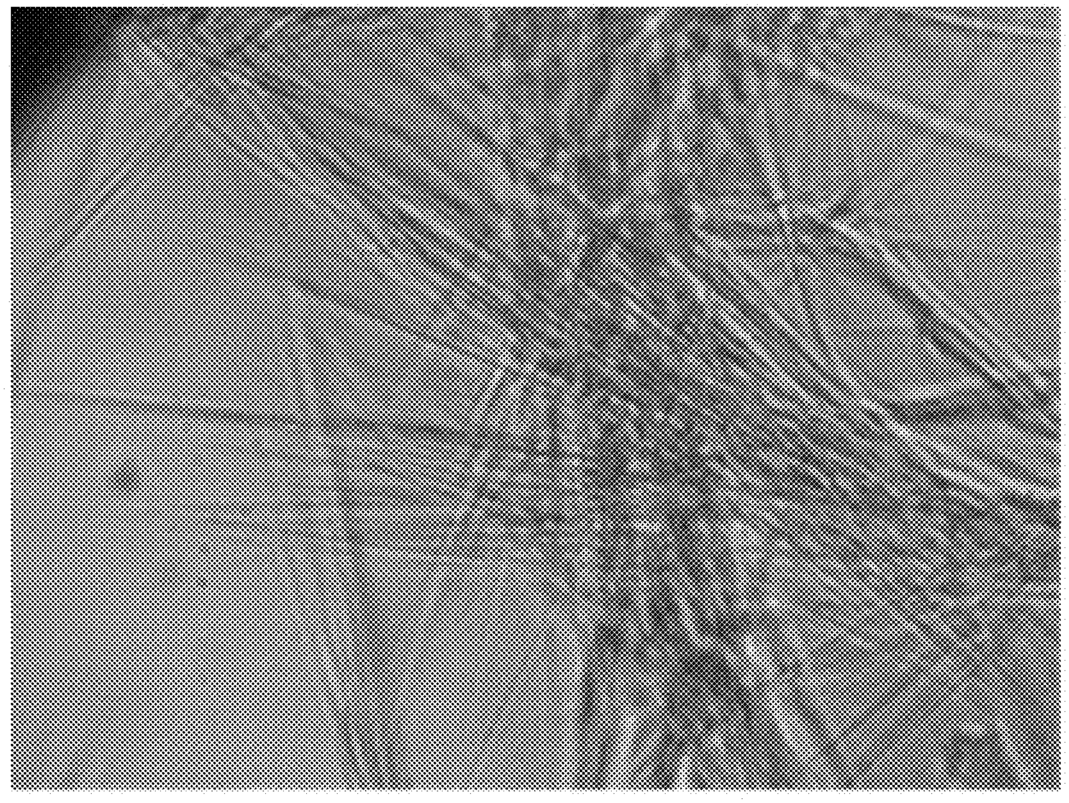
FIG. 51 Trastuzumab Crystals by Example 7 Method 1

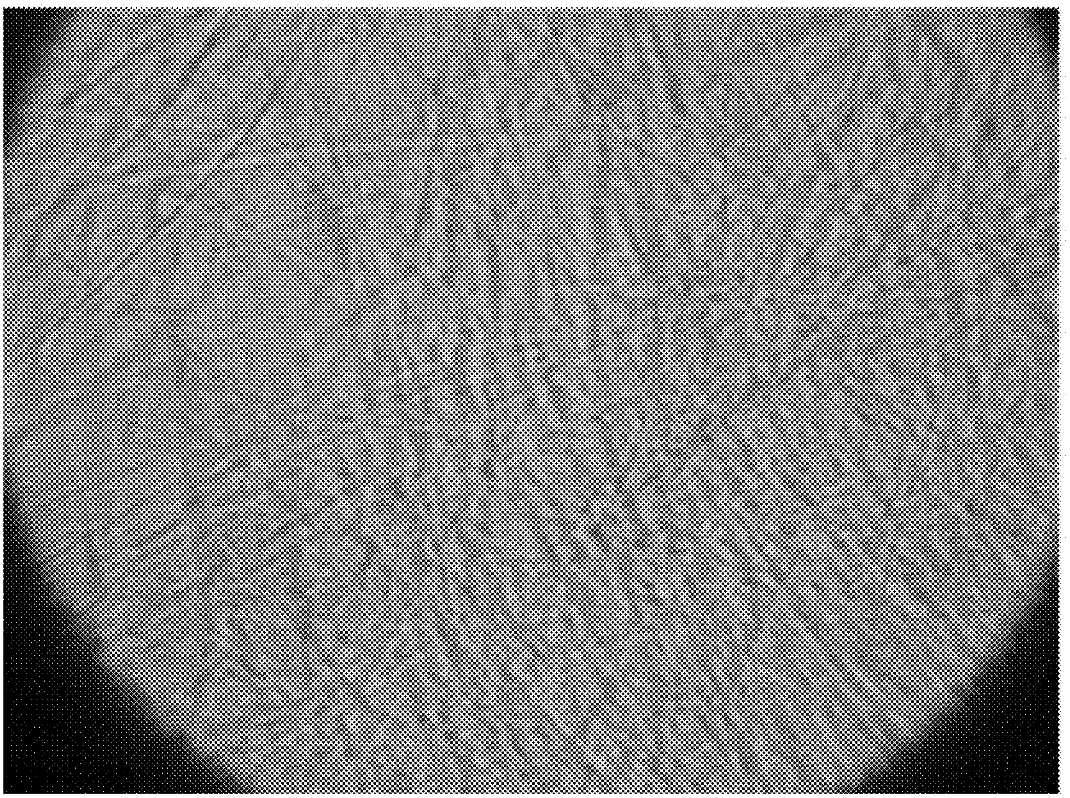
FIG. 52 Trastuzumab Crystals by Example 7 Method 2

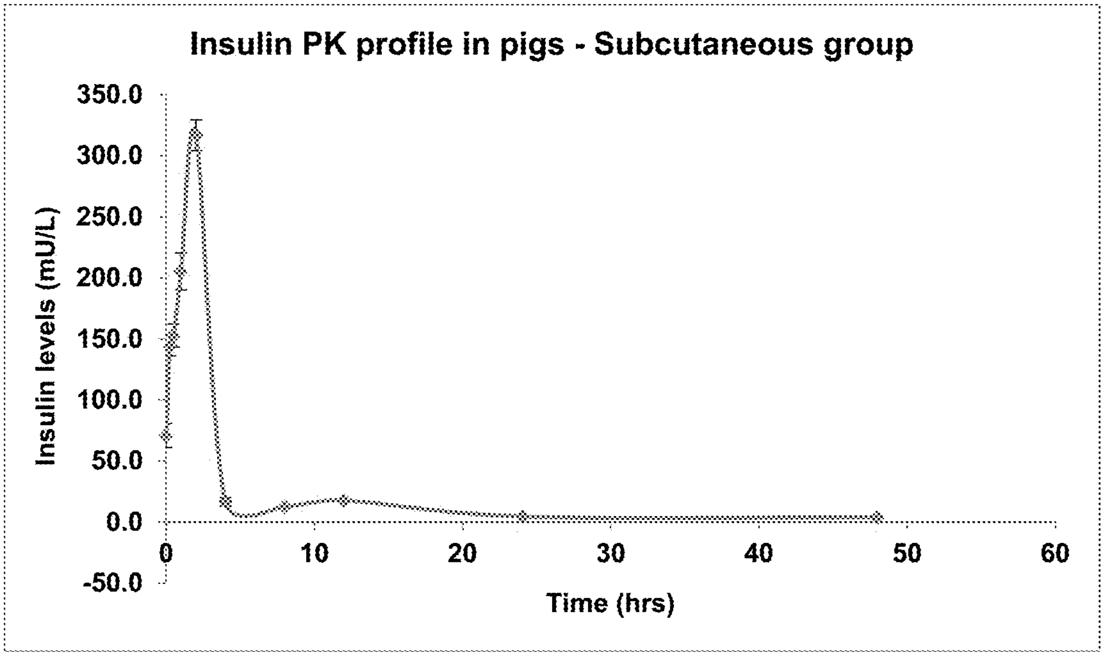
FIG. 53 Human Insulin R – Pharmacokinetic Profile of Subcutaneous Injection in Pigs

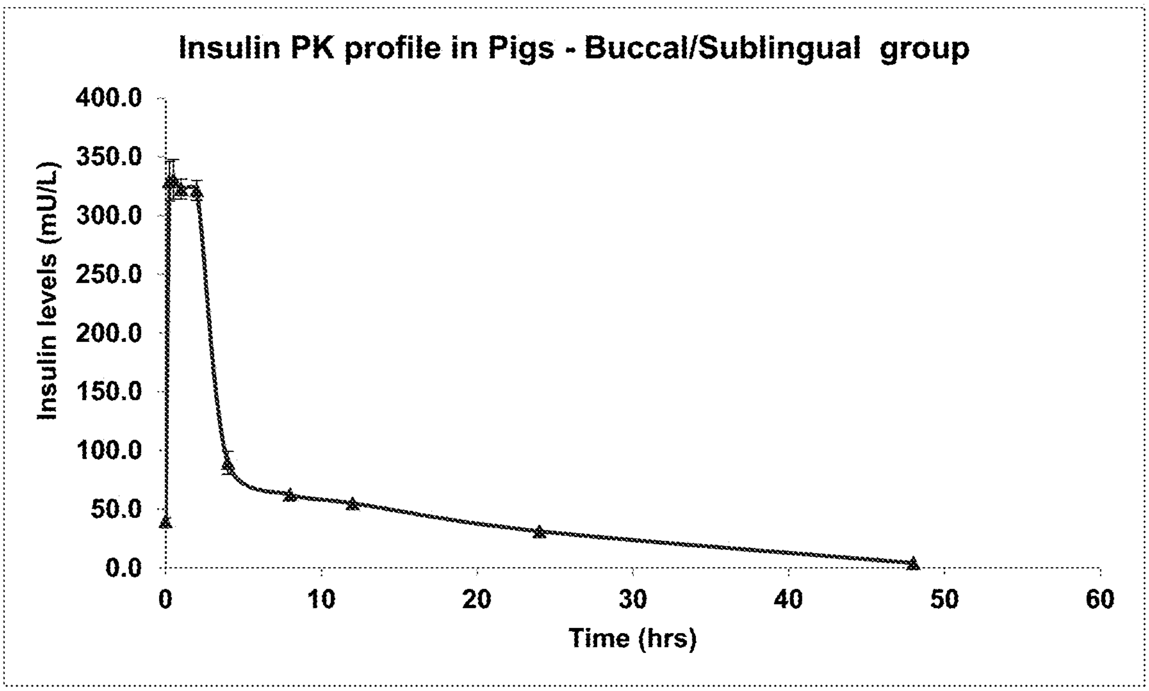
FIG. 54 Human Insulin R – Pharmacokinetic Profile of Buccal/Sublingual Delivery in Pigs

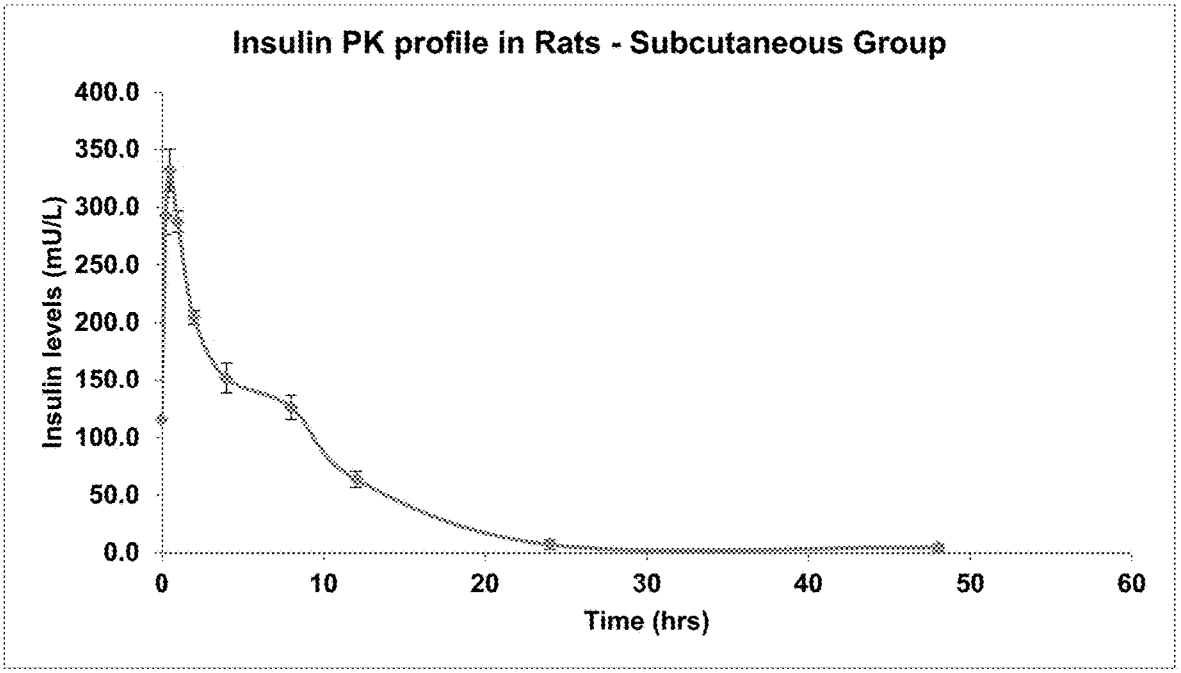
FIG. 55 Human Insulin R – Pharmacokinetic Profile of Subcutaneous Injection in Rats

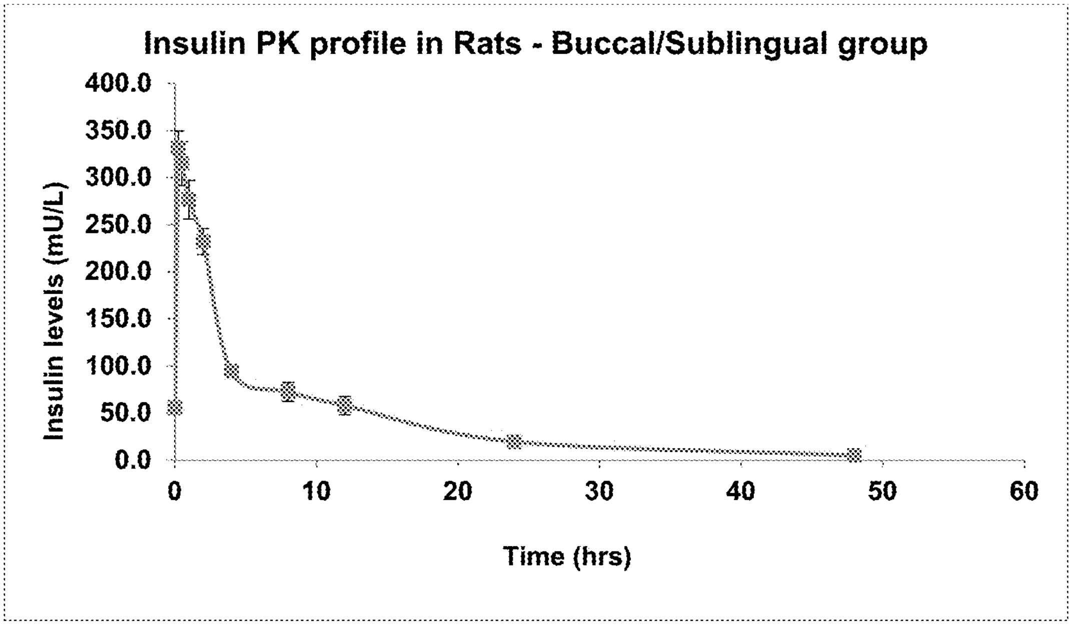
FIG. 56 Human Insulin R – Pharmacokinetic Profile of Buccal/Sublingual Delivery in Rats

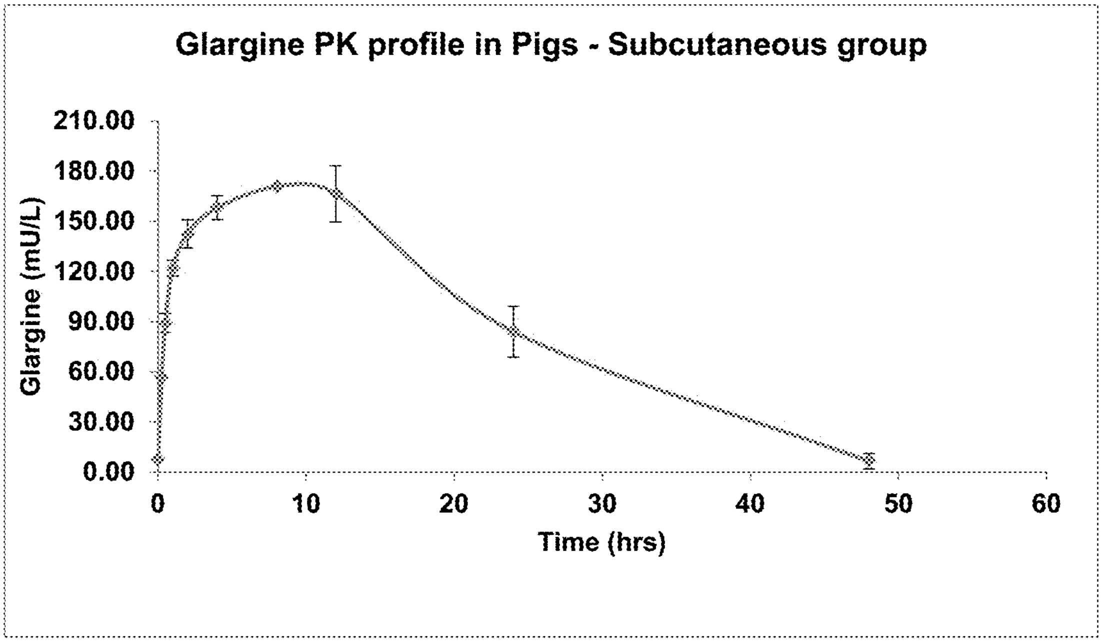
FIG. 57 Lantus/Insulin Glargine – Pharmacokinetic Profile of Subcutaneous Injection in Pigs

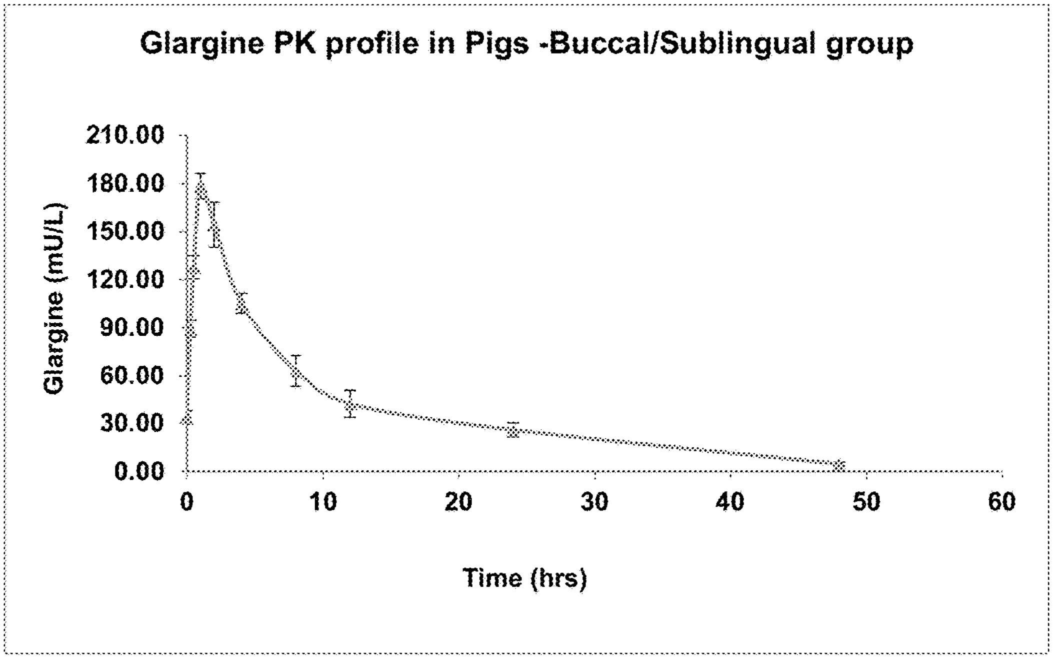
FIG. 58 Lantus/Insulin Glargine – Pharmacokinetic Profile of Buccal/Sublingual Delivery in Pigs

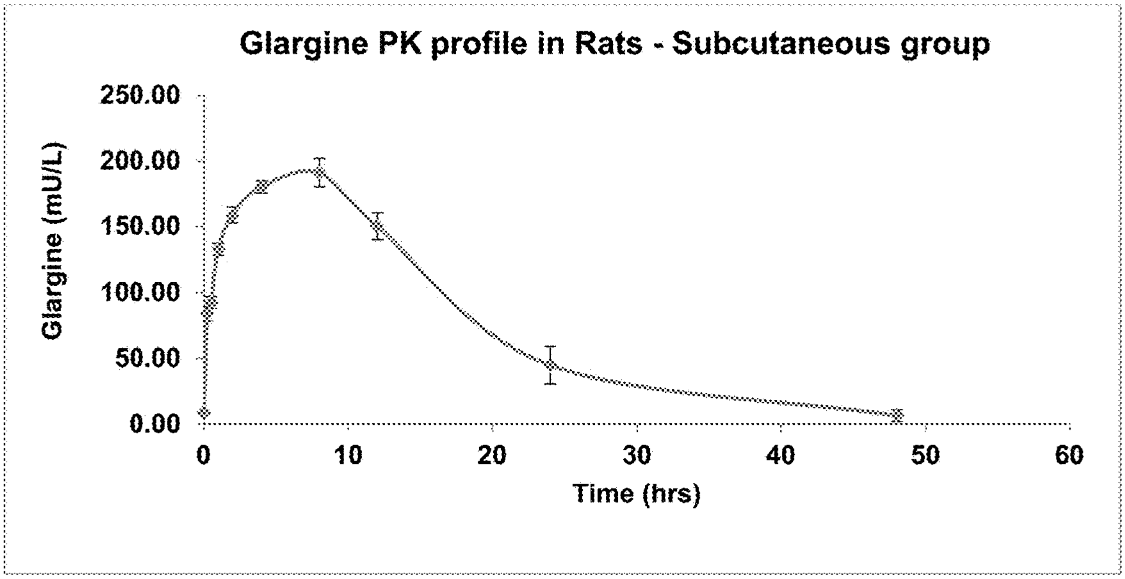
FIG. 59. Lantus/Insulin Glargine – Pharmacokinetic Profile of Subcutaneous Injection in Rats

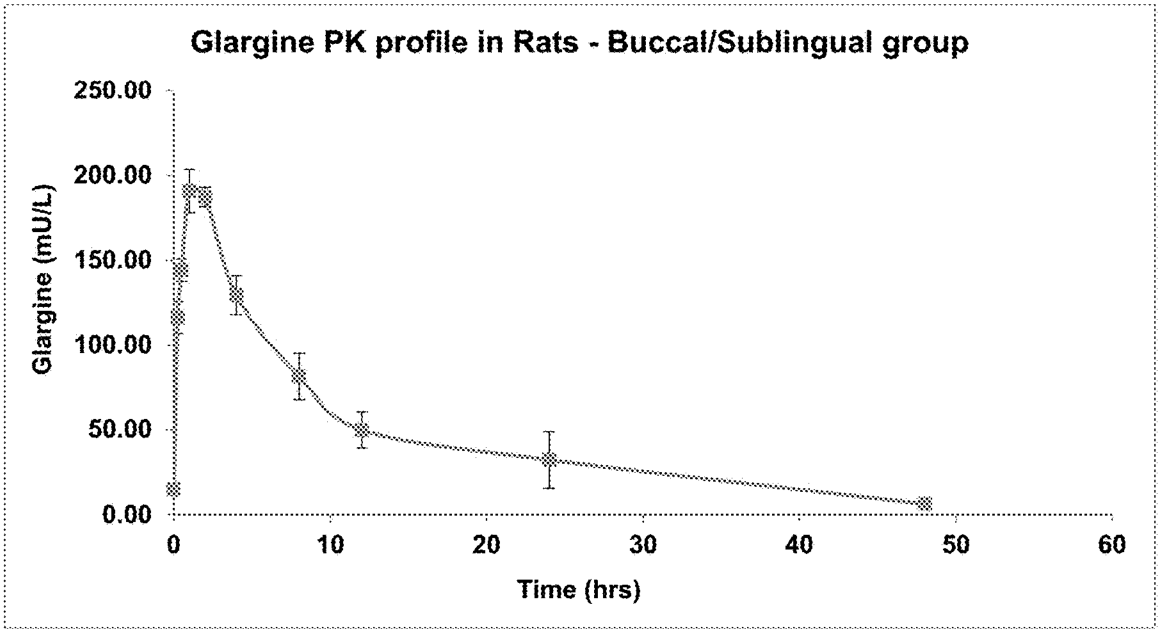
FIG. 60. Lantus/Insulin Glargine – Pharmacokinetic profile of Buccal/Sublingual Delivery in Rats

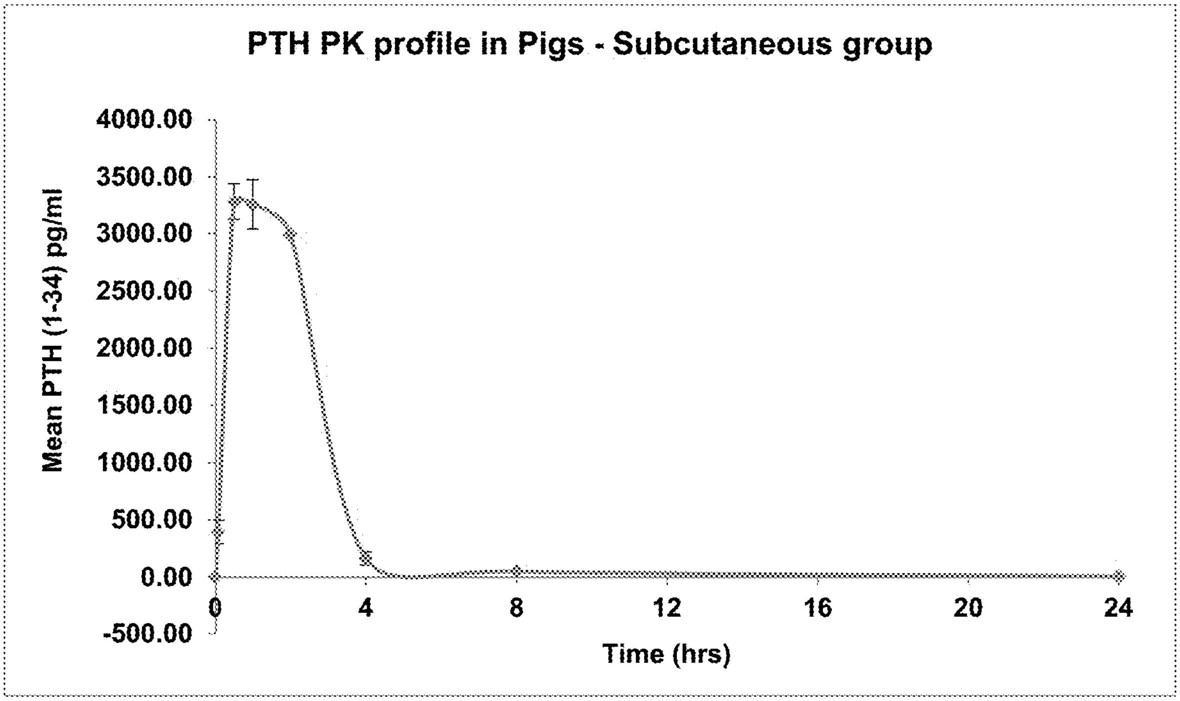
FIG. 61 PTH – Pharmacokinetic Profile of Subcutaneous Injection in Pigs

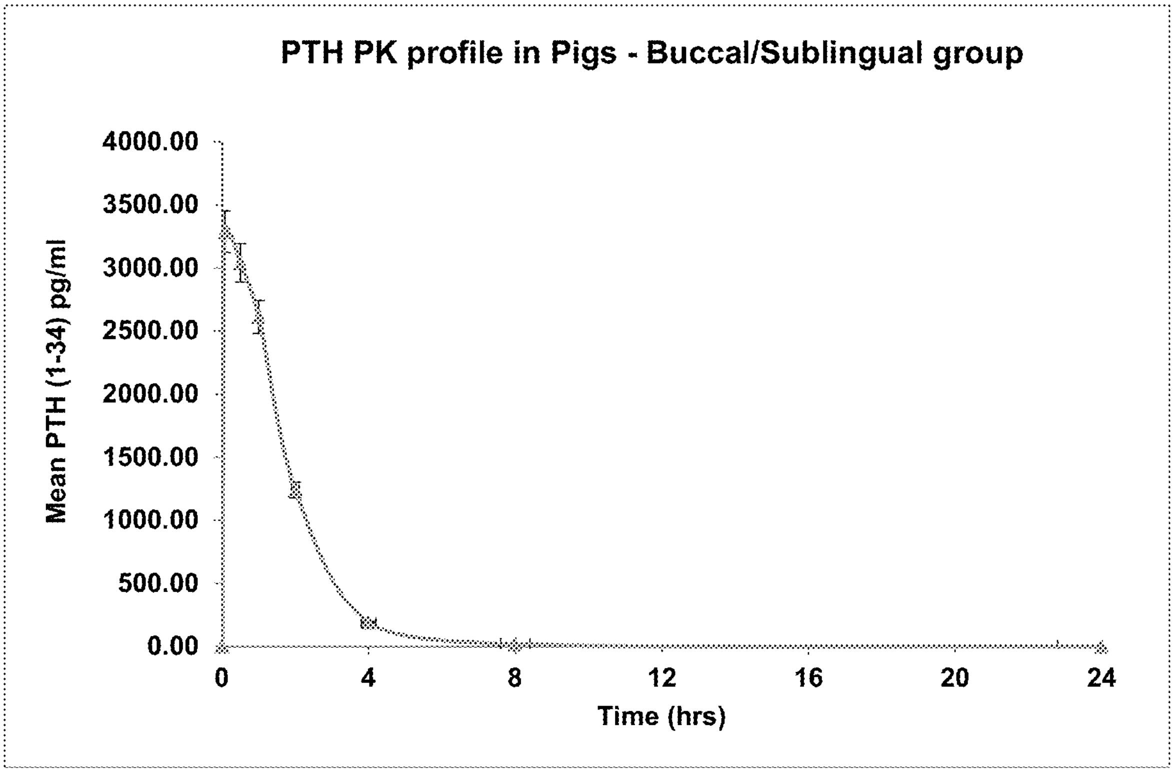
FIG. 62 PTH – Pharmacokinetic Profile of Buccal/Sublingual Delivery in Pigs

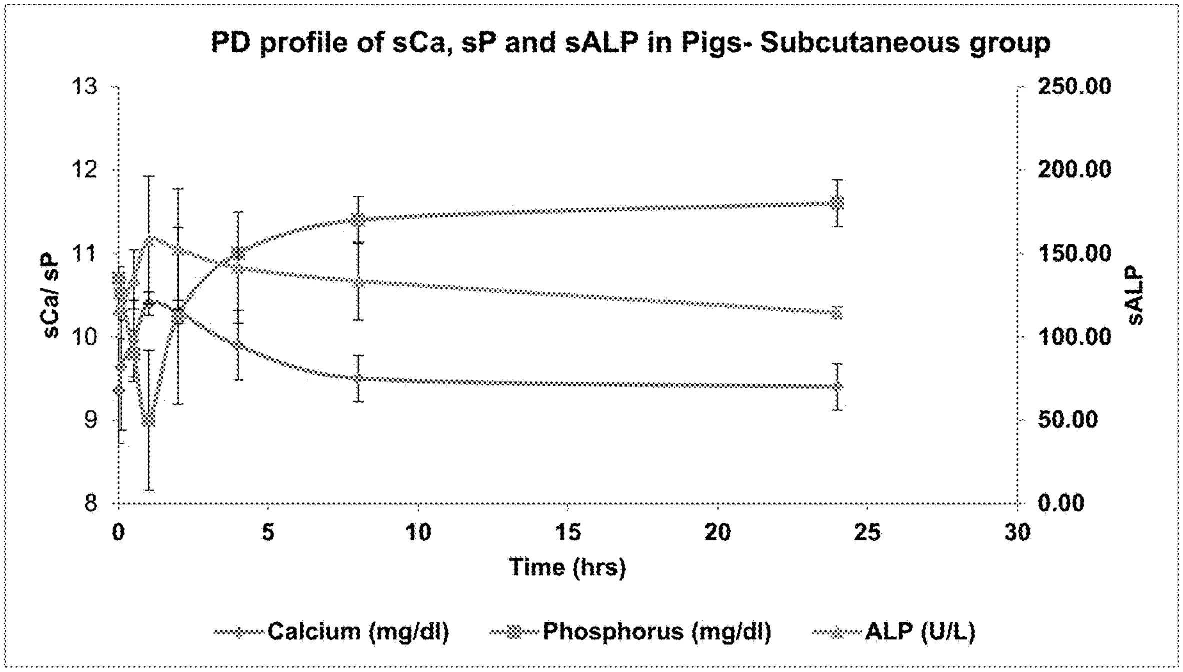
FIG. 63 Pharmacodynamics Analysis of PTH in Subcutaneous Group

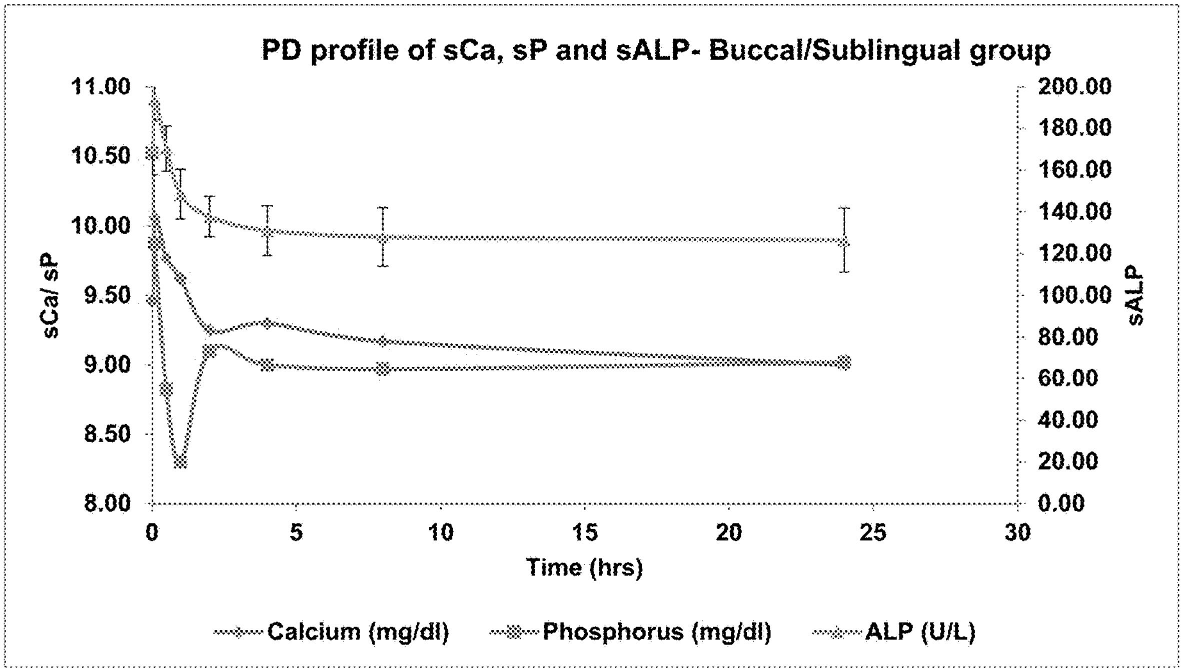
FIG. 64 Pharmacodynamics Analysis of PTH in Buccal/Sublingual Group

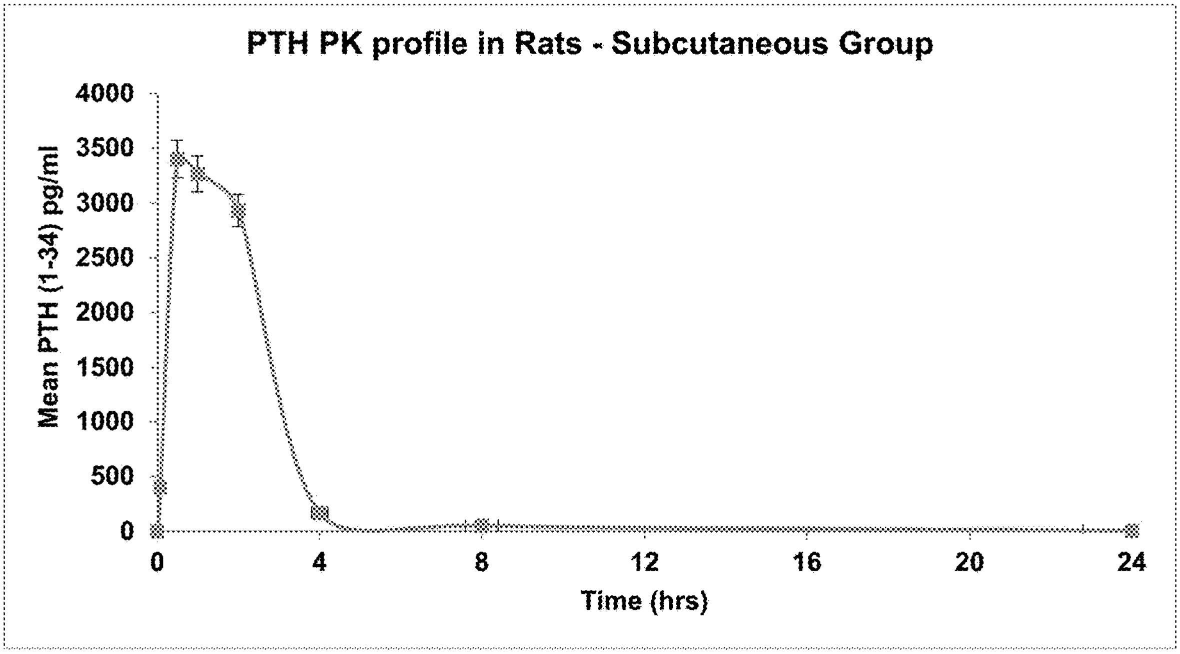
FIG. 65 PTH – Pharmacokinetic Profile of Subcutaneous Injection in Rats

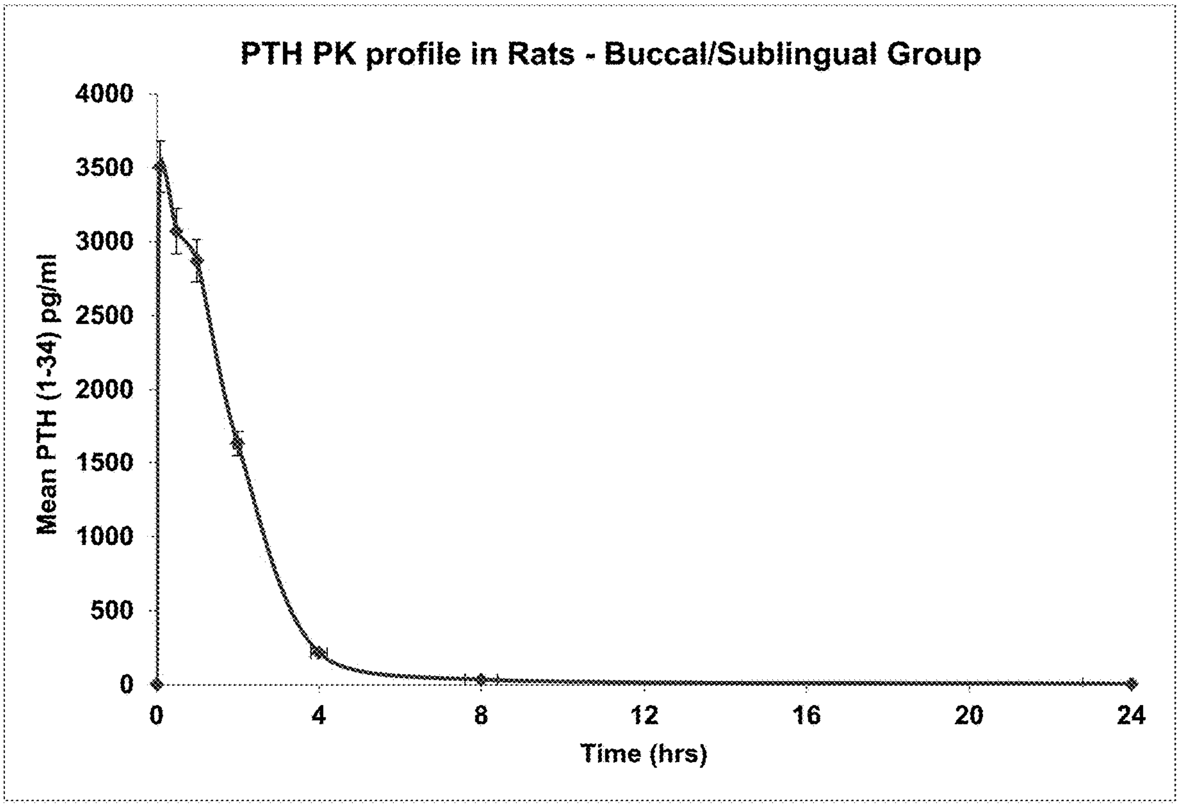
FIG. 66 PTH – Pharmacokinetic Profile of Buccal/Sublingual Delivery in Rats

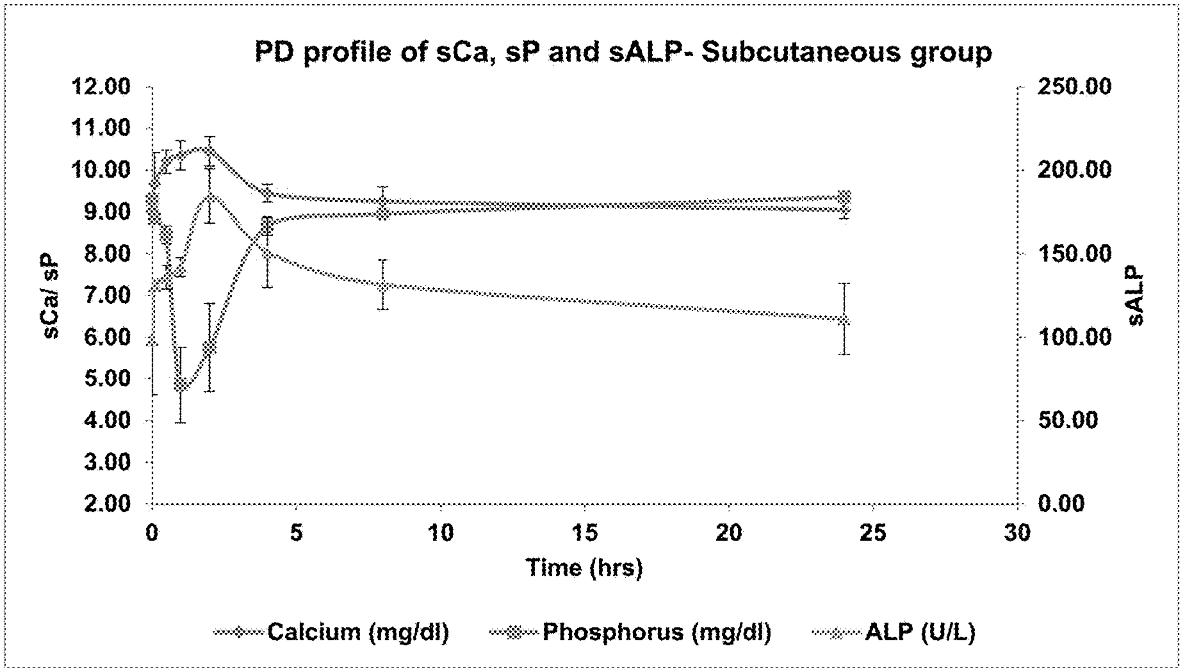
FIG. 67 Pharmacodynamics Analysis of PTH in Injectable Group

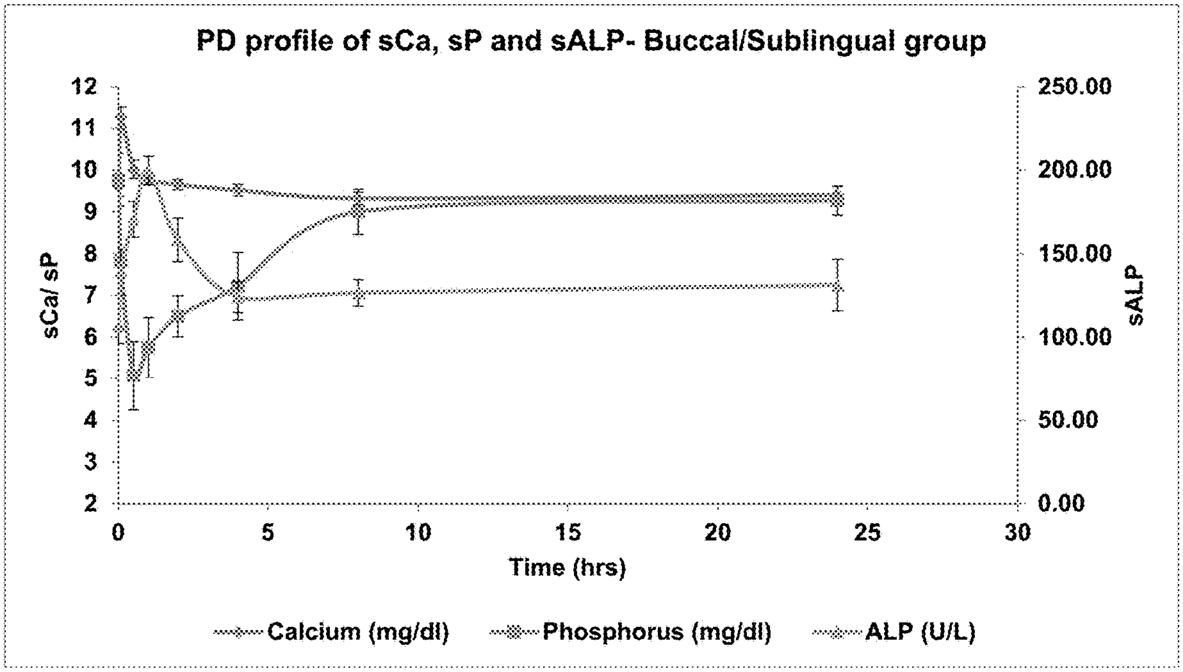
FIG. 68 Pharmacodynamics Analysis of PTH in Buccal/Sublingual Group

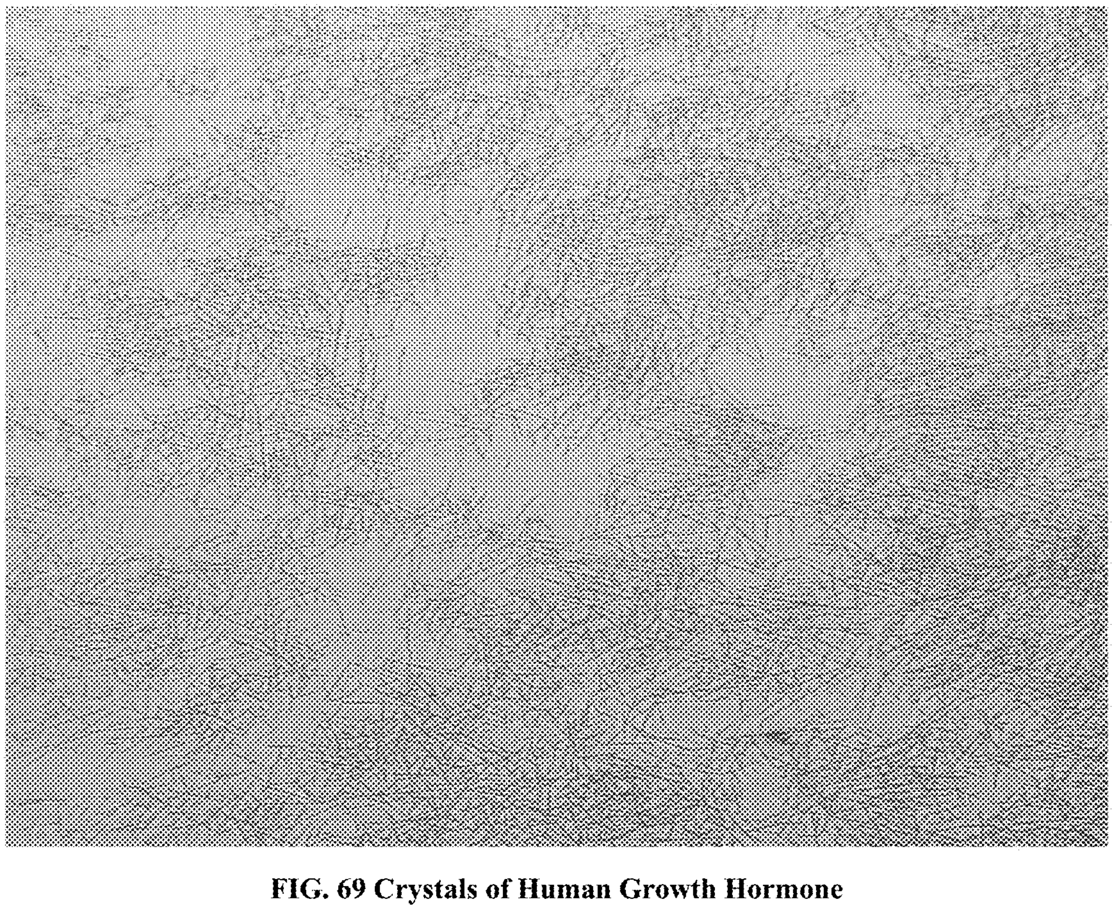
FIG. 69 Crystals of Human Growth Hormone

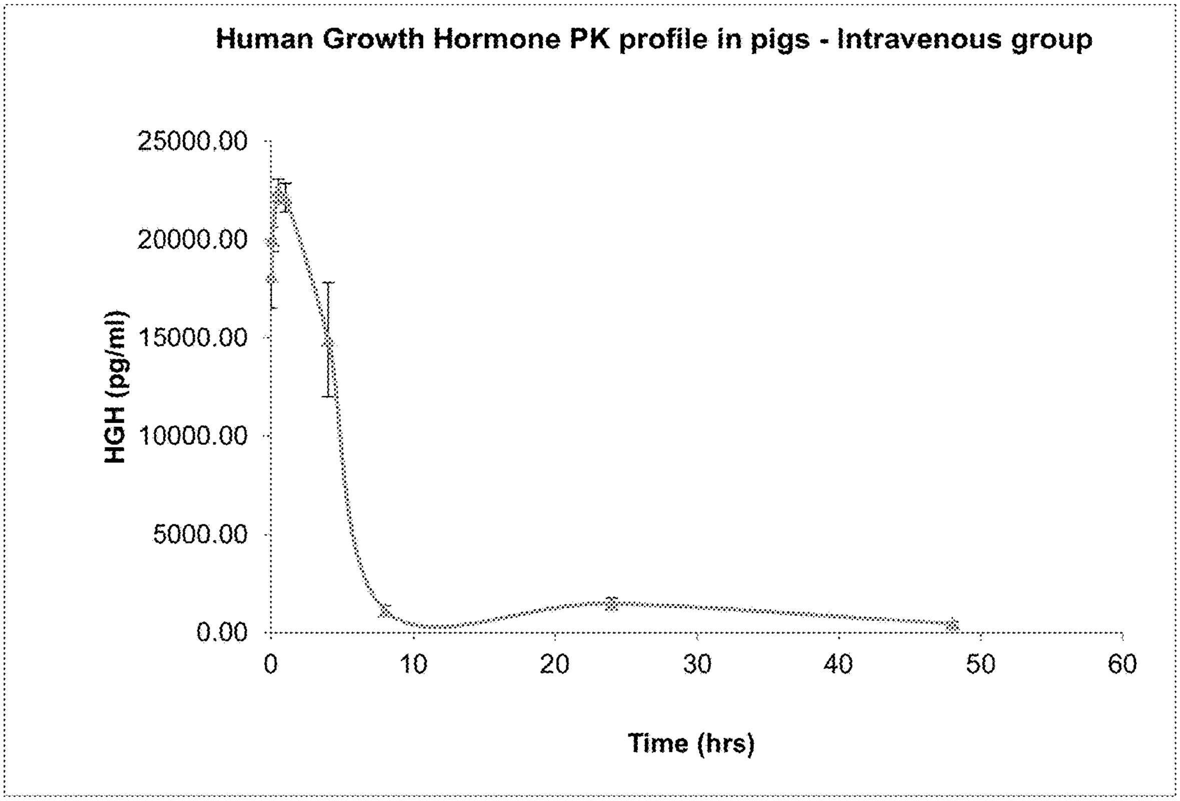
FIG. 70 Human Growth Hormone – Pharmacokinetic Profile of Intravenous Injection in Pigs

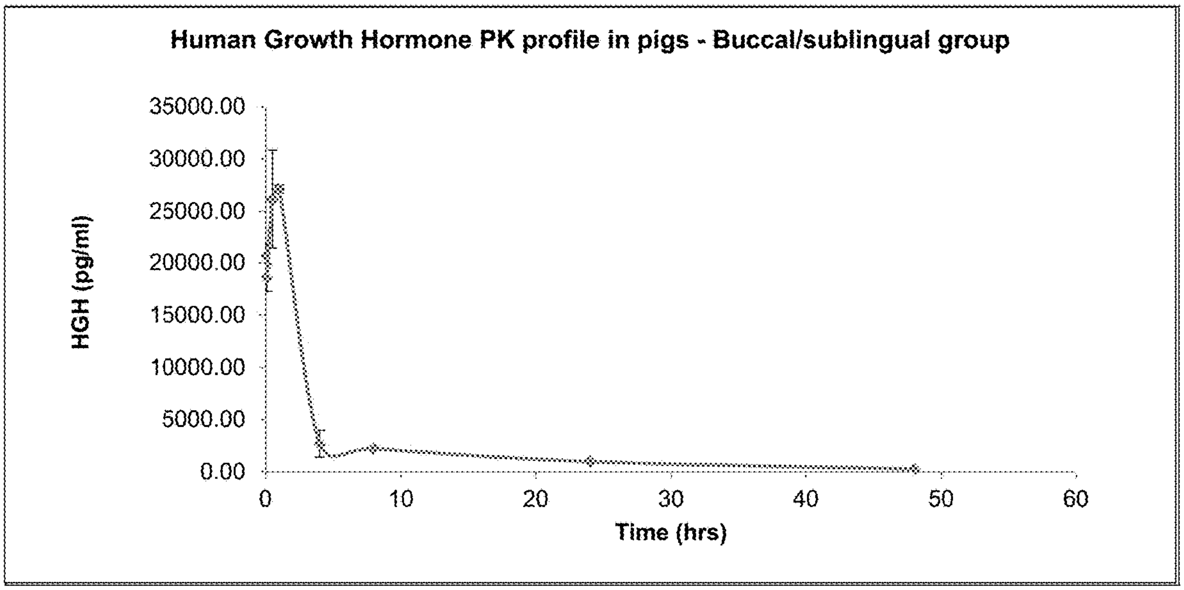
FIG. 71 Human Growth Hormone – Pharmacokinetic profile of hGH Crystals – Sugar Truffle Shell Form Buccal/Sublingual Delivery in Pigs

ORAL POLYPEPTIDE FORMULATIONS

CROSS-REFERENCE TO RELATED APPLICATION

This application claims priority to Indian Application No. 202241058760, filed Oct. 14, 2022 and Indian Application No. 202341022048, filed Mar. 27, 2023, the entirety of each of which is incorporated herein by reference.

BACKGROUND

Polypeptide therapeutics play an important role in medicine. Many current therapeutics include polypeptides such as enzymes, hormones, and antibodies. A typical route of administration for polypeptide therapeutics is intravenous or subcutaneous injection.

SUMMARY

The present disclosure provides, among other things, technologies (e.g., methods and compositions) for the administration (e.g., oral administration) of polypeptides, specifically including therapeutic polypeptides (e.g., antibody agents, enzymes, hormones, etc.).

Those skilled in the art are aware that therapeutic polypeptides are typically formulated as liquid solutions for administration by intravenous or subcutaneous injection. The present disclosure provides the surprising finding that certain formulations of polypeptides, e.g., specifically formulations of crystalline or amorphous polypeptides, can achieve effective systemic delivery of the polypeptides via oral administration of the formulations. Thus, the present disclosure provides, among other things, polypeptide formulations for oral delivery. In many embodiments, provided formulations comprise or otherwise utilize a polypeptide (e.g., a therapeutic polypeptide) in a crystalline (i.e., crystallized) or amorphous form. Thus, in many embodiments, the present disclosure provides oral formulations that include an amorphous polypeptide composition or a crystallized polypeptide composition (e.g., a powder form that includes amorphous polypeptide or crystallized polypeptide) and a pharmaceutically acceptable carrier.

In many embodiments, provided formulations are or comprise a polypeptide (e.g., a therapeutic polypeptide) in a non-liquid phase—e.g., such formulations may be gels, solids, suspensions (e.g., of solid particles), etc.

In some embodiments, a polypeptide formulation is or comprises a truffle formulation. In some embodiments, a truffle formulation comprises a pharmaceutically acceptable shell and a core that comprises an amorphous polypeptide composition or a crystallized polypeptide composition (e.g., a powder form that includes amorphous polypeptide or crystallized polypeptide). In some embodiments, a polypeptide formulation is or comprises a tablet formulation that comprises an amorphous polypeptide composition or a crystallized polypeptide composition (e.g., a powder form that includes amorphous polypeptide or crystallized polypeptide) and a pharmaceutically acceptable carrier. In some embodiments, a polypeptide formulation is or comprises a globule formulation that comprises an amorphous polypeptide composition or a crystallized polypeptide composition (e.g., a powder form that includes amorphous polypeptide or crystallized polypeptide) and a pharmaceutically acceptable carrier. In some embodiments, a polypeptide formulation is or comprises a candy formulation that comprises an amorphous polypeptide composition or a crystallized polypeptide composition (e.g., a powder form that includes amorphous polypeptide or crystallized polypeptide) and a pharmaceutically acceptable carrier.

The present disclosure includes the surprising discovery that oral administration of formulations disclosed herein, e.g., of truffle, tablet, globule, and/or candy formulations as described herein can successfully deliver polypeptides to the bloodstream. The present disclosure further includes the surprising discovery that polypeptides orally administered in a formulation as disclosed herein e.g., a truffle formulation, a tablet formulation, a globule formulation, a candy formulation, are efficiently delivered to the bloodstream, lymphatic system, and thoracic duct.

Advantages of formulations provided herein include that they can effectively deliver a wide range of polypeptides (e.g., of therapeutic polypeptides, such as antibody agents, enzymes, hormones, etc.) to the bloodstream after oral administration of such formulations. Thus, provided technologies have broad applicability and offer a new platform for polypeptide formulation. Upon reading the present disclosure, those skilled in the art will appreciate its generality and applicability to any or all polypeptides of interest.

The present disclosure demonstrates unexpectedly advantageous characteristics of provided formulations, including, in some embodiments, effectiveness in one or more of various modes of oral administration, e.g., buccal or sublingual administration. Indeed, the present disclosure documents that provided formulations can achieve desirable pharmacokinetic properties, including, for example, one or more of rate of delivery into the bloodstream, increased half-life, etc., and in some embodiments can achieve such properties via one or more of such oral administration modes.

In some embodiments, the present disclosure provides polypeptide formulations for oral delivery, which formulations include (i) a crystallized polypeptide composition or an amorphous polypeptide composition and (ii) a pharmaceutically acceptable carrier, optionally wherein the formulation is a truffle formulation comprising a core and a pharmaceutically acceptable shell, wherein the core comprises the crystallized polypeptide composition or amorphous polypeptide composition.

In some embodiments, the present disclosure provides polypeptide formulations for oral delivery that re tablet polypeptide formulations, which tablet polypeptide formulation comprises a crystallized polypeptide composition or an amorphous polypeptide composition and a pharmaceutically acceptable carrier.

In some embodiments, the present disclosure provides polypeptide formulations for oral delivery, which formulations are globule formulations that comprise a crystallized polypeptide composition or an amorphous polypeptide composition and a pharmaceutically acceptable carrier.

In some embodiments, the present disclosure provides polypeptide formulations for oral delivery, which formulations are candy formulations that comprise a crystallized polypeptide composition or an amorphous polypeptide composition and a pharmaceutically acceptable carrier, optionally wherein the candy formulation is in a form, for example, of candy gems, chewing gum, gummy candy, hard candy (e.g., drops, lollipops, lozenges, rock candy, stick candy, etc.) marshmallows, syrup, toffee, etc. In some embodiments, a candy formulation may be in the form of a drop, film, gel, patch, spray, wafer, etc.

In some embodiments, a provided formulation may be in the form of a dry powder (e.g., a dry spray). In some embodiments, a provided formulation may be in the form of a solid particle suspension. In some embodiments, a provided formulation may be in the form of a fast-dissolving tablet. In some embodiments, a provided formulation may be in the form of a fast-dissolving film.

In some embodiments, the present disclosure provides methods of delivering a polypeptide to the bloodstream of a subject, the method comprising a step of orally administering to the subject a polypeptide formulation including (i) a crystallized polypeptide composition or an amorphous polypeptide composition and (ii) a pharmaceutically acceptable carrier, optionally wherein the polypeptide formulation is a truffle formulation comprising a core and a pharmaceutically acceptable shell, wherein the core comprises the crystallized polypeptide composition or amorphous polypeptide composition. In certain embodiments, the polypeptide is delivered to the bloodstream via mouth tissue.

In some embodiments, the present disclosure provides methods delivering a polypeptide to mouth tissue of a subject, the method comprising a step of orally administering to the subject a polypeptide formulation including (i) a crystallized polypeptide composition or an amorphous polypeptide composition and (ii) a pharmaceutically acceptable carrier, optionally wherein the polypeptide formulation is a truffle formulation comprising a core and a pharmaceutically acceptable shell, wherein the core comprises the crystallized polypeptide composition or amorphous polypeptide composition. In certain aspects, the polypeptide is delivered to the bloodstream through buccal or sublingual administration.

In some embodiments, the present disclosure provides methods of producing a truffle formulation for oral delivery, the method comprising a step of placing within a shell a core comprising an amorphous polypeptide composition or a crystallized polypeptide composition. In some embodiments, the present disclosure provides methods of producing a tablet polypeptide formulation for oral delivery, the method comprising a step of mixing (i) a crystallized polypeptide composition or an amorphous polypeptide composition with (ii) a pharmaceutically acceptable carrier. In some embodiments, the present disclosure provides methods of producing a globule formulation for oral delivery, the method comprising a step of mixing (i) a crystallized polypeptide composition or an amorphous polypeptide composition with (ii) a pharmaceutically acceptable carrier. In some embodiments, the present disclosure provides methods of producing a candy formulation for oral delivery, the method comprising a step of mixing (i) a crystallized polypeptide composition or an amorphous polypeptide composition with (ii) a pharmaceutically acceptable carrier. In some embodiments, the present disclosure provides methods of producing a candy formulation for oral delivery, the method including mixing (i) a crystallized polypeptide composition or an amorphous polypeptide composition with (ii) a pharmaceutically acceptable carrier, wherein a pharmaceutically acceptable carrier comprises food ingredients, e.g., chocolate, cocoa, milk, milk product, natural dye, artificial dye, gum base, flavors, sweeteners, gelatin, starch, syrup, citric acid, sugar, etc.

In certain embodiments, a polypeptide amenable to formulation as described herein may be or comprise a therapeutic polypeptide. In some embodiments a polypeptide amenable to formulation as described herein may be or comprise, for example (i) an antibody agent (e.g., a monoclonal antibody, a bispecific antibody, etc.) or antigen-binding portion thereof; (ii) a fusion polypeptide; (iii) an immunoglobulin; (iv) an enzyme; (v) a hormone; (vi) a cytokine; or (vi) an analog or combination of any of the foregoing. In some embodiments, a polypeptide amenable to formulation as described herein may include one or more covalent modifications such as, for example, one or more of acetylation, acylation, amidation, fatty acids, glycation, glycosylation, lipidation, mannosylation, methylation, nitrosylation, phosphorylation, sulfation, palmitoylation, pegylation, prenylation, or a combinations thereof.

Among other contributions, the present disclosure provides an insight that provided formulations include a polypeptide component that, in some embodiments, is a single polypeptide that is in a crystallized or amorphous form. Alternatively, in some embodiments, the polypeptide in a provided formulation is a combination of two or more polypeptides; in some such embodiments, all such polypeptides are in a crystalline or amorphous form but in some embodiments, not all polypeptides in such polypeptide component need to be crystalline. That is, in some embodiments, less than all of the polypeptides in a polypeptide component of a provided formulation are crystalline. Without wishing to be bound by any particular theory, the present disclosure proposes that one (or more than one) polypeptide in a polypeptide component can act as a crystallization carrier with respect to one (or more than one) other polypeptide in the component.

In certain embodiments, a polypeptide component of a provided formulation is or comprises a polypeptide is selected from, for example, Abaloparatide (Tymlos), Adlyxin Lixisenatide®, Afamelanotide Scenesse®, Angiotensin II (Giapreza), Angiotension 11 antagonist, Anidulafungin, Atosiban, Aviptadil, Belantamab mafodotin-blmf (Blenrep™), Bentiromide, Beta-endorphin, Bivalirudin, Bradykynin, Bremelanotide Vyleesi®, Bursin, Calcitonin, Capreomycin, Carbetocin, Carfilzomib, Caspofungin, Ceruletide, Cholecystokynin, Cu-DOTATATE (Detectnet™), Dalbavancin, Daptomycin, Degarelix, Dulaglutide, Edotreotide, Edotreotide gallium Ga-68, Enfortumab Vedotin-Ejfv PADCEV®, Enfuvirtide, Etelcalcetide (Parsabiv), Exenatide, Ga DOTA-TOC, gallium Ga-68, Ga-PSMA-11, Glatiramer acetate, Glatiramer, Glucagon, Gonadorelin, Goserelin, Goserilin, Gramicidin, Human growth hormone, Icatibant, Imcivree™, Insulin degludec Tresiba®, Interferons, Interferon Alfa-2a, Recombinant, Interferon alfacon-1, Interferon Alfa-2b, Recombinant, Interferon beta-1b, Interferon beta-1a, Interferon alfa-n3, Interferon alfa-n1, Interferon gamma-1b, Peginterferon alfa-2b, Peginterferon alfa-2a, Insulin, Ixazomib Ninlar®, Lanreotide, Leuprorelin, Leuprotide, Linaclotide, Liraglutide, Lu DOTA-TATE Lutathera®, Lumasiran (Oxlumo™), Lupkynis™, LUPRON DEPOT, Lutetium Lu 177 dotatate4, Macimorelin (Macrilen), Micafungin, Mifamurtide, Mycappsa®, Scenesse®, Nesiritide, Octreotide, Oritavancin, Oxytocin, Pasireotide, Plecanatide Trulance®, Polatuzumab Vedotin-Piiq Polivy®, Pramlintide, Romidepsin, Voclosporin, Romiplostim, Rybelsus®, Sandostatin, Secretin human, Semaglutide, Sermorelin, Setmelanotide (Imcivree™), Somatuline, Taltirelin, Teduglutide, Telavancin, Teriparatide, Terlipressin, Tetracosactide, Bacitracin, Vancomycin, Thymalfasin, Mecasermin, Cetrorelix, Vasopressin, Victoza, Viltolarsen (Viltepso™), Vyleesi®, Zegalogue, Ziconotide, Lupkynis™, Zoladex, Desmopressin. Insulin degludec Tresiba®, Ixazomib Ninlar®, Macimorelin Macrilen®, 177Lu DOTA-TATE Lutathera®, 68Ga DOTA-TOC, Insulin recombinant, Exentide (Byetta), Lancreotide (Somatuline), Pramilintide (Symlin), Etanercept, Bevacizumab, Rituximab, Infliximab, Trastuzumab, Insulin glargine, Epoetin alfa, Darbepoetin alfa, Epoetin beta, Pegfilgrastim, Ranibizumab, Insulin aspart, Rhu insulin, Octocog alfa, Insulin lispro, Cetuximab, Eptacog alfa, Onabotulinumtoxin A, Filgrastin, Insulin detemir, Natalizumab, nsulin (humulin), Palivizumab, Bleomycin, Bortezomib Blenoxane, Buserelin, Carfilzomib, Cobicistat, Corticotropin, Cosyntropin, Cyclosporia, Dactinomycin, Depreotide, Eptifibatide, Ganirelix, Glutathion, Histrelin, Leuprolide, Lucinactant, Lypressin, Nafarelin, Pentagastrin, Pentetreotide, Polymyxin B, Protirelin, Saralasin, Secretin porcine, Sincalide, Somatorelin, Somatostatin, Teicoplanin, Triptorelin, Urofollitropin, Abarelix, Pegvisomant, Somatropin recombinant, Lutropin alfa, Follitropin beta, Menotropins, Thyrotropin Alfa, Choriogonadotropin alfa, Aldesleukin, Coagulation Factor IX, Antihemophilic Factor, Eptifibatide, Exenatide Bydureon, Lepirudin, Angiotensin 1-7, Boceprevir Victrelis, Kyprolis, Ciclosporin Ikervis, Ciclosporin Verkazia, Dalbavancin Xydalba, Lutetium (177Lu) oxodotreotide Lutathera, Ombitasvir (paritaprevir and ritonavir) Viekirax, Televancin Vibativ, Avexitide, Calcitonin gene-related peptide, Corticorelin, Leptin, Acleras-tide, Albusomatropin, Anamorelin, G17DT, Insulin peglispro, Lenomorelin, Selepressin, Somapacitan, Taspoglutide, Thymosin beta-4, Tirzepatide, Ularitide, Vosoritide, Zoptarelin doxorubicin, Bombesin, Cenderitide, Deslorelin, Gastric inhibitory polypeptide, MK-3207, Olcegepant, Pancreatic Polypeptide, Peptide YY (3-36), Pirnabine, Somatoprim, TT-232, BPI-3016, NBI-6024, Albiglutide, Taltirelin hydrate, Tesamorelin, Peginesatide, Cyclosporin A, Chiasma, Plecanotide, Colistin sulfate, Tyrothricin, Pancrelipase, Tilactase, Sacrosidase, Diamine oxidase, NOBEX insulin by the Palmitoylatios, Thymopentin, β-LGDP, PTH1-34, BSA, sCT, hGH, BSM, Captopril, Enfurvitide, Streptokinase, Dolcanatide, Efpeglenation-Sanofi, MEDI4166-Astra Zeneca, or PF-06836922 (MOD-4023)-Pfizer, or derivative variant thereof, optionally where the polypeptide is natural, synthetic, or engineered.

In certain embodiments, a polypeptide amenable to formulation as described herein has a molecular weight between about 100 Da and about 25 kDa, optionally where the molecular weight is between about 100 Da and about 1 kDa, about 100 Da and about 2 kDa, about 100 Da and about 3 kDa, about 100 Da and about 4 kDa, about 100 Da and about 5 kDa, about 100 Da and about 10 kDa, about 100 Da and about 15 kDa, or about 100 Da and about 20 kDa. In certain embodiments, a polypeptide has a molecular weight between about 25 kDa and about 1,000 kDa, optionally where the molecular weight is between about 25 kDa and about 500 kDa, about 100 kDa and about 500 kDa, about 120 kDa and about 250 kDa, or about 150 kDa and about 300 kDa.

In certain embodiments, a polypeptide formulation provided herein includes about 1 μg to about 2,000 mg of polypeptide (e.g., of polypeptide component, which may, in some embodiments, be a single polypeptide), optionally where the polypeptide formulation includes about 1 μg to about 1,000 mg, about 1 μg to about 500 mg, about 1 μg to about 400 mg, about 1 μg to about 300 mg, about 1 μg to about 200 mg, about 1 μg to about 100 mg, about 1 μg to about 50 mg, about 1 μg to about 25 mg, about 1 μg to about 20 mg, about 1 μg to about 15 mg, about 1 μg to about 10 mg, about 1 μg to about 5 mg, about 1 μg to about 1 mg, about 1 μg to about 500 μg, about 1 μg to about 250 μg, about 1 μg to about 200 μg, about 1 μg to about 150 μg, about 1 μg to about 100 μg, about 1 μg to about 50 μg, about 1 mg to about 1,000 mg, about 1 mg to about 500 mg, about 1 mg to about 400 mg, about 1 mg to about 300 mg, about 1 mg to about 200 mg, about 1 mg to about 100 mg, about 1 mg, to about 50 mg, about 1 mg to about 25 mg of polypeptide (e.g., of polypeptide component, which may, in some embodiments, be a single polypeptide).

In certain embodiments, a provided formulation includes crystals of polypeptide having an average particle size of less than 25 microns, e.g., less than 20, 15, 10, 5, 4, 3, 2, 1, or 0.5 microns, optionally where the crystals of polypeptide have an average particle size that is between 0.5 microns and 1, 2, 3, 4, 5, 10, 15, 20, or 25 microns or where the crystals of polypeptide have an average particle size that is between 1 micron and 1, 2, 3, 4, 5, 10, 15, 20, or 25 microns.

In certain embodiments, a provided formulation includes amorphous polypeptide particles of polypeptide having an average particle size of less than 25 microns, e.g., less than 20, 15, 10, 5, 4, 3, 2, 1, or 0.5 microns, optionally where the particles of polypeptide have an average particle size that is between 0.5 microns and 1, 2, 3, 4, 5, 10, 15, 20, or 25 microns or where such particles have an average particle size that is between 1 micron and 1, 2, 3, 4, 5, 10, 15, 20, or 25 microns.

In certain embodiments, a polypeptide formulation includes lyophilized polypeptide. In certain embodiments, a polypeptide formulation includes microcrystals of polypeptide. In certain embodiments, a polypeptide formulation includes a powder including crystallized polypeptide.

In certain embodiments, a core (e.g., of a truffle, tablet, globule, candy formulation) is a viscous solution. In certain embodiments, such a core comprises crystallized polypeptide composition. In certain embodiments, a core comprises amorphous polypeptide composition.

In certain embodiments, a shell (e.g., of a truffle formulation) is or comprises sugar. In certain embodiments, a shell is or comprises cane sugar. In certain embodiments, a shell is or comprises palm sugar. In certain embodiments, a shell is or comprises lactose. In certain embodiments, a shell is or comprises xylitol. In certain embodiments, a shell is or comprises milk sugar. In certain embodiments, a shell is cane sugar. In certain embodiments, a shell is palm sugar. In certain embodiments, a shell is hollow. In certain embodiments, a shell is hollow and a core is situated in empty space of a shell. In certain embodiments, a truffle formulation comprises a shell and a core, wherein a shell is hollow and a core is situated in empty space of a shell. In certain embodiments, a truffle shell is hollow and shell is fully filled with space of a core. In certain embodiments, a truffle shell is hollow and the shell is partially filled with space of a core.

In certain embodiments, a polypeptide formulation is formulated for delivery via the gut, optionally where a polypeptide formulation is a capsule. In certain embodiments, a polypeptide formulation is formulated for delivery via the stomach and/or intestine. In certain embodiments, a polypeptide formulation includes an enteric coating.

In certain embodiments, a core (e.g., of a truffle formulation) includes, in addition to polypeptide (i.e., crystalline or amorphous polypeptide), comprises one or more excipients or additives selected from the group consisting of aggregation-reducing agents, sugars or sugar alcohols, polysaccharides, stabilizers, hyaluronidase, buffering agents, preservatives, carriers, antioxidants, chelating agents, natural or synthetic polymers, cryoprotectants, lyoprotectants, surfactants, bulking agents, acidifying agents, ingredients to reduce injection site discomfort, antifoaming agents, alkalizing agents, vehicles, aggregation inhibitors, solubilizing agents, tonicity modifiers, permeation enhancers, muco bioadhesive agents, and stabilizing agents and combinations thereof.

In certain embodiments, one or more excipients or additives are individually or cumulatively present in a provided formulation at a concentration between 0.1 mM and about 1,000 mM, between about 0.1 mM and about 500 mM, between about 0.1 mM and about 200 mM, or between about 0.1 mM and about 100 mM.

In certain embodiments, a provided formulation includes one or more aggregation-reducing agent(s)s, such as may be selected from the group consisting of nicotinic acid, caffeine citrate, caffeine nicotinate, caffeine, octyl-β-D-glucopyranoside, and n-dodecyl-β-D-maltoside and optionally in combination with one or more of arginine, tryptophan, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA (aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfo-butyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino)hexanoic acid (NBD-X), methyl acetyl phosphate (MAP), citraconic anhydride, pyrophosphate, citrate, and combinations thereof.

Alternatively or additionally, in some embodiments, a provided formulation may include a tonicity modifier(s), for example which may be selected from the group consisting of arginine, cysteine, histidine, glycine, sodium chloride, potassium chloride, sodium citrate, saccharides such as sucrose, glucose, dextrose, glycerin or mannitol, and combinations thereof.

Alternatively or additionally, in some embodiments, a provided formulation may include an antioxidant(s), for example which may be selected from the group consisting of glycine, lysine, EDTA, DTPA, sorbitol, mannitol, ascorbic acid, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, sodium thiosulfate, sulfur dioxide, tocopherol, and combinations thereof.

Alternatively or additionally, in some embodiments, a provided formulation may include a lyoprotectant(s), for example which may be selected from the group consisting of sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; propylene glycol, glycerol, poly(ethylene glycol), or poly(propylene glycol); gelatin, dextrins, modified starch, carboxymethyl cellulose, and combinations thereof.

Alternatively or additionally, in some embodiments, a provided formulation may include a permeation enhancer(s), for example which may be selected from the group consisting of bile salts, e.g., tri-hydroxy salts sodium cholate, sodium glyco-cholate, sodium taurocholate and di-hydroxy salt, sodium deoxy cholate, sodium glyco-deoxy Cholate, sodium tauro-deoxy cholate; fatty acids, their salt and esters, e.g., oleic acid, lauric acid, cod liver oil extract, sodium laurate, sodium caprate, glyceryl monostearate, di-ethylene glycol mono ethyl ether and various sucrose fatty acid esters, medium-chain fatty acid glycerides, polycaprolactoneomega-3 fatty acids, lecithin (phosphatidylcholine), lysophosphatidylcholine; surfactants, e.g., sodium dodecyl (lauryl) sulphate, poly sorbates (polysorbate 80), laureths, brijs and benzalkonium chloride; complexing agents, e.g., cyclodextrins, dextran sulphate, dextran sulphate, sodium edetate; complexing agents, e.g., cyclodextrins, dextran sulphate, dextran sulphate, sodium edetate, co-solvents, e.g., ethanol and propylene glycol, combination of 1% oleic acid and 5%/10% polyethylene glycol 200, 2% glyceryl mono laurate and 40% alcohol, sodium caprate and alcohol or propylene glycol, 10% lauric acid in propylene glycol, polyoxyethylene, 2,3-lauryl ether, menthol, sodium caprate, sodium caprylate, sodium glycodeoxycholate, glycol; polysaccharides, e.g., chitosan and chitosan glutamate; and others such as, aprotinin, benzalkonium chloride, cetylpyridinium chloride, cetyltrimethyl ammonium bromide, sodium salicylate, lysophosphatidylcholine, methoxysalicylate, methyloleate, sodium edta, sulfoxides, various alkyl glycosides, ethylenediamide tetra acetic acid (edta), tartaric acid; lyotropic salts, such as magnesium sulfate; propylene glycol, glycerol, poly(ethylene glycol), or poly(propylene glycol); gelatin, dextrins, modified starch, carboxymethyl cellulose, and combinations thereof.

Alternatively or additionally, in some embodiments, a provided formulation may include an absorption enhancer(s), for example which may be selected from the group consisting of surfactants, cholesterol, glycerides, salicylates, bile salts, chelating agents, sodium caprate, a salt of capric acid and other includes N-(5-chlorosalicylol)-8-aminocaprylic acid (5-CNAC), 4-((4-chloro-2-hydroxybenzoyl))-amino) butanoic acid (4-CNAB) and N-(8-(2-hydroxybenzoyl))-amino) caprylic acid, also known as salcaprozate sodium (SNAC, caprylic acid, C8, castor oil, medium chain, acyl carnitine, EDTA, glyceryl monolaurate, bovine β-casein, tocopherol succinate glycol chitosan conjugates, lecithins, glyceryl monostearate (GMS), chitosan and alginate, PLGA, silica, stearic acid, oleic acid, hydrogenated castor oil, and glyceryl trimyristate, etoposide phosphate (Vepesid®), sulindac (Clinoril®), enalapril maleate (Vasotec®), ramipril (Altace®), olmesartan medoxomil (Benicar®), valacyclovir (Valtrex®), midodrine (Amatine®), gabapentin enacarbil (Horizant®), sulfasalazine (Azulfidine®); or Alternatively or additionally, in some embodiments, a provided formulation may include a muco bioadhesive agent(s), for example which may be selected from the group consisting of sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; propylene glycol, glycerol, poly(ethylene glycol), or poly(propylene glycol); gelatin, dextrins, modified starch, carboxymethyl cellulose, and combinations thereof. mucoadhesive system such as from naturae, e.g., gelatin, agarose, chitosan, hyaluronic acid and synthetic polymers, e.g., polyvinylpyrolidone (PVP), polyacrylates, polyvinyl alcohol, sodium carboxymethyl cellulose (SCMC) and pectin, all anionic-type polymers, chitosan (cationic type), and hydroxypropyl methylcellulose (HPMC) as a nonionic polymer, polyacrylic acid (PAA) derivatives (CP934, CP940, PCP), 15% CMC and 35% CP, copolymers of acrylic acid and poly(ethylene glycol) monomethylether monomethacrylate (PEGMM), eudragitl NE40D is a neutral poly(ethylacrylate methylmethacrylate, hydrophilic polymers, e.g., methocel K4M, methocel K15M, SCMC 400, Cekol 700, Cekol 10000, CP934P, CP971P and CP974P, carboxyvinyl polymer and triethanolamine, HPC (hydroxy propyl celluose), CP (carbopol 934P), carbopol (CP) EX-55 CMC (sodium carboxymethyl cellulose), HPMC (hydroxy propyl methyl cellulose), HEC (hydroxy ethyl cellulose), PIP [poly (isoprene)], PIB [poly(Isobutylene)], xanthum gum, locust bean gum, pectin, polycarbophil, benzyl esters, hydroxyethylcellulose, poly(acrylic acid), poly(acrylic acid-co-acrylamide), poly(acrylic acid-co-methyl methacrylate), poly (acrylic acid-co-butylacrylate), HEMA copolymerized with Polymeg® (polytetramethylene glycol), Cydot® (bioadhesive polymeric blend of CP and PIB), formulation consisting of PVP, cetylpyridinium chloride (as stabilizer), chitosan chloride, polyethylene oxide, polymethylvinylether/maleic anhydride (PME/MA), and tragacanth, poly ethyleneglycol monomethylether monomethacrylate, drum dried waxy maize starch (DDWM), carbopol 974P, and sodium stearylfumarate, and cellulose derivatives; hydrogels-acrylic acid (polar) and butyl acrylate (apolar), and combinations thereof.

Definitions

A, An, The: As used herein, "a", "an", and "the" refer to one or to more than one (i.e., to at least one) of the grammatical object of the article. By way of example, "an element" discloses embodiments of exactly one element and embodiments including more than one element.

About: As used herein, term "about", when used in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referenced value.

Administration: As used herein, the term "administration" typically refers to administration of a composition to a subject or system to achieve delivery of an agent that is, or is included in, the composition.

Agent: As used herein, the term "agent" may refer to any chemical entity, including without limitation any of one or more of an atom, molecule, compound, amino acid, polypeptide, nucleotide, nucleic acid, polypeptide complex, liquid, solution, saccharide, polysaccharide, lipid, or combination or complex thereof.

Amino acid: In its broadest sense, as used herein, refers to any compound and/or substance that can be incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with a typical or canonical amino acid structure. For example, in some embodiments, an amino acid can be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification can, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" can be used to refer to a free amino acid; in some embodiments it can be used to refer to an amino acid residue of a polypeptide.

Amorphous: As used herein, the term "amorphous" generally refers to a non-crystalline solid form of polypeptide, sometimes referred to as an amorphous solid" or "amorphous precipitate", which typically has no, or essentially no, molecular lattice structure characteristic of the crystalline solid state.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Antibody: As used herein, the term "antibody" refers to a polypeptide that includes one or more canonical immunoglobulin sequence elements sufficient to confer specific binding to a particular antigen (e.g., a heavy chain variable domain, a light chain variable domain, and/or one or more CDRs). Thus, the term antibody includes, without limitation, human antibodies, non-human antibodies, synthetic and/or engineered antibodies, fragments thereof, and agents including the same. Antibodies can be naturally occurring immunoglobulins (e.g., generated by an organism reacting to an antigen). Synthetic, non-naturally occurring, or engineered antibodies can be produced by recombinant engineering, chemical synthesis, or other artificial systems or methodologies known to those of skill in the art.

As is well known in the art, typical human immunoglobulins are approximately 150 kD tetrameric agents that include two identical heavy (H) chain polypeptides (about 50 kD each) and two identical light (L) chain polypeptides (about 25 kD each) that associate with each other to form a structure commonly referred to as a "Y-shaped" structure. Typically, each heavy chain includes a heavy chain variable domain (VH) and a heavy chain constant domain (CH). The heavy chain constant domain includes three CH domains: CH1, CH2 and CH3. A short region, known as the "switch", connects the heavy chain variable and constant regions. The "hinge" connects CH2 and CH3 domains to the rest of the immunoglobulin. Each light chain includes a light chain variable domain (VL) and a light chain constant domain (CL), separated from one another by another "switch." Each variable domain contains three hypervariable loops known as "complement determining regions" (CDR1, CDR2, and CDR3) and four somewhat invariant "framework" regions (FR1, FR2, FR3, and FR4). In each VH and VL, the three CDRs and four FRs are arranged from amino-terminus to carboxy-terminus in the following order: FR1, CDR1, FR2, CDR2, FR3, CDR3, and FR4. The variable regions of a heavy and/or a light chain are typically understood to provide a binding moiety that can interact with an antigen. Constant domains can mediate binding of an antibody to various immune system cells (e.g., effector cells and/or cells that mediate cytotoxicity), receptors, and elements of the complement system. Heavy and light chains are linked to one another by a single disulfide bond, and two other disulfide bonds connect the heavy chain hinge regions to one another, so that the dimers are connected to one another and the tetramer is formed. When natural immunoglobulins fold, the FR regions form the beta sheets that provide the structural framework for the domains, and the CDR loop regions from both the heavy and light chains are brought together in three-dimensional space so that they create a single hypervariable antigen binding site located at the tip of the Y structure.

In some embodiments, an antibody is polyclonal, monoclonal, monospecific, or multispecific antibodies (including bispecific antibodies). In some embodiments, an antibody includes at least one light chain monomer or dimer, at least one heavy chain monomer or dimer, at least one heavy chain-light chain dimer, or a tetramer that includes two heavy chain monomers and two light chain monomers. Moreover, the term “antibody” can include (unless otherwise stated or clear from context) any art-known constructs or formats utilizing antibody structural and/or functional features including without limitation intrabodies, domain antibodies, antibody mimetics, Zybodies®, Fab fragments, Fab' fragments, F(ab')2 fragments, Fd' fragments, Fd fragments, isolated CDRs or sets thereof, single chain antibodies, single-chain Fvs (scFvs), disulfide-linked Fvs (sdFv), polypeptide-Fc fusions, single domain antibodies (e.g., shark single domain antibodies such as IgNAR or fragments thereof), cameloid antibodies, camelized antibodies, masked antibodies (e.g., Probodies®), affybodies, anti-idiotypic (anti-Id) antibodies (including, e.g., anti-anti-Id antibodies), Small Modular ImmunoPharmaceuticals (“SMIPs™”), single chain or Tandem diabodies (TandAb®), VHHs, Anticalins®, Nanobodies® minibodies, BiTE®s, ankyrin repeat proteins or DARPINs®, Avimers®, DARTs, TCR-like antibodies, Adnectins®, Affilins®, Trans-Bodies®, Affibodies®, TrimerX®, MicroProteins, Fynomers®, Centyrins®, and KALBITOR®s, CARs, engineered TCRs, and antigen-binding fragments of any of the above.

In various embodiments, an antibody includes one or more structural elements recognized by those skilled in the art as a complementarity determining region (CDR) or variable domain. In some embodiments, an antibody can be a covalently modified (“conjugated”) antibody (e.g., an antibody that includes a polypeptide including one or more canonical immunoglobulin sequence elements sufficient to confer specific binding to a particular antigen, where the polypeptide is covalently linked with one or more of a therapeutic agent, a detectable moiety, another polypeptide, a glycan, or a polyethylene glycol molecule). In some embodiments, antibody sequence elements are humanized, primatized, chimeric, etc, as is known in the art.

An antibody including a heavy chain constant domain can be, without limitation, an antibody of any known class, including but not limited to, IgA, secretory IgA, IgG, IgE and IgM, based on heavy chain constant domain amino acid sequence (e.g., alpha (α), delta (δ), epsilon (ε), gamma (γ) and mu (μ)). IgG subclasses are also well known to those in the art and include but are not limited to human IgG1, IgG2, IgG3 and IgG4. “Isotype” refers to the Ab class or subclass (e.g., IgM or IgG1) that is encoded by the heavy chain constant region genes. As used herein, a “light chain” can be of a distinct type, e.g., kappa (κ) or lambda (λ), based on the amino acid sequence of the light chain constant domain. In some embodiments, an antibody has constant region sequences that are characteristic of mouse, rabbit, primate, or human immunoglobulins. Naturally-produced immunoglobulins are glycosylated, typically on the CH2 domain. As is known in the art, affinity and/or other binding attributes of Fc regions for Fc receptors can be modulated through glycosylation or other modification. In some embodiments, an antibody may lack a covalent modification (e.g., attachment of a glycan) that it would have if produced naturally. In some embodiments, antibodies produced and/or utilized in accordance with the present invention include glycosylated Fc domains, including Fc domains with modified or engineered such glycosylation.

Antibody fragment: As used herein, an “antibody fragment” refers to a portion of an antibody or antibody agent as described herein, and typically refers to a portion that includes an antigen-binding portion or variable region thereof. An antibody fragment can be produced by any means. For example, in some embodiments, an antibody fragment can be enzymatically or chemically produced by fragmentation of an intact antibody or antibody agent. Alternatively, in some embodiments, an antibody fragment can be recombinantly produced (i.e., by expression of an engineered nucleic acid sequence. In some embodiments, an antibody fragment can be wholly or partially synthetically produced. In some embodiments, an antibody fragment (particularly an antigen-binding antibody fragment) can have a length of at least about 50, 60, 70, 80, 90, 100, 110, 120, 130, 140, 150, 160, 170, 180, 190 amino acids or more, in some embodiments at least about 200 amino acids.

Associated with: Two events or entities are “associated” with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically “associated” with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, or a combination thereof.

Between or From: As used herein, the term “between” refers to content that falls between indicated upper and lower, or first and second, boundaries (or “bounds”), inclusive of the boundaries. Similarly, the term “from”, when used in the context of a range of values, indicates that the range includes content that falls between indicated upper and lower, or first and second, boundaries, inclusive of the boundaries.

Bioavailability: As used herein, the term “bioavailability” can refer to the degree to which a substance, e.g., a polypeptide such as an antibody or antibody fragment, administered to an in vivo subject, becomes available to a tissue to which the substance is targeted (e.g., the bloodstream and/or plasma). Bioavailability can refer to the degree to which a substance that has been administered to an in vivo subject is delivered to blood of the subject. Bioavailability can refer to the ability of a substance to perform a function in the subject. Bioavailability can be measured in a number of ways, e.g., as the concentration of a substance in the bloodstream or plasma. In some embodiments, bioavailability can be assessed, for example, by comparing the "area under the curve" (AUC) in a plot of the plasma concentration as a function of time (area under the plasma concentration curve from time zero to a time where the plasma concentration returns to baseline levels). AUC can be calculated, for example, using the linear trapezoidal rule. "AUC0-t" refers to the area under the plasma concentration curve from time zero to a time, t, later, for example to the time of reaching baseline.

Cancer: As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In some embodiments, a cancer can include one or more tumors. In some embodiments, a cancer can be or include cells that are precancerous (e.g., benign), malignant, pre-metastatic, metastatic, and/or non-metastatic. In some embodiments, a cancer can be or include a solid tumor. In some embodiments, a cancer can be or include a hematologic tumor.

Crystalline: As used herein, the term "crystalline" or "crystal" refers to a material whose constituents (such as atoms, molecules, or ions) are arranged in a highly ordered microscopic structure, forming a crystal lattice that extends in all directions. In many embodiments, presence of crystalline material can be detected, for example, by X-ray diffraction (e.g., by X-ray Powder Diffraction analysis, XRPD).

Engineered: As used herein, the term "engineered" refers to the aspect of having been manipulated by the hand of man. For example, a polynucleotide is considered to be "engineered" when two or more sequences, that are not linked together in that order in nature, are manipulated by the hand of man to be linked to one another in the engineered polynucleotide. Those of skill in the art will appreciate that an "engineered" nucleic acid or amino acid sequence can be a recombinant nucleic acid or amino acid sequence. In some embodiments, an engineered polynucleotide includes a coding sequence and/or a regulatory sequence that is found in nature operably linked with a first sequence but is not found in nature operably linked with a second sequence, which is in the engineered polynucleotide and operably linked in with the second sequence by the hand of man. In some embodiments, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution, deletion, or mating). As is common practice and is understood by those of skill in the art, progeny or copies, perfect or imperfect, of an engineered polynucleotide or cell are typically still referred to as "engineered" even though the direct manipulation was of a prior entity.

Excipient: As used herein, "excipient" refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

"Improve," "increase," "inhibit," or "reduce": As used herein, the terms "improve", "increase", "inhibit", and "reduce", and grammatical equivalents thereof, indicate qualitative or quantitative difference from a reference.

Muco bioadhesive agent: As used herein, the term "muco bioadhesive agent" refers to an agent which increases the contact time between a material (e.g., a drug, an active ingredient of a drug, a polypeptide formulation as described herein or polypeptide released therefrom) and mucus or mucous membrane. In some embodiments, a muco bioadhesive agent prolongs the retention of a material at a site of application. In some embodiments, a muco bioadhesive agent alters the rate of release of a material for improved therapeutic outcome.

Oral administration: As used herein, the term "oral administration" refers to a route of administration where a substance is taken through the mouth. In some embodiments, oral administration is or comprises buccal administration. In some embodiments, oral administration is or comprises sublingual administration. In some embodiments, oral administration is or comprises spray to mouth. In some embodiments, oral administration is via a patch. In some embodiments, oral administration is via application of a film. In some embodiments, oral administration involves administration of drops. In some embodiments, oral administration is or comprises application of a gels. In some embodiments, oral administration is via a wafer. In some embodiments, oral administration is via a capsule. In some embodiments, oral administration is via a tablet. In some embodiments, oral administration is via a suspension. In some embodiments, oral administration is via a formulation as described herein.

Permeation enhancer: As used herein, the term "permeation enhancer" refers to an agent whose presence or level correlates with improved transport of a material, e.g., a drug product or active ingredient thereof, a polypeptide formulation as described herein or a polypeptide component thereof, etc, across an epithelial barrier. In some embodiments, an epithelial barrier is or comprises a mucosal membrane.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutical composition or formulation: As used herein, the term "pharmaceutical composition" or "formulation" refers to a composition in which a therapeutic agent is formulated together with one or more pharmaceutically acceptable carriers.

Polypeptide: As used herein, "polypeptide" refers to any polymeric chain of two or more amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may be or include of natural amino acids, non-natural amino acids, or both. In some embodiments, a polypeptide may be or include only natural amino acids or only non-natural amino acids. In some embodiments, a polypeptide can include D-amino acids, L-amino acids, or both. In some embodiments, a polypeptide may include only L-amino acids. In some embodiments, a polypeptide may include one or more pendant groups or other modifications, e.g., one or more amino acid side chains, e.g., at the polypeptide's N-terminus, at the polypeptide's C-terminus, at non-terminal amino acids, or at any combination thereof. In some embodiments, such pendant groups or modifications may be selected from acetylation, amidation, lipidation, methylation, phosphorylation, glycosylation, glycation, sulfation, mannosylation, nitrosylation, acylation, palmitoylation, prenylation, pegylation, etc., including combinations thereof. In some embodiments, a polypeptide may be cyclic, and/or may include a cyclic portion.

In some embodiments, the term "polypeptide" may be appended to a name of a reference polypeptide, activity, or structure to indicate a class of polypeptides that share a relevant activity or structure. For such classes, the present specification provides and/or those skilled in the art will be aware of exemplary polypeptides within the class whose amino acid sequences and/or functions are known. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that can in some embodiments be or include a characteristic sequence element) that shows very high sequence identity, often greater than 90% or even 95%, 96%, 97%, 98%, or 99%. Such a conserved region usually encompasses at least 3-4 and in some instances up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide can be or include a fragment of a parent polypeptide. In some embodiments, a useful polypeptide may be or include a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Reference: As used herein, "reference" refers to a standard or control relative to which a comparison is performed. For example, in some embodiments, an agent, sample, sequence, subject, animal, or individual, or population thereof, or a measure or characteristic representative thereof, is compared with a reference, an agent, sample, sequence, subject, animal, or individual, or population thereof, or a measure or characteristic representative thereof. In some embodiments, a reference is a measured value. In some embodiments, a reference is an established standard or expected value. In some embodiments, a reference is a historical reference. A reference can be quantitative of qualitative. Typically, as would be understood by those of skill in the art, a reference and the value to which it is compared represents measure under comparable conditions. Those of skill in the art will appreciate when sufficient similarities are present to justify reliance on and/or comparison. In some embodiments, an appropriate reference may be an agent, sample, sequence, subject, animal, or individual, or population thereof, under conditions those of skill in the art will recognize as comparable, e.g., for the purpose of assessing one or more particular variables (e.g., presence or absence of an agent or condition), or a measure or characteristic representative thereof.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2,000 g/mol, less than about 1500 g/mol, less than about 1,000 g/mol, less than about 800 g/mol, or less than about 500 g/mol. In some embodiments, a small molecule is not a polymer. In some embodiments, a small molecule does not include a polymeric moiety. In some embodiments, a small molecule is not and/or does not include a polypeptide. In some embodiments, a small molecule is not and/or does not include a polynucleotide (e.g., is not an oligonucleotide). In some embodiments, a small molecule is not and/or does not include a polysaccharide; for example, in some embodiments, a small molecule is not a glycoprotein, proteoglycan, glycolipid, etc.). In some embodiments, a small molecule is not a lipid. In some embodiments, a small molecule is a modulating agent (e.g., is an inhibiting agent or an activating agent). In some embodiments, a small molecule is biologically active. In some embodiments, a small molecule is detectable (e.g., includes at least one detectable moiety). In some embodiments, a small molecule is a therapeutic agent.

Subject: As used herein, the term "subject" refers to an organism, typically a mammal (e.g., a human, rat, or mouse). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject is not suffering from a disease, disorder or condition. In some embodiments, a subject does not display any symptom or characteristic of a disease, disorder, or condition. In some embodiments, a subject has one or more features characteristic of susceptibility to or risk of a disease, disorder, or condition. In some embodiments, a subject is a subject that has been tested for a disease, disorder, or condition, and/or to whom therapy has been administered. In some instances, a human subject can be interchangeably referred to as a "patient" or "individual." A subject administered an agent associated with treatment of a disease, disorder, or condition with which the subject is associated can be referred to as a subject in need of the agent, i.e., as a subject in need thereof.

Therapeutic agent: As used herein, the term "therapeutic agent" refers to any agent that elicits a desired pharmacological effect when administered to a subject. In some embodiments, an agent is considered to be a therapeutic agent if it demonstrates a statistically significant effect across an appropriate population. In some embodiments, the appropriate population can be a population of model organisms or a human population. In some embodiments, an appropriate population can be defined by various criteria, such as a certain age group, gender, genetic background, preexisting clinical conditions, etc. In some embodiments, a therapeutic agent is a substance that can be used for treatment of a disease, disorder, or condition. In some embodiments, a therapeutic agent is an agent that has been or is required to be approved by a government agency before it can be marketed for administration to humans. In some embodiments, a therapeutic agent is an agent for which a medical prescription is required for administration to humans.

Therapeutically effective amount: As used herein, "therapeutically effective amount" refers to an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that a therapeutically effective amount does not necessarily achieve successful treatment in every particular treated individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is administered for the purpose of achieving any such result. In some embodiments, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments, treatment can be of a subject who has been diagnosed as suffering from the relevant disease, disorder, and/or condition. In some embodiments, treatment can be of a subject known to have one or more susceptibility factors that are statistically correlated with increased risk of development of the relevant disease, disorder, or condition.

BRIEF DESCRIPTION OF THE DRAWING

FIG. 1 is a set of four images showing hollow sugar truffles.

FIG. 2 is an image showing microparticles of insulin produced by a typical crystallization approach known to those of skill in the art.

FIG. 3 is an image showing microparticles of insulin produced by a typical crystallization approach known to those of skill in the art.

FIG. 4 is an image showing microparticles of insulin produced by a typical crystallization approach known to those of skill in the art.

FIG. 5 is an image showing microparticles of insulin produced by a typical crystallization approach known to those of skill in the art.

FIG. 6 is an image showing microparticles of insulin produced by a typical crystallization approach known to those of skill in the art.

FIG. 7 is an image showing microparticles of insulin produced by a typical crystallization approach known to those of skill in the art.

FIG. 8 is an image showing microparticles of insulin produced by a typical crystallization approach known to those of skill in the art.

FIG. 9 is an image showing microparticles of insulin produced by a typical crystallization approach known to those of skill in the art.

FIG. 10A and FIG. 10B are images showing microparticles of Lantus/insulin glargine produced by a typical crystallization approach known to those of skill in the art.

FIG. 11 is an image showing microparticles of parathyroid hormone (PTH) produced by a typical crystallization approach known to those of skill in the art.

FIG. 12 is an image showing microparticles of parathyroid hormone (PTH) produced by a typical crystallization approach known to those of skill in the art.

FIG. 13 is an image showing microparticles of parathyroid hormone (PTH) produced by a typical crystallization approach known to those of skill in the art.

FIG. 14 is an image showing microparticles of parathyroid hormone (PTH) produced by a typical crystallization approach known to those of skill in the art.

FIG. 15 is an image showing microparticles of parathyroid hormone (PTH) produced by a typical crystallization approach known to those of skill in the art.

FIG. 16 is an image showing microparticles of parathyroid hormone (PTH) produced by a typical crystallization approach known to those of skill in the art.

FIG. 17 is an image showing microparticles of parathyroid hormone (PTH) produced by a typical crystallization approach known to those of skill in the art.

FIG. 18 is an image showing microparticles of parathyroid hormone (PTH) produced by a typical crystallization approach known to those of skill in the art.

FIG. 19 is an image showing microparticles of parathyroid hormone (PTH) produced by a typical crystallization approach known to those of skill in the art.

FIG. 20 is an image showing microparticles of parathyroid hormone (PTH) produced by a typical crystallization approach known to those of skill in the art.

FIG. 21 is an image showing microparticles of liraglutide produced by a typical crystallization approach known to those of skill in the art.

FIG. 22 is an image showing microparticles of liraglutide produced by a typical crystallization approach known to those of skill in the art.

FIG. 23 is an image showing microparticles of liraglutide produced by a typical crystallization approach known to those of skill in the art.

FIG. 24 is an image showing microparticles of liraglutide produced by a typical crystallization approach known to those of skill in the art.

FIG. 25 is an image showing microparticles of liraglutide produced by a typical crystallization approach known to those of skill in the art.

FIG. 26 is an image showing microparticles of liraglutide produced by a typical crystallization approach known to those of skill in the art.

FIG. 27 is an image showing microparticles of liraglutide produced by a typical crystallization approach known to those of skill in the art.

FIG. 28 is an image showing microparticles of liraglutide produced by a typical crystallization approach known to those of skill in the art.

FIG. 29 is an image showing microparticles of liraglutide produced by a typical crystallization approach known to those of skill in the art.

FIG. 30 is an image showing microparticles of octreotide produced by a typical crystallization approach known to those of skill in the art.

FIG. 31 is an image showing microparticles of octreotide produced by a typical crystallization approach known to those of skill in the art.

FIG. 32 is an image showing microparticles of octreotide produced by a typical crystallization approach known to those of skill in the art.

FIG. 33 is an image showing microparticles of octreotide produced by a typical crystallization approach known to those of skill in the art.

FIG. 34 is an image showing microparticles of octreotide produced by a typical crystallization approach known to those of skill in the art.

FIG. 35 is an image showing microparticles of octreotide produced by a typical crystallization approach known to those of skill in the art.

FIG. 36 is an image showing microparticles of octreotide produced by a typical crystallization approach known to those of skill in the art.

FIG. 37 is an image showing microparticles of octreotide produced by a typical crystallization approach known to those of skill in the art.

FIG. 38 is an image showing microparticles of octreotide produced by a typical crystallization approach known to those of skill in the art.

FIG. 39 is an image showing microparticles of octreotide produced by a typical crystallization approach known to those of skill in the art.

FIG. 40 is an image showing microparticles of octreotide produced by a typical crystallization approach known to those of skill in the art.

FIG. 41 is an image showing microparticles of octreotide produced by a typical crystallization approach known to those of skill in the art.

FIG. 42 is an image showing microparticles of octreotide produced by a typical crystallization approach known to those of skill in the art.

FIG. 43 is an image showing microparticles of octreotide produced by a typical crystallization approach known to those of skill in the art.

FIG. 44 is an image showing microparticles of octreotide produced by a typical crystallization approach known to those of skill in the art.

FIG. 45 is an image showing microparticles of octreotide produced by a typical crystallization approach known to those of skill in the art.

FIG. 46 is an image showing microparticles of octreotide produced by a typical crystallization approach known to those of skill in the art.

FIG. 47 is an image showing microparticles of octreotide produced by a typical crystallization approach known to those of skill in the art.

FIG. 48 is an image showing microparticles of octreotide produced by a typical crystallization approach known to those of skill in the art.

FIG. 49 is an image showing microparticles of octreotide produced by a typical crystallization approach known to those of skill in the art.

FIG. 50 is an image showing microparticles of octreotide produced by a typical crystallization approach known to those of skill in the art.

FIG. 51 is an image showing microparticles of trastuzumab produced by a typical crystallization approach known to those of skill in the art.

FIG. 52 is an image showing microparticles of trastuzumab produced by a typical crystallization approach known to those of skill in the art.

FIG. 53 is a graph showing plasma concentration of insulin over time following subcutaneous administration of a standard of care formulation of human insulin R to pigs.

FIG. 54 is a graph showing plasma concentration of insulin over time following buccal/sublingual administration of a formulation as provided herein to pigs.

FIG. 55 is a graph showing plasma concentration of insulin over time following subcutaneous administration of a standard of care formulation of human insulin R to rats.

FIG. 56 is a graph showing plasma concentration of insulin over time following buccal/sublingual administration of a formulation as provided herein to rats.

FIG. 57 is a graph showing plasma concentration of insulin glargine over time following subcutaneous administration of a standard of care formulation of Lantus/insulin glargine to pigs.

FIG. 58 is a graph showing plasma concentration of Lantus/insulin glargine over time following buccal/sublingual administration of a formulation as provided herein to pigs.

FIG. 59 is a graph showing plasma concentration of Lantus/insulin glargine over time following subcutaneous administration of a standard of care formulation of Lantus/insulin glargine to rats.

FIG. 60 is a graph showing plasma concentration of Lantus/insulin glargine over time following buccal/sublingual administration of a formulation as provided herein to rats.

FIG. 61 is a graph showing plasma concentration of PTH over time following subcutaneous administration of a standard of care formulation of PTH to pigs.

FIG. 62 is a graph showing plasma concentration of PTH over time following buccal/sublingual administration of a formulation as provided herein to pigs.

FIG. 63 is a graph showing plasma concentration of calcium, phosphorus, and ALP over time following subcutaneous administration of a standard of care formulation of PTH to pigs.

FIG. 64 is a graph showing plasma concentration of calcium, phosphorus, and ALP over time following buccal/sublingual administration of a formulation as provided herein to pigs.

FIG. 65 is a graph showing plasma concentration of PTH over time following subcutaneous administration of a standard of care formulation of PTH to rats.

FIG. 66 is a graph showing plasma concentration of PTH over time following buccal/sublingual administration of a formulation as provided herein to rats.

FIG. 67 is a graph showing plasma concentration of calcium, phosphorus, and ALP over time following subcutaneous administration of a standard of care formulation of PTH to rats.

FIG. 68 is a graph showing plasma concentration of calcium, phosphorus, and ALP over time following buccal/sublingual administration of a formulation as provided herein to rats.

FIG. 69 is an image showing microparticles of human growth hormone.

FIG. 70 is a graph showing plasma concentration of human growth hormone over time following intravenous injection to pigs.

FIG. 71 is graph showing plasma concentration of human growth hormone over time following administration of human growth hormone in truffle shell form through buccal/sublingual delivery to pigs.

DETAILED DESCRIPTION

Extensive effort has been expended by the pharmaceutical industry to bring polypeptide therapeutics to market. Clinical trials have included hundreds of polypeptides for treatment of multiple different conditions. However, clinical use of polypeptides has been hampered by numerous obstacles to their successful delivery. Bioavailability, stability, and therapeutic efficacy are among the factors considered in the development of formulations for polypeptide delivery.

Many polypeptides are traditionally administered by parenteral routes such as subcutaneous, intramuscular, or intravenous injection. The present disclosure identifies a source of a problem with prior technologies for administration of polypeptides, e.g., therapeutic polypeptides in their reliance primarily on parenteral strategies. The present disclosure provides an insight that oral administration would generally be preferable to injection of polypeptide therapeutics, among other things for patient acceptance, home use, and compliance with long-term regimens. Further, the present disclosure provides an insight that certain forms of polypeptide formulation are suitable for oral administration of polypeptides and can effectively achieve polypeptide delivery.

The present disclosure provides a variety of formulations that achieve systemic delivery of polypeptides via oral administration of the formulation. For example, in at least one aspect, the present disclosure provides a truffle formulation which comprises a shell and a core comprising polypeptide situated in a shell. In another aspect, the present disclosure provides a tablet formulation. In another aspect, the present disclosure provides a globule formulation. In another aspect, the present disclosure provides a candy formulation.

The present disclosure provides an insight that polypeptide compositions as described herein, e.g., truffle, globule, tablet, candy, etc. optionally comprise food ingredients and can be particularly desirable and/or effective for oral administration. In at least one aspect, polypeptide compositions comprising food ingredients as described herein have improved flavor, more attractive appearance, and/or are easier to handle compared to other formulations for oral administration, and compared to parental formulations. These advantages among others could cause oral formulations of polypeptide products to have therapeutic and commercial value distinct from and/or greater than those of other formulations, specifically including parenteral formulations.

Despite tremendous efforts to achieve oral delivery of polypeptides, parenteral delivery remains the major mode of administration for polypeptide therapeutics. While oral delivery has been achieved for administration of various small molecules, the difficulty of oral delivery of polypeptides is a problem recognized by those of skill in the art. Intrinsic physicochemical and biological properties, including large molecular size, poor permeation through gastrointestinal membrane, poor stability attributed to low pH of gastric fluid, and susceptibility to proteolytic enzymes are among the factors that render oral delivery of polypeptides highly challenging. In various trials, it has been observed that orally administered polypeptides demonstrated bioavailability of less than 1%. See, e.g., International Journal of Pharmaceutics, 447 (2013) 75-93. In some embodiments, a higher target bioavailability (e.g., at least 30%-50%) is preferred for therapeutic efficacy.

Efforts to improve polypeptide stability and performance have included chemical modification of polypeptides such as PEGylation, hyperglycosylation, and mannosylation or use of colloidal carriers including microparticles, nanoparticles, liposomes, carbon nanotubes and micelles. Despite such efforts, parenteral administration of polypeptides has persisted as the norm. The present disclosure provides solutions to the long-standing difficulty of formulating polypeptides for oral administration.

Various compositions of the present disclosure can include a core within a pharmaceutically acceptable shell. In some embodiments, a core exists in a truffle formulation as described herein. In some embodiments, a core exists in a tablet formulation as described herein and a core of such tablet is coated with a coating as described herein. In some embodiments, a core exists in a globule formulation as described herein. In some embodiments, a core exists in a candy formulation as described herein. In various embodiments, the core includes an amorphous polypeptide composition or a crystallized polypeptide composition.

Pharmaceutically Acceptable Carriers

Formulations provided herein can include a pharmaceutically acceptable carrier. As used herein, the term "pharmaceutically acceptable carrier" refers to a pharmaceutically-acceptable material, composition, or vehicle, such as a liquid or solid filler, diluent, excipient, or solvent encapsulating material, that facilitates formulation of an agent (e.g., a pharmaceutical agent), modifies bioavailability of an agent, or facilitates transport of an agent from one organ or portion of a subject to another. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients; oils, such as peanut oil, cottonseed oil, virgin coconut oil, almond oil, wheatgerm oil, any edible oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; food ingredients, e.g., chocolate, cocoa, milk, milk product, natural dye, artificial dye, gum base, flavors, sweeteners, gelatin, starch, syrup, citric acid, and other non-toxic compatible substances employed in pharmaceutical formulations. Excipients can include a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, cocoa butter, suppository waxes, glycerol, propylene, glycol, water, ethanol, or the like. In various embodiments, one or more pharmaceutically acceptable carriers are selected from the group consisting of aggregation-reducing agents, sugars or sugar alcohols, polysaccharides, stabilizers, hyaluronidase, buffering agents, preservatives, carriers, antioxidants, chelating agents, natural or synthetic polymers, cryoprotectants, lyoprotectants, surfactants, bulking agents, acidifying agents, ingredients to reduce injection site discomfort, antifoaming agents, alkalizing agents, vehicles, aggregation inhibitors, permeation enhancers, muco bioadhesive agents, solubilizing agents, tonicity modifiers, and stabilizing agents and combinations thereof.

In various embodiments, aggregation-reducing agents can include one or more of nicotinic acid, caffeine citrate, caffeine nicotinate, caffeine, octyl-β-D-glucopyranoside, and n-dodecyl-β-D-maltoside and optionally in combination with one or more of arginine, tryptophan, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA (aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfobutyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino) hexanoic acid (NBD-X), methyl acetyl phosphate (MAP), citraconic anhydride, pyrophosphate, citrate, and combinations thereof.

In various embodiments, tonicity modifiers can include one or more of arginine, cysteine, histidine, glycine, sodium chloride, potassium chloride, sodium citrate, saccharides such as sucrose, glucose, dextrose, glycerin or mannitol, and combinations thereof.

In various embodiments, antioxidants can include one or more of glycine, lysine, EDTA, DTPA, sorbitol, mannitol, ascorbic acid, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, sodium thiosulfate, sulfur dioxide, tocopherol, and combinations thereof.

In various embodiments, lyoprotectants can include one or more of sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; propylene glycol, glycerol, poly(ethylene glycol), or poly(propylene glycol); gelatin, dextrins, modified starch, carboxymethyl cellulose, and combinations thereof.

In various embodiments, permeation enhancer(s) can include one or more of bile salts, e.g., tri-hydroxy salts sodium cholate, sodium glyco-cholate, sodium taurocholate and di-hydroxy salt, sodium deoxy cholate, sodium glycodeoxy Cholate, sodium tauro-deoxy cholate; fatty acids, their salt and esters, e.g., oleic acid, lauric acid, cod liver oil extract, sodium laurate, sodium caprate, glyceryl monostearate, di-ethylene glycol mono ethyl ether and various sucrose fatty acid esters, medium-chain fatty acid glycerides, polycaprolactoneomega-3 fatty acids, lecithin (phosphatidylcholine), lysophosphatidylcholine; surfactants, e.g., sodium dodecyl (lauryl) sulphate, poly sorbates (polysorbate 80), laureths, brijs and benzalkonium chloride; complexing agents, e.g., cyclodextrins, dextran sulphate, dextran sulphate, sodium edetate; complexing agents, e.g., cyclodextrins, dextran sulphate, dextran sulphate, sodium edetate, co-solvents, e.g., ethanol and propylene glycol, combination of 1% oleic acid and 5%/10% polyethylene glycol 200, 2% glyceryl mono laurate and 40% alcohol, sodium caprate and alcohol or propylene glycol, 10% lauric acid in propylene glycol, polyoxyethylene, 2,3-lauryl ether, menthol, sodium caprate, sodium caprylate, sodium glycodeoxycholate, glycol; polysaccharides, e.g., chitosan and chitosan glutamate; and others such as, aprotinin, benzalkonium chloride, cetylpyridinium chloride, cetyltrimethyl ammonium bromide, sodium salicylate, lysophosphatidylcholine, methoxysalicylate, methyloleate, sodium edta, sulfoxides, various alkyl glycosides, ethylene-diamide tetra acetic acid (edta), tartaric acid; lyotropic salts, such as magnesium sulfate; propylene glycol, glycerol, poly(ethylene glycol), or poly (propylene glycol); gelatin, dextrins, modified starch, carboxymethyl cellulose, and combinations thereof.

In various embodiments, absorption enhancer(s) can include surfactants, cholesterol, glycerides, salicylates, bile salts, chelating agents, sodium caprate, a salt of capric acid and other includes N-(5-chlorosalicylol)-8-aminocaprylic acid (5-CNAC), 4-((4-chloro-2 -hydroxybenzoyl))-amino) butanoic acid (4-CNAB) and N-(8-(2-hydroxybenzoyl))-amino) caprylic acid, also known as salcaprozate sodium (SNAC, caprylic acid, C8, castor oil, medium chain, acyl carnitine, EDTA, glyceryl monolaurate, bovine β-casein, tocopherol succinate glycol chitosan conjugates, lecithins, glyceryl monostearate (GMS), chitosan and alginate, PLGA, silica, stearic acid, oleic acid, hydrogenated castor oil, and glyceryl trimyristate, etoposide phosphate (Vepesid®), sulindac (Clinoril®), enalapril maleate (Vasotec®), ramipril (Altace®), olmesartan medoxomil (Benicar®), valacyclovir (Valtrex®), midodrine (Amatine®), gabapentin enacarbil (Horizant®), sulfasalazine (Azulfidine®), and combinations thereof.

In various embodiments, muco bioadhesive agent(s) can include sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; propylene glycol, glycerol, poly(ethylene glycol), or poly(propylene glycol); gelatin, dextrins, modified starch, carboxymethyl cellulose, and combinations thereof mucoadhesive system such as from naturae, e.g., gelatin, agarose, chitosan, hyaluronic acid and synthetic polymers, e.g., polyvinylpyrolidone (PVP), polyacrylates, polyvinyl alcohol, sodium carboxymethyl cellulose (SCMC) and pectin, all anionic-type polymers, chitosan (cationic type), and hydroxypropyl methylcellulose (HPMC) as a nonionic polymer, polyacrylic acid (PAA) derivatives (CP934, CP940, PCP), 15% CMC and 35% CP, copolymers of acrylic acid and poly(ethylene glycol) monomethylether monomethacrylate (PEGMM), eudragitl NE40D is a neutral poly(ethylacrylate methylmethacrylate, hydrophilic polymers, e.g., methocel K4M, methocel K15M, SCMC 400, Cekol 700, Cekol 10000, CP934P, CP971P and CP974P, carboxyvinyl polymer and triethanolamine, HPC (hydroxy propyl celluose), CP (carbopol 934P), carbopol (CP) EX-55 CMC (sodium carboxymethyl cellulose), HPMC (hydroxy propyl methyl cellulose), HEC (hydroxy ethyl cellulose), PIP [poly (isoprene)], PIB [poly(Isobutylene)], xanthum gum, locust bean gum, pectin, polycarbophil, benzyl esters, hydroxyethylcellulose, poly(acrylic acid), poly(acrylic acid-co-acrylamide), poly(acrylic acid-co-methyl methacrylate), poly (acrylic acid-co-butylacrylate), HEMA copolymerized with Polymeg® (polytetramethylene glycol), Cydot® (bioadhesive polymeric blend of CP and PIB), formulation consisting of PVP, cetylpyridinium chloride (as stabilizer), chitosan chloride, polyethylene oxide, polymethylvinylether/maleic anhydride (PME/MA), and tragacanth, poly ethyleneglycol monomethylether monomethacrylate, drum dried waxy maize starch (DDWM), carbopol 974P, and sodium stearylfumarate, and cellulose derivatives; hydrogels-acrylic acid (polar) and butyl acrylate (apolar), and combinations thereof.

In various embodiments, pharmaceutically acceptable carriers expressly exclude a pharmaceutically active agent. In various embodiments, pharmaceutically acceptable carriers expressly exclude one or more, or all, polypeptides.

Crystallized and Amorphous Polypeptides

The present disclosure includes oral formulations that include a polypeptide component that is or comprises one or more polypeptides. Typically, a polypeptide component will be or comprise a polypeptide in a crystalline (e.g., crystallized) form or in an amorphous form. Thus, in many embodiments, provide formulations include a polypeptide (e.g., present in an amorphous polypeptide composition or a crystallized polypeptide composition) and a pharmaceutically acceptable carrier.

Those skilled in the art will appreciate that pharmaceutical agents, e.g., polypeptides, often can exist in a variety of solid forms, including polymorph, solvate, hydrate, salt, co-crystal and amorphous forms. In certain embodiments, provided formulations include a polypeptide component in which at least one, and in some embodiments all, polypeptide(s) is in such a form. In some embodiments, a polypeptide component consists of crystalline polypeptide(s). In some embodiments, a polypeptide component is amorphous (e.g., consists of amorphous polypeptide(s)).

Amorphous polypeptide compositions can include compositions in which polypeptide molecules are disordered or essentially disordered. Amorphous polypeptides can lack or essentially lack long-range order of the positions of the atoms. In various embodiments, an amorphous polypeptide can be more soluble than a crystallized form of the same polypeptide. In certain embodiments, an amorphous polypeptide is a composition that has not been crystallized and/or has not been processed according to a method of crystallization. In certain embodiments, an amorphous polypeptide composition can include short-range order, residual crystallinity, polymorphic states, and regions of different density, none of which necessarily constitute long-range order. In various embodiments an amorphous polypeptide composition can include a fraction of crystallized polypeptide, e.g., a fraction of crystallized polypeptide that is less than 20% total polypeptide (e.g., less than 20%, 15%, 10%, 9%, 8%, 7%, 6%, 5%, 4%, 3%, 2%, 1%, 0.5%, or 0.1% crystallized polypeptide) by mass, volume, or mols. Techniques for determining the degree of crystallinity include XRD, DSC, solution calorimetry, water sorption, isothermal calorimetry, and thermally stimulated current (TSC). In various embodiments, an amorphous polypeptide compositions does not diffract X-rays in a coherent manner and/or powder X-ray diffraction patterns are broad halos with no or very few characteristic peaks.

In various embodiments, an amorphous polypeptide composition includes an average and/or maximum particle size of less than 25 microns, e.g., less than 20, 15, 10, 5, 4, 3, 2, 1, 0.5, or 0.1 microns, optionally wherein the particles have an average and/or maximum particle size that is between 0.1 microns and 0.5, 1, 2, 3, 4, 5, 10, 15, 20, or 25 microns or wherein the particles of polypeptide have an average and/or maximum particle size that is between 0.1 micron and 0.1, 0.5, 1, 2, 3, 4, 5, 10, 15, 20, or 25 microns. In various embodiments, particles of a polypeptide composition are microparticles or nanoparticles of polypeptide.

In some embodiments, amorphous polypeptide compositions include compositions that include a high proportion of amorphous and/or non-crystallized polypeptide (e.g., of a polypeptide characterized by a particular amino acid sequence) relative to other agents or types of agents. In various embodiments, an amorphous polypeptide composition includes at least 1%, 2%, 3%, 4%, 5%, 6%, 7%, 8%, 9%, 10%, 20%, 30%, 40%, 50%, 60%, 70%, 75%, 80%, 85%, 90%, 95%, 96%, 97%, 98%, 99%, or 100% amorphous and/or non-crystallized polypeptide (e.g., of a polypeptide characterized by a particular amino acid sequence) by weight, mole ratio, or volume of the composition or of polypeptide present in the composition. In various embodiments, an amorphous polypeptide composition can be characterized by an amount of amorphous and/or non-crystallized polypeptide (e.g., of a polypeptide characterized by a particular amino acid sequence) that is in a range between a lower bound of 1%, 2%, 3%, 4%, 5%, 6%, 7%, 8%, 9%, 10%, 20%, 30%, 40%, 50%, 60%, 70%, 75%, 80%, 85%, or 90% by weight, mole ratio, or volume of the composition or of polypeptide present in the composition and an upper bound of 10%, 20%, 30%, 40%, 50%, 60%, 70%, 75%, 80%, 85%, 90%, 95%, 96%, 97%, 98%, 99%, or 100% by weight, mole ratio, or volume of the composition or of polypeptide present in the composition.

In various embodiments, an amorphous polypeptide composition is free, or substantially free, of non-polypeptide agents (and/or of agents other than amorphous polypeptide), e.g., where the amorphous polypeptide composition includes no more than 1%, 2%, 3%, 4%, 5%, 10%, 15%, 20%, 25%, or 30% of non-polypeptide agents (and/or of agents other than amorphous polypeptide) by weight, by mole ratio, or by volume. In various embodiments, an amorphous polypeptide composition includes no more than 1%, 2%, 3%, 4%, 5%, 10%, 15%, 20%, 25%, 30%, 40%, 50%, 60%, 70%, 75%, 80%, 85%, 90%, or 95% of non-polypeptide agents (and/or of agents other than amorphous polypeptide) by weight, by mole ratio, or by volume. In various embodiments, an amorphous polypeptide composition includes particles of one or more particular polypeptides and is free or substantially free of other polypeptide agents (optionally including crystallized form(s) of the one or more particular polypeptides), e.g., where the amorphous polypeptide composition includes no more than 1%, 2%, 3%, 4%, 5%, 10%, 15%, 20%, 25%, or 30% of other polypeptide agents by weight, by mole ratio, or by volume. In various embodiments, an amorphous polypeptide composition includes no more than 1%, 2%, 3%, 4%, 5%, 10%, 15%, 20%, 25%, 30%, 40%, 50%, 60%, 70%, 75%, 80%, 85%, 90%, or 95% of other polypeptide agents by weight, by mole ratio, or by volume. In various embodiments, an amorphous polypeptide composition includes particles of one or more particular polypeptides and is free or substantially free of other agents (optionally including crystallized form(s) of the one or more particular polypeptides), e.g., where the amorphous polypeptide composition includes no more than 1%, 2%, 3%, 4%, 5%, 10%, 15%, 20%, 25%, or 30% of other agents by weight, by mole ratio, or by volume. In various embodiments, an amorphous polypeptide composition includes no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

In various embodiments, an amorphous polypeptide composition includes particles of one or more particular polypeptides where the particles of the one or more particular polypeptides are free, or substantially free, of non-polypeptide agents, e.g., where the particles include no more than 1%, 2%, 3%, 4%, 5%, 10%, 15%, 20%, 25%, or 30% of non-polypeptide agents by weight, by mole ratio, or by volume. In various embodiments, an amorphous polypeptide composition includes particles of one or more particular polypeptides where the particles of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of non-polypeptide agents by weight, by mole ratio, or by volume. In various embodiments, an amorphous polypeptide composition includes particles of one or more particular polypeptides where the particles of the one or more particular polypeptides are free, or substantially free, of other polypeptides, e.g., where the particles of the one or more particular polypeptides include no more than 1%, 2%, 3%, 4%, 5%, 10%, 15%, 20%, 25%, or 30% of other polypeptides by weight, by mole ratio, or by volume. In various embodiments, an amorphous polypeptide composition includes particles of one or more particular polypeptides where the particles of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other polypeptides by weight, by mole ratio, or by volume. In various embodiments, an amorphous polypeptide composition includes particles of one or more particular polypeptides where the particles of the one or more particular polypeptides are free, or substantially free, of other agents (optionally including non-crystallized form(s) of the one or more particular polypeptides), e.g., where the particles of the one or more particular polypeptides include no more than 1%, 2%, 3%, 4%, 5%, 10%, 15%, 20%, 25%, or 30% of other agents by weight, by mole ratio, or by volume. In various embodiments, an amorphous polypeptide composition includes particles of one or more particular polypeptides where the particles of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

In some embodiments, processes for production of amorphous polypeptide compositions can include one or more of, for example, molecular quenching of melts, rapid precipitation by antisolvent addition, freeze-drying, spray-drying, spray-freeze-drying, precipitation in supercritical fluids, solid-dispersion, and solid-state chemical reactions (degradation) of crystalline precursors. For example, freeze drying of a protein/PEG blend solution and subsequent removal of PEG from the matrix has proven to yield precipitated protein particles in amorphous form. Processes that introduce mechanical or chemical stress (grinding, milling, and wet granulation) can render crystalline materials fully or partially amorphous.

In some embodiments, an amorphous polypeptide composition can be a hydrated form or prepared from a hydrated form. Hydrated forms can include an alcohol (e.g., ethanol). In some embodiments, an amorphous polypeptide composition is a solvated form or prepared form a solvated form. Exemplary solvents can include, for example, an acidic solvent or an organic solvent. In some embodiments, a solvent can include DMSO, DMF, acetic acid, acetonitrile, methanol, propanol, isopropanol, acetone, anisole, 1-butanol, 2-butanol, butyl acetate, fer/-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, tetrahydrofuran, ethanol, and/or water. Certain methods of preparing amorphous polypeptide compositions can include removal of a solvent by rapid solvent evaporation from a solvated form, spray drying, roller drying, solvent precipitation, or freeze drying. In some embodiments, an amorphous polypeptide composition includes a cation such as a 2+ charged cation (e.g., $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, or $Zn^{2+}$).

In some embodiments, crystal formation can include assembly of non-crystalline solid agents into a crystalline solid form. In some embodiments, crystal formation can utilize various molecular interactions, including, e.g., hydrogen bonding, p stacking, and Vander Waals Forces. Hydrogen bond formation is often responsible for intermolecular interactions in molecular solids. Crystallization is typically considered with respect to small molecule agents, and rarely considered with respect to polypeptides. Polypeptides typically lack well-defined conformation in solution. In certain embodiments, an amorphous polypeptide composition or a crystallized polypeptide composition is a powder form that includes crystals of polypeptide.

In various embodiments, a crystallized polypeptide composition includes crystals of polypeptide having an average and/or maximum particle size of less than 25 microns, e.g., less than 20, 15, 10, 5, 4, 3, 2, 1, 0.5, or 0.1 microns, optionally wherein the crystals of polypeptide have an average and/or maximum particle size that is between 0.1 microns and 0.5, 1, 2, 3, 4, 5, 10, 15, 20, or 25 microns or wherein the crystals of polypeptide have an average and/or maximum particle size that is between 0.1 micron and 0.1, 0.5, 1, 2, 3, 4, 5, 10, 15, 20, or 25 microns. In various embodiments, crystals of a crystallized polypeptide composition are microcrystals or nanocrystals of polypeptide.

In some embodiments, crystallized polypeptide compositions include compositions that include a high proportion of crystallized polypeptide (e.g., of a polypeptide characterized by a particular amino acid sequence) relative to other agents or types of agents. In various embodiments, a crystallized polypeptide composition includes at least 1%, 2%, 3%, 4%, 5%, 6%, 7%, 8%, 9%, 10%, 20%, 30%, 40%, 50%, 60%, 70%, 75%, 80%, 85%, 90%, 95%, or 100% crystallized polypeptide (e.g., of a polypeptide characterized by a particular amino acid sequence) by weight, by mole ratio, or by volume of the composition or of polypeptide present in the composition. In various embodiments, a crystallized polypeptide composition can be characterized by an amount of crystallized polypeptide (e.g., of a polypeptide characterized by a particular amino acid sequence) that is between that is between a lower bound of 1%, 2%, 3%, 4%, 5%, 6%, 7%, 8%, 9%, 10%, 20%, 30%, 40%, 50%, 60%, 70%, 75%, 80%, 85%, or 90% by weight, mole ratio, or volume of the composition or of polypeptide present in the composition and an upper bound of 10%, 20%, 30%, 40%, 50%, 60%, 70%, 75%, 80%, 85%, 90%, 95%, 96%, 97%, 98%, 99%, or 100% by weight, mole ratio, or volume of the composition or of polypeptide present in the composition.

In various embodiments, a crystallized polypeptide composition is free, or substantially free, of non-polypeptide agents e.g., where the crystallized polypeptide composition includes no more than 1%, 2%, 3%, 4%, 5%, 10%, 15%, 20%, 25%, or 30% of non-polypeptide agents by weight, by mole ratio, or by volume. In various embodiments, a crystallized polypeptide composition includes no more than 1%, 2%, 3%, 4%, 5%, 10%, 15%, 20%, 25%, 30%, 40%, 50%, 60%, 70%, 75%, 80%, 85%, 90%, or 95% of non-polypeptide agents by weight, by mole ratio, or by volume. In various embodiments, a crystallized polypeptide composition includes crystals of one or more particular polypeptides and is free or substantially free of other polypeptide agents (optionally including non-crystallized form(s) of the one or more particular polypeptides), e.g., where the crystallized polypeptide composition includes no more than 1%, 2%, 3%, 4%, 5%, 10%, 15%, 20%, 25%, or 30% of other polypeptide agents by weight, by mole ratio, or by volume. In various embodiments, a crystallized polypeptide composition includes crystals of one or more particular polypeptides and includes no more than 1%, 2%, 3%, 4%, 5%, 10%, 15%, 20%, 25%, 30%, 40%, 50%, 60%, 70%, 75%, 80%, 85%, 90%, or 95% of other polypeptide agents by weight, by mole ratio, or by volume. In various embodiments, a crystallized polypeptide composition includes crystals of one or more particular polypeptides and is free or substantially free of other agents (optionally including non-crystallized form (s) of the one or more particular polypeptides), e.g., where the crystallized polypeptide composition includes no more than 1%, 2%, 3%, 4%, 5%, 10%, 15%, 20%, 25%, or 30% of other agents by weight, by mole ratio, or by volume. In various embodiments, a crystallized polypeptide composition includes crystals of one or more particular polypeptides and includes no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

In various embodiments, a crystallized polypeptide composition includes crystals of one or more particular polypeptides where the crystals of the one or more particular polypeptides are free, or substantially free, of non-polypeptide agents, e.g., where the crystals include no more than 1%, 2%, 3%, 4%, 5%, 10%, 15%, 20%, 25%, or 30% of non-polypeptide agents by weight, by mole ratio, or by volume. In various embodiments, a crystallized polypeptide composition includes crystals of one or more particular polypeptides where the crystals include no more than 1%, 2%, 3%, 4%, 5%, 10%, 15%, 20%, 25%, 30%, 40%, 50%, 60%, 70%, 75%, 80%, 85%, 90%, or 95% of non-polypeptide agents by weight, by mole ratio, or by volume. In various embodiments, a crystallized polypeptide composition includes crystals of one or more particular polypeptides where the crystals of the one or more particular polypeptides are free, or substantially free, of other polypeptides, e.g., where the crystals of the one or more particular polypeptides include no more than 1%, 2%, 3%, 4%, 5%, 10%, 15%, 20%, 25%, or 30% of other polypeptides by weight, by mole ratio, or by volume. In various embodiments, a crystallized polypeptide composition includes crystals of one or more particular polypeptides where the crystals of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other polypeptides by weight, by mole ratio, or by volume. In various embodiments, a crystallized polypeptide composition includes crystals of one or more particular polypeptides where the crystals of the one or more particular polypeptides are free, or substantially free, of other agents (optionally including non-crystallized form(s) of the one or more particular polypeptides), e.g., where the crystals of the one or more particular polypeptides include no more than 1%, 2%, 3%, 4%, 5%, 10%, 15%, 20%, 25%, or 30% of other agents by weight, by mole ratio, or by volume. In various embodiments, a crystallized polypeptide composition includes crystals of one or more particular polypeptides where the crystals of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

In some embodiments, polypeptide crystals can be prepared from a polypeptide sample. Polypeptide crystals can be prepared form a polypeptide sample that is substantially pure of other agents and/or contaminants. Polypeptide crystals can be prepared from an amorphous material, e.g., a lyophilized material that is amorphous or an amorphous solid that has been precipitated. In some embodiments, polypeptide crystals can be prepared from a mixture of amorphous and crystalline material, e.g., a lyophilized material that is a mixture of amorphous and crystalline material or a mixture of amorphous and crystalline solids that has been precipitated. In various embodiments, polypeptide crystals can be prepared form a polypeptide sample having a polypeptide concentration between 0.1 and 200 mg/mL, e.g., having a polypeptide concentration between a lower bound of 0.1, 1, 5, 10, 15, 20, 25, 50, 75, or 100 mg/mL and an upper bound of 15, 20, 25, 50, 75, 100, 125, 150, 175, or 200 mg/mL.

In some embodiments, means of polypeptide crystallization can include, without limitation, one or more of, evaporation, slow diffusion (e.g., vapor diffusion at ambient or low temperature), slow cooling, slurrying, hanging drop, sitting drop, seeded crystal development, and/or other crystallization methods known in the art. Those of skill in the art will appreciate that many crystallization methods are well understood and known in the art, such that polypeptide crystallization is generally straightforward. Those of skill in the art will further appreciate that polypeptide crystallization is especially straight forward where a particular crystal size is not required, where large crystals are not required, where a particular crystalline form is not required, and/or where perfectly regular crystals are not required, any or all of which can characterize various embodiments as described herein.

In some embodiments, crystalline polypeptides can be prepared by mixing a polypeptide in a suitable solvent (e.g., water) and then causing the polypeptide to return to the solid phase. For example, polypeptides can form crystals when precipitated from an aqueous solution (e.g., of ammonium sulfate). In certain exemplary embodiments, a polypeptide-saturated solution is prepared by increasing the concentration of the polypeptide in the solution. At maximal solubility, polypeptide precipitation can occur and the precipitant can be crystalline. Slow precipitation can produce small numbers of larger crystals while more rapid precipitation can produce very large numbers of small crystals, such that the rate of precipitation is therefore not critical to the production of crystals in general.

In some embodiments, evaporation (e.g., slow evaporation) is a common means of crystallizing polypeptides. Precipitation of a polypeptide can occur by allowing the solvent of a solution of polypeptide to evaporate (e.g., slowly evaporate) until the solution reaches saturation, thereby allowing polypeptide precipitation to occur.

In some embodiments, cooling (e.g., slow cooling) is another method of crystallizing polypeptides. Precipitation of a polypeptide can occur by allowing a solution of polypeptide to cool (e.g., slowly cool), thereby reducing the maximum solubility of the polypeptide in the solution and inducing precipitation to occur.

In some embodiments, vapor diffusion and batch methods are also commonly employed in polypeptide crystallization. In vapor diffusion, a drop containing a mixture of precipitant and unprecipitated polypeptide is sealed in a chamber with pure precipitant. Water vapor then diffuses out of the drop until the osmolarity of the drop and the precipitant are equal. The dehydration of the drop causes a slow concentration of both polypeptide and precipitant until equilibrium can be achieved, favoring crystallization. Vapor diffusion can be performed in either hanging-drop or sitting-drop format. A hanging-drop method can involve a drop of polypeptide solution placed on an inverted cover slip, which is then suspended above the reservoir. A sitting-drop method can position a drop on a pedestal that is separated from the reservoir. Both of these methods require sealing of the environment so that equilibration between the drop and reservoir can occur.

In some embodiments, a batch method relies on bringing a polypeptide directly into the nucleation zone by mixing polypeptide with the appropriate amount of precipitant. Various Examples provided herein include batch crystallization. Batch crystallization is different from continuous crystallization in that the withdrawal of crystal product for the batch system is made only once at the end of the batch run. Batch crystallization may also include the semibatch system, in which one or more feed solutions are added to the crystallizer at a constant or variable rate throughout all or part of the batch. In various embodiments, batch crystallization can vary in volume from, e.g., 1 microliter (e.g., in an Eppendorf tube) to a liter or more (e.g., thousands of liters). In various embodiments, no vapor diffusion method is involved. In various embodiments, no evaporation is involved. In various embodiments, batch crystallization includes slowly adding precipitating reagents (e.g., with stirring if necessary, depending on batch size).

Typically, seeds of crystallizing material can be added early in the batch process in order to improve reproducibility and product quality. When a desired amount of solid has been formed, slurry is typically transferred to a solid-liquid separation unit.

In some embodiments, dialysis is another method commonly employed in polypeptide crystallization. This technique utilizes diffusion and equilibration of precipitant molecules through a semi-permeable membrane as a means of gradually approaching the concentration at which the macromolecule crystallizes. Dialysis tubes can be used in the case of large amounts of polypeptide being available.

In some embodiments, microdialysis buttons, also known as Cambridge buttons, offer a convenient way to produce crystals from a small amount of sample. A polypeptide sample is placed inside a small chamber on top of the button and the sample is covered with a dialysis membrane of appropriate molecular weight cut-off. The apparatus is then immersed in a reservoir containing precipitant solution. Equilibration of precipitant molecules can occur through the membrane.

In some embodiments, free interface diffusion can also be used to crystallize polypeptide. This technique can include carefully layering precipitant solution on top of concentrated polypeptide solution in a capillary, the ends of which are then sealed with wax. Narrow diameter of the capillary minimizes mixing from natural convection in the system. Thus, precipitant and polypeptide slowly inter-diffuse and the system reaches the equilibrium by a phenomenon called counter-diffusion. When the solutions initially come into contact and diffusive mixing occurs, the region of the polypeptide solution in the neighborhood of the interface becomes supersaturated and ideal conditions for nuclei formation are created. As time proceeds, the two solutions inter-diffuse along the axis of the capillary and dilute each other, thus promoting the dissolution of the smaller nuclei and the growth of the larger ones. The achievement, by the free liquid diffusion, of transient nucleation conditions in most cases allows to obtain high quality crystals. Thus free interface diffusion can be view as a rational crystallization approach to minimize supersaturation and impurity levels at the crystal growth front and to ensure steadiness of both values. A variant of free interface diffusion method is referred to as liquid bridge method, in which method a drop of polypeptide sample and a drop of precipitant solution are placed in close proximity on a cover glass and connected by a thin liquid bridge. The liquid diffusion between the two droplets, sealed from air, may induce crystal growth.

In some instances, crystallization nucleation can be induced by use of a material such as a nucleating agent, nucleant, or seed. Nucleation can occur on the surface of a nucleating agent, nucleant, or seed, which induces a higher local concentration of macromolecules, lowers the energy barrier for nucleation and bypasses kinetic barriers of spontaneous nucleation; a lower level of supersaturation can be required under such circumstances.

In some embodiments, pharmaceutical co-crystals can be crystalline materials comprised of a pharmaceutically active ingredient and one or more co-crystal formers ("coformers"), such that the active ingredient and coformers are together in the same crystal lattice. Co-crystals are distinguished from salts because unlike salts, the components that co-exist in the co-crystal lattice with a defined stoichiometry interact nonionically. In addition, co-crystals differ from polymorphs, which are defined as including 1) single-component crystalline forms that have different arrangements or conformations of the molecules in the crystal lattice, 2) amorphous forms, and 3) multicomponent phases such as solvate and hydrate forms. Co-crystals are similar to solvates at least in that both contain more than one component in the lattice. In some embodiments, an amorphous polypeptide composition or a crystallized polypeptide composition does not include co-crystallized polypeptide. In some embodiments, an amorphous polypeptide composition or a crystallized polypeptide composition includes co-crystallized polypeptide.

Those of skill in the art will appreciate that a number of crystallization conditions can be adjusted to increase or decrease efficiency and/or purity of crystallization. For instance, crystallization conditions that can be adjusted include solubilization systems (aqueous systems and/or organic solvent systems), pH, counterions, salts, temperature, excipients, coformers, and polypeptide concentration. Modulating and testing ranges for these factors is trivial for those of skill in the art. In the art of crystallization, it is considered typical to sample a wide variety of crystallization conditions. Moreover, as those of skill in the art will appreciate, the present disclosure does not necessarily require that the most efficient form of crystallization be identified, only that crystals can be formed.

In some embodiments, crystallized polypeptide compositions can include a plurality of crystallized polypeptides. In various embodiments, crystallized polypeptides can be characterized by high concentration, high purity, and/or high stability. Any suitable methods known in the art can be used to characterize provided crystallized polypeptide compositions, including but not limited to X-ray powder diffraction (XRPD), differential scanning calorimetry (DSC), thermogravimetric analysis (TGA), high-performance liquid chromatography (HPLC), liquid chromatography-mass spectrometry (LCMS), laser diffraction, hot stage microscopy, polarized light microscopy, and the like.

In various embodiments, an amorphous polypeptide composition or a crystallized polypeptide composition is free, or substantially free, of one or more, or any, precipitation reagents, optionally wherein the precipitation reagents includes one or more of salts, organic solvents, or polymers, optionally where the salts can include a salt selected from ammonium sulfate, citrate salts, and cetyltrimethylammonium salts, the organic solvents can include an organic solvent selected from 2-methyl-2,4-pentanediol or 2-Methyl-2, 4-pentanediol, and/or the polymers can include a polymer that is a polyethylene glycol.

In various embodiments, an amorphous polypeptide composition or a crystallized polypeptide composition includes polypeptide crystals that are free, or substantially free, of one or more, or any, precipitation reagents, optionally wherein the precipitation reagents includes one or more of salts, organic solvents, or polymers, optionally where the salts can include a salt selected from ammonium sulfate, citrate salts, and cetyltrimethylammonium salts, the organic solvents can include an organic solvent selected from 2-methyl-2,4-pentanediol or 2-Methyl-2, 4-pentanediol, and/or the polymers can include a polymer that is a polyethylene glycol.

Except where otherwise specified, those of skill in the art will appreciate that references relating to crystallization in the art refer to crystallization of molecules that are not polypeptides, e.g., to crystallization of molecules that are small molecules, e.g., small molecule therapeutics.

In various applications, peptide crystallization can produce well-ordered crystals with generally uniform content. While the present disclosure includes polypeptide compositions that include well-ordered crystals, the present disclosure also specifically includes the recognition that formulations do not require crystals having a particular or consistent size or character. In various embodiments, crystallized polypeptide compositions include one or more crystalline forms of a polypeptide (e.g., one or more polymorphs or hydrates of a polypeptide).

Those of skill in the art will appreciate from the present disclosure that compositions and methods provided herein are useful for the delivery of a wide variety of polypeptides. Among other things, the present disclosure provides the recognition that a wide range of polypeptides with different characteristics (e.g., molecular weight, molecule size, hydrophilicity, lipophilicity, modification patterns, preparation methods, etc.) can be utilized in formulations and methods as described herein. Those skilled in the art will appreciate that polypeptides useful in formulations, compositions, and methods as described herein can be grouped into different categories in a variety of ways.

In some embodiments, a polypeptide is a stapled peptide. In some embodiments, a polypeptide is a cyclic peptide generated through cyclization. In some embodiments, a polypeptide is a peptide comprising bicycles through chemical linkage.

In some embodiments, a polypeptide is a hydrophobic peptide. In some embodiments, a polypeptide is a hydrophilic peptide.

In some embodiments, a polypeptide is a peptide comprising dual agonists.

In some embodiments, a polypeptide is generated through Phage display technology. In some embodiments, a polypeptide is generated through peptidomimetics approach. In some embodiments, a polypeptide is a polypeptide is generated through genetic engineering. In some embodiments, a polypeptide is generated from antibodies (e.g., antibody fragments) with a molecular weight of less than 60 k Da. In some embodiments, a polypeptide is generated through non-ribosomal method. In some embodiments, a polypeptide is rationally designed based on protein-protein interaction.

In some embodiments, a polypeptide is a polypeptide comprising sustained release properties.

In some embodiments, a polypeptide is able to establish intramolecular hydrogen bonding.

In some embodiments, a polypeptide is a peptide comprising pH dependent solubility and/or stability.

Those skilled in the art will appreciate that formulations or methods described herein provide surprisingly improved properties and such surprisingly improved properties are observed across a wide range of polypeptide formulations comprising polypeptides with different characteristics (e.g., molecular weight, molecule size, hydrophilicity, lipophilicity, modification patterns, preparation methods, etc.). For example, those of skill in the art will appreciate from the present disclosure that compositions and methods provided herein are advantageous at least in part because they deliver polypeptides to the bloodstream and/or plasma after oral administration, e.g., buccal/sublingual administration, e.g., with advantageous pharmacokinetic properties.

In some embodiments, a polypeptide amenable to formulation as described herein has a molecular weight that may be, for example, at least about 25 kDa, 50 kDa, 100 kDa, 150 kDa, 200 kDa, 250 kDa, 300 kDa, 400 kDa, 500 kDa, 1,000 kDa, 2,000 kDa or greater. In some embodiments, a polypeptide has a molecular weight within a range, for example, from about 100 to about 1,000 kDa, e.g., from about 25 kDa to about 1,000 kDa, about 25 kDa to about 500 kDa, about 100 kDa to about 500 kDa, about 125 kDa to about 250 kDa, about 125 kDa to about 175 kDa, or about 150 kDa to about 300 kDa. In various embodiments, a polypeptide can have a molecular weight having a lower bound of e.g., about 100, 150, 200, 250, 300, 350, 400, 450, or 500 kDa and an upper abound of, e.g., about 100, 150, 200, 250, 300, 350, 400, 450, 500, 750, or 1,000 kDa.

In some embodiments, a polypeptide amenable to formulation as described herein has a molecular weight that may be, for example, between about 100 Da and 25 kDa, optionally wherein the molecular weight is between about 100 Da and about 1 kDa, about 100 Da and about 2 kDa, about 100 Da and about 3 kDa, about 100 Da and about 4 kDa, about 100 Da and about 5 kDa, about 100 Da and about 10 kDa, about 100 Da and about 15 kDa, or about 100 Da and about 20 kDa, In various embodiments, a polypeptide can have a molecular weight within a range having a lower bound of e.g., about 100 Da, 150 Da, 200 Da, 250 Da, 300 Da, 400 Da, 500 Da, 600 Da, 700 Da, 800 Da, 900 Da, 1 kDa, 2 kDa, 3 kDa, 4 kDa, or 5 kDa and an upper abound of, e.g., about 250 Da, 300 Da, 400 Da, 500 Da, 600 Da, 700 Da, 800 Da, 900 Da, 1 kDa, 2 kDa, 3 kDa, 4 kDa, 5 kDa, 10 kDa, 15 kDa, 20 kDa, 25 kDa, 50 kDa, 100 kDa, 150 kDa, 200 kDa, 300 kDa, 500 kDa, 800 kDa, 1,000 kDa, 1,500 kDa, or 2,000 kDa, wherein the upper bound of the range is higher than the lower bound of the range.

In some embodiments, a polypeptide amenable to formulation as described herein has a molecular weight that may be, for example, between about 500 Da and 70 kDa. In some embodiments, a polypeptide has a molecular weight that may be, for example, between about 5 kDa and 2,000 kDa.

In some embodiments, a polypeptide has a molecular weight that may be, for example, between about 10 kDa and 500 kDa. In some embodiments, a polypeptide has a molecular weight that may be, for example, between about 20 kDa and 500 kDa. In some embodiments, a polypeptide has a molecular weight that may be, for example, between about 100 kDa and 150 kDa. In some embodiments, a polypeptide has a molecular weight that may be, for example, between about 150 kDa and 200 kDa.

In some embodiments, a polypeptide amenable to formulation as described herein can include, e.g., about 3 to about 1,000 amino acids, e.g., about 10 to about 500, about 10 to about 250, about 10 to about 100, about 100 to about 1,000, about 100 to about 750, about 100 to about 500, about 100 to about 250, about 250 to about 1,000, about 250 to about 750, or about 250 to about 500 amino acids. In various embodiments, polypeptides can include a number of amino acids within a range having a lower bound of, e.g., about 3, 10, 20, 30, 40, 50, 75, 100, 150, 200, 250, 300, 350, 400, 450, or 500 amino acids and an upper abound of, e.g., about 100, 150, 200, 250, 300, 350, 400, 450, 500, 750, or 1,000 amino acids, the lower bound being smaller than the upper bound.

In various embodiments, a polypeptide amenable to formulation as described herein can be a therapeutic polypeptide, e.g., an antibody agent, or antigen-binding portion thereof, an enzyme (e.g., a replacement enzyme), a hormone, a cytokine, etc., e.g., for administration to a subject in need thereof. Those of skill in the art will be familiar with the identities and character of a wide variety of therapeutic polypeptides.

In various embodiments, polypeptides can be or include recombinant polypeptides, isolated or synthetic polypeptides, cytoskeletal proteins, extracellular matrix proteins, plasma proteins, coagulation factors, acute phase proteins, hemoproteins, cell adhesion proteins, transmembrane transport proteins, synport/antiport proteins, hormones, growth factors, receptors, transmembrane receptors, intracellular receptors, DNA-binding proteins, transcription regulation proteins, RNA-binding proteins, immune system proteins, nutrient storage and transport proteins, chaperone proteins, enzymes, glycoproteins, phosphoproteins, membrane proteins, transport proteins, or lipoproteins, antibodies, recombinant antibodies, antibody fragments, monoclonal antibodies, modified enzymes, pegylated polypeptides, therapeutic polypeptides, storage polypeptides, enzymes, growth factors or hormones, immunomodifiers, anti-infectives, antiproliferatives, vaccines or other therapeutics, prophylactic, diagnostic polypeptides, and combinations thereof.

In various embodiments, a polypeptide can be or include an antibody or antibody fragment. In some embodiments, an antibody is a monoclonal antibody or fragment thereof. In some embodiments, an antibody is a polyclonal antibody or fragment thereof. In some embodiments, an antibody is natural, synthetic, or engineered.

Antibody fragments include Fab fragments (a single Fab that is isolated from a complete antibody by digestion with the enzyme papain) and F(ab')2 fragments (two Fabs covalently-bound to each other, produced by digesting the antibody with the enzyme pepsin). Fab fragments are monospecific, while F(ab')2 fragments are bispecific. Antibody fragments include double-stranded Fv (dsFv) fragments and single-chain Fv (scFv) fragments (the "v" stands for "variable" in both cases). A dsFv fragment consists of a Fab fragment minus the constant regions, i.e., consisting only of the variable regions of a heavy and light chain covalently bound to each other. A scFv fragment is a single polypeptide chain, consisting of the variable region of a heavy chain linked via a peptide linker to the variable region of a light chain. Classically, both dsFv and scFv fragments are monovalent (and thus mono-specific). However, two dsFv fragments or two scFv fragments can themselves be linked to form a bispecific fragment (which would be analogous to a F(ab')2 fragment without the constant regions). Furthermore, it is possible to link two dsFv fragments or scFv fragments with different antigen-binding sites (i.e., different specificities), to form a bi-specific fragment. Such fragments may be used as either research tools or therapeutic or diagnostic reagents.

In some embodiments, an antibody is an immunoglobulin. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids which are primarily responsible for antigen recognition. The carboxy-terminal portion of each chain defines an invariable region primarily responsible for effector function. The four chains are arranged in a classic "Y" model. The bottom "leg" of the "Y" is called the Fc region ("c" stands for "crystallizable" or, alternatively, "complement-binding") and is used to anchor the antibody within cell membranes, and is also used to bind macrophage cells and thus activate complementation. The two "arms" at the top of the "Y" are called Fab regions (the "ab" stands for "antigen-binding"). Each Fab region contains an invariable region (at the junction of the Fab and the Fc regions) and a variable region (which extends to the tip of the "Y" or Fc region). Each variable region contains identical antigen-binding sites (at regions within the variable regions called "hypervariable" regions) at each tip of the "Y". The term "hypervariable" region refers to amino acid residues from a complementarity-determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)). "Framework" or FR residues are the remaining variable region residues other than the hypervariable region residues. Each Fab region has one antigen-binding site, and the complete antibody molecule therefore has two antigen-binding sites (i.e., is "bivalent"). The two antigen-binding sites on a naturally occurring antibody are identical to each other, and therefore the antibody is specific for one antigen (i.e., is "monospecific").

Antibodies can be assigned to different classes depending on the amino acid sequence of the invariable domain of their heavy chains. Heavy chains are classified as mu ($\mu$), delta ($\Delta$), gamma ($\gamma$), alpha ($\alpha$), and epsilon ($\varepsilon$), and define the antibody's isotype as IgM, IgD, IgG, IgA, and IgE, respectively. Typically, IgG, IgE and IgD occur as monomers, while IgA can occur as not only a monomer, but also a dimer or trimer, and IgM can occur as a pentamer. Several of the above may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activities. Human light chains are classified as kappa ($\kappa$) and lambda ($\lambda$) light chains. Within light and heavy chains, the variable and invariable regions are joined by a "J" region of about 12 or more amino acids, with the heavy chain additionally encompassing a "D" region of about 10 more amino acids (See generally, Fundamental Immunology, Ch. 7 (Paul, W., ed., 2nd ed. Raven Press, N.Y. (1989)).

In some embodiments, a polypeptide may be a chimeric antibody. Though naturally occurring antibodies are derived from a single species, engineered antibodies and antibody fragments may be derived from more than one species of animal, i.e., may be chimeric. Mouse (murine)/human chimeric antibodies have been generated, though other combinations are possible. Chimeric antibodies have been further broken down into two subtypes: chimeric and humanized. Chimeric murine/human antibodies typically contain approximately 75% human and 25% mouse amino acid sequences, respectively. The human sequences represent invariable regions of an antibody while the mouse sequences represent variable regions (and thus contain the antigen-binding sites) of an antibody. The general rationale for using such chimeras is to retain antigen specificity of a mouse antibody but reduce the immunogenicity of a mouse antibody (a murine antibody would cause an immune response against it in species other than the mouse) and thus be able to employ a chimera in human therapies. Chimeric antibodies also include those which include CDR regions from different human antibodies. CDR regions, also called hypervariable regions, are sequences within variable regions of antibody molecules that generate antigen-binding sites. CDR regions are so-named because the binding site is complementary in shape and charge distribution to the epitope recognized on an antigen. Alternatively, chimeric antibodies include framework regions from one antibody and CDR regions from another antibody. Chimeric antibodies also include those which include CDR regions from at least two different human antibodies. Humanized antibodies typically contain approximately 90% (or more) human amino acid sequences. In this scenario, the only murine sequences present are those for a hypervariable region (that are the actual antigen-binding sites contained within a variable region). Humanized antibodies have minimal mouse immunogenicity as compared with chimeric antibodies.

Examples of antibodies and antibody fragments include, without limitation, Idarucizumab (Praxbind®) Raxibacumab (ABTHRAX®), Atezolizumab (TECENTRIQ®, RG7446 (Roche)), Ofatumumab (Arzerra®), Obinutuzumab (GAZYVA®, GA101 (Roche)), Bezlotoxumab (ZINPLAVA™), Necitumumab (Portrazza™), Obiltoxaximab (ANTHIM®), Olaratumab (Lartruvo™), Rituximab (RITUXAN®, ABP 798 (Amgen), MabThera®, GP2013 (Novartis)), Tositumomab (Bexxar®), Trastuzumab (HERCEPTIN®, ABP 980 (Amgen), HERTRAZ™, CANMAB™), Pertuzumab (PERJETA®, RG1273 (Roche)), Tocilizumab (ACTEMRA®), Bevacizumab (AVASTIN®, ABP 215 (Amgen)), Daratumumab (Darzalex®), Elotuzumab (EMPLICITI™), Siltuximab (SYLVANT™), Panitumumab (Vectibix®), Vedolizumab (Entyvio®), Eculizumab (Soliris®), Natalizumab (TYSABRI®), Cetuximab (ERBITUX®), Ipilimumab (YERVOY®), Reslizumab (CINQAIR®), Pembrolizumab (KEYTRUDA®), Nivolumab (OPDIVO®), Infliximab (REMICADE®, ABP 710 (Amgen), FLIXABI®), Abciximab (ReoPro®), Evolocumab (Repatha®), Secukinumab (Cosentyx®), Certolizumab pegol (Cimzia®), Ixekizumab (TALTZ™), Omalizumab (Xolair®), Canakinumab (Ilaris®), Alirocumab (Praluent®), Daclizumab (ZINBRYTA™, ZENAPAX®), Denosumab (XGEVA®), Denosumab (Prolia®), Mepolizumab (Nucala), Ustekinumab (Stelara®), Golimumab (Simponi®), Adalimumab (HIMIRA®, ABP501 (Amgen), GP2017 (Novartis)), Ramucirumab (CYRAMZA®), Ranibizumab (LUCENTIS®, RG3645 (Roche & Novartis)), Efalizumab (Raptiva®) Palivizumab (Synagis®), Ado-trastuzumab emtansine (KADCYLA™) Alemtuzumab (Campath®), Alemtuzumab (LEMTRADA™), Basiliximab (Simulect®), Belimumab (Benlysta®), Blinatumomab (BLINCYTO®), Brentuximab vedotin (Adcetris), Capromab pendetide (ProstaScint®), Dinutuximab (Unituxin), Elotuzumab (EMPLICITI™), Gemtuzumab ozogamicin (Mylotarg), Ibritumomab tiuxetan (Zevalin®), Itolizumab (Alzumab™), Muromonab (Orthoclone OKT3®), Nimotuzumab (Theracim®), Nofetumomab (Verluma®), and biosimilars and combinations thereof. In various embodiments, examples of antibodies and antibody fragments include, without limitation, Abciximab, Palivizumab, Murumonab-CD3, Gemtuzumab, Trastuzumab, Basiliximab, Daclizumab, Etanercept, Ibritumomab, and/or Tiuxetan Examples of antibodies and antibody fragments include, without limitation, anti-cytokine antibodies, anti-CD antigen antibodies (e.g. anti-CD3, -CD20 (Rituximab), anti-CD25, anti-CD52, anti-CD33, and anti-CD11a), anti-TNF-α (e.g., Infliximab), anti-rattlesnake venom, anti-ICAM (e.g., anti-ICAM-1 and anti-ICAM-3), anti-growth factor antibodies (e.g., anti-VEGF), anti-growth factor receptor antibodies (e.g., anti-HER2/neu (Trastuzumab), and anti-EGFR), anti-immunoglobulin antibodies (e.g., anti-IgE), anti-polyclonal Ab antibodies, anti-viral antibodies (e.g., anti-CMV, anti-HIV (anti-gp120), anti-HBV, anti-RSV (anti-F glycoprotein)), anti-complement antibodies (e.g., anti-C5), anti-clotting factor antibodies (e.g., anti-gpIIb/IIIa and anti-Factor VII), anti-interleukin antibodies (e.g., anti-IL-5, anti-IL-4, and anti-IL-8), antibodies targeted to the Major Histocompatability Complex (e.g., anti-HLA), anti-idiotypic antibodies, anti-integrin antibodies (e.g., anti-β-2-integrin), anti-17-IA cell surface antigen, anti-α4β7, anti-VLA-4, anti-CBL, and combinations thereof.

In some embodiments, a polypeptide is a biosimilar antibody. A biosimilar is generally similar to the reference either physiochemically or biologically, both in terms of safety and efficacy. A biosimilar can be evaluated against a reference using one or more in vitro studies. In vitro comparisons may be combined with in vivo data demonstrating similarity of pharmacokinetics, pharmacodynamics, and/or safety. Clinical evaluations can include comparisons of pharmacokinetic properties (e.g., AUC0-inf, AUC0-t, Cmax, tmax, Ctrough); pharmacodynamic endpoints; or similarity of clinical efficacy (e.g., using randomized, parallel group comparative clinical trials). Differences between a biosimilar and a reference can include post-translational modification, e.g. by conjugating one or more biochemical groups such as a phosphate, various lipids and carbohydrates; by proteolytic cleavage following translation; by changing the chemical nature of an amino acid (e.g., formylation); or by many other mechanisms. Other post-translational modifications can be a consequence of manufacturing process operations—for example, glycation may occur with exposure of the product to reducing sugars. In other cases, storage conditions may be permissive for certain degradation pathways such as oxidation, deamidation, or aggregation.

Those skilled in the art will be aware of a variety of contexts in which antibodies can generally be used therapeutically, e.g., for the treatment of cancer, inflammation, cardiovascular disease, and transplant rejection, by virtue of their specific target-binding properties and/or target neutralization, e.g., binding and/or neutralization of targets associated with disease states. For example, the monoclonal antibody Infliximab binds to tumor necrosis factor and neutralizes its role in inflammation by blocking its interaction with a cell surface receptor. Rituximab targets malignant B lymphocytes by binding to their cell surface CD20 antigen. Clinically relevant antibodies may also be classified according to the therapeutic area in which they are to be employed. In some embodiments, a clinical antibody employed for therapeutic use may include those for treating cancers (e.g., pancreatic cancer), inflammatory diseases (e.g., autoimmune diseases, arthritis), cardiovascular diseases (e.g., strokes), infectious disease (e.g., HIV/AIDS), respiratory diseases (e.g., asthma), tissue transplantation rejection and organ transplantation rejection. In some embodiments, a clinical antibody is employed for radioimmunotherapy.

In various embodiments, a polypeptide can be or include a polypeptide replacement therapy, an enzyme (such as a therapeutic replacement enzyme), and/or a fusion polypeptide. Examples of polypeptides and/or enzymes include, e.g., an antibody (e.g., an anti-HER2 antibody, e.g., trastuzumab), a GLP-1 receptor agonist, human glucagon-like peptide-1 (GLP-1) or an analog thereof (e.g., a synthetic analog, e.g., liraglutide), parathyroid hormone or an analog thereof (e.g., recombinant human parathyroid hormone analog, e.g., teriparatide), human growth hormone (e.g., Norditropin NordiFlex® R (human growth hormone (human recombinant)), insulin or an analog thereof (e.g., Humulin®), rituximab, bevacizumab, cetuximab, etanercept, infliximab, or an analog or derivative thereof. Examples of enzymes, e.g., for replacement enzyme therapy, can include agalsidase beta, agalsidase alfa, imiglucerase, aliglucerase alfa, velaglucerase alfa, alglucerase, sebelipase alpha, laronidase, idursulfase, elosulfase alpha, galsulfase, pancrelipase, sapropterin, eliglustat, galsulfase, asfotase alfa, pegvaliase, elapegademase, and/or sacrosidase. Examples of replacement polypeptides include Factor I, Factor II, Factor III, Factor IV, Factor V, Factor VI, Factor VII, Factor VIII, Factor IX, Factor X, Factor XI, Factor XII, Factor XIII, and/or von Willebrand factor. Examples of fusion polypeptides can include, e.g., etanercept, aflibercept, rilonacept, alefacept, romiplostim, abatacept/belatacept, and/or denileukin-diftitox. The present disclosure includes analogs and modified forms of polypeptides disclosed herein, e.g., that include one or more pendant groups or modifications, e.g., pegylation, acetylation, amidation, lipidation, methylation, phosphorylation, glycosylation, glycation, sulfation, mannosylation, nitrosylation, acylation, palmitoylation, prenylation, or combinations thereof. In various particular embodiments, a polypeptide includes one or more pendant groups or modifications selected from pegylation and/or fatty acids. Those skilled in the art will appreciate that the modified polypeptides of the present disclosure encompass polypeptides with non-natural amino acids, with altered amino acids, with altered intramolecular binding properties, with chemical modification of the backbone.

In some embodiments, a polypeptide is conjugated with another molecule, e.g., small molecules (e.g., fluorophores, chelating agents and therapeutics), oligosaccharides, lipids (e.g., ionizable cationic lipids), oligonucleotides, antibodies, etc. In some embodiments, a polypeptide is conjugated to a ligand that targets a site of therapeutic relevance. In some embodiments, a polypeptide is conjugated to a ligand that targets a cell surface receptor, e.g., carbohydrate receptors, lipoprotein receptors, transferring receptors, receptors involved cell adhesion, etc. In some embodiments, a polypeptide is conjugated to a cell penetrating peptide. In some embodiments, a polypeptide is conjugated to an albumin binding peptide. In some embodiments, a polypeptide is conjugated to an albumin binding antibody fragment. In some embodiments, a polypeptide is conjugated to a passive or active transport enhancers. In some embodiments, a polypeptide is conjugated to a mucoadhesive device.

In some embodiments, a polypeptide of the present disclosure is insulin or an analog thereof (e.g., Humulin®). In some embodiments, a polypeptide of the present disclosure is lantus/insulin glargine. In some embodiments, a polypeptide of the present disclosure is parathyroid hormone (PTH). In some embodiments, a polypeptide of the present disclosure is liraglutide. In some embodiments, a polypeptide of the present disclosure is octreotide acetate. In some embodiments, a polypeptide of the present disclosure is trastuzumab. In some embodiments, a polypeptide of the present disclosure is human growth hormone (e.g., Norditropin NordiFlex® R (human growth hormone (human recombinant). In some embodiments, a polypeptide of the present disclosure is adalimumab. In some embodiments, a polypeptide of the present disclosure is semaglutide.

The present disclosure further relates to engineered and/or biosimilar forms of therapeutic polypeptides, which such forms may, for example, show at least 80% sequence identity with their reference polypeptide, e.g., at least 80%, 85%, 90%, 95%, 96%, 97%, 98%, or 99% identity with such reference polypeptide.

The present disclosure further includes the recognition that polypeptides, including, e.g., antibodies and/or antibody fragments, are generally not referred to as "small molecules" or "compounds" in the art. Accordingly, because small molecules and compounds can have very different physical and pharmacokinetic properties than polypeptides as disclosed herein, e.g., than antibodies and/or antibody fragments, prior art disclosures relating to small molecules and compounds would not be understood as applicable by those of skill in the art to the formulations and methods relating to polypeptides as disclosed herein.

Formulations

As appreciated by those skilled in the art, in some aspects, a polypeptide formulation as described herein is in a form suitable for oral administration, e.g., buccal/sublingual administration. In some embodiments, a provided formulation is a truffle formulation. In some embodiments, a provided formulation is a tablet formulation. In some embodiments, a provided formulation is a tablet formulation, a globule formulation. In some embodiments, a provided formulation is a candy formulation. In some embodiments, a provided formulation may be in the form of a dry powder (e.g., a dry spray). In some embodiments, a provided formulation may be in the form of a solid particle suspension. In some embodiments, a provided formulation may be in the form of a fast-dissolving tablet. In some embodiments, a provided formulation may be in the form of a fast-dissolving film.

In various embodiments, a polypeptide formulation as described herein, e.g., a truffle formulation, a tablet formulation, a globule formulation, a candy formulation, can include a coating. In some embodiments, a coating is or comprises an enteric coating. An enteric coating is typically a barrier that controls the location of a recipients body (e.g., digestive system, e.g., gut, e.g., small and/or large intestine) in which an oral formulation's core is exposed and/or to which the oral formulation's core is delivered. Many enteric coatings are insoluble at a low pH but dissolve, swells, or becomes soluble at a higher pH in the intestinal tract. Typical materials used for enteric coatings can include CAP (cellulose acetate phthalate), CAT (cellulose acetate trimellitate), PVAP (poly(vinyl acetate phthalate)) and HPMCP (hydroxypropyl methylcellulose phthalate), poly(methacrylic acid-co-methyl methacrylate), fatty acids, waxes, shellac (e.g., esters of aleuritic acid), plastics, and plant fibers. In various embodiments, the dissolution pH of an enteric coating can be between, e.g., about 4.5 and about 7, e.g., about 4.5 to about 5.5, about 4.5 to about 6.0, about 5.5 to about 7.0, about 5.0, about 6.2, or about 7.0. In various embodiments an enteric coating has a pH release that is within a range that has a lower bound of about 4.5, 5.0, 5.5, or 6.0 and an upper bound of about 5.0, 5.5, 6.0, 6.5, 7.0, or 7.5.

The present disclosure expressly includes the recognition that enteric coatings are not necessary for delivery of a polypeptide disclosed herein according to various embodiments methods and compositions as described herein to reach the bloodstream, plasma, lymphatic system, and/or thoracic duct, e.g., in therapeutically effective amounts.

In various embodiments, a formulation that includes an amorphous polypeptide composition or a crystallized polypeptide composition is or includes a bioadhesive formulation, e.g., in or on the surface of a formulation, e.g., truffle, tablet, globule, or candy formulation. In various embodiments, a bioadhesive formulation adheres to a specific biological location such as a mucosal lining (mucoadhesion). Bioadhesive dosage forms can improve the oral absorption of polypeptide agent by delivering it in small doses over an extended period and/or localizing it in the intestine by bioadhesion. Various bioadhesive polymers can be broadly as specific or nonspecific. Specific bioadhesive polymers (e.g., lectins, and fimbrins) have the ability to adhere to specific chemical structures within the biological molecules while the nonspecific bioadhesive polymers (e.g., polyacrylic acid [PAA] and cyanoacrylates) have the ability to bind with both the cell surfaces and the mucosal layer. Further examples of bioadhesive polymers include CMC sodium, Carbopol, Polycarbophil, Tragacanth, Sodium alginate, HPMC, Gum karaya, Gelatin, Guar gum, Pectin, Acacia, Chitosan, and hydroxypropyl cellulose. Examples of bioadhesive polymers can include Hydrophilic polymers (e.g., Methyl Cellulose, hydroxyethyl cellulose, HPMC, Na CMC, and carbomers), Thiolated polymers (e.g., Chitosan-iminothiolane, PAA-cysteine, PAA-homocysteine, chitosan-thioglycolic acid, chitosan-thioethylamidine, alginate-cysteine, poly (methacrylic acid)-cysteine and sodium carboxymethylcellulose-cysteine), Lectin-based polymers (e.g., Lentil lectin, peanut agglutinin, and *Ulex europaeus* agglutinin), Polyox WSR (e.g., WSR N-10, WSR N-80, WSR N-205, and WSR N-750), and other polymers such as tomato lectin, PAA-co-PEG, and PSA.

The present disclosure includes methods and compositions that include a polypeptide formulation for oral delivery including a core within a pharmaceutically acceptable shell, where the core includes a polypeptide composition (e.g., an amorphous polypeptide composition or a crystallized polypeptide composition).

In various embodiments, a core comprises about 1 mg to 2,000 mg of polypeptide (e.g., crystalized polypeptide or amorphous polypeptide). In various embodiments, a core comprises about 1 mg to 1,000 mg, 1 mg to 500 mg, 1 mg to 400 mg, 1 mg to 300 mg, 1 mg to 200 mg, or 1 mg to 100 mg of crystalized polypeptide or amorphous polypeptide. In some embodiments the formulation includes an amount of crystalized polypeptide or amorphous polypeptide that is within a range having a lower bound of, e.g., 1, 5, 10, 15, 20, 25, 30, 35, 40, 45, 50, 75, 100, 150, 200, 250, 300, 350, 400, 450, or 500 mg crystalized polypeptide or amorphous polypeptide and an upper bound of 100, 150, 200, 250, 300, 350, 400, 450, 500, 1,000, or 2,000 mg crystalized polypeptide or amorphous polypeptide. In various embodiments, a core comprises about 50 μg to 2,000 mg of a polypeptide, optionally wherein the polypeptide formulation includes about 50 μg to 1,000 mg, 50 μg to 500 mg, 50 μg to 400 mg, 50 μg to 300 mg, 50 μg to 200 mg, 50 μg to 100 mg, 50 μg to 50 mg, 50 μg to 25 mg, 50 μg to 20 mg, 50 μg to 15 mg, 50 μg to 10 mg, 50 μg to 5 mg, 50 μg to 1 mg, 50 μg to 500 μg, 1 mg to 1,000 mg, 1 mg to 500 mg, 1 mg to 400 mg, 1 mg to 300 mg, 1 mg to 200 mg, 1 mg to 100 mg, 1 mg, to 50 mg, 1 mg to 25 mg crystalized polypeptide or amorphous polypeptide. In various embodiments, a core comprises about 1 μg to 2,000 mg of a polypeptide, optionally wherein the polypeptide formulation includes about 1 μg to 1,000 mg, 1 μg to 500 mg, 1 μg to 400 mg, 1 μg to 300 mg, 1 μg to 200 mg, 1 μg to 100 mg, 1 μg to 50 mg, 1 μg to 25 mg, 1 μg to 20 mg, 1 μg to 15 mg, 1 μg to 10 mg, 1 μg to 5 mg, 1 μg to 1 mg, 1 μg to 500 μg, 1 μg to 250 μg, 1 μg to 200 μg, 1 μg to 150 μg, 1 μg to 100 μg, 1 μg to 50 μg of the crystalized polypeptide or amorphous polypeptide. In some embodiments the formulation includes an amount of crystalized polypeptide or amorphous polypeptide that is within a range having a lower bound of, e.g., 1 μg, 5 μg, 10 μg, 15 μg, 20 μg, 25 μg 50 μg, 100 μg, 200 μg, 300 μg, 400 μg, 500 μg, 600 μg, 700 μg, 800 μg, 900 μg, 1 mg, 2 mg, 3 mg, 4 mg, 5 mg, 10 mg, or 25 mg crystalized polypeptide or amorphous polypeptide and an upper bound of 500 μg, 600 μg, 700 μg, 800 μg, 900 μg, 1 mg, 2 mg, 3 mg, 4 mg, 5 mg, 10 mg, 25 mg, 50 mg, 100 mg, 500 mg, 1,000 mg, or 2,000 mg crystalized polypeptide or amorphous polypeptide.

In various embodiments, one or more pharmaceutically acceptable carriers are present in a formulation (e.g., a truffle, a tablet, a globule, or a candy formulation) or a core thereof at a concentration between 0.1 mM and about 1,000 mM, between about 0.1 mM and about 500 mM, between about 0.1 mM and about 200 mM, or between about 1 mM and about 100 mM. In various embodiments, one or more pharmaceutically acceptable carriers are present in a formulation (e.g., a truffle, a tablet, a globule, or a candy formulation) or a core thereof at a concentration within a range having a lower bound of 0.1, 1, 5, 10, 20, 30, 40, 50, 75, or 100 mM and an upper bound of 10, 20, 30, 40, 50, 75, 100, 150, 200, 250 or 500 mM.

In some embodiments, a polypeptide formulation as described herein is in a shape of sphere, cube, cone, cylinder, half sphere, torus, pyramid, triangular prism, hexagonal prism, cuboid, hexagonal pyramid, hallow cylinder, octahedron, diamond, star prism, hexagonal diamond, star pyramid, pentagonal prism, L shape prism, dodecahedron, tetrahedron, or icosahedron, or a modification thereof, or a combination thereof.

Those skilled in the art, reading the present disclosure will appreciate that, in some embodiments, a suitable means of administration for a particular provided formulation to a particular subject may be selected upon consideration, among other things, of, for example age and/or condition of a subject. Similarly, in some embodiments, unit dose, appropriate dosing regimen, and/or total dose to be administered may be selected based on sound medical judgment taking into consideration, for example, any designated or approved range is provided, weight, age, condition, and other characteristics of a patient, etc.

Those skilled in the art, reading the present disclosure will appreciate that, in some embodiments, it may be feasible to administer certain provided formulations by other routes. In some embodiments, certain provided formulations (e.g., truffle, tablet, globule, candy formulations) can be administered rectally as suppository formulations.

Suppository Formulations

Certain suppository formulations can include an amorphous polypeptide composition or a crystallized polypeptide composition and suppository excipients, e.g., a lipophilic base (e.g., cocoa butter, coconut oil, virgin coconut oil, almond oil, wheatgerm oil, any edible oil, hydrogenated vegetable oils, and hard fats) or hydrophilic base (e.g., glycerinated gelatin and polyethylene glycols). Lipophilic bases are immiscible with body fluids and readily melt at body temperature to release the drug on the mucosal surface, whereas hydrophilic bases need to dissolve in the physiological fluids for drug release. Suppository formulations can include solid, semi-solid, and liquid forms.

In various embodiments, a suppository formulation includes a semi-solid dosage form such as a gel or foam. A rectal gel can be a semi-solid formulations that contain a solvent trapped within a polymer network to create a viscous consistency. Viscosity of a gel can be modified by the addition of co-solvents (e.g., glycerin and propylene glycol) and electrolytes.

In various embodiments, a suppository formulation includes a liquid suppository, e.g., a liquid suppository including thermosensitive polymers (e.g., poloxamers), mucoadhesive polymers (e.g., carbopol, sodium alginate, polycarbophil, hydroxypropyl methylcellulose, hydroxyethyl cellulose, and methylcellulose), or a combination of thermosensitive and mucoadhesive polymers. Suppositories can further include, e.g., cellulose ether polymers (e.g., hydroxypropyl methylcellulose, hydroxyethyl cellulose, and methylcellulose).

In various embodiments, a suppository formulation includes a foam such as a colloidal dosage form with a hydrophilic liquid continuous phase containing a foaming agent and a gaseous dispersion phase distributed throughout. Following rectal administration, certain such formulations transition from a foam state to a liquid or semi-solid state on the mucosal surface. Foaming agents include amphiphilic substances that are important for foam generation and stabilization.

Exemplary Formulations

Truffle Formulations

In some embodiments, the present disclosure provides truffle formulations comprising a core and a pharmaceutically acceptable shell.

In some embodiments, core includes an amorphous polypeptide composition or a crystallized polypeptide composition as described herein. In a provided truffle formulation, such a core can be situated in a shell. In some embodiments, a core comprises crystallized polypeptide composition. In some embodiments, a core comprises an amorphous polypeptide composition.

In some embodiments, a shell is or comprises sugar. In some embodiments, a shell is or comprises cane sugar. In some embodiments, a shell is or comprises palm sugar. In certain embodiments, a shell is or comprises lactose. In certain embodiments, a shell is or comprises xylitol. In certain embodiments, a shell is or comprises milk sugar. In some embodiments, a shell is cane sugar. In some embodiments, a shell is palm sugar.

In some embodiments, a shell includes hardshell and soft shell. In various embodiments, a shell is a gelatin shell or hydroxypropyl methylcellulose (HPMC) shell. Exemplary shell materials can include polymers such as poly(glycolic acid) (PGA), poly(lactic acid) (PLA) and its copolymers, poly(lactide-co-glycolide) (PLGA), and non-ionic cellulose ethers such as hydroxypropylcellulose (HPC) and hydroxypropyl methylcellulose (HPMC). In some embodiments a capsule is a vegetable capsule.

In some embodiments, shell of a truffle formulation can be produced from a single piece of gelatin. Gelatin can be used to surround a core not based on water, as water would dissolve the gelatin. Once ingested, the shell dissolves, exposing the core.

In some embodiments, shell of a truffle formulation can be filled with a core including dry ingredients in powder form. In some such embodiments, a shell may be formed, its body is first filled with a core composition, and then the shell closed with the cap. Once ingested, the shell dissolves, exposing the core.

In some embodiments, a shell is hollow. In some embodiments, a shell is partially filled with space of a core. In some embodiments, a shell is partially fully with space of a core.

In some embodiments, a polypeptide formulation as described herein is in a shape of sphere, or a modification thereof. In some embodiments, a truffle formulation as described herein is in a shape of sphere, or a modification thereof.

Tablet Formulations

In some embodiments, the present disclosure provides a tablet formulation comprising a crystallized polypeptide composition or an amorphous polypeptide composition and a pharmaceutically acceptable carrier. In some embodiments, a tablet formulation as described herein is prepared by pressing a mixture of a crystallized polypeptide composition or an amorphous polypeptide composition and a pharmaceutically acceptable carrier.

Alternatively or additionally, in some embodiments, a tablet formulation as described herein is coated with a pharmaceutically acceptable coating. In some embodiments, a coating is or comprises food ingredient. In some embodiments, a coating comprises or is an enteric coating.

Globule Formulations

In some embodiments, the present disclosure provides a globule formulation comprising a crystallized polypeptide composition or an amorphous polypeptide composition and a pharmaceutically acceptable carrier. In some embodiments, a globule formulation comprises a suspension of solid particles, wherein such solid particles comprise a crystallized polypeptide composition or an amorphous polypeptide composition and optionally one or more pharmaceutically acceptable carriers.

Alternatively or additionally, in some embodiments, a globule formulation as described herein is coated with a pharmaceutically acceptable coating. In some embodiments, a coating is or comprises food ingredient. In some embodiments, a coating comprises or is an enteric coating.

Candy Formulations

In some embodiments, the present disclosure provides a candy formulation comprising crystallized polypeptide composition or amorphous polypeptide composition and a pharmaceutically acceptable carrier.

In some embodiments, a candy formulation comprises one or more food ingredients, e.g., chocolate, cocoa, milk, milk product, natural dye, artificial dye, gum base, flavors, sweeteners, gelatin, starch, syrup, citric acid, sugar, etc.

In some embodiments, a candy formulation comprises about 50% w/w of sugar. In some embodiments, a candy formulation comprises about 60% w/w of sugar. In some embodiments, a candy formulation comprises about 70% w/w of sugar. In some embodiments, a candy formulation comprises about 80% w/w of sugar. In some embodiments, a candy formulation comprises about 90% w/w of sugar. In some embodiments, a candy formulation comprises about 91% w/w of sugar. In some embodiments, a candy formulation comprises about 92% w/w of sugar. In some embodiments, a candy formulation comprises about 93% w/w of sugar. In some embodiments, a candy formulation comprises about 94% w/w of sugar. In some embodiments, a candy formulation comprises about 95% w/w of sugar. In some embodiments, a candy formulation comprises about 96% w/w of sugar. In some embodiments, a candy formulation comprises about 97% w/w of sugar. In some embodiments, a candy formulation comprises about 98% w/w of sugar. In some embodiments, a candy formulation comprises about 99% w/w of sugar.

In some embodiments, a candy formulation comprises more than about 50% w/w of sugar. In some embodiments, a candy formulation comprises more than about 60 w/w of sugar. In some embodiments, a candy formulation comprises more than about 70% w/w of sugar. In some embodiments, a candy formulation comprises more than about 80% w/w of sugar. In some embodiments, a candy formulation comprises more than about 90% w/w of sugar. In some embodiments, a candy formulation comprises more than about 95% w/w of sugar. In some embodiments, a candy formulation comprises more than about 99% w/w of sugar. In some embodiments, a candy formulation comprises more than about 99.9% w/w of sugar.

In some embodiments, a candy formulation comprises less than about 50% w/w of sugar. In some embodiments, a candy formulation comprises less than about 40 w/w of sugar. In some embodiments, a candy formulation comprises less than about 30% w/w of sugar. In some embodiments, a candy formulation comprises less than about 20% w/w of sugar. In some embodiments, a candy formulation comprises less than about 10% w/w of sugar. In some embodiments, a candy formulation comprises less than about 5% w/w of sugar. In some embodiments, a candy formulation comprises less than about 3% w/w of sugar. In some embodiments, a candy formulation comprises less than about 2% w/w of sugar. In some embodiments, a candy formulation comprises less than about 1% w/w of sugar. In some embodiments, a candy formulation comprises less than about 0.5% w/w of sugar. In some embodiments, a candy formulation comprises less than about 0.1% w/w of sugar.

In some embodiments, a candy formulation is in a form of, for example, of candy gems, chewing gum, gummy candy, hard candy (e.g., drops, lollipops, lozenges, rock candy, stick candy, etc.) marshmallows, syrup, toffee, etc. In some embodiments, a candy formulation may be in the form of a drop, film, gel, patch, spray, wafer, etc.

Suppository Formulations

The present disclosure further includes suppositories suitable for rectal delivery. In various embodiments, suppositories melt or dissolve upon administration. In various embodiments, a suppository includes a shell (e.g., a cane sugar shell disclosed herein) that surrounds a core. In various embodiments, a suppository does not include a shell-core structure. Suppositories can be formed from waxy matter, structured glycerin, hydrogenated vegetable oil, polyethylene glycol wax derivative, or poloxamer-based mixtures. In various embodiments, a suppository is solid at ambient temperature but rapidly melts at body temperature. Emulsifiers may be used to increase the solubility of crystallized polypeptide or amorphous polypeptide in the suppository mass and/or accelerate the dispersal of crystallized polypeptide or amorphous polypeptide after the suppository melts.

Polypeptide formulations as described herein are suitable for oral administration or rectal administration.

Polypeptide Delivery and Applications

Compositions and methods provided by present disclosure include formulations for oral administration to a subject, which oral administration, in various embodiments, results in delivery of a polypeptide to e.g., thoracic duct, lymphatic system, small and/or large intestine, and/or bloodstream of a subject. Without wishing to be bound by any particular scientific theory or the knowledge of the present inventors, the present disclosure is the first utilization of oral formulations provided herein to deliver a polypeptide to the bloodstream via buccal/sublingual administration.

Without wishing to be bound by any particular scientific theory, the present inventors have surprisingly discovered that polypeptides orally administered polypeptide formulations as described herein, e.g., truffle, tablet, globule, or candy formulations, are efficiently delivered to the bloodstream, e.g., via buccal/sublingual administration. Accordingly, the present disclosure provides a platform or system of general, including compositions and methods disclosed herein, for delivery of diverse polypeptides to the thoracic duct, lymphatic system, small and/or large intestine, and/or blood stream.

The present disclosure provides compositions and methods, e.g., for delivery of a polypeptide to a subject, e.g., to the thoracic duct, lymphatic system, small and/or large intestine, and/or blood stream of the subject. In various embodiments, composition or method as described herein delivers polypeptide to bloodstream with beneficial pharmacokinetic characteristics. In various embodiments, beneficial pharmacokinetic characteristics can result from distribution of a polypeptide through mouth tissue, e.g., via buccal/sublingual administration. Accordingly, the present disclosure specifically includes methods and compositions for delivery of a polypeptide to mouth tissue, e.g., via buccal/sublingual administration.

In various embodiments, a polypeptide of a provided formulation is characterized in that after administration according to the present disclosure, a polypeptide delivered to bloodstream thereby has a median, mean, or modal half-life in a plurality of serum samples, systems, and/or across polypeptide molecules after administration (e.g., across a plurality of subjects after oral administration of a polypeptide formulation to each subject) of at least 0.5 hours, optionally wherein the half-life is at least 1, 2, 5, 10, 15, 20, 25, 30, 35, 40, 45, 50, 55, 60 hours, or more, optionally wherein the median, mean, or modal half-life is in a range having a lower bound of 1, 2, 5, 10, or 15 hours and an upper bound of 20, 25, 30, 35, 40, 45, 50, 55, 60 hours, or more. In various embodiments, after oral administration to a subject of a polypeptide formulation as described herein, the polypeptide delivered to bloodstream by a provided formulation has a half-life of at least 0.5 hours, optionally wherein the half-life is at least 1, 2, 5, 10, 15, 20, 25, 30, 35, 40, 45, 50, 55, or 60 hours, or more, optionally wherein the half-life is in a range having a lower bound of 1, 2, 5, 10, or 15 hours and an upper bound of 20, 25, 30, 35, 40, 45, 50, 55, 60 hours, or more.

In various embodiments, a polypeptide of a provided formulation is characterized in that after administration according to the present disclosure, a polypeptide delivered to bloodstream by such provided formulation has a median, mean, or modal half-life across a plurality of samples, systems, and/or polypeptide molecules (e.g., across a plurality of subjects after oral administration of the polypeptide formulation to each subject) that is at least 10% greater than the median, mean, or modal half-life achieved by injection (e.g., intravenous administration) of the polypeptide (e.g., according to a standard of care route of administration for the polypeptide), optionally wherein the median, mean, or modal half-life of the polypeptide delivered to bloodstream by a provided formulation (e.g., after oral administration) is at least 20%, 30%, 40%, 50%, 60%, 70%, 80%, 90%, 100%, 2-fold, 3-fold, or 4-fold, greater than the median, mean, or modal half-life achieved by injection (e.g., intravenous administration) of the polypeptide (e.g., according to a standard of care route of administration for the polypeptide). In various embodiments, after oral administration to a subject of the polypeptide formulation, the polypeptide delivered to bloodstream by a provided formulation has a half-life that is at least 10% greater than the half-life achieved by injection (e.g., intravenous administration) of the polypeptide (e.g., according to a standard of care route of administration for the polypeptide), optionally wherein the half-life of the polypeptide delivered to bloodstream by a provided formulation after oral administration to the subject is at least 20%, 30%, 40%, 50%, 60%, 70%, 80%, 90%, 100%, 2-fold, 3-fold, or 4-fold, greater than the half-life achieved by injection (e.g., intravenous administration) of the polypeptide (e.g., according to a standard of care route of administration for the polypeptide).

In various embodiments, a polypeptide of a provided formulation is characterized in that after administration according to the present disclosure, a polypeptide delivered thereby has a median, mean, or modal $T_{max}$ across a plurality of samples, systems, and/or polypeptide molecules (e.g., across a plurality of subjects after oral administration of the polypeptide formulation to each subject) that is at least 10% greater than the median, mean, or modal $T_{max}$ achieved by injection (e.g., intravenous administration) of the polypeptide (e.g., according to a standard of care route of administration for the polypeptide), optionally wherein the median, mean, or modal $T_{max}$ of the polypeptide of the polypeptide formulation (e.g., after oral administration) is at least 20%, 30%, 40%, 50%, 60%, 70%, 80%, 90%, 100%, 2-fold, 3-fold, or 4-fold, 5-fold, 10-fold, or 20-fold greater than the median, mean, or modal $T_{max}$ achieved by injection (e.g., intravenous administration) of the polypeptide (e.g., according to a standard of care route of administration for the polypeptide). In various embodiments, after oral administration to a subject of the polypeptide formulation, the polypeptide of the polypeptide formulation has a $T_{max}$ that is at least 10% greater than the $T_{max}$ achieved by injection (e.g., intravenous administration) of the polypeptide (e.g., according to a standard of care route of administration for the polypeptide), optionally wherein the $T_{max}$ of the polypeptide of the polypeptide formulation after oral administration to the subject is at least 20%, 30%, 40%, 50%, 60%, 70%, 80%, 90%, 100%, 2-fold, 3-fold, or 4-fold, 5-fold, 10-fold, or 20-fold greater than the $T_{max}$ achieved by injection (e.g., intravenous administration) of the polypeptide (e.g., according to a standard of care route of administration for the polypeptide).

In various embodiments, a polypeptide of a polypeptide formulation is characterized in that after administration according to the present disclosure, a polypeptide delivered thereby has a median, mean, or modal bioavailability across a plurality of samples, systems, and/or polypeptide molecules (e.g., across a plurality of subjects after oral administration of the polypeptide formulation to each subject) that is at least 1% of the median, mean, or modal bioavailability achieved by injection (e.g., subcutaneous administration) of the polypeptide (e.g., according to a standard of care route of administration for the polypeptide), optionally wherein the median, mean, or modal bioavailability of the polypeptide of the polypeptide formulation (e.g., after oral administration) is at least 1%, 1.5%, 2%, 3%, 4%, 5%, 10%, 20%, 30%, 40%, 50%, 60%, 70%, 80%, 90%, 100%, 2-fold, 3-fold, 4-fold, or 5-fold of the median, mean, or modal bioavailability achieved by injection (e.g., subcutaneous administration) of the polypeptide (e.g., according to a standard of care route of administration for the polypeptide). In various embodiments, after oral administration to a subject of a polypeptide formulation, the polypeptide of the polypeptide formulation has an bioavailability that is at least 1% of the bioavailability achieved by injection (e.g., subcutaneous administration) of the polypeptide (e.g., according to a standard of care route of administration for the polypeptide), optionally wherein the bioavailability of the polypeptide of the polypeptide formulation after oral administration to the subject is at least 1%, 1.5%, 2%, 3%, 4%, 5%, 10%, 20%, 30%, 40%, 50%, 60%, 70%, 80%, 90%, 100%, 2-fold, 3-fold, 4-fold, or 5-fold of the bioavailability achieved by injection (e.g., subcutaneous administration) of the polypeptide (e.g., according to a standard of care route of administration for the polypeptide). In various embodiments, a polypeptide of a polypeptide formulation is characterized in that after administration according to the present disclosure, an active polypeptide delivered thereby has a median, mean, or modal bioavailability across a plurality of samples, systems, and/or polypeptide molecules (e.g., across a plurality of subjects after oral administration of the polypeptide formulation to each subject) that is at least 1%, e.g., at least about 1%, about 1.5%, about 2%, about 3%, about 4%, about 5%, about 10%, about 20%, about 30%, about 40%, about 50%, about 60%, about 70%, about 80%, about 90%, about 100%, in some embodiments, provided formulations achieve oral bioavailability above about 5%, or within a range of about 10%-20% oral bioavailability, or about 15%.

In various embodiments, a polypeptide of a polypeptide formulation is characterized in that after administration according to the present disclosure, a polypeptide delivered thereby has a median, mean, or modal $C_{max}$ across a plurality of samples, systems, and/or polypeptide molecules (e.g., across a plurality of subjects after oral administration of the polypeptide formulation to each subject) that is at least 10% less than the median, mean, or modal $C_{max}$ achieved by injection (e.g., subcutaneous administration) of the polypeptide (e.g., according to a standard of care route of administration for the polypeptide), optionally wherein the median, mean, or modal $C_{max}$ of the polypeptide of the polypeptide formulation (e.g., after oral administration) is at least 20%, 30%, 40%, 50%, 60%, 70%, 80%, or 90%, less than the median, mean, or modal $C_{max}$ achieved by injection (e.g., subcutaneous administration) of the polypeptide (e.g., according to a standard of care route of administration for the polypeptide). In various embodiments, after oral administration to a subject of a polypeptide formulation, the polypeptide of the polypeptide formulation has a $C_{max}$ that is at least 10% less than the $C_{max}$ achieved by injection (e.g., subcutaneous administration) of the polypeptide (e.g., according to a standard of care route of administration for the polypeptide), optionally wherein the $C_{max}$ of the polypeptide of the polypeptide formulation after oral administration to the subject is at least 20%, 30%, 40%, 50%, 60%, 70%, 80%, or 90%, less than the $C_{max}$ achieved by injection (e.g., subcutaneous administration) of the polypeptide (e.g., according to a standard of care route of administration for the polypeptide).

In various embodiments, a method can include administering a composition and/or formulation as described herein to a subject in need thereof, where the composition and/or formulation includes a polypeptide for treatment of a disease or condition from which the subject suffers.

Further disclosed herein are methods of treating a disease or disorder in mammals, including administering to the mammal a composition and/or formulation as described herein that includes a therapeutically effective amount of a polypeptide, and optionally wherein a composition and/or formulation further includes a pharmaceutically acceptable viscosity-reducing agent, aggregation-reducing agent, or other additive as described above; and wherein a therapeutic formulation is effective for treatment of a diseases or disorder. In some embodiments, an excipient compound is essentially pure.

Those skilled in the art will be aware of appropriate applications of any particular provided formulation, for example based on the polypeptide(s) it delivers and/or its therapeutic usage. For example, therapeutic polypeptides are currently approved to treatment of diseases, conditions, or disorders such as breast cancer, gastric cancer, Non-Hodgkin's Lymphoma, urothelial carcinoma & solid tumors, Metastatic colorectal cancer, Non-squamous non-small cell lung cancer, Metastatic breast cancer, Hodgkin lymphoma, Biliary cancer, Acute myeloid Leukemia, prostate cancer, multiple myeloma, solid tumors of bone, neuroblastoma, pancreatic cancer, acute myelogenous leukemia, metastatic melanoma, metastatic squamous non-small cell cancer, Anaplastic astrocytoma; Brain cancer, Glioblastoma, Glioma, Head and neck cancer, Merkel cell carcinoma, Nasopharyngeal cancer, Oesophageal cancer, Hepatocellular carcinoma, refractory euroblastoma, Osteosarcoma, Peritoneal cancer, Fallopian tube cancer, Mesothelioma, Metastatic Melanoma, Renal Cell Carcinoma, NR-LU-10 for cancer, lupus, Chronic Lymphocytic Leukemia, soft tissue sarcoma, ovarian cancer, bladder cancer, esophageal cancer, gastric nasopharyngeal cancer, adrenocortical carcinoma, HER2-positive breast cancer, adenocarcinoma, Granulomatosis with Polyangiitis (GPA), microscopic polyangiitis, idiopathic pulmonary fibrosis, focal segmental glomerulosclerosis, Prolactinoma, and combinations thereof.

In some embodiments, a therapeutic use for a composition and/or formulation as described herein can include treatment and/or detection of an autoimmune disease such as Rheumatoid Arthritis (RA), Osteoarthritis, Juvenile Idiopathic Arthritis (JIA), Psoriatic Arthritis (PsA), Ankylosing Spondylitis (AS), Crohn's Disease (CD), Ulcerative Colitis (UC), Plaque Psoriasis (Ps), systemic lupus erythematosus, Lupus nephritis, Familial Cold Autoinflammatory Syndrome (FCAS), Sjogren's syndrome, and combinations thereof.

In some embodiments, a therapeutic polypeptide as described herein can be used for treatment and/or detection of another immunologically-related disorder such as Leukopaenia, paroxysmal nocturnal hemoglobinuria (PNH), atypical hemolytic uremic syndrome (aHUS), thrombotic microangiopathy (TMA), Inflammatory bowel disease, ulcerative colitis and transplantation rejection, surgery-related, life-threatening, uncontrolled bleeding, and combinations thereof.

In some embodiments, a therapeutic polypeptide as described herein can be used for treatment and/or detection of an infectious disease like *Clostridium difficile* infection, respiratory syncytial virus (RSV) disease, Anthrax, Flu virus infection, Influenza Virus infection, Hepatitis B virus infection, Rabies virus infection, invasive *Candida* infection, bacterial septic shock, HIV infection, Nosocomial pneumonia, Staphylococcal infections, STEC (Shiga-like toxin-producing *Escherichia coli* or *E. coli* serotype O121) infection causing diarrhea and HUS (hemolytic-uremic syndrome), Cytomegalovirus, Botulism, Ebola Virus, and combinations thereof.

In some embodiments, a therapeutic polypeptide as described herein can be used for treatment and/or detection of a cardiovascular disease such as cardiac ischemic complications, percutaneous coronary intervention, Acute myocardial infarction, pulmonary embolism, deep vein thrombosis, arterial thrombosis or embolism, occlusion of arteriovenous cannula, thrombocytopenia with chronic immune (idiopathic) thrombocytopenic purpura (ITP), and combinations thereof.

In some embodiments, a therapeutic polypeptide as described herein can be used for treatment and/or detection of an ophthalmic disorder such as Age-Related Macular Degeneration (AMD), Macular Edema, Retinal Vein Occlusion (RVO), Diabetic Macular Edema, Neuromyelitis optica, and combinations thereof.

In some embodiments, a therapeutic polypeptide as described herein can be used for treatment and/or detection of a respiratory disorder such as asthma, chronic idiopathic urticaria, acute bronchospasm or status asthmaticus, Chronic obstructive pulmonary disease, and combinations thereof.

In some embodiments, a therapeutic polypeptide as described herein can be used for treatment and/or detection of a metabolic disorder like hyperlipidemia, Diabetes mellitus type-1 and 2, Hypercholesterolaemia, dyslipidemia, and combinations thereof.

In some embodiments, a therapeutic polypeptide as described herein can be used for treatment and/or detection of a genetic disorder like Haemophilia A and B, Prader-Willi syndrome, Turner syndrome, Cryopyrin-Associated Periodic Syndromes (CAPS), Muckle-Wells Syndrome (MWS), X-linked hypophosphatemia, Sickle-cell pain crisis, and combinations thereof.

In some embodiments, a therapeutic polypeptide as described herein can be used for treatment and/or detection of a bone-related ailment like Osteoporosis, aplastic anaemia, and combinations thereof.

In some embodiments, a therapeutic polypeptide as described herein can be used for treatment and/or detection of other disorders including removal of venom; Alzheimer's disease, Back pain (Sciatic nerve pain), Migraine, Atopic dermatitis, Duchenne muscular dystrophy, Hepatic fibrosis, Cystic Fibrosis, *Pseudomonas aeruginosa* Infections, Ventilator-associated pneumonia, and combinations thereof.

In various embodiments, the present disclosure provides a method of producing a formulation as described herein, including, e.g., steps of (1) preparing a core including an amorphous polypeptide composition or a crystallized polypeptide composition, and (2) placing the core in a pharmaceutically acceptable shell. In various embodiments, the present disclosure provides a method of producing a tablet formulation for oral delivery, the method including mixing (i) a crystallized polypeptide composition or an amorphous polypeptide composition with (ii) a pharmaceutically acceptable carrier. In various embodiments, the present disclosure provides a method of producing a globule formulation for oral delivery, the method including mixing (i) a crystallized polypeptide composition or an amorphous polypeptide composition with (ii) a pharmaceutically acceptable carrier. In various embodiments, the present disclosure provides a method of producing a candy formulation for oral delivery, the method including mixing (i) a crystallized polypeptide composition or an amorphous polypeptide composition with (ii) a pharmaceutically acceptable carrier. In various embodiments, the present disclosure provides a method of producing a formulation as described herein, including, e.g., steps of (1) crystallizing a polypeptide to produce an amorphous polypeptide composition or a crystallized polypeptide composition; (2) preparing a core including the crystalized polypeptide or amorphous polypeptide composition, and (3) placing the core in a pharmaceutically acceptable shell.

EXAMPLES

The following Examples demonstrate methods and compositions for oral administration of polypeptides that include a polypeptide and a pharmaceutically acceptable carrier. The following Examples further demonstrate advantages of oral formulations as described herein including improved half-life and bioavailability (e.g., faster onset of action), even achieving oral bioavailability that is at least about 1% or more (e.g., at least about 5%, or even 10% or more) of that observed when the active polypeptide is administered by injection.

Among other things, the present Examples provide various polypeptide formulations and testing of polypeptide formulations useful for buccal/sublingual administration.

Still further, present Examples confirm that formulations and methods as described herein can be applicable to a wide range of polypeptides with different characteristics. Formulations and methods comprising a wide range of polypeptides each provide improved half-life and bioavailability. For example, the present Examples demonstrate that formulations comprising polypeptides across a broad range of molecular weight, e.g., from about 4 K Da to about 22 K Da, (insulin MW: 5808 Da, Lantus MW: 6063 Da, PTH MW: 4114 Da, hGH MW: 22,124.76 Da) each provided greater than 7% bioavailability when compared to SC or IV administration.

Furthermore, present Examples confirm that provided technologies successfully formulate different forms or variants of the same polypeptide agent. For example, Examples 9-11 document application of provided technologies to different forms of insulin (i.e., natural insulin to Lantus). As can be seen, provided technologies achieve improved bioavailability notwithstanding the structural change from insulin to Lantus, which shifts the isoelectric point from a pH of 5.4 to 6.7, making Lantus more soluble at an acidic pH than insulin.

Additionally, present Examples confirm that formulations provided herein are applicable not only to water soluble polypeptides, e.g., PTH, but also to polypeptides that are less water soluble, e.g., insulin and Lantus, and polypeptides that need binding to cell receptors to cross cell membranes.

The present Examples utilize batch crystallization to produce crystallized polypeptide compositions. As those of skill in the art will appreciate from the present disclosure that the specific production method, size, size distribution, shape, and shape distribution of crystals is not an essential feature for the successful formulation of polypeptides in accordance with the methods and compositions provided herein. The present Examples expressly demonstrate that oral formulations as described herein can be advantageously produced.

Example 1: Production of Cane Sugar/Palm Sugar Truffle Shells

In order to deliver the peptide/protein through buccal or sublingual route to systemic circulation, the peptide/protein were enclosed in sugar truffles or globules. The sugar truffles or globules, which are commercially available, are made up of 100% cane sugar. Sugar truffles or globules, grade 60 (SBL Quality Globules, India), which are pharmaceutical grade, were taken and drilled to make a hole in order to produce truffle shells (FIG. 1). A known amount of peptide/protein were weighed and transferred to these shells and then sealed using palm sugar in order to create a perfect sugar truffle or globule. The shells were able to hold up to 5 mg of protein/peptide. Now, the protein/peptide were inside the shell covered with sugar.

Truffles or globules work as a vehicle to transfer the peptide/protein to systemic circulation. Sugar truffles or globules do not alter the properties of drug substances. Due to their readily soluble nature, they are easy to administer in any age group. Commercial truffles or globules are available in different sizes. Their sizes are denoted in No., which start with No. 10, 20, 30, 40, etc. The diameter of size no. 10 measures 1 mm, of no. 20 measures 2 mm, and so on. So, the size of the sugar truffle shell can be altered in order to fit different amount of peptide/protein.

Alternatively, instead of cane sugar, either lactose or xylitol or milk sugar can be used in the preparation of sugar globules/truffle shells. Cocoa truffle shells—such as 100% dark chocolate or Callebaut®'s caramelly and creamy milk chocolate, Callebaut's creamy white chocolate or any other truffle shells can also be used to prepare the peptide/protein containing shells or tablets.

Example 2: Crystallization of Insulin

The present Example demonstrates formation of crystallized insulin for use in an oral formulation as disclosed herein. Humulin® R is a peptide/protein hormone structurally identical to human insulin synthesized through rDNA technology in a non-disease-producing laboratory strain of *Escherichia coli* bacteria. Humulin® R is indicated as an adjunct to diet and exercise to improve glycemic control in adults and children with type 1 and type 2 diabetes mellitus. Humulin®, when used subcutaneously, is usually given three or more times daily before meals. The present Example includes the recognition that insulin is exemplary of peptide/proteins for which an oral formulation would be advantageous.

The present Example utilizes Humulin® R (insulin (human recombinant)) U-100 (100 units per mL). To produce insulin microparticles, Insulin (Sigma Chemical Company) was desalted using 0.01N NaOH as follows. 62 mg of insulin dissolved in 4 mL of 0.01N HCl, pH 2.0. The pH of the peptide/protein solution was increased by adding 10 uL of 0.1N NaOH each time until peptide/protein is precipitated. The precipitated peptide/protein was collected and washed twice in 5 mL of water, each time collecting the water separately. To the collected water 0.1N NaOH was added to collect the dissolved peptide/protein from water. Finally all precipitate was dissolved in 1 mL of 0.01N HCl. Insulin aliquots were then crystalized using a variety of methods described below.

Crystallization Method 1: A 500 μL aliquot of Insulin (~62 mg/mL), in water was mixed with 1000 μL of reagent containing 40% (v/v) PEG 300, 100 mM sodium cacodylate/hydrochloric acid (pH 6.5), 200 mM calcium acetate, and incubated at room temperature overnight. The final concentration of the insulin in solution was 15.5 mg/mL. This mixture was then mixed using a votex and left at room temperature. Insulin microparticles were obtained on the following day. See FIG. 2. 90% of the input Insulin was formed microparticles by this method.

Crystallization Method 2: A 500 μL aliquot of insulin (~62 mg/mL), in water was mixed with 1000 μL of reagent containing 40% (v/v) PEG 600, 100 mM sodium cacodylate/hydrochloric acid (pH 6.5), 200 mM calcium acetate, and incubated at room temperature overnight. The final concentration of the insulin in solution was 15.5 mg/mL. This mixture was then mixed using a votex and left at room temperature. Insulin microparticles were obtained on the following day. See FIG. 3. 90% of the input Insulin was formed microparticles by this method.

Crystallization Method 3: A 500 μL aliquot of insulin (~62 mg/mL), in water was mixed with 1000 μL of reagent containing 40% (v/v) 1,2-propanediol, 100 mM sodium acetate/acetic acid (pH 4.5), 50 mM calcium acetate, and incubated at room temperature overnight. The final concentration of the insulin in solution was 15.5 mg/mL. This mixture was then mixed using a votex and left at room temperature. Insulin microparticles were obtained on the following day. See FIG. 4. 90% of the input Insulin was formed microparticles by this method.

Crystallization Method 4: A 500 μL aliquot of insulin (~62 mg/mL), in water was mixed with 1000 μL of reagent containing 14.4% (w/v) PEG 8000, 80 mM sodium cacodylate/hydrochloric acid (pH 6.5), 160 mM calcium acetate, 20% (v/v) glycerol, and incubated at room temperature overnight. The final concentration of the insulin in solution was 15.5 mg/mL. This mixture was then mixed using a votex and left at room temperature. Insulin microparticles were obtained on the following day. See FIG. 5. 90% of the input Insulin was formed microparticles by this method.

Crystallization Method 5: A 500 μL aliquot of insulin (~62 mg/mL), in water was mixed with 1000 μL of reagent containing 20% (w/v) PEG 3000, 100 mM tris base/hydrochloric acid (pH 7.0), 200 mM Calcium acetate, and incubated at room temperature overnight. The final concentration of the insulin in solution was 15.5 mg/mL. This mixture was then mixed using a votex and left at room temperature. Insulin microparticles were obtained on the following day. See FIG. 6. 90% of the input Insulin was formed microparticles by this method.

Crystallization Method 6: A 500 μL aliquot of insulin (~62 mg/mL), in water was mixed with 1000 μL of reagent containing 20% (w/v) PEG 1000, 100 mM sodium cacodylate/hydrochloric acid (pH 6.5), 200 mM Magnesium chloride, and incubated at room temperature overnight. The final concentration of the insulin in solution was 15.5 mg/mL. This mixture was then mixed using a votex and left at room temperature. Insulin microparticles were obtained on the following day. See FIG. 7. 90% of the input Insulin was formed microparticles by this method.

Crystallization Method 7: A 500 μL aliquot of insulin (~62 mg/mL), in water was mixed with 1000 μL of reagent containing 10% (v/v) 2-propanol, 100 mM MES/sodium hydroxide (pH 6.0), 200 mM calcium acetate, and incubated at room temperature overnight. The final concentration of the insulin in solution was 15.5 mg/mL. This mixture was then mixed using a votex and left at room temperature. Insulin microparticles were obtained on the following day. See FIG. 8. 90% of the input Insulin was formed microparticles by this method.

Crystallization Method 8: A 500 μL aliquot of Insulin regular (Huminsulin-R) 100 IU/mL was mixed with 1000 μL of reagent containing 40% v/v Reagent alcohol, 10 mM tris base/HCl (pH 8.5), 50 mM magnesium chloride and left at room temperature. Cube shaped Insulin microparticles started appearing after 2-3 minutes of the set up. This mixture was then mixed using a votex and left at room temperature. Insulin microparticles were obtained on the following day See FIG. 9. 90% of the input Insulin was formed microparticles by this method.

Example 3: Crystallization of Lantus/Insulin Glargine

The present Example demonstrates formation of crystallized Lantus/insulin glargine for use in an oral formulation as disclosed herein. Insulin glargine is a synthetic version of human insulin that is FDA approved to treat adults and children with type 1 diabetes and adults with type 2 diabetes to improve and maintain glycemic control. Insulin glargine is a long-acting insulin injected once daily and provides a basal insulin level throughout the day. Insulin glargine has an onset of action of 1.5 to 2 hours. It has a long duration of action of up to 24 hours due to modifications of amino acids, including Asn to Gly at position 21 of the A chain and the addition of two Arg residues and positions 31 and 32 of the B chain. This arrangement allows the insulin to remain soluble at a pH of 4.0, which is the pH of the solution in which it is administered, and then become insoluble at physiologic pH. Once insulin glargine is injected into the body and introduced to the higher pH, the insoluble precipitate that forms slowly releases soluble protein over 24 hours. The present Example includes the recognition that Lantus/insulin glargine is exemplary of peptide/proteins for which an oral formulation would be advantageous.

The present Example utilizes insulin glargine (Lantus) (100 units per mL). To produce insulin glargine microparticles, the insulin glargine was treated as follows. About 1500 of insulin glargine (Lantus)-100 IU/mL was added to 100 μL of 1M sodium phosphate buffer, pH 6. The solution was mixed and Incubated for 2 minutes. The solution was then centrifuged for 30-60 sec at 10000×g and the supernatant was discarded. The pellet was then washed with 1500 μL of 10 mM sodium phosphate buffer, pH 6, and centrifuged again to separate the precipitate. The procedure was repeated for 2-3 times. The precipitate was then dissolved in 0.1N HCl such that the final protein concentration was 12.5 mg/mL. [Extinction co-efficient is 1.0675]. The solution was then filtered through 0.22 micron syringe filters. After filtration an equal volume of crystallization reagent containing 1M ammonium chloride in 1M sodium carbonate buffer, pH 10.5 was added and left at room temperature. Hexagonal shaped Insulin microparticles started appearing after 2-3 minutes of the set up. See FIG. 10. The crystals were then stored at 4° C. until use.

Example 4: Crystallization of PTH

The present Example demonstrates formation of crystallized PTH (1-34) for use in an oral formulation as disclosed herein. Teriparatide injection is a recombinant human parathyroid hormone analog (PTH 1-34). It has an identical sequence to the 34 N-terminal amino acids (the biologically active region) of the 84-amino acid human parathyroid hormone. Teriparatide injection is a recombinant version of parathyroid hormone used to treat men and postmenopausal women who have severe osteoporosis with a high risk of fractures. It works by stimulating new bone formation, which improves bone density and decreases the risk of spinal fractures. Teriparatide has a molecular weight of 4117.8 daltons.

Teriparatide is supplied as a sterile, colorless, clear, isotonic solution in a glass cartridge which is pre-assembled into a disposable delivery device (pen) for subcutaneous injection. Each prefilled delivery device is filled with 2.7 mL to deliver 3 mL. Each mL contains 250 mcg teriparatide (corrected for acetate, chloride, and water content), 0.41 mg glacial acetic acid, 0.1 mg sodium acetate (anhydrous), 45.4 mg mannitol, 3 mg meta cresol, and water for injection. In addition, hydrochloric acid solution 10% and/or sodium hydroxide solution 10% may have been added to adjust the product to pH 4. The present Example includes the recognition that PTH (1-34) is exemplary of peptide/proteins for which an oral formulation would be advantageous.

The present Example utilizes PTH (1-34). To produce PTH microparticles, PTH was dialyzed against water for 24 hours with three changes and lyophilized to get dry powder. The lyophilized powder of PTH was then dissolved in water at a concentration of 80 mg/mL. PTH aliquots were then crystalized using a variety of methods described below.

Crystallization Method 1: A 500 μL aliquot of PTH (80 mg/mL), in water was mixed with 1000 μL of reagent containing 2500 mM sodium chloride, 100 mM imidazole/hydrochloric acid (pH 8.0), and incubated at room temperature overnight. The final concentration of the PTH in solution was 26.67 mg/mL. This mixture was then mixed using a votex and left at room temperature. PTH microparticles were obtained on the following day. See FIG. 11. 90% of the input PTH was formed microparticles by this method.

Crystallization Method 2: A 500 μL aliquot of PTH (80 mg/mL), in water was mixed with 1000 μL of reagent containing 35% (v/v) MPD, 100 mM MES/sodium hydroxide (pH 6.0), 200 mM lithium sulfate, and incubated at room temperature overnight. The final concentration of the PTH in solution was 26.67 mg/mL. This mixture was then mixed using a votex and left at room temperature. PTH microparticles were obtained on the following day. See FIG. 12. 80% of the input PTH was formed microparticles by this method.

Crystallization Method 3: A 500 μL aliquot of PTH (80 mg/mL), in water was mixed with 1000 μL of reagent containing 2500 mM Sodium chloride, 100 mM tris base/hydrochloric acid pH 7.0, 200 mM magnesium chloride, and incubated at room temperature overnight. The final concentration of the PTH in solution was 26.67 mg/mL. This mixture was then mixed using a votex and left at room temperature. PTH microparticles were obtained on the following day. See FIG. 13. 85% of the input PTH was formed microparticles by this method.

Crystallization Method 4: A 500 μL aliquot of PTH (80 mg/mL), in water was mixed with 1000 μL of reagent containing 2.68M Sodium chloride, 3.35% (v/v) isopropanol, 0.1M HEPES/sodium hydroxide (pH 7.5), and incubated at room temperature overnight. The final concentration of the PTH in solution was 26.67 mg/mL. This mixture was then mixed using a votex and left at room temperature. PTH microparticles were obtained on the following day. See FIG. 14. 80% of the input PTH was formed microparticles by this method.

Crystallization Method 5: A 500 μL aliquot of PTH (80 mg/mL), in water was mixed with 1000 μL of reagent containing 1.7M lithium sulfate, 6.8% (v/v) MPD, 0.085M Imidazole/hydrochloric acid (pH 6.5), and incubated at room temperature overnight. The final concentration of the PTH in solution was 26.67 mg/mL. This mixture was then mixed using a votex and left at room temperature. PTH microparticles were obtained on the following day. See FIG. 15. 70% of the input PTH was formed microparticles by this method.

Crystallization Method 6: A 500 μL aliquot of PTH (80 mg/mL), in water was mixed with 1000 μL of reagent containing 1.5M Ammonium sulfate, 12% (v/v) isopropanol, 0.1M Imidazole/hydrochloric acid (pH 6.5), and incubated at room temperature overnight. The final concentration of the PTH in solution was 26.67 mg/mL. This mixture was then mixed using a votex and left at room temperature. PTH microparticles were obtained on the following day. See FIG. 16. 85% of the input PTH was formed microparticles by this method.

Crystallization Method 7: A 500 μL aliquot of PTH (80 mg/mL), in water was mixed with 1000 μL of reagent containing 30% (v/v) isopropanol, 30% (w/v) PEG 3350, 0.1M tris base/hydrochloric acid pH 8.5, and incubated at room temperature overnight. The final concentration of the PTH in solution was 26.67 mg/mL. This mixture was then mixed using a votex and left at room temperature. PTH microparticles were obtained on the following day. See FIG. 17. 80% of the input PTH was formed microparticles by this method.

Crystallization Method 8: A 500 μL aliquot of PTH (80 mg/mL), in water was mixed with 1000 μL of reagent containing 3.0M sodium formate, 4% (w/v) PEG 8000, 0.1M imidazole/hydrochloric acid pH 6.5, and incubated at room temperature overnight. The final concentration of the PTH in solution was 26.67 mg/mL. This mixture was then mixed using a votex and left at room temperature. PTH microparticles were obtained on the following day. See FIG. 18. 90% of the input PTH was formed microparticles by this method.

Crystallization Method 9: A 500 μL aliquot of PTH (80 mg/mL), in water was mixed with 1000 μL of reagent containing 2.0M sodium chloride, 5% (w/v) PEG 4000, 0.1M tris base/hydrochloric acid (pH 8.5), and incubated at room temperature overnight. The final concentration of the PTH in solution was 26.67 mg/mL. This mixture was then mixed using a votex and left at room temperature. PTH microparticles were obtained on the following day. See FIG. 19. 85% of the input PTH was formed microparticles by this method.

Crystallization Method 10: A 133 μL aliquot of PTH (70 mg/mL), in water was mixed with 50 μL of 1M HEPES buffer pH 7.5/7.7, 300 μL of 5M NaCl, 15 μL of 100% IPA and incubated at room temperature overnight. The final concentration of the PTH in solution was 18 mg/mL. This mixture was then mixed using a votex and left at room temperature. PTH microparticles were obtained on the following day. See FIG. 20. 85% of the input PTH was formed microparticles by this method.

Example 5: Crystallization of Liraglutide

The present Example demonstrates formation of crystallized liraglutide for use in an oral formulation as disclosed herein. Liraglutide is marketed under the brand name Victoza® (Novo Nordisk). Liraglutide is a synthetic analog of human glucagon-like peptide-1 (GLP-1) produced using recombinant technology and acts as a GLP-1 receptor agonist. Liraglutide is 97% homologous to native human GLP-1, substituting arginine for lysine at position 34. Liraglutide includes a C-16 fatty acid (palmitic acid) with a glutamic acid spacer on the remaining lysine residue at position 26 of the peptide precursor. Liraglutide's therapeutic effects including increasing insulin release from the pancreas and decreasing excessive glucagon release. The present Example includes the recognition that liraglutide is exemplary of peptide/proteins for which an oral formulation would be advantageous.

Liraglutide half-life is an important consideration in therapeutic use. Endogenous GLP-1 has a plasma half-life of 1.5-2 minutes due to degradation by the ubiquitous enzymes, dipeptidyl peptidase-4 (DPP4) and neutral endopeptidase (NEP). The half-life after intramuscular injection is approximately half an hour, so even administered this way, it has limited use as a therapeutic agent. The metabolically active forms of GLP-1 are the endogenous GLP-1-(7-36)NH2 and the more rare GLP-1-(7-37). Prolonged action of liraglutide is achieved by attaching a fatty acid molecule at one position of the GLP-1-(7-37) molecule, enabling it to both self-associate and bind to albumin. The active GLP-1 is then released from albumin at a slow, consistent rate.

For use in the present Example, liraglutide was acquired as VICTOZA, a clear, colorless or almost colorless solution. Each 1 mL of VICTOZA solution contains 6 mg of liraglutide and the following inactive ingredients: disodium phosphate dihydrate, 1.42 mg; propylene glycol, 14 mg; phenol, 5.5 mg; and water for injection. Each pre-filled pen contains a 3 mL solution of VICTOZA equivalent to 18 mg liraglutide (free-base, anhydrous).

To produce liraglutide microparticles, liraglutide was dialyzed against water for 24 hours with three changes and lyophilized to get dry powder. The lyophilized powder of liraglutide was then dissolved in water at a concentration of 80 mg/mL. Liraglutide aliquots were then crystalized using a variety of methods described below.

Crystallization Method 1: A 500 μL aliquot of liraglutide (80 mg/mL), in water was mixed with 1000 μL of reagent containing 1.34 M ammonium sulfate, 3.35% (v/v) PEG 400, 0.05M magnesium sulfate, 0.1M tris base/hydrochloric acid (pH 8.5), and incubated at room temperature overnight. The final concentration of the liraglutide in solution was 26.67 mg/mL. This mixture was then mixed using a votex and left at room temperature. Liraglutide microparticles were obtained on the following day. See FIG. 21. 75% of the input liraglutide was formed microparticles by this method.

Crystallization Method 2: A 500 μL aliquot of liraglutide (80 mg/mL), in water was mixed with 1000 μL of reagent containing 35% (v/v) MPD, 100 mM tris base/hydrochloric acid pH 7.0, 200 mM sodium chloride, and incubated at room temperature overnight. The final concentration of the liraglutide in solution was 26.67 mg/mL. This mixture was then mixed using a votex and left at room temperature. Liraglutide microparticles were obtained on the following day. See FIG. 22. 85% of the input liraglutide was formed microparticles by this method.

Crystallization Method 3: A 500 μL aliquot of liraglutide (80 mg/mL), in water was mixed with 1000 μL of reagent containing 1000 mM Ammonium phosphate dibasic 100 mM sodium citrate/citric acid pH 5.5, 200 mM sodium chloride, and incubated at room temperature overnight. The final concentration of the liraglutide in solution was 26.67 mg/mL. This mixture was then mixed using a votex and left at room temperature. Liraglutide microparticles were obtained on the following day. See FIG. 23. 90% of the input liraglutide was formed microparticles by this method.

Crystallization Method 4: A 500 μL aliquot of liraglutide (80 mg/mL), in water was mixed with 1000 μL of reagent containing 25% (w/v) PEG 1500, 100 mM SPG buffer (pH 8.5), and incubated at room temperature overnight. The final concentration of the liraglutide in solution was 26.67 mg/mL. This mixture was then mixed using a votex and left at room temperature. Liraglutide microparticles were obtained on the following day. See FIG. 24. 85% of the input liraglutide was formed microparticles by this method.

Crystallization Method 5: A 500 μL aliquot of Liraglutide (80 mg/mL), in water was mixed with 1000 μL of reagent containing 40% (v/v) ethylene glycol, 100 mM MES/sodium hydroxide pH 6.0, 200 mM zinc acetate, and incubated at room temperature overnight. The final concentration of the liraglutide in solution was 26.67 mg/mL. This mixture was then mixed using a votex and left at room temperature. Liraglutide microparticles were obtained on the following day. See FIG. 25. 75% of the input liraglutide was formed microparticles by this method.

Crystallization Method 6: A 500 μL aliquot of liraglutide (80 mg/mL), in water was mixed with 1000 μL of reagent containing 3M sodium chloride, 5% (v/v) MPD, 0.1M calcium chloride, 0.1M imidazole/hydrochloric acid (pH 6.5), and incubated at room temperature overnight. The final concentration of the liraglutide in solution was 26.67 mg/mL. This mixture was then mixed using a votex and left at room temperature. Liraglutide microparticles were obtained on the following day. See FIG. 26. 80% of the input liraglutide was formed microparticles by this method.

Crystallization Method 7: A 500 μL aliquot of liraglutide (80 mg/mL), in water was mixed with 1000 μL of reagent containing 0.429 M sodium chloride, 9.9% (v/v) isopropanol, 0.1M calcium chloride, 0.1M imidazole/hydrochloric acid pH 6.5, and incubated at room temperature overnight. The final concentration of the liraglutide in solution was 26.67 mg/mL. This mixture was then mixed using a votex and left at room temperature. Liraglutide microparticles were obtained on the following day. See FIG. 27. 70% of the input liraglutide was formed microparticles by this method.

Crystallization Method 8: A 500 μL aliquot of liraglutide (80 mg/mL), in water was mixed with 1000 μL of reagent containing 5.36% (v/v) MPD, 0.67M potassium phosphate dibasic/sodium phosphate monobasic pH 8.5, and incubated at room temperature overnight. The final concentration of the liraglutide in solution was 26.67 mg/mL. This mixture was then mixed using a votex and left at room temperature. Liraglutide microparticles were obtained on the following day. See FIG. 28. 85% of the input liraglutide was formed microparticles by this method.

Crystallization Method 9: A 500 μL aliquot of liraglutide (80 mg/mL), in water was mixed with 500 μL of reagent containing 4M sodium chloride, 5% (v/v) IPA, 0.1M HEPES/sodium hydroxide (pH 7.5), and incubated at room temperature overnight. The final concentration of the liraglutide in solution was 40 mg/mL. This mixture was then mixed using a votex and left at room temperature. Liraglutide microparticles were obtained on the following day. See FIG. 29. 85% of the input liraglutide was formed microparticles by this method.

Example 6: Crystallization of Octreotide Acetate

The present Example demonstrates formation of crystallized octreotide acetate for use in an oral formulation as disclosed herein. Octreotide is the acetate salt of a synthetic long-acting cyclic octapeptide with pharmacologic properties mimicking those of the natural hormone somatostatin. Octreotide is a more potent inhibitor of growth hormone, glucagon, and insulin than somatostatin. Octreotide is a peptide drug used to treat acromegaly as well as diarrhea associated with metastatic carcinoid tumors and vasoactive intestinal peptide secreting tumors. Sandostatin® is given by subcutaneous injection, usually 2 to 3 times per day. The present Example includes the recognition that insulin is exemplary of peptide/proteins for which an oral formulation would be advantageous.

The present Example utilizes commercially available octreotide acetate (Hemmo Pharmaceuticals, Pvt. Ltd., Thane, India), a lyophilized material. To produce octreotide microparticles, octreotide was dissolved in HPLC water. Octreotide aliquots were then crystalized using a variety of methods described below.

Crystallization Method 1: A 500 μL aliquot of octreotide acetate (~57 mg/mL) in water was mixed with 1000 μL of reagent containing 1600 mM sodium phosphate monobasic/400 mM potassium phosphate dibasic in a buffer of 100 mM sodium phosphate dibasic/citric acid pH 4.2 and incubated at room temperature. The final concentration of the octreotide in solution was 19 mg/mL. This mixture was then mixed using a votex mixer and left at room temperature. Needle shaped crystals were obtained within 2 days of the set up. See FIG. 30. Greater than 90% of the input Octreotide was formed microcrystals by this method.

Crystallization Method 2: A 500 μL aliquot of octreotide acetate (~57 mg/mL) in water was mixed with 1000 μL of reagent containing 1200 mM sodium phosphate monobasic/800 mM potassium phosphate dibasic in a buffer of 100 mM CAPS/sodium hydroxide (pH 10.5) containing 200 mM lithium sulfate and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 31. Greater than 90% of the input octreotide was formed microcrystals by this method.

Crystallization Method 3: A 500 μL aliquot of octreotide acetate (~57 mg/mL) in water was mixed with 1000 μL of reagent containing 2% (v/v) PEG 400 in a buffer of 100 mM sodium acetate/acetic acid (pH 5.5) containing 2000 mM ammonium sulfate and incubated overnight at room temperature. The final concentration of the octreotide in solution was 19 mg/mL. This mixture was then mixed using a votex mixer and left at room temperature. Broomstick shaped crystals are obtained within 2 days of the set up. See FIG. 32. Greater than 90% of the input Octreotide was formed microcrystals by this method.

Crystallization Method 4: A 500 μL aliquot of octreotide acetate (~57 mg/mL) in water was mixed with 1000 μL of reagent containing 2% (v/v) PEG 400, 2 M potassium phosphate dibasic/sodium phosphate monobasic pH 6.5 and incubated overnight at room temperature. The final concentration of the octreotide in solution was 19 mg/mL. This mixture was then mixed using a votex mixer and left at room temperature. Broomstick shaped crystals are obtained within 2 days of the set up. See FIG. 33. Greater than 90% of the input octreotide was formed microcrystals by this method.

Crystallization Method 5: A 500 μL aliquot of octreotide acetate (~57 mg/mL) in water was mixed with 1000 μL of reagent containing 1.34% (v/v) PEG 400, 1.34 M potassium phosphate dibasic/sodium phosphate monobasic (pH 6.5) and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 34. Greater than 80% of the input octreotide was formed microcrystals by this method.

Crystallization Method 6: A 500 μL aliquot of octreotide acetate (~57 mg/mL) in water was mixed with 1000 μL of reagent containing 5% (v/v) isopropanol, 2.5 M potassium phosphate dibasic/sodium phosphate monobasic (pH 5.5) and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 35. Greater than 60% of the input octreotide was formed microcrystals by this method.

Crystallization Method 7: A 500 μL aliquot of octreotide acetate (~57 mg/mL) in water was mixed with 1000 μL of reagent containing 3.35% (v/v) isopropanol, 1.675 M potassium phosphate dibasic/sodium phosphate monobasic pH 5.5 and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 36. Greater than 70% of the input Octreotide was formed microcrystals by this method.

Crystallization Method 8: A 500 μL aliquot of Octreotide acetate (~57 mg/mL) in water was mixed with 1000 μL of reagent containing 0.67% (v/v) PEG 4000, 0.67 M ammonium citrate/citric acid (pH 5.5) and incubated overnight at room temperature. The final concentration of the octreotide in solution was 19 mg/mL. This mixture was then mixed using a votex mixer and left at room temperature. Long needle shaped crystals are obtained within 2 days of the set up. See FIG. 37. Greater than 70% of the input octreotide was formed microcrystals by this method.

Crystallization Method 9: A 500 μL aliquot of Octreotide acetate (~57 mg/mL) in water was mixed with 1000 μL of reagent containing 0.5% (v/v) PEG 4000, 1M potassium phosphate dibasic/sodium phosphate monobasic (pH 7.5) and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 38. Greater than 60% of the input octreotide was formed microcrystals by this method.

Crystallization Method 10: A 500 μL aliquot of octreotide acetate (~57 mg/mL) in water was mixed with 1000 μL of reagent containing 0.34% (v/v) PEG 4000, 0.67M potassium phosphate dibasic/sodium phosphate monobasic pH 7.5 and incubated overnight at room temperature. The final concentration of the octreotide in solution was 19 mg/mL. This mixture was then mixed using a votex mixer and left at room temperature. Circular spike shaped crystals are obtained within 2 days of the set up. See FIG. 39. Greater than 70% of the input octreotide was formed microcrystals by this method.

Crystallization Method 11: A 500 μL aliquot of Octreotide acetate (~57 mg/mL) in water was mixed with 1000 μL of reagent containing 2M Sodium chloride, 5% (v/v) PEG 4000, 0.1M tris base/hydrochloric acid (pH 8.5) and incubated overnight at room temperature. The final concentration of the octreotide in solution was 19 mg/mL. This mixture was then mixed using a votex mixer and left at room temperature. Circular spike shaped crystals are obtained within 2 days of the set up. See FIG. 40. Greater than 60% of the input octreotide was formed microcrystals by this method.

Crystallization Method 12: A 500 μL aliquot of octreotide acetate (~57 mg/mL) in water was mixed with 1000 μL of reagent containing 2000 mM ammonium sulfate, 100 mM CAPS/sodium hydroxide pH 10.5, 200 mM lithium sulfate and incubated overnight at room temperature. The final concentration of the octreotide in solution was 19 mg/mL. This mixture was then mixed using a votex mixer and left at room temperature. Long needle shaped crystals are obtained within 2 days of the set up. See FIG. 41. Greater than 80% of the input octreotide was formed microcrystals by this method.

Crystallization Method 13: A 500 μL aliquot of octreotide acetate (~57 mg/mL) in water was mixed with 1000 μL of reagent containing 40% (v/v) PEG 400, 100 mM tris base/hydrochloric acid (pH 8.5), 200 mM lithium sulfate and incubated overnight at room temperature. The final concentration of the octreotide in solution was 19 mg/mL. This mixture was then mixed using a votex mixer and left at room temperature. Long needle shaped crystals are obtained within 2 days of the set up. See FIG. 42. Greater than 80% of the input octreotide was formed microcrystals by this method.

Crystallization Method 14: A 500 μL aliquot of octreotide acetate (~57 mg/mL) in water was mixed with 1000 μL of reagent containing 20% (w/v) polyacrylic acid 5100, 100 mM HEPES/sodium hydroxide (pH 7.0), 20 mM magnesium chloride and incubated overnight at room temperature. The final concentration of the octreotide in solution was 19 mg/mL. This mixture was then mixed using a votex mixer and left at room temperature. Circular spike shaped crystals are obtained within 2 days of the set up. See FIG. 43. Greater than 70% of the input Octreotide was formed microcrystals by this method.

Crystallization Method 15: A 500 μL aliquot of octreotide acetate (~57 mg/mL) in water was mixed with 1000 μL of reagent containing 1.34 M ammonium sulfate, 6.7% (v/v) glycerol, 0.05M magnesium sulphate, 0.1M imidazole/hydrochloric acid (pH 6.5) and incubated overnight at room temperature. The final concentration of the octreotide in solution was 19 mg/mL. This mixture was then mixed using a votex mixer and left at room temperature. Rice grain shaped crystals are obtained within 2 days of the set up. See FIG. 44. Greater than 50% of the input Octreotide was formed microcrystals by this method.

Crystallization Method 16: A 500 μL aliquot of octreotide acetate (~57 mg/mL) in water was mixed with 1000 μL of reagent containing 1000 mM sodium citrate tribasic, 100 mM CHES/sodium hydroxide (pH 9.5) and incubated overnight at room temperature. The final concentration of the octreotide in solution was 19 mg/mL. This mixture was then mixed using a votex mixer and left at room temperature. Plate shaped crystals are obtained within 2 days of the set up. See FIG. 45. Greater than 60% of the input Octreotide was formed microcrystals by this method.

Crystallization Method 17: A 500 μL aliquot of Octreotide acetate (~57 mg/mL) in water was mixed with 1000 μL of reagent containing 800 mM potassium phosphate dibasic, 100 mM HEPES/sodium hydroxide (pH 7.5), 800 mM sodium phosphate monobasic and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 46. Greater than 80% of the input Octreotide was formed microcrystals by this method.

Crystallization Method 18: A 500 μL aliquot of octreotide acetate (~57 mg/mL) in water was mixed with 1000 μL of reagent containing 2000 mM ammonium sulfate, 100 mM sodium citrate/citric acid (pH 5.5) and incubated overnight at room temperature. The final concentration of the Octreotide in solution was 19 mg/mL. This mixture was then mixed using a votex mixer and left at room temperature. Needle shaped crystals are obtained within 2 days of the set up. See FIG. 47. Greater than 90% of the input Octreotide was formed microcrystals by this method.

Crystallization Method 19: A 500 μL aliquot of octreotide acetate (~57 mg/mL) in water was mixed with 1000 μL of reagent containing 1260 mM ammonium sulfate, 100 mM HEPES/sodium hydroxide (pH 7.5) and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 48. Greater than 60% of the input Octreotide was formed microcrystals by this method.

Crystallization Method 20: A 500 μL aliquot of octreotide acetate (~57 mg/mL) in water was mixed with 1000 μL of reagent containing 2000 mM ammonium sulfate, 100 mM sodium acetate/hydrochloric acid pH 4.6 and incubated overnight at room temperature. The final concentration of the octreotide in solution was 19 mg/mL. This mixture was then mixed using a votex mixer and left at room temperature. Needle shaped crystals are obtained within 2 days of the set up. See FIG. 49. Greater than 80% of the input Octreotide was formed microcrystals by this method.

Crystallization Method 21: A 500 μL aliquot of octreotide acetate (~57 mg/mL) in water was mixed with 1000 μL of reagent containing 1.34M ammonium sulfate, 1.34% (v/v) PEG 400, 100 mM sodium acetate/acetic acid (pH 5.5) and incubated overnight at room temperature. The final concentration of the octreotide in solution was 19 mg/mL. This mixture was then mixed using a votex mixer and left at room temperature. Flower shaped crystals are obtained within 2 days of the set up. See FIG. 50. Greater than 70% of the input Octreotide was formed microcrystals by this method.

Example 7: Crystallization of Trastuzumab

The present Example demonstrates formation of crystallized trastuzumab for use in an oral formulation as disclosed herein. Trastuzumab is a humanized monoclonal antibody commercially available as Herclon® (Roche). Trastuzumab is an IgG1 kappa antibody that contains human framework regions with the complementarity-determining regions of a murine antibody (4D5) that binds with HER2. Trastuzumab has been widely used to treat breast cancer which overexpresses the extracellular domain of the epidermal growth factor receptor 2 protein, HER2. The present Example includes the recognition that trastuzumab is exemplary of peptide/proteins for which an oral formulation would be advantageous.

Trastuzumab antibody was stored in its original 440 mg vial as a sterile lyophilized powder and was subsequently dissolved in 5 mL of sterile water. The dissolved trastuzumab solution, containing 88 mg/mL trastuzumab, 39.6 mg L-histidine HCl, 25.6 mg L-histidine, 1600 mg α,α-trehalose dihydrate, and 7.2 mg polysorbate 20, USP.

To produce trastuzumab microparticles, a 500 μL aliquot of trastuzumab (88 mg/mL), in a buffer containing 3.96 mg/mL L-histidine HCl, 2.56 mg/mL L-histidine, 160 mg/mL α,α-trehalose dihydrate, and 0.72 mg/mL polysorbate 20, USP, was mixed with 1000 μL of reagent containing 20% PEG 300, 10% PEG 8000, 10% glycerol, 100 mM tris, (pH 8.5), and incubated at room temperature overnight. The final concentration of the trastuzumab in solution was 29.33 mg/mL. This mixture was then mixed using a votex and left at room temperature. Trastuzumab microparticles were obtained on the following day. See FIGS. 51 & 52. 95% of the input Trastuzumab was formed microparticles by this method.

Example 8: Crystallization of Human Growth Hormone

The present Example demonstrates formation of crystallized human growth hormone for use in an oral formulation as disclosed herein. Norditropin NordiFlex® R is a peptide/protein hormone structurally identical to human growth hormone synthesized through rDNA technology. Norditropin NordiFlex® R Injection acts as a replacement for growth hormone, and helps restore normal growth and development of bones and muscles in individuals suffering from growth hormone deficiency. It helps children grow taller and also enables muscle growth in both children as well as adults. The present Example includes the recognition that human growth hormone is exemplary of peptide/proteins for which an oral formulation would be advantageous.

The present Example utilizes Norditropin NordiFlex® R (human growth hormone (human recombinant)) (10 mg per mL). To produce human growth hormone microparticles, commercially available hGH (Human Growth Hormone Inj. Norditropin NordiFlex, 15 mg/1.5 mL) containing Somatropin 10 mg, mannitol 39 mg, histidine 1.1 mg, poloxamer 188 3.0 mg, phenol 3.0 mg, and water for injection in 1.0 mL with HCl and NaOH was buffer exchanged with 10 mM Tris·HCl buffer pH 8 and concentrated to 60 mg/mL using 10 kDa Vivaspin concentrator. Human growth hormone aliquots were then crystalized as described below.

Crystallization Method: To 500 μL aliquot of human growth hormone (~60 mg/mL) in 10 mM Tris·HCl buffer pH 8, Tris HCl (1 M, pH 8) was added to final concentration of 100 mM. Crystals of hGH were grown by adding calcium chloride 1M to the solution to a final concentration of 85 mM, and followed by IPA addition to a final concentration of 5% (v/v) and incubated at room temperature overnight. The final concentration of the human growth hormone in solution was 15.0 mg/mL. This mixture was then mixed using a votex and left at room temperature. Human growth hormone microparticles were obtained on the following day. See FIG. 69. 95% of the input human growth hormone was formed microparticles by this method.

Example 9: Pharmacokinetics Study of Insulin Formulation Containing/Enclosed in Sugar Truffle Shell in Minipigs The present Example demonstrates that oral formulations of insulin exemplary of oral formulations disclosed herein have therapeutically effective pharmacokinetic profiles, e.g., with advantageous properties as compared to parenteral administration of the same peptide/protein. The present example utilizes an insulin crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained Insulin regular, Humulin R (Humulin R (insulin human recombinant) U-100 is a sterile, clear, aqueous, and colorless solution that contains human insulin (rDNA origin) 100 units/mL, glycerin 16 mg/mL and meta-cresol 2.5 mg/mL, endogenous zinc (approximately 0.015 mg/100 units) and water for injection. The pH is 7.0 to 7.8. The insulin was dialyzed against water for 24 hours against water and lyophilized. The lyophilized insulin was reconstituted in dilute acid. The reconstituted insulin was then processed to prepare microparticles according to the procedure mentioned under Example 2. The microparticle insulin was then lyophilized after washing with cold isopropanol. The amount of lyophilized insulin was quantified against a reference standard using a C18 reverse phase HPLC column (gradient elution, solvent A (0.1% TFA in water, solvent B (0.1% TFA in acetonitrile)). The lyophilized insulin (dosage mentioned under Table 1) was then transferred to sugar truffle shell made from cane sugar or palm sugar. The shell was then sealed with coconut palm sugar (DEGA Farms). The samples were then stored at 4° C. until further use.

TABLE 1

Experimental Design for Pharmacokinetics Analysis

| | SC (Marketed Formulation) | Oral (Sugar Truffle Formulation) |
|---|---|---|
| No. of Minipigs (Yorkshire) 3 to 4 months old | 2 | 4 |
| Sex | Female | Female |
| Body Weight | 12 ± 1 kg | 12 ± 1 kg |
| Group | 1 | 2 |
| Test Item | Insulin | Insulin |
| Dose (mg) | 0.347 | 2.08 |
| Formulation | Liquid | Sugar Truffle Shell enclosing lyophilized Insulin |
| Route | SC (Subcutaneous) | PO (oral - Buccal/sublingual) |
| Feeding Status | Fasting overnight followed by 2 g/kg glucose solution challenge prior to test article administration | Fasting overnight followed by 2 g/kg glucose solution challenge prior to test article administration |
| Blood/plasma sample collection time | 0 min, 15 mins, 30 mins 1 hour, 2 hours, 4 hours, 8 hours, 12 hours, 24 hours and 48 hours post dose | 0 min, 15 mins, 30 mins 1 hour, 2 hours, 4 hours, 8 hours, 12 hours, 24 hours and 48 hours post dose |
| Analysis | Insulin INS ELISA kit ABBEXA | |

Pharmacokinetic analysis was conducted in Female Minipigs weighing 12±1 kg for 2 days. Experimental design is shown in Table 1. Pigs in the treatment group were fasted overnight prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 15 min, 30 min, 1 hour, 2 hours, 4 hours, 8 hours, 12 hours, 24 hours, and 48 hours into an EDTA-blood collection tubes for the separation of plasma to determine insulin levels by ELISA. Plasma samples collected at different time points were analyzed by ELISA kit according to ABBEXA protocol. This kit is based on sandwich enzyme-linked immuno-sorbent assay technology. An antibody, anti-insulin was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient INS will produce a blue colored product, which then changes to yellow after adding the acidic stop solution. The intensity of the yellow color is proportional to the INS amount bound on the plate. The Optical Density (OD) was measured spectrophotometrically at 450 nm in a microplate reader, from which the concentration of INS can be calculated.

The data in Table 2 and FIGS. 53 and 54 demonstrate average plasma concentration of Insulin at different time points. The full pharmacokinetic profile are shown in Table 3 and 4. Orally administered Insulin formulation showed 38% bioavailability when compared to SC. Insulin was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each Insulin dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t ½=ln 2/λz.

TABLE 2

Mean PK results of Human Insulin R formulations in Pigs

| Time (hours) | Subcutaneous - Human Insulin R | Buccal/Sublingual |
|---|---|---|
| 0 | 70.86 ± 9.79 | 39.8 ± 2.77 |
| 0.25 | 144.4 ± 8.22 | 329.3 ± 16.81 |
| 0.5 | 152.81 ± 9.45 | 330.95 ± 16.88 |
| 1 | 205.29 ± 15.18 | 322.62 ± 8.41 |
| 2 | 316.87 ± 12.65 | 321.48 ± 8.49 |
| 4 | 16.51 ± 3.35 | 89.61 ± 9.76 |
| 8 | 12.59 ± 1.15 | 62.58 ± 4.96 |
| 12 | 17.7 ± 2.73 | 55.17 ± 9.39 |
| 24 | 4.58 ± 0.76 | 31.36 ± 2.95 |
| 48 | 3.86 ± 0.06 | 4.24 ± 0.63 |

TABLE 3

Full Pharmacokinetic profile of subcutaneous Human Insulin R formulations in Pigs

| Parameter | Unit | Value | Parameter | Unit | Value |
|---|---|---|---|---|---|
| R | | −0.882 | AUMC 0-inf_obs | mU/L*h^2 | 15748.377 |
| R_adjusted | | 0.703 | AUMC 0-t/0-inf_obs | | 0.485 |
| NumRegPoints | | 5.000 | MRT 0-t | h | 6.938 |
| TimeRegStart | h | 4.000 | MRT 0-inf_obs | h | 13.028 |
| TimeRegEnd | h | 48.000 | Vz/F_obs | (mg)/(mU/L) | 0.008 |
| Lambda_z | 1/h | 0.036 | Cl/F_obs | (mg)/(mU/L)/h | 0.000 |
| t½ | h | 19.218 | Clast_pred | mU/L | 3.247 |
| Tmax | h | 2.000 | Clast_pred/Cmax | | 0.010 |
| Cmax | mU/L | 316.870 | AUC t-inf_pred | mU/L*h | 90.028 |
| Tlag | h | 0.000 | AUC 0-inf_pred | mU/L*h | 1191.812 |
| Tlast | h | 48.000 | AUC 0-t/0-inf_pred | | 0.924 |
| Clast_obs | mU/L | 3.860 | AUC 0-inf/D_pred | mU/L*h/(mg) | 3434.617 |
| Clast_obs/Cmax | | 0.012 | AUMC t-inf_pred | mU/L*h^2 | 6817.410 |
| AUC 0-t | mU/L*h | 1101.784 | AUMC 0-inf_pred | mU/L*h^2 | 14461.785 |
| AUC t-inf_obs | mU/L*h | 107.019 | AUMC 0-t/0-inf_pred | | 0.529 |
| AUC 0-inf_obs | mU/L*h | 1208.803 | MRT 0-inf_pred | h | 12.134 |
| AUC 0-t/0-inf_obs | | 0.911 | Vz/F_pred | (mg)/(mU/L) | 0.008 |
| AUC 0-inf/D_obs | mU/L*h/(mg) | 3483.581 | Cl/F_pred | (mg)/(mU/L)/h | 0.000 |
| AUMC 0-t | mU/L*h^2 | 7644.374 | | | |
| AUMC t-inf_obs | mU/L*h^2 | 8104.002 | | | |

TABLE 4

Full Pharmacokinetic profile of buccal/sublingual Human Insulin R formulations in Pigs

| Parameter | Unit | Value | Parameter | Unit | Value |
|---|---|---|---|---|---|
| R | | −0.991 | AUMC 0-inf_obs | mU/L*h^2 | 29582.246 |
| R_adjusted | | 0.977 | AUMC 0-t/0-inf_obs | | 0.867 |
| NumRegPoints | | 5.000 | MRT 0-t | h | 10.214 |
| TimeRegStart | h | 4.000 | MRT 0-inf_obs | h | 11.492 |
| TimeRegEnd | h | 48.000 | Vz/F_obs | (mg)/(mU/L) | 0.002 |
| Lambda_z | 1/h | 0.068 | Cl/F_obs | (mg)/(mU/L)/h | 0.000 |
| t½ | h | 10.234 | Clast_pred | mU/L | 4.739 |
| Tmax | h | 0.500 | Clast_pred/Cmax | | 0.014 |
| Cmax | mU/L | 330.950 | AUC t-inf_pred | mU/L*h | 69.975 |
| Tlag | h | 0.000 | AUC 0-inf_pred | mU/L*h | 2581.437 |
| Tlast | h | 48.000 | AUC 0-t/0-inf_pred | | 0.973 |
| Clast_obs | mU/L | 4.240 | AUC 0-inf/D_pred | mU/L*h/(mg) | 7439.299 |
| Clast_obs/Cmax | | 0.013 | AUMC t-inf_pred | mU/L*h^2 | 4391.997 |
| AUC 0-t | mU/L*h | 2511.461 | AUMC 0-inf_pred | mU/L*h^2 | 30044.996 |
| AUC t-inf_obs | mU/L*h | 62.603 | AUMC 0-t/0-inf_pred | | 0.854 |
| AUC 0-inf_obs | mU/L*h | 2574.064 | MRT 0-inf_pred | h | 11.639 |
| AUC 0-t/0-inf_obs | | 0.976 | Vz/F_pred | (mg)/(mU/L) | 0.002 |
| AUC 0-inf/D_obs | mU/L*h/(mg) | 7418.052 | Cl/F_pred | (mg)/(mU/L)/h | 0.000 |
| AUMC 0-t | mU/L*h^2 | 25652.999 | | | |
| AUMC t-inf_obs | mU/L*h^2 | 3929.247 | | | |

Example 10: Pharmacokinetics Study of Insulin Formulation Containing/Enclosed in Sugar Truffle Shell in Rats/SD The present Example demonstrates that oral formulations of insulin exemplary of oral formulations disclosed herein have therapeutically effective pharmacokinetic profiles, e.g., with advantageous properties as compared to parenteral administration of the same peptide/protein. The present example demonstrates an insulin crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained Insulin regular, Humulin R (Humulin R (insulin human recombinant) U-100 is a sterile, clear, aqueous, and colorless solution that contains human insulin (rDNA origin) 100 units/mL, glycerin 16 mg/mL and meta-cresol 2.5 mg/mL, endogenous zinc (approximately 0.015 mg/100 units) and water for injection. The pH is 7.0 to 7.8. The insulin was dialyzed against water for 24 hrs against water and lyophilized. The lyophilized insulin was reconstituted in dilute acid. The reconstituted insulin was then processed to prepare microparticles according to the procedure mentioned under Example 2. The microparticle insulin was then lyophilized after washing with cold isopropanol. The amount of lyophilized insulin was quantified against a reference standard using a C18 reverse phase HPLC column (gradient elution, solvent A (0.1% TFA in water, solvent B (0.1% TFA in acetonitrile)). The lyophilized insulin (dosage mentioned under Table 5) was then transferred to sugar truffle shell made from cane sugar or palm sugar. The shell was then sealed with coconut palm sugar (DEGA Farms). The samples were then stored at 4° C. until further use.

TABLE 5

Experimental Design for Pharmacokinetics Analysis

| | SC (Marketed Formulation) | Oral (Sugar Truffle Formulation) |
|---|---|---|
| No. of SD rats, 8 to 10 weeks old | 2 | 4 |
| Sex | Female | Female |
| Body Weight | 220-250 gms | 220-250 gms |
| Group | 1 | 2 |
| Test Item | Insulin | Insulin |
| Dose (mg) | 0.087 | 0.52 |
| Formulation | Liquid | Sugar Truffle Shell enclosing lyophilized Insulin |

TABLE 5-continued

Experimental Design for Pharmacokinetics Analysis

| | SC (Marketed Formulation) | Oral (Sugar Truffle Formulation) |
|---|---|---|
| Route | SC (Subcutaneous) | PO (oral - Buccal/sublingual) |
| Feeding Status | Fasting overnight followed by 2 g/kg glucose solution challenge prior to test article administration | Fasting overnight followed by 2 g/kg glucose solution challenge prior to test article administration |
| Blood/plasma sample collection time | 0 min, 15 mins, 30 mins 1 hour, 2 hours, 4 hours, 8 hours, 12 hours, 24 hours and 48 hours post dose | 0 min, 15 mins, 30 mins 1 hour, 2 hours, 4 hours, 8 hours, 12 hours, 24 hours and 48 hours post dose |
| Analysis | Insulin INS ELISA kit ABBEXA | |

Pharmacokinetic analysis was conducted in Female rats weighing 220-250 grams for 2 days. Experimental design is shown in Table 5. Rats in the oral treatment group was fasted overnight prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 15 min, 30 min, 1 hour, 2 hours, 4 hours, 8 hours, 12 hours, 24 hours, and 48 hours into an EDTA-blood collection tubes for the separation of plasma to determine insulin levels by ELISA. Plasma samples collected at different time points were analyzed by ELISA kit according to ABBEXA protocol. This kit is based on sandwich enzyme-linked immuno-sorbent assay technology. An antibody, anti-insulin was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient INS will produce a blue colored product, which then changes to yellow after adding the acidic stop solution. The intensity of the yellow color is proportional to the INS amount bound on the plate. The Optical Density (OD) was measured spectrophotometrically at 450 nm in a microplate reader, from which the concentration of INS can be calculated.

The data in Table 6 and FIGS. 55 and 56 demonstrate average plasma concentration of Insulin at different time points. The full pharmacokinetic profile are shown in Tables 7 and 8. Orally administered Insulin formulation showed 16% bioavailability when compared to SC. Insulin was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each Insulin dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t½=ln 2/λz.

TABLE 6

Mean PK results of Human Insulin R formulations in Rats

| Time (hours) | Subcutaneous - Human Insulin R | Buccal/Sublingual |
|---|---|---|
| 0 | 115.34 ± 1.07 | 55.57 ± 5.63 |
| 0.25 | 292.44 ± 16.08 | 331.52 ± 18.17 |
| 0.5 | 332.03 ± 18.28 | 315 ± 23.38 |
| 1 | 287.79 ± 9.26 | 276.63 ± 20.53 |
| 2 | 204.5 ± 5.86 | 232.19 ± 13.83 |
| 4 | 151.79 ± 13.25 | 94.11 ± 3.66 |
| 8 | 126.01 ± 10.46 | 72.37 ± 10.05 |
| 12 | 63.66 ± 6.97 | 57.82 ± 9.72 |
| 24 | 6.98 ± 4.19 | 19.39 ± 2.71 |
| 48 | 4.42 ± 2.87 | 4.8 ± 2.3 |

TABLE 7

Full Pharmacokinetic profile of Subcutaneous Human Insulin R formulations in Rats

| Parameter | Unit | Value | Parameter | Unit | Value |
|---|---|---|---|---|---|
| R | | −0.94 | AUMC 0-t/0-inf_obs | | 0.87 |
| R_adjusted | | 0.87 | MRT 0-t | h | 7.74 |
| NumRegPoints | | 8.00 | MRT 0-inf_obs | h | 8.70 |
| TimeRegStart | h | 0.50 | Vz/F_obs | (mg)/(mU/L) | 0.00 |
| TimeRegEnd | h | 48.00 | Cl/F_obs | (mg)/(mU/L)/h | 0.00 |
| Lambda_z | 1/h | 0.10 | Clast_pred | mU/L | 2.36 |
| t½ | h | 7.21 | Clast_pred/Cmax | | 0.01 |
| Tmax | h | 0.50 | AUC t-inf_pred | mU/L*h | 24.58 |
| Cmax | mU/L | 332.03 | AUC 0-inf_pred | mU/L*h | 2406.58 |

TABLE 7-continued

| Full Pharmacokinetic profile of Subcutaneous Human Insulin R formulations in Rats | | | | | |
|---|---|---|---|---|---|
| Parameter | Unit | Value | Parameter | Unit | Value |
| Tlag | h | 0.00 | AUC 0-t/0-inf_pred | | 0.99 |
| Tlast | h | 48.00 | AUC 0-inf/D_pred | mU/L*h/(mg) | 6935.40 |
| Clast_obs | mU/L | 4.42 | AUMC t-inf_pred | mU/L*h^2 | 1435.63 |
| Clast_obs/Cmax | | 0.01 | AUMC 0-inf_pred | mU/L*h^2 | 19871.95 |
| AUC 0-t | mU/L*h | 2382.00 | AUMC 0-t/0-inf_pred | | 0.93 |
| AUC t-inf_obs | mU/L*h | 45.98 | MRT 0-inf_pred | h | 8.26 |
| AUC 0-inf_obs | mU/L*h | 2427.98 | Vz/F_pred | (mg)/(mU/L) | 0.00 |
| AUC 0-t/0-inf_obs | | 0.98 | Cl/F_pred | (mg)/(mU/L)/h | 0.00 |
| AUC 0-inf/D_obs | mU/L*h/(mg) | 6997.06 | | | |
| AUMC 0-t | mU/L*h^2 | 18436.32 | | | |
| AUMC t-inf_obs | mU/L*h^2 | 2685.22 | | | |
| AUMC 0-inf_obs | mU/L*h^2 | 21121.54 | | | |

TABLE 8

| Full Pharmacokinetic profile of buccal/sublingual Human Insulin R formulations in Rats | | | | | |
|---|---|---|---|---|---|
| Parameter | Unit | Value | Parameter | Unit | Value |
| R | | −0.996 | AUMC t-inf_obs | mU/L*h^2 | 4357.035 |
| R_adjusted | | 0.990 | AUMC 0-inf_obs | mU/L*h^2 | 25478.020 |
| NumRegPoints | | 5.000 | AUMC 0-t/0-inf_obs | | 0.829 |
| TimeRegStart | h | 4.000 | MRT 0-t | h | 9.580 |
| TimeRegEnd | h | 48.000 | MRT 0-inf_obs | h | 11.202 |
| Lambda_z | 1/h | 0.069 | Vz/F_obs | (mg)/(mU/L) | 0.003 |
| t½ | h | 10.064 | Cl/F_obs | (mg)/(mU/L)/h | 0.000 |
| Tmax | h | 0.250 | Clast_pred | mU/L | 4.481 |
| Cmax | mU/L | 331.520 | Clast_pred/Cmax | | 0.014 |
| Tlag | h | 0.000 | AUC t-inf_pred | mU/L*h | 65.056 |
| Tlast | h | 48.000 | AUC 0-inf_pred | mU/L*h | 2269.755 |
| Clast_obs | mU/L | 4.800 | AUC 0-t/0-inf_pred | | 0.971 |
| Clast_obs/Cmax | | 0.014 | AUC 0-inf/D_pred | mU/L*h/(mg) | 4364.913 |
| AUC 0-t | mU/L*h | 2204.699 | AUMC t-inf_pred | mU/L*h^2 | 4067.241 |
| AUC t-inf_obs | mU/L*h | 69.691 | AUMC 0-inf_pred | mU/L*h^2 | 25188.226 |
| AUC 0-inf_obs | mU/L*h | 2274.390 | AUMC 0-t/0-inf_pred | | 0.839 |
| AUC 0-t/0-inf_obs | | 0.969 | MRT 0-inf_pred | h | 11.097 |
| AUC 0-inf/D_obs | mU/L*h/(mg) | 4373.827 | Vz/F_pred | (mg)/(mU/L) | 0.003 |
| AUMC 0-t | mU/L*h^2 | 21120.985 | Cl/F_pred | (mg)/(mU/L)/h | 0.000 |

Example 11: Pharmacokinetics Study of Lantus/Insulin Glargine Formulation Containing/Enclosed in Sugar Truffle Shell in Minipigs The present Example demonstrates that oral formulations of insulin glargine exemplary of oral formulations disclosed herein have therapeutically effective pharmacokinetic profiles, e.g., with advantageous properties as compared to parenteral administration of the same peptide/protein. The present example demonstrates an insulin glargine crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained Lantus, insulin glargine (Monocomponent insulin glargine recombinant) is a sterile, clear, aqueous, and colorless solution that contains insulin glargine (rDNA origin) 100 units/mL, and meta-cresol 2.7 mg/mL, and water for injection. The Lantus was processed to prepare microparticles according to the procedure mentioned under Example 3. The microparticle Lantus/insulin glargine was then lyophilized after washing with cold isopropanol. The amount of lyophilized insulin glargine was quantified against a reference standard using a C18 reverse phase HPLC column (gradient elution, solvent A (0.1% TFA in water, solvent B (0.1% TFA in acetonitrile)). The lyophilized Lantus/glargine (dosage mentioned under Table 9) was then transferred to sugar truffle shell made from cane sugar or palm sugar. The shell was then sealed with coconut palm sugar (DEGA Farms). The samples were then stored at 4° C. until further use.

TABLE 9

Experimental Design for Pharmacokinetics Analysis

| | SC (Marketed Formulation) | Oral (Sugar Truffle Formulation) |
|---|---|---|
| No. of Minipigs (Yorkshire) 3 to 4 months old | 2 | 4 |
| Sex | Female | Female |
| Body Weight | 12 ± 1 kg | 12 ± 1 kg |
| Group | 1 | 2 |
| Test Item | Lantus/Glargine | Lantus/Glargine |
| Dose (mg) | 0.364 | 2.18 |
| Formulation | Liquid | Sugar Truffle Shell enclosing lyophilized Lantus/Glargine |
| Route | SC (Subcutaneous) | PO (oral - Buccal/sublingual) |
| Feeding Status | Fasting overnight followed by 2 g/kg glucose solution challenge prior to test article administration | Fasting overnight followed by 2 g/kg glucose solution challenge prior to test article administration |
| Blood/plasma sample collection time | 0 min, 15 mins, 30 mins 1 hour, 2 hours, 4 hours, 8 hours, 12 hours, 24 hours and 48 hours post dose | 0 min, 15 mins, 30 mins 1 hour, 2 hours, 4 hours, 8 hours, 12 hours, 24 hours and 48 hours post dose |
| Analysis | Glargine ELISA kit Creative Diagnostics | |

Pharmacokinetic analysis was conducted in Female Minipigs weighing 12±1 kg for 2 days. Experimental design is shown in Table 9. Pigs in the oral treatment group was fasted overnight prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 15 min, 30 min, 1 hour, 2 hours, 4 hours, 8 hours, 12 hours, 24 hours, and 48 hours into an EDTA-blood collection tubes for the separation of plasma to determine Lantus levels by ELISA. Plasma samples collected at different time points were analyzed by ELISA kit according to Creative Diagnostics protocol. This kit is based on sandwich enzyme-linked immuno-sorbent assay technology. An antibody, anti-insulin/glargine was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient Glargine will produce a blue colored product, which then changes to yellow after adding the acidic stop solution. The intensity of the yellow color is proportional to the glargine amount bound on the plate. The Optical Density (OD) was measured spectrophotometrically at 450 nm in a microplate reader, from which the concentration of Glargine can be calculated.

The data in Table 10 and FIGS. 57 and 58 demonstrate average plasma concentration of Lantus/insulin glargine at different time points. The full pharmacokinetic profile are shown in Tables 11 and 12. Orally administered Lantus/insulin glargine formulation showed 7% bioavailability when compared to SC. Lantus/insulin glargine was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each Lantus/insulin glargine dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t ½=ln 2/λz.

TABLE 10

Mean PK results of Glargine formulations in Pigs

| Time (hours) | Subcutaneous - Glargine | Buccal/Sublingual |
|---|---|---|
| 0 | 7.86 ± 0.64 | 33.85 ± 4.15 |
| 0.25 | 56.92 ± 0.76 | 89.57 ± 5.28 |
| 0.5 | 89.27 ± 5.66 | 127.88 ± 7.19 |
| 1 | 122 ± 4.75 | 178.44 ± 7.95 |
| 2 | 142.49 ± 8.42 | 154.37 ± 14.07 |
| 4 | 158.18 ± 7.17 | 105.41 ± 6.17 |
| 8 | 170.71 ± 0.86 | 63.03 ± 9.77 |
| 12 | 166.4 ± 16.76 | 42.31 ± 8.42 |
| 24 | 83.97 ± 15.22 | 26.04 ± 4.34 |
| 48 | 6.57 ± 4.6 | 4.73 ± 1.21 |

TABLE 11

Full Pharmacokinetic profile of Subcutaneous Lantus/Glargine formulations in Minipigs

| Parameter | Unit | Value | Parameter | Unit | Value |
|---|---|---|---|---|---|
| R | | −0.991 | AUMC t-inf_obs | mU/L*h^2 | 4197.791 |
| R_adjusted | | 0.966 | AUMC 0-inf_obs | mU/L*h^2 | 68131.696 |
| NumRegPoints | | 3.000 | AUMC 0-t/0-inf_obs | | 0.938 |
| TimeRegStart | h | 12.000 | MRT 0-t | h | 14.423 |
| TimeRegEnd | h | 48.000 | MRT 0-inf_obs | h | 15.127 |
| Lambda_z | 1/h | 0.092 | Vz/F_obs | (mg)/(mU/L) | 0.001 |
| t½ | h | 7.525 | Cl/F_obs | (mg)/(mU/L)/h | 0.000 |
| Tmax | h | 8.000 | Clast_pred | mU/L | 7.148 |
| Cmax | mU/L | 170.710 | Clast_pred/Cmax | | 0.042 |
| Tlag | h | 0.000 | AUC t-inf_pred | mU/L*h | 77.596 |
| Tlast | h | 48.000 | AUC 0-inf_pred | mU/L*h | 4510.400 |
| Clast_obs | mU/L | 6.570 | AUC 0-t/0-inf_pred | | 0.983 |
| Clast_obs/Cmax | | 0.038 | AUC 0-inf/D_pred | mU/L*h/(mg) | 12289.917 |
| AUC 0-t | mU/L*h | 4432.804 | AUMC t-inf_pred | mU/L*h^2 | 4566.968 |
| AUC t-inf_obs | mU/L*h | 71.323 | AUMC 0-inf_pred | mU/L*h^2 | 68500.874 |
| AUC 0-inf_obs | mU/L*h | 4504.127 | AUMC 0-t/0-inf_pred | | 0.933 |
| AUC 0-t/0-inf_obs | | 0.984 | MRT 0-inf_pred | h | 15.187 |
| AUC 0-inf/D_obs | mU/L*h/(mg) | 12272.825 | Vz/F_pred | (mg)/(mU/L) | 0.001 |
| AUMC 0-t | mU/L*h^2 | 63933.906 | Cl/F_pred | (mg)/(mU/L)/h | 0.000 |

TABLE 12

Full Pharmacokinetic profile of buccal/sublingual Lantus/Glargine formulations in Minipigs

| Parameter | Unit | Value | Parameter | Unit | Value |
|---|---|---|---|---|---|
| R | | −0.995 | AUMC t-inf_obs | mU/L*h^2 | 4794.993 |
| R_adjusted | | 0.985 | AUMC 0-inf_obs | mU/L*h^2 | 26738.908 |
| NumRegPoints | | 4.000 | AUMC 0-t/0-inf_obs | | 0.821 |
| TimeRegStart | h | 8.000 | MRT 0-t | h | 11.720 |
| TimeRegEnd | h | 48.000 | MRT 0-inf_obs | h | 13.731 |
| Lambda_z | 1/h | 0.063 | Vz/F_obs | (mg)/(mU/L) | 0.024 |
| t½ | h | 11.001 | Cl/F_obs | (mg)/(mU/L)/h | 0.001 |
| Tmax | h | 1.000 | Clast_pred | mU/L | 4.955 |
| Cmax | mU/L | 178.440 | Clast_pred/Cmax | | 0.028 |
| Tlag | h | 0.000 | AUC t-inf_pred | mU/L*h | 78.644 |
| Tlast | h | 48.000 | AUC 0-inf_pred | mU/L*h | 1950.918 |
| Clast_obs | mU/L | 4.730 | AUC 0-t/0-inf_pred | | 0.960 |
| Clast_obs/Cmax | | 0.027 | AUC 0-inf/D_pred | mU/L*h/(mg) | 672.730 |
| AUC 0-t | mU/L*h | 1872.274 | AUMC t-inf_pred | mU/L*h^2 | 5023.113 |
| AUC t-inf_obs | mU/L*h | 75.072 | AUMC 0-inf_pred | mU/L*h^2 | 26967.028 |
| AUC 0-inf_obs | mU/L*h | 1947.346 | AUMC 0-t/0-inf_pred | | 0.814 |
| AUC 0-t/0-inf_obs | | 0.961 | MRT 0-inf_pred | h | 13.823 |
| AUC 0-inf/D_obs | mU/L*h/(mg) | 671.499 | Vz/F_pred | (mg)/(mU/L) | 0.024 |
| AUMC 0-t | mU/L*h^2 | 21943.916 | Cl/F_pred | (mg)/(mU/L)/h | 0.001 |

Example 12: Pharmacokinetics Study of Lantus/Insulin Glargine Formulation Containing/Enclosed in Sugar Truffle Shell in Rats/SD The present Example demonstrates that oral formulations of insulin/glargine exemplary of oral formulations disclosed herein have therapeutically effective pharmacokinetic profiles, e.g., with advantageous properties as compared to parenteral administration of the same peptide/protein. The present example demonstrates an insulin/glargine crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained Lantus/insulin glargine (Monocomponent insulin glargine recombinant) is a sterile, clear, aqueous, and colorless solution that contains insulin glargine (rDNA origin) 100 units/mL, and meta-cresol 2.7 mg/mL, and water for injection. The Lantus was processed to prepare microparticles according to the procedure mentioned under Example 3. The microparticle insulin/glargine was then lyophilized after washing with cold isopropanol. The amount of lyophilized insulin glargine was quantified against a reference standard using a C18 reverse phase HPLC column (gradient elution, solvent A (0.1% TFA in water, solvent B (0.1% TFA in acetonitrile)). The lyophilized insulin/glargine (dosage mentioned under Table 13) was then transferred to sugar truffle shell made from cane sugar or palm sugar. The shell was then sealed with coconut palm sugar (DEGA Farms). The samples were then stored at 4° C. until further use.

TABLE 13

Experimental Design for Pharmacokinetics Analysis

| | SC (Marketed Formulation) | Oral (Sugar Truffle Formulation) |
|---|---|---|
| No. of SD rats, 8 to 10 weeks old | 2 | 4 |
| Sex | Female | Female |
| Body Weight | 220-250 gms | 220-250 gms |
| Group | 1 | 2 |
| Test Item | Lantus/Glargine | Lantus/Glargine |
| Dose (mg) | 0.091 | 0.546 |
| Formulation | Liquid | Sugar Truffle Shell enclosing lyophilized Lantus/Glargine |
| Route | SC (Subcutaneous) | PO (oral - Buccal/sublingual) |
| Feeding Status | Fasting overnight followed by 2 g/kg glucose solution challenge prior to test article administration | Fasting overnight followed by 2 g/kg glucose solution challenge prior to test article administration |
| Blood/plasma sample collection time | 0 min, 15 mins, 30 mins 1 hour, 2 hours, 4 hours, 8 hours, 12 hours, 24 hours and 48 hours post dose | 0 min, 15 mins, 30 mins 1 hour, 2 hours, 4 hours, 8 hours, 12 hours, 24 hours and 48 hours post dose |
| Analysis | Glargine ELISA kit | Creative Diagnostics |

Pharmacokinetic analysis was conducted in Female rats weighing 220-250 grams for 2 days. Experimental design is shown in Table 13. Rats in the oral treatment group was fasted overnight prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 15 min, 30 min, 1 hour, 2 hours, 4 hours, 8 hours, 12 hours, 24 hours, and 48 hours into an EDTA-blood collection tubes for the separation of plasma to determine insulin/glargine levels by ELISA. Plasma samples collected at different time points were analyzed by ELISA kit according to Creative Diagnostics protocol. This kit is based on sandwich enzyme-linked immuno-sorbent assay technology. An antibody, anti-insulin/glargine was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient glargine will produce a blue colored product, which then changes to yellow after adding the acidic stop solution. The intensity of the yellow color is proportional to the glargine amount bound on the plate. The Optical Density (OD) was measured spectrophotometrically at 450 nm in a microplate reader, from which the concentration of glargine can be calculated.

TABLE 14

Mean PK results of Glargine formulations in Rats

| Time (hours) | Subcutaneous - Glargine | Buccal/Sublingual |
|---|---|---|
| 0 | 8.97 ± 1.52 | 14.93 ± 3.76 |
| 0.25 | 83.73 ± 5.4 | 116.32 ± 9.45 |

TABLE 14-continued

Mean PK results of Glargine formulations in Rats

| Time (hours) | Subcutaneous - Glargine | Buccal/Sublingual |
|---|---|---|
| 0.5 | 92.37 ± 4.44 | 144.21 ± 6.61 |
| 1 | 132.81 ± 4.55 | 190.78 ± 12.73 |
| 2 | 158.84 ± 6.03 | 187.29 ± 5.64 |
| 4 | 180.65 ± 4.67 | 129.5 ± 11.5 |
| 8 | 191.45 ± 10.87 | 81.46 ± 13.85 |

TABLE 14-continued

| Mean PK results of Glargine formulations in Rats | | |
|---|---|---|
| Time (hours) | Subcutaneous - Glargine | Buccal/Sublingual |
| 12 | 150.38 ± 10.16 | 49.83 ± 10.63 |
| 24 | 44.83 ± 14.26 | 32.17 ± 16.68 |
| 48 | 6.55 ± 4.42 | 6.26 ± 2.73 |

The data in Table 14 and FIGS. 59 & 60 demonstrate average plasma concentration of insulin glargine at different time points. The full pharmacokinetic profile are shown in Tables 15 and 16. Orally administered Insulin/glargine formulation showed 10% bioavailability when compared to SC. Insulin glargine was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each Insulin/glargine dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t ½=ln 2/λz.

TABLE 15

Full Pharmacokinetic profile of Subcutaneous Lantus/insulin glargine formulations in Rats

| Parameter | Unit | Value | Parameter | Unit | Value |
|---|---|---|---|---|---|
| R | | −0.999 | AUMC t-inf_obs | mU/L*h^2 | 4568.77 |
| R_adjusted | | 0.996 | AUMC 0-inf_obs | mU/L*h^2 | 51037.397 |
| NumRegPoints | | 4.000 | AUMC 0-t/0-inf_obs | | 0.910 |
| TimeRegStart | h | 8.000 | MRT 0-t | h | 12.258 |
| TimeRegEnd | h | 48.000 | MRT 0-inf_obs | h | 13.197 |
| Lambda_z | 1/h | 0.086 | Vz/F_obs | (mg)/(mU/L) | 0.000 |
| t½ | h | 8.100 | Cl/F_obs | (mg)/(mU/L)/h | 0.000 |
| Tmax | h | 8.000 | Clast_pred | mU/L | 6.349 |
| Cmax | mU/L | 191.450 | Clast_pred/Cmax | | 0.033 |
| Tlag | h | 0.000 | AUC t-inf_pred | mU/L*h | 74.194 |
| Tlast | h | 48.000 | AUC 0-inf_pred | mU/L*h | 3865.084 |
| Clast_obs | mU/L | 6.550 | AUC 0-t/0-inf_pred | | 0.981 |
| Clast_obs/Cmax | | 0.034 | AUC 0-inf/D_pred | mU/L*h/(mg) | 42473.447 |
| AUC 0-t | mU/L*h | 3790.890 | AUMC t-inf_pred | mU/L*h^2 | 4428.341 |
| AUC t-inf_obs | mU/L*h | 76.545 | AUMC 0-inf_pred | mU/L*h^2 | 50897.061 |
| AUC 0-inf_obs | mU/L*h | 3867.435 | AUMC 0-t/0-inf_pred | | 0.913 |
| AUC 0-t/0-inf_obs | | 0.980 | MRT 0-inf_pred | h | 13.168 |
| AUC 0-inf/D_obs | mU/L*h/(mg) | 42499.285 | Vz/F_pred | (mg)/(mU/L) | 0.000 |
| AUMC 0-t | mU/L*h^2 | 46468.720 | Cl/F_pred | (mg)/(mU/L)/h | 0.000 |

TABLE 16

Full Pharmacokinetic profile of buccal/sublingual Lantus/Glargine formulations in Rats

| Parameter | Unit | Value | Parameter | Unit | Value |
|---|---|---|---|---|---|
| R | | −0.993 | AUMC t-inf_obs | mU/L*h^2 | 6555.665 |
| R_adjusted | | 0.979 | AUMC 0-inf_obs | mU/L*h^2 | 33742.529 |
| NumRegPoints | | 4.000 | AUMC 0-t/0-inf_obs | | 0.806 |
| TimeRegStart | h | 8.000 | MRT 0-t | h | 11.944 |
| TimeRegEnd | h | 48.000 | MRT 0-inf_obs | h | 14.188 |
| Lambda_z | 1/h | 0.061 | Vz/F_obs | (mg)/(mU/L) | 0.005 |
| t½ | h | 11.291 | Cl/F_obs | (mg)/(mU/L)/h | 0.000 |
| Tmax | h | 1.000 | Clast_pred | mU/L | 6.480 |
| Cmax | mU/L | 190.780 | Clast_pred/Cmax | | 0.034 |
| Tlag | h | 0.000 | AUC t-inf_pred | mU/L*h | 105.557 |
| Tlast | h | 48.000 | AUC 0-inf_pred | mU/L*h | 2381.762 |
| Clast_obs | mU/L | 6.260 | AUC 0-t/0-inf_pred | | 0.956 |
| Clast_obs/Cmax | | 0.033 | AUC 0-inf/D_pred | mU/L*h/(mg) | 2977.202 |
| AUC 0-t | mU/L*h | 2276.205 | AUMC t-inf_pred | mU/L*h^2 | 6786.186 |
| AUC t-inf_obs | mU/L*h | 101.971 | AUMC 0-inf_pred | mU/L*h^2 | 33973.051 |
| AUC 0-inf_obs | mU/L*h | 2378.176 | AUMC 0-t/0-inf_pred | | 0.800 |
| AUC 0-t/0-inf_obs | | 0.957 | MRT 0-inf_pred | h | 14.264 |

TABLE 16-continued

| Full Pharmacokinetic profile of buccal/sublingual Lantus/Glargine formulations in Rats | | | | | |
|---|---|---|---|---|---|
| Parameter | Unit | Value | Parameter | Unit | Value |
| AUC 0-inf/D_obs | mU/L*h/(mg) | 2972.720 | Vz/F_pred | (mg)/(mU/L) | 0.005 |
| AUMC 0-t | mU/L*h^2 | 27186.864 | Cl/F_pred | (mg)/(mU/L)/h | 0.000 |

Example 12: Pharmacokinetics Study of PTH (1-34) Formulation Containing/Enclosed in Sugar Truffle Shell in Minipigs The present Example demonstrates that oral formulations of PTH (1-34) exemplary of oral formulations disclosed herein have therapeutically effective pharmacokinetic profiles, e.g., with advantageous properties as compared to parenteral administration of the same peptide/protein. The present example demonstrates a PTH (1-34) crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained PTH (1-34) (synthetic PTH (1-34) from PRIVEEL PEPTIDES) is a lyophilized white powder (>95% purity). The PTH (1-34) was processed to prepare microparticles according to the procedure mentioned under Example 4. The microparticle PTH (1-34) was then lyophilized after washing with cold isopropanol. The amount of lyophilized PTH was quantified against a reference standard using a C18 reverse phase HPLC column (gradient elution, solvent A (0.1% TFA in water, solvent B (0.1% TFA in acetonitrile)). The lyophilized PTH (1-34) (dosage mentioned under Table 17) was then transferred to sugar truffle shell made from cane sugar or palm sugar. The shell was then sealed with coconut palm sugar (DEGA Farms). The samples were then stored at 4° C. until further use.

TABLE 17

| Experimental Design for Pharmacokinetics and Pharmacodynamics Analysis | | |
|---|---|---|
| | SC (Marketed Formulation) | Oral (Sugar Truffle Formulation) |
| No. of Minipigs (Yorkshire) 3 to 4 months old | 2 | 4 |
| Sex | Female | Female |
| Body Weight | 12 ± 1 kg | 12 ± 1 kg |
| Group | 1 | 2 |
| Test Item | PTH (1-34) | PTH (1-34) |
| Dose (mg) | 0.04 | 0.49 |
| Formulation | Liquid | Sugar Truffle Shell enclosing lyophilized PTH |
| Route | SC (Subcutaneous) | PO (oral - Buccal/sublingual) |
| Feeding Status | Fasting overnight or Fed State | Fasting overnight or Fed State |
| Blood/plasma sample collection time | 0 min, 5 mins, 30 mins 1 hour, 2 hours, 4 hours, 8 hours, 12 hours and 24 hours hours post dose | 0 min, 5 mins, 30 mins 1 hour, 2 hours, 4 hours, 8 hours, 12 hours and 24 post dose |

TABLE 17-continued

| Experimental Design for Pharmacokinetics and Pharmacodynamics Analysis | | |
|---|---|---|
| | SC (Marketed Formulation) | Oral (Sugar Truffle Formulation) |
| Analysis | PTH (1-34) ELISA kit Creative Diagnostics | |
| Pharmaco-dynamics | Serum Calcium, serum phosphate and serum alkaline phosphatase | |

Pharmacokinetic analysis was conducted in Female Minipigs weighing 12±1 kg for 2 days. Experimental design is shown in Table 17. Pigs in the oral treatment group was either fasted overnight or fed prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 5 min, 30 min, 1 hour, 2 hours, 4 hours, 8 hours, and 24 hours into an EDTA-blood collection tubes for the separation of plasma to determine PTH (1-34) levels by ELISA. Plasma samples collected at different time points were analyzed by ELISA kit according to Creative Diagnostics protocol. This kit is based on sandwich enzyme-linked immuno-sorbent assay technology. An antibody, anti-PTH (1-34) was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient PTH (1-34) will produce a blue colored product, which then changes to yellow after adding the acidic stop solution. The intensity of the yellow color is proportional to the PTH (1-34) amount bound on the plate. The Optical Density (OD) was measured spectrophotometrically at 450 nm in a microplate reader, from which the concentration of PTH (1-34) can be calculated.

For pharmacodynamics analysis of serum calcium, serum phosphorous and alkaline phosphatase, blood samples were collected at aforementioned time points 0 min, 5 min, 30 min, 1 hour, 2 hours, 4 hours, 8 hours, and 24 hours and serum was separated. The serum calcium and serum phosphorous were estimated using Siemen's RAPIDCHEM 744 Electrolyte Analyzer and for serum ALP Siemen's Dimension Expand Plus was used.

TABLE 18

| Mean PTH (1-34) levels summary table (Pigs) in pg/mL | | | | | | | | |
|---|---|---|---|---|---|---|---|---|
| Group | 0 min | 5 min | 30 min | 1 hour | 2 hour | 4 hour | 8 hour | 24 hour |
| GI - Subcutaneous | 0.002 | 394.271 | 3283.757 | 3258.430 | 2989.814 | 163.724 | 49.988 | 6.435 |
| GII - Buccal/sublingual | 0.000 | 3288.655 | 3041.555 | 2612.290 | 1240.205 | 189.325 | 17.765 | 0.000 |

TABLE 19

| Full Pharmacokinetic profile of Subcutaneous PTH (1-34) formulations in Minipigs | | | | | |
|---|---|---|---|---|---|
| Parameter | Unit | Value | Parameter | Unit | Value |
| R | | −0.984 | AUMC t-inf_obs | pg/mL*h^2 | 1292.445 |
| R_adjusted | | 0.935 | AUMC 0-inf_obs | pg/mL*h^2 | 20668.040 |
| NumRegPoints | | 3.000 | AUMC 0-t/0-inf_obs | | 0.937 |
| TimeRegStart | h | 4.000 | MRT 0-t | h | 2.022 |
| TimeRegEnd | h | 24.000 | MRT 0-inf_obs | h | 2.148 |
| Lambda_z | 1/h | 0.152 | Vz/F_obs | (μg)/(pg/mL) | 0.027 |
| t½ | h | 4.554 | Cl/F_obs | (μg)/(pg/mL)/h | 0.004 |
| Tmax | h | 0.500 | Clast_pred | pg/mL | 6.035 |
| Cmax | pg/mL | 3283.757 | Clast_pred/Cmax | | 0.002 |
| Tlag | h | 0.000 | AUC t-inf_pred | pg/mL*h | 39.650 |
| Tlast | h | 24.000 | AUC 0-inf_pred | pg/mL*h | 9619.819 |
| Clast_obs | pg/mL | 6.435 | AUC 0-t/0-inf_pred | | 0.996 |
| Clast_obs/Cmax | | 0.002 | AUC 0-inf/D_pred | pg/mL*h/(μg) | 240.495 |
| AUC 0-t | pg/mL*h | 9580.170 | AUMC t-inf_pred | pg/mL*h^2 | 1212.104 |
| AUC t-inf_obs | pg/mL*h | 42.278 | AUMC 0-inf_pred | pg/mL*h^2 | 20587.700 |
| AUC 0-inf_obs | pg/mL*h | 9622.448 | AUMC 0-t/0-inf_pred | | 0.941 |
| AUC 0-t/0-inf_obs | | 0.996 | MRT 0-inf_pred | h | 2.140 |
| AUC 0-inf/D_obs | pg/mL*h/(μg) | 240.561 | Vz/F_pred | (μg)/(pg/mL) | 0.027 |
| AUMC 0-t | pg/mL*h^2 | 19375.595 | Cl/F_pred | (μg)/(pg/mL)/h | 0.004 |

TABLE 20

| Full Pharmacokinetic profile of buccal/sublingual PTH (1-34) formulations in Minipigs | | | | | |
|---|---|---|---|---|---|
| Parameter | Unit | Value | Parameter | Unit | Value |
| R | | −0.995 | AUMC t-inf_obs | pg/mL*h^2 | 235.606 |
| R_adjusted | | 0.988 | AUMC 0-inf_obs | pg/mL*h^2 | 9236.909 |
| NumRegPoints | | 5.000 | AUMC 0-t/0-inf_obs | | 0.974 |
| TimeRegStart | h | 0.500 | MRT 0-t | h | 1.355 |
| TimeRegEnd | h | 8.000 | MRT 0-inf_obs | h | 1.385 |
| Lambda_z | 1/h | 0.709 | Vz/F_obs | (mg)/(pg/mL) | 0.000 |
| t½ | h | 0.977 | Cl/F_obs | (mg)/(pg/mL)/h | 0.000 |
| Tmax | h | 0.080 | Clast_pred | pg/mL | 15.641 |
| Cmax | pg/mL | 3288.655 | Clast_pred/Cmax | | 0.005 |
| Tlag | h | 0.000 | AUC t-inf_pred | pg/mL*h | 22.045 |
| Tlast | h | 8.000 | AUC 0-inf_pred | pg/mL*h | 6666.354 |
| Clast_obs | pg/mL | 17.765 | AUC 0-t/0-inf_pred | | 0.997 |
| Clast_obs/Cmax | | 0.005 | AUC 0-inf/D_pred | pg/mL*h/(mg) | 13604.805 |
| AUC 0-t | pg/mL*h | 6644.309 | AUMC t-inf_pred | pg/mL*h^2 | 207.435 |
| AUC t-inf_obs | pg/mL*h | 25.039 | AUMC 0-inf_pred | pg/mL*h^2 | 9208.738 |
| AUC 0-inf_obs | pg/mL*h | 6669.348 | AUMC 0-t/0-inf_pred | | 0.977 |
| AUC 0-t/0-inf_obs | | 0.996 | MRT 0-inf_pred | h | 1.381 |
| AUC 0-inf/D_obs | pg/mL*h/(mg) | 13610.915 | Vz/F_pred | (mg)/(pg/mL) | 0.000 |
| AUMC 0-t | pg/mL*h^2 | 9001.303 | Cl/F_pred | (mg)/(pg/mL)/h | 0.000 |

TABLE 21

Pharmacodynamics data of PTH in Yorkshire Pigs - Subcutaneous group

| Group 1 | Time (hours) | sCa | sP | sALP |
|---|---|---|---|---|
| Subcutaneous | 0 | 9.35 ± 0.63 | 10.7 ± 0.14 | 116.5 ± 6.36 |
| (40 μg) | 0.08 | 9.65 ± 0.77 | 10.52 ± 0.17 | 119.5 ± 2.12 |
| | 0.5 | 9.95 ± 0.49 | 9.8 ± 0.28 | 134.5 ± 17.67 |
| | 1 | 10.4 ± 0.14 | 9 ± 0.84 | 158 ± 38.18 |
| | 2 | 10.3 ± 0.14 | 10.25 ± 1.06 | 152.5 ± 36.06 |
| | 4 | 9.9 ± 0.42 | 11 ± 0 | 141.5 ± 33.23 |
| | 8 | 9.5 ± 0.28 | 11.4 ± 0.28 | 133.5 ± 23.33 |
| | 24 | 9.4 ± 0.28 | 11.6 ± 0.28 | 114.5 ± 3.53 |

TABLE 22

Pharmacodynamics data of PTH in Yorkshire Pigs - Buccal/Sublingual group

| Group 2 | Time (hours) | sCa | sP | sALP |
|---|---|---|---|---|
| Sugar | 0 | 9.46 ± 0.4 | 10.52 ± 0.33 | 170.55 ± 12.85 |
| Truffle | 0.08 | 10.05 ± 0.17 | 9.87 ± 0.15 | 193.5 ± 9.32 |
| Shell | 0.5 | 9.77 ± 0.12 | 8.82 ± 0.17 | 170.25 ± 10.81 |
| (0.49 mg) | 1 | 9.62 ± 0.04 | 8.3 ± 0.16 | 148.5 ± 11.9 |
| | 2 | 9.25 ± 0.26 | 9.1 ± 0.49 | 137.75 ± 9.67 |
| | 4 | 9.3 ± 0.34 | 9 ± 0.11 | 131 ± 11.91 |
| | 8 | 9.17 ± 0.26 | 8.97 ± 0.17 | 128 ± 14.02 |
| | 24 | 9 ± 0.18 | 9.02 ± 0.14 | 126.5 ± 15.28 |

The data in Table 18 and FIGS. 61 & 62 demonstrate average plasma concentration of PTH (1-34) at different time points. The full pharmacokinetic profile are shown in Tables 19 and 20. Orally administered PTH (1-34) formulation showed 6% bioavailability when compared to SC. PTH (1-34) was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each PTH (1-34) dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t ½=ln 2/λz.

The pharmacodynamics data in subcutaneous and buccal/Sublingual groups are shown in Tables 21 and 22 and in FIGS. 63 and 64. The PD data clearly indicates the effect on serum calcium, serum phosphorous and serum alkaline phosphatase when PTH was given by buccal/sublingual route.

Example 13: Pharmacokinetics Study of PTH (1-34) Formulation Containing/Enclosed in Sugar Truffle Shell in Rats/SD The present Example demonstrates that oral formulations of PTH (1-34) exemplary of oral formulations disclosed herein have therapeutically effective pharmacokinetic profiles, e.g., with advantageous properties as compared to parenteral administration of the same peptide/protein. The present example demonstrates a PTH (1-34) crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained PTH (1-34) (synthetic PTH (1-34) from PRIVEEL PEPTIDES) is a lyophilized white powder (>95% purity). The PTH (1-34) was processed to prepare microparticles according to the procedure mentioned under Example 4. The microparticle PTH (1-34) was then lyophilized after washing with cold isopropanol. The amount of lyophilized PTH was quantified against a reference standard using a C18 reverse phase HPLC column (gradient elution, solvent A (0.1% TFA in water, solvent B (0.1% TFA in acetonitrile)). The lyophilized PTH (1-34) (dosage mentioned under Table 23) was then transferred to sugar truffle shell made from cane sugar or palm sugar. The shell was then sealed with coconut palm sugar (DEGA Farms). The samples were then stored at 4° C. until further use.

TABLE 23

Experimental Design for Pharmacokinetics Analysis

| | SC (Marketed Formulation) | Oral (Sugar Truffle Formulation) |
|---|---|---|
| No. of SD rats, 8 to 10 weeks old | 2 | 4 |
| Sex | Female | Female |
| Body Weight | 220-250 gms | 220-250 gms |
| Group | 1 | 2 |
| Test Item | PTH (1-34) | PTH (1-34) |
| Dose (mg) | 0.04 | 0.49 |
| Formulation | Liquid | Sugar Truffle Shell enclosing lyophilized PTH |
| Route | SC (Subcutaneous) | PO (oral - Buccal/sublingual) |
| Feeding Status | Fasting overnight or Fed State | Fasting overnight or Fed State |
| Blood/plasma sample collection time | 0 min, 5 mins, 30 mins 1 hour, 2 hours, 4 hrs, 8 hours, 12 hours, and 24 hours post dose | 0 min, 5 mins, 30 mins 1 hour, 2 hours, 4 hours, 8 hours, 12 hours and 24 hours post dose |
| Analysis | PTH (1-34) ELISA kit Creative Diagnostics | |
| Pharmacodynamics | Serum Calcium, serum phosphate and serum alkaline phosphatase | |

Pharmacokinetic analysis was conducted in female rats weighing 220-250 grams for 2 days. Experimental design is shown in Table 23. Rats in the oral treatment group was either fasted overnight or fed prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 15 min, 30 min, 1 hour, 2 hours, 4 hours, 8 hours, 12 hours, 24 hours, and 48 hours into an EDTA-blood collection tubes for the separation of plasma to determine PTH (1-34) levels by ELISA. Plasma samples collected at different time points were analyzed by ELISA kit according to Creative Diagnostics protocol. This kit is based on sandwich enzyme-linked immuno-sorbent assay technology. An antibody, anti-PTH (1-34) was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient PTH (1-34) will produce a blue colored product, which then changes to yellow after adding the acidic stop solution. The intensity of the yellow color is proportional to the PTH (1-34) amount bound on the plate. The Optical Density (OD) was measured spectrophotometrically at 450 nm in a microplate reader, from which the concentration of PTH (1-34) can be calculated.

For pharmacodynamics analysis of serum calcium, serum phosphorous and alkaline phosphatase, blood samples were collected at aforementioned time points 0 min, 5 min, 30 min, 1 hour, 2 hours, 4 hours, 8 hours, and 24 hours and serum was separated. The serum calcium and serum phosphorous were estimated using Siemen's RAPIDCHEM 744 Electrolyte Analyzer and for serum ALP Siemen's Dimension Expand Plus was used.

TABLE 24

Mean PTH (1-34) levels summary table (Rats) in pg/mL

| Group | 0 min | 5 min | 30 min | 1 hour | 2 hour | 4 hour | 8 hour | 24 hour |
|---|---|---|---|---|---|---|---|---|
| GI - Subcutaneous | 0.002 | 403.478 | 3401.092 | 3265.822 | 2932.064 | 167.201 | 50.851 | 6.201 |
| GII - Buccal/sublingual | 0.000 | 3509.400 | 3070.365 | 2870.515 | 1634.220 | 214.435 | 33.695 | 6.020 |

TABLE 25

Full Pharmacokinetic profile of Subcutaneous PTH (1-34) formulations in Rats

| Parameter | Unit | Value | Parameter | Unit | Value |
|---|---|---|---|---|---|
| R | | −0.985 | AUMC t-inf_obs | pg/mL*h^2 | 1216.009 |
| R_adjusted | | 0.940 | AUMC 0-inf_obs | pg/mL*h^2 | 20516.940 |
| NumRegPoints | | 3.000 | AUMC 0-t/0-inf_obs | | 0.941 |
| TimeRegStart | h | 4.000 | MRT 0-t | h | 2.016 |
| TimeRegEnd | h | 24.000 | MRT 0-inf_obs | h | 2.134 |
| Lambda_z | 1/h | 0.155 | Vz/F_obs | (μg)/(pg/mL) | 0.013 |
| t½ | h | 4.465 | Cl/F_obs | (μg)/(pg/mL)/h | 0.002 |
| Tmax | h | 0.500 | Clast_pred | pg/mL | 5.821 |
| Cmax | pg/mL | 3401.092 | Clast_pred/Cmax | | 0.002 |
| Tlag | h | 0.000 | AUC t-inf_pred | pg/mL*h | 37.497 |
| Tlast | h | 24.000 | AUC 0-inf_pred | pg/mL*h | 9610.050 |
| Clast_obs | pg/mL | 6.201 | AUC 0-t/0-inf_pred | | 0.996 |
| Clast_obs/Cmax | | 0.002 | AUC 0-inf/D_pred | pg/mL*h/(μg) | 480.502 |
| AUC 0-t | pg/mL*h | 9572.553 | AUMC t-inf_pred | pg/mL*h^2 | 1141.464 |
| AUC t-inf_obs | pg/mL*h | 39.945 | AUMC 0-inf_pred | pg/mL*h^2 | 20442.395 |
| AUC 0-inf_obs | pg/mL*h | 9612.499 | AUMC 0-t/0-inf_pred | | 0.944 |
| AUC 0-t/0-inf_obs | | 0.996 | MRT 0-inf_pred | h | 2.127 |
| AUC 0-inf/D_obs | pg/mL*h/(μg) | 480.625 | Vz/F_pred | (μg)/(pg/mL) | 0.013 |
| AUMC 0-t | pg/mL*h^2 | 19300.931 | Cl/F_pred | (μg)/(pg/mL)/h | 0.002 |

TABLE 26

Full Pharmacokinetic profile of buccal/sublingual PTH (1-34) formulations in Rats

| Parameter | Unit | Value | Parameter | Unit | Value |
|---|---|---|---|---|---|
| R | | −0.910 | AUMC t-inf_obs | pg/mL*h^2 | 614.328 |
| R_adjusted | | 0.795 | AUMC 0-inf_obs | pg/mL*h^2 | 14870.906 |
| NumRegPoints | | 7.000 | AUMC 0-t/0-inf_obs | | 0.959 |
| TimeRegStart | h | 0.080 | MRT 0-t | h | 1.800 |
| TimeRegEnd | h | 24.000 | MRT 0-inf_obs | h | 1.872 |
| Lambda_z | 1/h | 0.271 | Vz/F_obs | (mg)/(pg/mL) | 0.000 |
| t½ | h | 2.555 | Cl/F_obs | (mg)/(pg/mL)/h | 0.000 |
| Tmax | h | 0.080 | Clast_pred | pg/mL | 2.875 |
| Cmax | pg/mL | 3509.400 | Clast_pred/Cmax | | 0.001 |
| Tlag | h | 0.000 | AUC t-inf_pred | pg/mL*h | 10.599 |
| Tlast | h | 24.000 | AUC 0-inf_pred | pg/mL*h | 7932.948 |
| Clast_obs | pg/mL | 6.020 | AUC 0-t/0-inf_pred | | 0.999 |
| Clast_obs/Cmax | | 0.002 | AUC 0-inf/D_pred | pg/mL*h/(mg) | 16189.690 |
| AUC 0-t | pg/mL*h | 7922.349 | AUMC t-inf_pred | pg/mL*h^2 | 293.438 |
| AUC t-inf_obs | pg/mL*h | 22.189 | AUMC 0-inf_pred | pg/mL*h^2 | 14550.016 |
| AUC 0-inf_obs | pg/mL*h | 7944.538 | AUMC 0-t/0-inf_pred | | 0.980 |
| AUC 0-t/0-inf_obs | | 0.997 | MRT 0-inf_pred | h | 1.834 |

TABLE 26-continued

Full Pharmacokinetic profile of buccal/sublingual PTH (1-34) formulations in Rats

| Parameter | Unit | Value | Parameter | Unit | Value |
|---|---|---|---|---|---|
| AUC 0-inf/D_obs | pg/mL*h/(mg) | 16213.344 | Vz/F_pred | (mg)/(pg/mL) | 0.000 |
| AUMC 0-t | pg/mL*h^2 | 14256.578 | Cl/F_pred | (mg)/(pg/mL)/h | 0.000 |

TABLE 27

Pharmacodynamics data of PTH in Rats - Subcutaneous group

| Group 1 | Time (hours) | sCa | sP | sALP |
|---|---|---|---|---|
| Subcutaneousl (40 μg) | 0 | 9.05 ± 0.07 | 9.3 ± 0.28 | 98.5 ± 33.23 |
| | 0.08 | 9.65 ± 0.77 | 8.85 ± 0.07 | 131 ± 1.41 |
| | 0.5 | 10.2 ± 0.28 | 8.45 ± 0.21 | 136 ± 7.07 |
| | 1 | 10.35 ± 0.35 | 4.85 ± 0.91 | 142 ± 5.65 |
| | 2 | 10.45 ± 0.35 | 5.75 ± 1.06 | 184.5 ± 16.26 |
| | 4 | 9.45 ± 0.21 | 8.65 ± 0.21 | 151 ± 21.21 |
| | 8 | 9.25 ± 0.35 | 8.95 ± 0.07 | 131.5 ± 14.84 |
| | 24 | 9.05 ± 0.21 | 9.35 ± 0.07 | 111 ± 21.21 |

TABLE 28

Pharmacodynamics data of PTH in Rats - Buccal/Sublingual group

| Group 2 | Time (hours) | sCa | sP | sALP |
|---|---|---|---|---|
| Sugar Truffle Shell (0.49 mg) | 0 | 9.62 ± 0.25 | 9.77 ± 0.63 | 106.75 ± 10.53 |
| | 0.08 | 11.25 ± 0.26 | 7.8 ± 0.31 | 138.75 ± 13.72 |
| | 0.5 | 10.02 ± 0.22 | 5.07 ± 0.82 | 170.5 ± 10.66 |
| | 1 | 9.77 ± 0.12 | 5.75 ± 0.72 | 199.75 ± 8.46 |
| | 2 | 9.65 ± 0.12 | 6.5 ± 0.49 | 158.25 ± 13.07 |
| | 4 | 9.52 ± 0.14 | 7.22 ± 0.81 | 124 ± 9.2 |
| | 8 | 9.32 ± 0.15 | 9 ± 0.54 | 126.5 ± 7.93 |
| | 24 | 9.4 ± 0.21 | 9.27 ± 0.35 | 131.25 ± 15.45 |

The data in Table 24 and FIGS. 65 & 66 demonstrate average plasma concentration of PTH (1-34) at different time points. The full pharmacokinetic profile are shown in Table 25 and 26. Orally administered PTH (1-34) formulation showed 7% bioavailability when compared to SC. PTH (1-34) was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each PTH (1-34) dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t ½=ln 2/λz.

The pharmacodynamics data in subcutaneous and buccal/Sublingual groups of rats are shown in Tables 27 and 28 and in FIGS. 67 and 68. The PD data clearly indicates the effect on serum calcium, serum phosphorous and serum alkaline phosphatase when PTH was given by buccal/sublingual route.

Example 14: Pharmacokinetics Study of hGH (Human Growth Hormone) Formulation Containing/Enclosed in Sugar Truffle Shell in Minipigs The present Example demonstrates that oral formulations of hGH exemplary of oral formulations disclosed herein have therapeutically effective pharmacokinetic profiles, e.g., with advantageous properties as compared to parenteral administration of the same peptide/protein. The present example demonstrates a hGH crystal powder formulation enclosed in sugar truffle shell, demonstrating that enteric formulation is not required for advantageous application of formulations as described herein.

The present Example includes an oral formulation of crystallized peptide/protein prepared as follows: Commercially obtained hGH (Human Growth Hormone Inj., Norditropin NordiFlex, 15 mg/1.5 mL) is a solution containing Somatropin 10 mg, mannitol 39 mg, histidine 1.1 mg, poloxamer 188 3.0 mg, phenol 3.0 mg, and water for injection in 1.0 mL with HCl and NaOH. The hGH was processed to prepare microparticles according to the procedure mentioned under Example 8. The microparticle hGH was then lyophilized after washing with cold isopropanol. The amount of lyophilized hGH was quantified against a reference standard using a C18 reverse phase HPLC column (gradient elution, solvent A (0.1% TFA in water, solvent B (0.1% TFA in acetonitrile)). The lyophilized hGH (dosage mentioned under Table 1) was then transferred to sugar truffle shell made from cane sugar or palm sugar. The shell was then sealed with coconut palm sugar (DEGA Farms). The samples were then stored at 4° C. until further use.

TABLE 29

Experimental Design for Pharmacokinetics and Pharmacodynamics Analysis

| | SC (Marketed Formulation) | Oral (Sugar Truffle Formulation) |
|---|---|---|
| No. of Minipigs (Yorkshire) 3 to 4 months old | 2 | 4 |
| Sex | Female | Female |
| Body Weight | 12 ± 1 kg | 12 ± 1 kg |
| Group | 1 | 2 |
| Test Item | hGH | hGH |
| Dose (mg) | 0.33 | 2.5 |
| Formulation | Liquid | Sugar Truffle Shell enclosing lyophilized hGH |
| Route | IV (Intravenous) | PO (oral - Buccal/sublingual) |
| Feeding Status | Fasting overnight or Fed State | Fasting overnight or Fed State |
| Blood/plasma sample collection time | 0 min, 5 mins, 30 mins 1 hour, 4 hours, 8 hours, 24 hours, and 48 hours post dose | 0 min, 5 mins, 30 mins, 1 hour, 4 hours, 8 hours, 24 hours and 48 hours post dose |
| Analysis | hGH ELISA kit Creative Diagnostics | |

Pharmacokinetic analysis was conducted in Female Minipigs weighing 12±1 kg for 2 days. Experimental design is shown in Table 29. Pigs in the oral treatment group was either fasted overnight or fed prior to the test sample administration. All the test animals in the treatment groups were administered with respective test formulation to the pre-designated animals. The animal was restrained and its head was held vertically, the jaws were pulled away, the tongue was gently lifted with a forceps followed by placement of a polypeptide formulation as described herein buccally/sublingually. After placing a polypeptide formulation as described herein, the snout was held together for about 1-2 mins to prevent the chewing of the polypeptide formulation. The time of dosage of each animal was noted. Blood samples were collected at aforementioned time points 0 min, 5 min, 30 min, 1 hour, 4 hours, 8 hours, 24 hours and 48 hours into an EDTA-blood collection tubes for the separation of plasma to determine hGH levels by ELISA. Plasma samples collected at different time points were analyzed by ELISA kit according to Creative Diagnostics protocol. This kit is based on sandwich enzyme-linked immuno-sorbent assay technology. An antibody, anti-hGH was pre-coated onto a 96-well plate. Standards, test samples, and biotin-conjugated reagent were added to the wells and incubated. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient hGH will produce a blue colored product, which then changes to yellow after adding the acidic stop solution. The intensity of the yellow color is proportional to the hGH amount bound on the plate. The Optical Density (OD) was measured spectrophotometrically at 450 nm in a microplate reader, from which the concentration of hGH can be calculated.

TABLE 30

Mean hGH levels summary table (Pigs) in pg/mL

| Time (hrs) | GI- IV | GII- Buccal/sublingual |
|---|---|---|
| 0 | 18144.54 ± 1619.64 | 20672.24 ± 1140.76 |
| 0.08 | 20014.87 ± 620.32 | 18582.31 ± 1303.34 |
| 0.5 | 22513.2 ± 562.85 | 26137.66 ± 4718.88 |
| 1 | 22130.7 ± 728.54 | 27123.44 ± 382.69 |
| 4 | 14910.13 ± 2908.87 | 2681.8 ± 1281.33 |
| 8 | 1159.19 ± 226.15 | 2208.63 ± 86.73 |
| 24 | 1495.55 ± 291.77 | 971.98 ± 38.36 |
| 48 | 463.04 ± 90.34 | 256.84 ± 13.49 |

TABLE 31

Full Pharmacokinetic profile of Intravenous hGH formulations in Minipigs

| Parameter | Unit | Value | Parameter | Unit | Value |
|---|---|---|---|---|---|
| R | | −0.838 | AUMC t-inf_obs | pg/ml*h^2 | 365646.123 |
| R_adjusted | | 0.629 | AUMC 0-inf_obs | pg/ml*h^2 | 1696005.242 |
| NumRegPoints | | 6.000 | AUMC 0-t/0-inf_obs | | 0.784 |
| TimeRegStart | h | 0.500 | MRT 0-t | h | 8.635 |
| TimeRegEnd | h | 48.000 | MRT 0-inf_obs | h | 10.596 |
| Lambda_z | 1/h | 0.077 | Vz_obs | (mg)/(pg/ml) | 0.000 |
| t½ | h | 8.980 | Cl_obs | (mg)/(pg/ml)/h | 0.000 |
| Tmax | h | 0.500 | Vss_obs | (mg)/(pg/ml) | 0.000 |
| Cmax | pg/ml | 22513.200 | Clast_pred | pg/ml | 314.650 |
| C0 | pg/ml | 18144.540 | Clast_pred/Cmax | | 0.014 |
| Tlast | h | 48.000 | AUC t-inf_pred | pg/ml*h | 4076.251 |
| Clast_obs | pg/ml | 463.040 | AUC 0-inf_pred | pg/ml*h | 158135.382 |
| Clast_obs/Cmax | | 0.021 | AUC 0-t/0-inf_pred | | 0.974 |
| AUC 0-t | pg/ml*h | 154059.131 | AUC 0-inf/D_pred | pg/ml*h/(mg) | 479198.128 |
| AUC t-inf_obs | pg/ml*h | 5998.634 | AUMC t-inf_pred | pg/ml*h^2 | 248467.457 |
| AUC 0-inf_obs | pg/ml*h | 160057.765 | AUMC 0-inf_pred | pg/ml*h^2 | 1578826.575 |
| AUC 0-t/0-inf_obs | | 0.963 | AUMC 0-t/0-inf_pred | | 0.843 |
| AUC 0-inf/D_obs | pg/ml*h/(mg) | 485023.532 | MRT 0-inf_pred | h | 9.984 |
| AUMC 0-t | pg/ml*h^2 | 1330359.118 | | | |

TABLE 32

Full Pharmacokinetic profile of buccal/sublingual hGH formulations in Minipigs

| Parameter | Unit | Value | Parameter | Unit | Value |
|---|---|---|---|---|---|
| R | | −1.000 | AUMC t-inf_obs | pg/ml*h^2 | 320994.350 |
| R_adjusted | | 0.999 | AUMC 0-inf_obs | pg/ml*h^2 | 1203569.518 |
| NumRegPoints | | 4.000 | AUMC 0-t/0-inf_obs | | 0.733 |
| TimeRegStart | h | 4.000 | MRT 0-t | h | 7.419 |
| TimeRegEnd | h | 48.000 | MRT 0-inf_obs | h | 9.725 |
| Lambda_z | 1/h | 0.053 | Vz/F_obs | (mg)/(pg/ml) | 0.000 |
| t½ | h | 12.982 | Cl/F_obs | (mg)/(pg/ml)/h | 0.000 |
| Tmax | h | 1.000 | Clast_pred | pg/ml | 260.848 |
| Cmax | pg/ml | 27123.440 | Clast_pred/Cmax | | 0.010 |
| Tlag | h | 0.000 | AUC t-inf_pred | pg/ml*h | 4885.479 |
| Tlast | h | 48.000 | AUC 0-inf_pred | pg/ml*h | 123841.570 |
| Clast_obs | pg/ml | 256.840 | AUC 0-t/0-inf_pred | | 0.961 |
| Clast_obs/Cmax | | 0.009 | AUC 0-inf/D_pred | pg/ml*h/(mg) | 49536.628 |
| AUC 0-t | pg/ml*h | 118956.091 | AUMC t-inf_pred | pg/ml*h^2 | 326004.060 |
| AUC t-inf_obs | pg/ml*h | 4810.404 | AUMC 0-inf_pred | pg/ml*h^2 | 1208579.228 |

TABLE 32-continued

| Full Pharmacokinetic profile of buccal/sublingual hGH formulations in Minipigs | | | | | |
|---|---|---|---|---|---|
| Parameter | Unit | Value | Parameter | Unit | Value |
| AUC 0-inf_obs | pg/ml*h | 123766.495 | AUMC 0-t/0-inf_pred | | 0.730 |
| AUC 0-t/0-inf_obs | | 0.961 | MRT 0-inf_pred | h | 9.759 |
| AUC 0-inf/D_obs | pg/ml*h/(mg) | 49506.598 | Vz/F_pred | (mg)/(pg/ml) | 0.000 |
| AUMC 0-t | pg/ml*h^2 | 882575.168 | Cl/F_pred | (mg)/(pg/ml)/h | 0.000 |

The data in Table 30 and FIGS. 70 & 71 demonstrate average plasma concentration of hGH at different time points. The full pharmacokinetic profile are shown in Tables 31 and 32. Orally administered hGH formulation showed 10% bioavailability when compared to IV. hGH was analyzed in plasma using a specific enzyme linked immunosorbent assay (ELISA). Pharmacokinetic endpoints were determined using noncompartmental methods using PK Solutions software. AUC was approximated using the trapezoidal rule on the observed concentrations. C max for each hGH dose was derived as the maximum of all valid concentrations, and t max was then determined as the corresponding time point to C max. The terminal elimination rate constant (λz) was estimated by log-linear regression on the terminal part of the concentration-time curve, and t ½ was then calculated as t ½=ln 2/X z.

Other Embodiments

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

What is claimed is:

1. A polypeptide formulation comprising:

a core comprising a crystallized polypeptide component consisting of a pharmaceutically active polypeptide; and a pharmaceutically acceptable shell consisting of lactose or cane sugar that dissolves when placed buccally or sublingually, so that the pharmaceutically active crystallized polypeptide component is released into mouth tissue and is absorbed through such mouth tissue into the bloodstream, such that once in the bloodstream, at least 5% bioavailability of administered pharmaceutically active polypeptide, compared to injection, is achieved.

2. The polypeptide formulation of claim 1, wherein the pharmaceutically active polypeptide is selected from Abaloparatide, Lixisenatide, Afamelanotide, Angiotensin II, Angiotensin II antagonist, Anidulafungin, Atosiban, Aviptadil, Belantamab mafodotin-blmf, Bentiromide, Beta-endorphin, Bivalirudin, Bradykiynin, Bremelanotide, Bursin, Calcitonin, Capreomycin, Carbetocin, Carfilzomib, Caspofungin, Ceruletide, Cholecystokynin, Cu-DOTATATE, Dalbavancin, Daptomycin, Degarelix, Dulaglutide, Edotreotide, Edotreotide gallium Ga-68, Enfortumab Vedotin-Ejfv, Enfuvirtide, Etelcalcetide, Exenatide, Ga DOTA-TOC, gallium Ga-68, Ga-PSMA-11, Glatiramer acetate, Glatiramer, Glucagon, Gonadorelin, Goserilin, Gramicidin, Human growth hormone, Icatibant, Insulin degludec, Interferons, Interferon Alfa-2a, Recombinant Interferon alfacon-1, Interferon Alfa-2b, Recombinant Interferon beta-1b, Interferon beta-1a, Interferon alfa-n3, Interferon alfa-n1, Interferon gamma-1b, Peginterferon alfa-2b, Peginterferon alfa-2a, Insulin, Ixazomib, Lanreotide, Leuprorelin, Leuprotide, Linaclotide, Liraglutide, Lumasiran, Lutetium Lu 177 dotatate, Macimorelin, Micafungin, Mifamurtide, Nesiritide, Octreotide, Oritavancin, Oxytocin, Pasireotide, Plecanatide, Polatuzumab Vedotin-Piiq, Pramlintide, Romidepsin, Voclosporin, Romiplostim, octreotide acetate, Secretin human, Semaglutide, Sermorelin, Setmelanotide, Taltirelin, Teduglutide, Telavancin, Teriparatide, Terlipressin, Tetracosactide, Bacitracin, Vancomycin, Thymalfasin, Mecasermin, Cetrorelix, Vasopressin, Viltolarsen, Ziconotide, Desmopressin, 177Lu DOTA-TATE, 68Ga DOTA-TOC, Insulin recombinant, Exenatide, Lancreotide, Etanercept, Bevacizumab, Rituximab, Infliximab, Trastuzumab, Insulin glargine, Epoetin alfa, Darbepoetin alfa, Epoetin beta, Pegfilgrastim, Ranibizumab, Insulin aspart, Rhu insulin, Octocog alfa, Insulin lispro, Cetuximab, Eptacog alfa, Onabotulinumtoxin A, Filgrastin, Insulin detemir, Natalizumab, Insulin, Palivizumab, Bleomycin, Bortezomib Blenoxane, Buserelin, Carfilzomib, Cobicistat, Corticotropin, Cosyntropin, Dactinomycin, Depreotide, Eptifibatide, Ganirelix, Glutathion, Histrelin, Leuprolide, Lucinactant, Lypressin, Nafarelin, Pentagastrin, Pentetreotide, Polymyxin B, Protirelin, Saralasin, Secretin porcine, Sincalide, Somatorelin, Somatostatin, Teicoplanin, Triptorelin, Urofollitropin, Abarelix, Pegvisomant, Somatropin recombinant, Lutropin alfa, Follitropin beta, Menotropins, Thyrotropin Alfa, Choriogonadotropin alfa, Aldesleukin, Coagulation Factor IX, Antihemophilic Factor, Eptifibatide, Exenatide, Lepirudin, Angiotensin 1-7, Boceprevir, Ciclosporin, Ciclosporin, Dalbavancin, Lutetium (177Lu) oxodotreotide, Ombitasvir, paritaprevir, ritonavir, Televancin, Avexitide, Calcitonin gene-related peptide, Corticorelin, Leptin, Aclerastide, Albusomatropin, Anamorelin, G17DT, Insulin peglispro, Lenomorelin, Selepressin, Somapacitan, Taspoglutide, Thymosin beta-4, Tirzepatide, Ularitide, Vosoritide, Zoptarelin doxorubicin, Bombesin, Cenderitide, Deslorelin, Gastric inhibitory polypeptide, MK-3207, Olcegepant, Pancreatic Polypeptide, Peptide YY (3-36), Pirnabine, Somatoprim, TT-232, BPI-3016, NBI-6024, Albiglutide, Taltirelin hydrate, Tesamorelin, Peginesatide, Cyclosporin A, Plecanotide, Colistin sulfate, Tyrothricin, Pancrelipase, Tilactase, Sacrosidase, Diamine oxidase, insulin by the Palmitoylation, Thymopentin, 6-LGDP, PTH1-34, BSA, sCT, hGH, BSM, Captopril, Enfurvitide, Streptokinase, Dolcanatide, Efpeglenation, MEDI4166, or PF-06836922 (MOD-4023).

3. The polypeptide formulation of claim 1, wherein the pharmaceutically active polypeptide is insulin, parathyroid hormone (PTH), human growth hormone, liraglutide, octreotide acetate, or trastuzumab.

4. The polypeptide formulation of claim 1, wherein the pharmaceutically active polypeptide has a molecular weight between about 500 Da to about 200 kDa.

5. The polypeptide formulation of claim 1, wherein the polypeptide formulation comprises about 1 μg to about 500 mg of the pharmaceutically active polypeptide.

6. The polypeptide formulation of claim 1, wherein the crystallized polypeptide component consists of crystals of the pharmaceutically active polypeptide having an average particle size of less than 25 microns.

7. The polypeptide formulation of claim 1, wherein the pharmaceutically active polypeptide-comprises lyophilized polypeptide.

8. The polypeptide formulation of claim 1, wherein the crystallized polypeptide component is in a powder form.

9. The polypeptide formulation of claim 1, wherein the shell consists of cane sugar.

10. The polypeptide formulation of claim 1, wherein the shell is hollow.

11. The polypeptide formulation of claim 1, wherein the shell is hollow and the shell is fully filled with space from the core.

12. The polypeptide formulation of claim 1, wherein the shell is hollow and the shell is partially filled with space from the core.

13. The polypeptide formulation of claim 1, wherein the formulation is in a shape of sphere, cube, cone, cylinder, half sphere, torus, pyramid, triangular prism, hexagonal prism, cuboid, hexagonal pyramid, hallow cylinder, octahedron, diamond, star prism, hexagonal diamond, star pyramid, pentagonal prism, L shape prism, dodecahedron, tetrahedron, or icosahedron, or a combination thereof.

14. The polypeptide formulation of claim 1, wherein the formulation is in a shape of sphere.

15. The polypeptide formulation of claim 1, wherein the core further comprises one or more excipients or additives selected from the group consisting of aggregation-reducing agents, sugars or sugar alcohols, polysaccharides, stabilizers, hyaluronidase, buffering agents, preservatives, carriers, antioxidants, chelating agents, natural or synthetic polymers, cryoprotectants, lyoprotectants, surfactants, bulking agents, acidifying agents, ingredients to reduce injection site discomfort, antifoaming agents, alkalizing agents, vehicles, aggregation inhibitors, solubilizing agents, tonicity modifiers, stabilizing agents and combinations thereof.

16. The polypeptide formulation of claim 15, wherein:

(i) the aggregation-reducing agent(s) s are selected from the group consisting of nicotinic acid, caffeine citrate, caffeine nicotinate, caffeine, octyl-β-D-glucopyranoside, and n-dodecyl-β-D-maltoside;

(ii) the tonicity modifier(s) are selected from the group consisting of arginine, cysteine, histidine, glycine, sodium chloride, potassium chloride, sodium citrate, saccharides;

(iii) the antioxidant(s) are selected from the group consisting of glycine, lysine, ethylene-diamidetetraacetic acid (EDTA), diethylenetriaminepentaacetic acid (DTPA), sorbitol, mannitol, ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sulfur dioxide, tocopherol, and combinations thereof;

(iv) the lyoprotectant(s) are selected from the group consisting of sucrose, lactose, trehalose, dextran, erythritol, arabitol, xylitol, sorbitol, maltose, lactulose, maltulose, glucitol, maltitol, lactitol, isomaltulose, mannitol, amino acids, lyotropic salts, gelatin, dextrins, modified starch, carboxymethyl cellulose, and combinations thereof;

(v) permeation enhancer(s) are selected from the group consisting of bile salts, fatty acids, sodium laurate, sodium caprate, glyceryl monostearate, di-ethylene glycol mono ethyl ether, sucrose fatty acid esters, medium-chain fatty acid glycerides, polycaprolactoneomega-3 fatty acids, lecithin, phosphatidylcholine, lysophosphatidylcholine, surfactants, complexing agents, co-solvents, polysaccharides, aprotinin, benzalkonium chloride, cetylpyridinium chloride, cetyltrimethyl ammonium bromide, sodium salicylate, lysophosphatidylcholine, methoxysalicylate, methyloleate, sodium EDTA, sulfoxides, alkyl glycosides, EDTA, tartaric acid, lyotropic salts, propylene glycol, glycerol, polyethylene glycol, poly propylene glycol, gelatin, dextrins, modified starch, carboxymethyl cellulose, and combinations thereof;

(vi) absorption enhancer(s) are selected from the group consisting of surfactants, cholesterol, glycerides, salicylates, bile salts, chelating agents, sodium caprate, a salt of capric acid, and combinations thereof; or (vii) muco bioadhesive agent(s) are selected from the group consisting of sucrose, lactose, trehalose, dextran, erythritol, arabitol, xylitol, sorbitol, maltose, lactulose, maltulose, glucitol, maltitol, lactitol, isomaltulose, mannitol, amino acids, lyotropic salts, propylene glycol, glycerol, polyethylene glycol, polypropylene glycol, gelatin, dextrins, modified starch, carboxymethyl cellulose, anionic polymers, chitosan, hydroxypropyl methylcellulose (HPMC), polyacrylic acid (PAA), 15% carboxymethyl cellulose, 35% carbomer, copolymers of acrylic acid, polyethylene glycol monomethylether monomethacrylate (PEGMM), neutral polyethylacrylate methylmethacrylate, hydrophilic polymers, carboxyvinyl polymer, triethanolamine, hydroxy propyl cellulose (HPC), sodium carboxymethyl cellulose, hydroxy propyl methyl cellulose (HPMC), hydroxy ethyl cellulose (HEC), poly isoprene (PIP), poly Isobutylene (PIB), xanthan gum, locust bean gum, pectin, polycarbophil, benzyl esters, hydroxyethylcellulose, polyacrylic acid, polyacrylic acid-co-acrylamide, polyacrylic acid-co-methyl methacrylate, polyacrylic acid-co-butylacrylate, 2-hydroxyethyl methacrylate (HEMA) copolymerized with polytetramethylene glycol, bioadhesive polymeric blend of CP and PIB, cetylpyridinium chloride, chitosan chloride, polyethylene oxide, polymethylvinylether, maleic anhydride, tragacanth, poly ethyleneglycol monomethylether monomethacrylate, drum dried waxy maize starch (DDWM), carboxypolymethylene, sodium stearylfumarate, cellulose, hydrogels-acrylic acid, butyl acrylate, and combinations thereof.

17. The polypeptide formulation of claim 1, wherein the pharmaceutically active polypeptide has a molecular weight between about 500 Da to about 70 kDa.

18. A method of administering a therapeutic polypeptide to a subject in need thereof, the method comprising:

sublingually administering to the subject a polypeptide formulation comprising: a core and a pharmaceutically acceptable shell consisting of lactose or cane sugar wherein:

the core comprises a polypeptide component consisting of the therapeutic polypeptide that is unmodified or is modified by one or more of acetylation, acylation, amidation, glycation, glycosylation, lipidation, mannosylation, methylation, nitrosylation, phosphorylation, sulfation, palmitoylation, pegylation, and prenylation, which polypeptide is in a crystallized form; and the shell dissolves when placed buccally or sublingually, so that the crystallized polypeptide component is released into mouth tissue and is absorbed through such mouth tissue into the bloodstream, such that once in the bloodstream, at least 5% bioavailability of administered therapeutic polypeptide, compared to injection, is achieved.

* * * * *